United States Patent [19]
Cramp

[11] Patent Number: 5,859,283
[45] Date of Patent: Jan. 12, 1999

[54] INTERMEDIATES TO HERBICIDAL 4-SUBSTITUTED ISOXAZOLES

[75] Inventor: Susan Mary Cramp, Ongar, England

[73] Assignee: Rhone-Poulenc Agriculture Limited, Ongar, England

[21] Appl. No.: 22,051

[22] Filed: Feb. 11, 1998

Related U.S. Application Data

[62] Division of Ser. No. 848,909, May 1, 1997, Pat. No. 5,747,424, which is a division of Ser. No. 460,093, Jun. 2, 1995, Pat. No. 5,656,573, which is a continuation of Ser. No. 108,792, Aug. 19, 1993, abandoned, which is a continuation-in-part of Ser. No. 850,035, Mar. 12, 1992, abandoned, which is a continuation-in-part of Ser. No. 580,795, Sep. 11, 1990, abandoned, and a continuation-in-part of Ser. No. 850,031, Mar. 12, 1992, abandoned, which is a continuation-in-part of Ser. No. 790,175, Nov. 12, 1991, abandoned, and a continuation-in-part of Ser. No. 742,381, Aug. 8, 1991, abandoned, and a continuation-in-part of Ser. No. 850,128, Mar. 12, 1992, abandoned, and a continuation-in-part of Ser. No. 850,424, Mar. 12, 1992, abandoned.

[30] Foreign Application Priority Data

Sep. 11, 1989 [GB] United Kingdom .................. 89 20519

[51] Int. Cl.$^6$ .................................................... C07C 69/74
[52] U.S. Cl. ........................... 560/124; 560/123; 560/121
[58] Field of Search .................................... 560/124, 123, 560/121

[56] References Cited

U.S. PATENT DOCUMENTS

| | | | |
|---|---|---|---|
| 3,658,838 | 4/1972 | Kiehne et al. | 260/310 R |
| 3,865,863 | 2/1975 | Field et al. | 260/465 E |
| 4,031,246 | 6/1977 | Collins et al. | 424/331 |
| 4,093,736 | 6/1978 | Collins | 424/282 |
| 4,173,650 | 11/1979 | Hanifin, Jr. et al. | 548/247 |
| 4,364,956 | 12/1982 | Clark et al. | 424/269 |
| 4,562,187 | 12/1985 | Tegeler et al. | 548/248 |
| 4,680,401 | 7/1987 | Grohe | 546/153 |
| 4,699,992 | 10/1987 | Grohe et al. | 558/405 |
| 4,725,595 | 2/1988 | Schriewer et al. | 514/211 |
| 4,782,156 | 11/1988 | Grohe | 546/153 |
| 4,829,075 | 5/1989 | Ehrhardt et al. | 548/248 X |
| 4,841,059 | 6/1989 | Schriewer et al. | 546/312 |
| 4,902,795 | 2/1990 | Schriewer et al. | 544/182 |
| 4,914,228 | 4/1990 | Grohe | 560/103 |
| 4,977,263 | 12/1990 | Schriewer et al. | 544/329 |
| 4,990,646 | 2/1991 | Grohe | 558/405 |
| 5,059,614 | 10/1991 | Lepage et al. | 548/245 |

FOREIGN PATENT DOCUMENTS

| | | |
|---|---|---|
| 0002480 | 6/1979 | European Pat. Off. . |
| 0129846 | 1/1985 | European Pat. Off. . |
| 0168737 | 1/1986 | European Pat. Off. . |
| 0176846 | 4/1986 | European Pat. Off. . |
| 0220523 | 5/1987 | European Pat. Off. . |
| 0229635 | 7/1987 | European Pat. Off. . |
| 0241232 | 10/1987 | European Pat. Off. . |
| 0248399 | 12/1987 | European Pat. Off. . |
| 0371876 | 6/1990 | European Pat. Off. . |
| 0418175 | 3/1991 | European Pat. Off. . |
| 0476761 | 3/1992 | European Pat. Off. . |
| 2023474 | 8/1970 | France . |
| 2453168 | 10/1980 | France . |
| 2330913 | 1/1974 | Germany . |
| 86-180728 | 8/1986 | Japan . |
| 1268745 | 3/1972 | United Kingdom . |
| 1274578 | 5/1972 | United Kingdom . |
| 1298535 | 12/1972 | United Kingdom . |
| 1304558 | 1/1973 | United Kingdom . |
| 1305863 | 2/1973 | United Kingdom . |
| 2018247 | 10/1979 | United Kingdom . |
| 2098593 | 11/1982 | United Kingdom . |

OTHER PUBLICATIONS

Grothaus et al., *J. Am. Chem. Soc.* 58, 1334–1336 (1936).
Eiden et al, *Arch. Pharmaz.* 306, 929–933 (1973) (includes English abstract).
Sokolov et al, *Chemical Abstracts*, vol. 61, No. 9486a (1964).
Kochetkov et al., *Chemical Abstracts*, vol. 55, No. 18707g (1961).
Ataka et al, *Chemical Abstracts*, vol. 111, No. 11, Sep. 10, 1989, p. 730, abstract No. 97105j.
Kampe, *Angewandte Chemie,* International Edition, vol. 21, No. 7, Jul. 1982, pp. 540–541.
Menozzi et al, *Journal of Heterocyclic Chemistry*, vol. 20, No. 3, May–Jun. 1983, pp. 645–648.
Renfrow et al, *The Journal of Organic Chemistry*, pp. 150–153 (1968).
Sandifer et al, *J. Heterocyclic Chem.* 13, pp. 607–608 (1976).
Ashton et al, *J. Med. Chem.*, 27, pp. 1245–1253 (1984).
Fouli et al, *Journal f. prakt. Chemie,* Band 329, Heft 6, pp. 1116–1122 (1987).
Kochetkov et al, *Zh. Obs. Khm* 30, (11), pp. 3675–3682 (1960) —English translation, pp. 3641–3646.
Oikawa et al, *J. Org. Chem.,* vol. 43, No. 10, pp. 2087–2088 (1978).
Carabateas et al, *Chemical Abstracts*, vol. 98, 160694f (1983).
Broggini et al, *Chemical Abstracts,* vol. 115, 183156r (1991).
Broggini et al, *J. Chem. Soc. Perkin Trans.* 1, 1843–1846 (1991).
Kalish et al, *J. Het. Chem.,* vol. 12 (1), pp. 49–57 (1975).
Sokolov et al, *Zhurnal Obs. Khim.,* vol. 347, pp. 2207–2209 (1964), English translation pp. 2217–2219.
Takashima et al, "Preparation of isoxazole derivatives as herbicides", Chemical Abstracts No. 125:275855, 1996.

*Primary Examiner*—Deborah C. Lambkin
*Attorney, Agent, or Firm*—Burns, Doane, Swecker & Mathis, L.L.P.

[57] ABSTRACT

4-Substituted isoxazole derivatives of formula I:

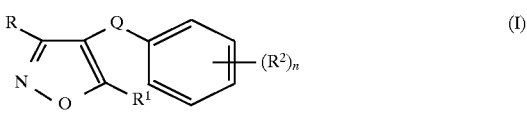

wherein R, R$^1$, R$^2$, Q and n have the meanings defined in the description, which possess valuable herbicidal properties and intermediates useful in their preparation.

7 Claims, No Drawings

INTERMEDIATES TO HERBICIDAL 4-SUBSTITUTED ISOXAZOLES

CROSS-REFERENCE TO RELATED APPLICATIONS

This application is a divisional of application Ser. No. 08/848,909, filed May 1, 1997, U.S. Pat. No. 5,747,424, which is a divisional of application Ser. No. 08/460,093, filed Jun. 2, 1995, U.S. Pat. No. 5,656,573, which is a continuation of application Ser. No. 08/108,792, filed Aug. 19, 1993, now abandoned, which is a continuation-in-part of prior application Ser. No. 07/850,035 filed Mar. 12, 1992, now abandoned, which is a continuation-in-part of application Ser. No. 07/580,795, filed Sep. 11, 1990, now abandoned; and Ser. No. 07/850,031 filed Mar. 12, 1992, now abandoned, which is a continuation-in-part of application Ser. No. 07/790,175, filed Nov. 12, 1991, now abandoned, and Ser. No. 07/742,381, filed Aug. 8, 1991, now abandoned, and Ser. Nos. 07/850,128 and 07/850,424, both filed Mar. 12, 1992, and now abandoned. All or the prior applications are incorporated by reference herein in their entireties and relied upon.

BACKGROUND OF THE INVENTION

1. Field of Invention

This invention relates to 4-substituted isoxazole derivatives, compositions containing them, processes for their preparation, intermediates in their synthesis, and their use as herbicides.

2. Discussion of Prior Art

In U.S. Pat. No. 4,173,650 (American Cyanamid Co) is described the 4-benzoylisoxazole 4-(4-fluorobenzoyl)-5-metylisoxazole, which is used as an intermediate to compounds having anti-inflammatory activity.

D. Grothaus (J. Amer. Chem Soc., 1936 58 1334) describes the preparation of 5-amino-4-(4-bromobenzoyl) isoxazole. Neither of the above publications claim any use of the compounds as herbicides.

SUMMARY OF THE INVENTION

The present invention relates to 4-substituted isoxazole derivatives of formula I:

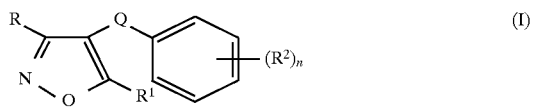

wherein R, $R^1$, $R^2$, Q and n have the meanings as defined below, which possess valuable herbicidal properties.

DESCRIPTION OF PREFERRED EMBODIMENTS

In one embodiment, the invention provides compounds of formula I above wherein

R represents hydrogen;

$R^1$ represents:
  straight- or branched-chain alkyl, alkenyl or alkynyl having up to 6 carbon atoms, optionally substituted by one or more halogens;
  or cycloalkyl having from 3 to 6 carbon atoms, optionally bearing one or more substituents selected from the group consisting of $R^{93}$, halogen and —$CO_2R^{96}$; or
  cycloalkenyl having from 3 to 6 carbon atoms, optionally bearing one or more substituents selected from the group consisting of $R^{93}$, halogen and —$CO_2R^{96}$; or
  an aryl or aralkyl (e.g. benzyl) group, preferably of the formula $(R^2)_q$-phenyl-(—$CR^{93}R^{94}$—)$_p$— (aryl contains 6 to 10 carbon atoms; aralkyl generally contains 7 to 11 carbon atoms); or
  a member of the group consisting of —$CO_2R^{93}$, —$COR^{93}$, cyano, nitro, —$NR^{93}R^{94}$ and halogen (F,Cl,Br,I);

$R^2$ represents:
  a member of the group consisting of nitro, cyano, halogen (F,Cl,Br,I), $R^{95}$, —$S(O)_mR^{95}$, —$SO_2NR^{93}R^{94}$, —$CO_2R^{93}$, —$COR^{93}$, —$CONR^{93}R^{94}$, —$CSNR^{93}R^{94}$, —$OR^{95}$, $C_1$–$C_3$ alkyl substituted by —$OR^{95}$; and —$O(CH_2)_rOR^{97}$;

n represents an integer from 1 to 5;

Q represents C=O;

$R^{93}$ and $R^{94}$, which can be the same or different, each represents:
  hydrogen or straight- or branched-chain alkyl having up to 6 carbon atoms, optionally substituted by one or more halogens;

$R^{95}$ represents:
  straight- or branched-chain alkyl having up to 6 carbon atoms, optionally substituted by one or more halogens;

$R^{96}$ is as defined for $R^{93}$ but does not represent hydrogen;

$R^{97}$ represents straight- or branched-chain alkyl having up to 4 carbon atoms, optionally substituted by one or more halogens;

m represents zero, 1 or 2;

p represents zero or 1;

q represents zero or an integer from 1 to 5; and r represents 1, 2 or 3;

and agriculturally acceptable salts thereof, which possess valuable herbicidal properties.

It is to be understood that when n is an integer from 2 to 5, the substituents $R^2$ may be the same or different, and also the substituents $R^2$, $R^{93}$ and $R^{94}$ may be the same or different.

Furthermore, in certain cases the substituents $R^1$, $R^2$, $R^{93}$, $R^{94}$, $R^{95}$, $R^{96}$ and $R^{97}$ contribute to optical and/or stereoisomerism. All such forms are embraced by the present invention.

The compound of formula I wherein Q is C=O, R is hydrogen, $R^1$ is methyl and $(R^2)_n$ is 4-fluoro is not considered as part of the invention, nor is the compound wherein Q is C=O, R is hydrogen, $R^1$ is $NH_2$ and $(R^2)_n$ is 4-bromo, but compositions containing them and their uses as herbicides are considered as a part of the invention.

By the term 'agriculturally acceptable salts' is meant salts the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts. Suitable acid addition salts of the compounds of formula I, which may be formed when the compounds incorporate an amino radical, include salts with inorganic acids, for example hydrochlorides, sulphates, phosphates and nitrates and salts with organic acids, for example acetic acid. It is to be understood that where reference is made in the present specification to the compounds of formula I, such reference is intended to include also the salts with agriculturally acceptable acids or bases of compounds of formula I where appropriate.

In this first embodiment, among the compounds and/or the compositions and/or the method of use of the invention, it is preferred to use the compounds of formula I wherein $R^1$ is alkyl or cycloalkyl and n is 2 or 3. Preferably one of the groups represented by $(R^2)_n$ is in the ortho position on the phenyl ring.

In this first embodiment, further preferred compounds of formula I are those wherein:

$R^1$ is alkyl optionally substituted by halogen; or cycloalkyl optionally substituted by alkyl or halogen, and/or, $R^2$ is halogen; nitro; $R^{95}$; —S(O)$_m$R$^{95}$; alkyl substituted by —OR$^{95}$; or —COOR$^{93}$, wherein $R^{93}$ is not hydrogen; and/or $R^{95}$ is alkyl (with 1 to 3 carbon atoms) optionally substituted by fluorine or chlorine.

In this first embodiment, a further preferred class of compounds of formula I are those wherein:

$R^1$ represents straight- or branched-chain alkyl having up to 4 carbon atoms; or cycloalkyl having 3 or 4 carbon atoms, optionally substituted by straight- or branched-chain alkyl having up to 4 carbon atoms;

one of the groups $R^2$ represents halogen, or a member selected from the group consisting of $R^{95}$, —OR$^{95}$, —S(O)$_m$R$^{95}$ and nitro, in the 2-position of the phenyl ring;

one of the groups $R^2$ represents —O(CH$_2$)$_r$—OR$^{97}$, in the 3-position of the phenyl ring;

the 4-position of the phenyl ring is unsubstituted or substituted by a group $R^2$, wherein $R^2$ represents halogen or a member selected from the group consisting of $R^{95}$, —OR$^{95}$, —S(O)$_m$R$^{95}$ and nitro;

$R^{95}$ represents straight- or branched-chain alkyl having from one to four carbon atoms, optionally substituted by one or more halogens;

and r represents an integer from 1 to 3;

which show unexpected and high herbicidal action in comparison with known compounds against important weed species including cockelbur (*Xanthium strumarium*).

In this first embodiment, a further preferred class of compounds of formula I are those having one or more of the following characteristics:

a) $R^1$ represents methyl, ethyl, 1-methylethyl, cyclopropyl or 1-methylcyclopropyl;

b) one of the groups $R^2$ represents a member selected from the group consisting of chlorine, bromine, fluorine, $R^{95}$ and —S(O)$_m$R$^{95}$, in the 2-position of the phenyl ring;

c) one of the groups $R^2$ represents —O(CH$_2$)$_r$—OR$^{97}$, in the 3-position of the phenyl ring;

d) the 4-position of the phenyl ring is unsubstituted or substituted by a group $R^2$, wherein $R^2$ represents chlorine, bromine or fluorine, or a group selected from $R^{95}$ and —S(O)$_m$R$^{95}$;

e) $R^{97}$ represents a straight- or branched-chain alkyl having from one to four carbon atoms;

f) n represents 2 or 3;

g) r represents two or three;

with the proviso that either the 2-position or the 4-position of the phenyl ring is substituted by a group —SO$_2$R$^{95}$.

In this first embodiment, a further preferred class of compounds of formula I because of their herbicidal properties are those wherein:

a) $R^1$ represents 1-methylethyl, 1-methylcyclopropyl or cyclopropyl;

b) one of the groups $R^2$ represents halogen or a member selected from the group consisting of $R^{95}$, —OR$^{95}$, —S(O)$_m$R$^{95}$ and nitro, in the 2-position of the phenyl ring;

c) one of the groups $R^2$ represents —O(CH$_2$)$_r$—OR$^{97}$, in the 3-position of the phenyl ring;

d) one of the groups $R^2$ represents chlorine, bromine or fluorine or a member selected from the group consisting of $R^{95}$ and —S(O)$_m$R$^{95}$, in the 4-position of the phenyl ring;

e) $R^{95}$ represents methyl, ethyl or trifluoromethyl; and f) $R^{97}$ represents methyl or ethyl.

In this first embodiment, a particularly preferred class of compounds of formula I because of their herbicidal properties are those wherein;

a) $R^1$ represents cyclopropyl;

b) one of the groups $R^2$ represents chlorine, bromine or fluorine; or a member selected from the group consisting of methyl, trifluoromethyl and —S(O)$_m$CH$_3$, in the 2-position of the phenyl ring;

c) one of the groups $R^2$ represents —O(CH$_2$)$_r$—OR$^{97}$, in the 3-position of the phenyl ring;

d) one of the groups $R^2$ represents chlorine, bromine or fluorine or a member selected from the group consisting of methyl, trifluoromethyl and —S(O)$_m$CH$_3$; and e) r represents two;

with the proviso that either the 2-position or the 4-position of the phenyl ring is substituted by a group —S(O)$_m$R$^{95}$.

In this first embodiment, other preferred compounds of formula I are those wherein $R^1$ is an aryl or aralkyl group, particularly when $R^1$ has the formula $[(R^2)_q$-phenyl]-(CR$^{93}$R$^{94}$)$_p$—, wherein p is zero or 1, q is zero or an integer from 1 to 5, and $R^2$, $R^{93}$ and $R^{94}$ are as defined above.

In a second embodiment, the invention provides compounds of formula I above wherein:

R represents:
straight- or branched-chain alkyl, alkenyl or alkynyl having up to 6 carbon atoms, optionally substituted by one or more halogens;

or cycloalkyl having from 3 to 6 carbon atoms, optionally bearing one or more substituents selected from the group consisting of $R^{85}$, halogen and —CO$_2$R$^{83}$; or a member selected from the group consisting of —CO$_2$R$^{83}$, —COR$^{85}$, cyano, nitro, —CONR$^{84}$R$^{86}$, halogen, —CO$_2$R$^{87}$ and —COSR$^{88}$;

$R^1$ represents:
hydrogen, or
straight- or branched-chain alkyl, alkenyl or alkynyl having up to 6 carbon atoms, optionally substituted by one or more halogens; or
cycloalkyl having from 3 to 6 carbon atoms, optionally bearing one or more substituents selected from $R^{85}$ and halogen;

$R^2$ represents:
halogen, or
a member selected from the group consisting of $R^{85}$, —SR$^{85}$, —SOR$^{85}$, —SO$_2$R$^{85}$, —SO$_2$NR$^{84}$R$^{86}$, —CO$_2$R$^{83}$, —COR$^{85}$, —CONR$^{86}$R$^{84}$, —CSNR$^{84}$R$^{86}$, —OR$^{85}$, nitro, cyano, —O(CH$_2$)$_s$—OR$^{85}$, and straight- or branched-chain alkyl having up to 6 carbons which is substituted by —OR$^{85}$;

n represents an integer from 1 to 5;

Q represents C=O;

$R^{83}$, $R^{84}$ and $R^{86}$, which can be the same or different, each represents:
hydrogen, or
straight- or branched-chain alkyl having up to 6 carbon atoms, optionally substituted by one or more halogens;

$R^{87}$ represents:
straight- or branched-chain alkenyl or alkynyl having from three to six carbon atoms, optionally substituted by one or more halogens or one or more groups —$OR^{85}$, —$SR^{85}$ or —$CO_2R^{83}$; or
a group $Ar(CH_2)_t$—, wherein Ar is phenyl optionally bearing one or more groups $R^2$; or
a group —$N=CR^{81}R^{82}$, wherein
$R^{81}$ represents hydrogen or straight- or branched-chain alkyl having up to six carbon atoms, and
$R^{82}$ represents straight- or branched-chain alkyl having up to six carbon atoms, or phenyl optionally bearing one or more groups $R^2$;
or $R^{81}$ and $R^{82}$ together with the carbon atom to which they are attached form a 5- or 6-membered ring which can have up to two heteroatoms in the ring selected from nitrogen, oxygen and sulfur;

$R^{88}$ represents:
straight- or branched-chain alkyl, alkenyl, or alkynyl having up to six carbon atoms, optionally substituted by one or more halogens or one or more groups —$OR^{85}$, —$SR^{85}$ or —$CO_2R^{83}$; or
phenyl optionally bearing one or more groups $R^2$;

$R^{85}$ represents:
straight- or branched-chain alkyl having up to 6 carbon atoms, optionally substituted by one or more halogens;

s represents an integer from 1 to 3;

t represents zero or an integer from 1 to 3;

provided that R and $R^1$ do not simultaneously represent methyl;

and agriculturally acceptable salts thereof, which possess valuable herbicidal properties.

When n represents an integer from 2 to 5, the substituents $R^2$ may be the same or different.

Furthermore, in certain cases the substituents R, $R^1$, $R^2$, $R^{81}$, $R^{82}$, $R^{83}$, $R^{84}$, $R^{85}$, $R^{86}$, $R^{87}$ and $R^{88}$ contribute to optical isomerism and/or stereoisomerism. All such forms are embraced by the present invention.

By the term "agriculturally acceptable salts" is meant salts, the cations of which are known and accepted in the art for the formation of salts for agricultural or horticultural use. Preferably the salts are water-soluble.

Suitable salts formed by compounds of formula I which are acidic, i.e. compounds containing one or more carboxy groups, with bases include alkali metal (e.g sodium and potassium) salts, alkaline earth metal (e.g. calcium and magnesium) salts, ammonium and amine (e.g diethanolamine, triethanolamine, octylamine, dioctylmethylamine and morpholine) salts.

It is to be understood that where reference is made in the present specification to the compounds of formula I, such reference is intended to include salts where the context so permits.

Herbicidal compositions comprising a compound of formula I wherein Q is C=O and R and $R^1$ simultaneously represent methyl and the use of such compounds for the control of the growth of weeds constitute part of the invention as hereafter defined.

In this second embodiment, a preferred class of compounds of formula I are those wherein:
R represents:
straight- or branched-chain alkyl, alkenyl or alkynyl having up to 6 carbon atoms, optionally substituted by one or more halogens;
or cycloalkyl having from 3 to 6 carbon atoms, optionally bearing one or more substituents selected from $R^{85}$, halogen and —$CO_2R^{83}$; or
a member selected from the group consisting of —$CO_2R^{83}$, —$COR^{85}$, cyano, nitro, —$CONR^{84}R^{86}$ and halogen.

Particularly important classes of compounds of formula I because of their herbicidal properties include those which exhibit one or more of the following features:

(a) R represents:
straight- or branched-chain alkyl having up to 6 carbon atoms, optionally substituted by one or more halogens, for example methyl, ethyl, 1-methylethyl or trifluoromethyl; or
cycloalkyl having from 3 to 6 carbon atoms, for example cyclopropyl or 1-methylcyclopropyl; or
a member selected from the group consisting of —$COR^{85}$, —$CO_2R^{83}$ and halogen, preferably bromine;

(b) $R^1$ represents:
straight- or branched-chain alkyl having up to 6 carbon atoms, for example methyl or 1-methylethyl; or
cycloalkyl having 3 or 4 carbon atoms, optionally bearing one or more $R^{85}$ groups, for example cyclopropyl or 1-methylcyclopropyl;

(c) $R^2$ represents:
halogen, particularly chlorine, fluorine or bromine, or alkyl having up to 6 carbons substituted by —$OR^{85}$; or
a member selected from the group consisting of $R^{85}$, nitro, —$CO_2R^{83}$, —$SOR^{85}$, —$SR^{85}$, —$SO_2R^{85}$ and —$OR^{85}$;

(d) at least one group $R^2$ occupies an ortho position adjacent to the carbonyl group linking the phenyl and isoxazolyl rings;

(e) $R^{83}$ represents:
straight or branched-chain alkyl having up to 6 carbon atoms, for example methyl or ethyl;

(f) $R^{84}$ represents hydrogen;

(g) $R^{85}$ represents straight- or branched-chain alkyl having up to 6 carbon atoms, optionally substituted by one or more halogens, for example methyl or trifluoromethyl;

and agriculturally acceptable salts thereof.

In this second embodiment, a further preferred class of compounds of formula I are those which include one or more of the following features:
R represents —$CO_2R^{83}$ or —$COR^{85}$, most preferably —$CO_2R^{83}$;
$R^1$ represents straight- or branched-chain alkyl having up to 6 carbon atoms, e.g. methyl, ethyl, 1-methylethyl; or cycloalkyl having 3 or 4 carbon atoms, optionally substituted by one or more groups $R^{85}$, e.g. cyclopropyl or 1-methylcyclopropyl;
$R^2$ represents halogen. preferably chlorine or bromine; or alkyl having up to 6 carbon atoms, substituted by —$OR^{85}$; or
a member selected from the group consisting of $R^{85}$, nitro, —$CO_2R^{83}$, —$SR^{85}$, —$SOR^{85}$, —$SO_2R^{85}$, —$OR^{85}$ and —$O(CH_2)_sOR^{85}$;

$R^{83}$ represents straight- or branched-chain alkyl having up to 6 carbon atoms;

$R^{84}$ represents hydrogen:

$R^{85}$ represents straight- or branched-chain alkyl having up to 3 carbon atoms, optionally substituted by one or more halogens;

one of the groups $R^2$ is in the ortho position of the phenyl ring;

and n represents 2 or 3.

In this second embodiment, a further preferred class of compounds of formula I are those wherein:

(a) R represents —$CO_2R^{87}$ or —$COSR^{88}$;

(b) $R^{87}$ represents:
straight- or branched-chain alkenyl or alkynyl having from three to six carbon atoms, optionally substituted by one or more halogens; or
a group $Ar(CH_2)_t$— wherein Ar is phenyl optionally bearing up to three substituents selected from halogen, $R^{85}$, —$OR^{85}$, nitro, cyano, —$SR^{85}$, —$S(O)R^{85}$ and —$SO_2R^{85}$; or
a group —N=$CR^{81}R^{82}$, wherein $R^{82}$ represents:
straight- or branched-chain alkyl having up to six carbon atoms; or phenyl optionally bearing up to three substituents selected from halogen, $R^{85}$, —$OR^{85}$, nitro cyano, —$SR^{85}$, —$S(O)R^{85}$ and —$SO_2R^{85}$;

(c) $R^{88}$ represents:
straight- or branched-chain alkyl, alkenyl or alkynyl having up to six carbon atoms, optionally substituted by one or more halogens;
or phenyl optionally bearing up to three substituents selected from halogen, $R^{85}$, —$OR^{85}$, nitro, cyano, —$SR^{85}$, —$S(O)R^{85}$ and —$SO_2R^{85}$; and/or (d) $R^{85}$ represents alkyl having one or two carbon atoms, optionally substituted by one or more halogens.

In this second embodiment, a further preferred class of compounds of formula I are those wherein;

R represents —$CO_2R^{87}$;

$R^{87}$ represents straight- or branched-chain alkenyl or alkynyl having from three to six carbon atoms, optionally substituted by one or more chlorine, bromine or fluorine; and $R^{85}$ represents methyl, ethyl or trifluoromethyl.

In this second embodiment, a further preferred class of compounds of formula I are those wherein:

R represents —$CO_2R^{87}$;

$R^{87}$ represents:
a group $Ar(CH_2)_t$— wherein Ar is phenyl optionally bearing up to three substituents selected from chlorine, bromine, fluorine, methyl, methoxy, trifluoromethyl, trifluoromethoxy, cyano and nitro;

$R^{85}$ represents methyl, ethyl or trifluoromethyl.

In this second embodiment, a further preferred class of compounds of formula I are those wherein:

R represents —$CO_2R^{87}$;

$R^{87}$ represents a group —N=$CR^{81}R^{82}$, wherein $R^{81}$ represents hydrogen or straight- or branched-chain alkyl having up to four carbon atoms; and $R^{82}$ represents straight- or branched-chain alkyl group having up to four carbon atoms, or phenyl optionally bearing up to three substituents selected from chlorine, bromine, fluorine, methyl, methoxy, trifluoromethyl, trifluoromethoxy, cyano and nitro.

In this second embodiment, a further preferred class of compounds of formula I are those wherein;

R represents —$COSR^{88}$;

$R^{88}$ represents:
straight- or branched-chain alkyl, alkenyl or alkynyl having up to six carbon atoms, optionally substituted by one or more halogens;
or phenyl optionally bearing up to three substituents selected from methyl, methoxy, trifluoromethyl, trifluoromethoxy, nitro and cyano.

In a third embodiment, the invention provides compounds of formula I above wherein:

R represents hydrogen;

$R^1$ represents:
straight- or branched-chain alkyl, alkenyl or alkynyl having up to 6 carbon atoms, optionally substituted by one or more halogens;
or cycloalkyl having from 3 to 6 carbon atoms, optionally substituted by one or more $R^{75}$ groups, or by one or more halogens, or by a substituent —$COOR^{75}$; or
cycloalkenyl having 5 or 6 carbon atoms, optionally substituted by one or more $R^{75}$ groups, or by one or more halogens or by a substituent —$COOR^{75}$; or
an aryl or aralkyl (e.g. benzyl) group of the formula —$[(R^2)_x\text{phenyl}]\text{-}[C(R^{73})(R^{74})]_u$ (aryl is generally $C_6$–$C_{10}$; aralkyl is generally $C_7$–$C_{11}$); or
—$COOR^{75}$; or
—$COR^{73}$; or
cyano or nitro; or
—$NR^{73}R^{74}$; or
halogen (i.e. F, Cl, Br, I);

$R^2$ represents:
nitro or cyano; or
halogen (i.e. F, Cl, Br, I); or
a group $R^{75}$; or
—$S(O)_vR^{75}$; or
—$SO_2NR^{73}R^{74}$; or
—$COOR^{75}$; or
—$COR^{73}$; or
—$CONR^{73}R^{74}$ or —$CSNR^{73}R^{74}$; or
—$OR^{75}$; or
$C_1$–$C_3$ alkyl, substituted by —$OR^{75}$;

n represents an integer from 1 to 5;

Q represents —$CR^{61}R^{71}$—;

$R^{73}$ and $R^{74}$ which may be the same or different, each represents:
hydrogen or straight- or branched-chain alkyl having up to 6 carbon atoms, optionally substituted by one or more halogens;

$R^{75}$ represents:
straight- or branched-chain alkyl having up to 6 carbon atoms, optionally substituted by one or more halogens;

$R^{61}$ represents:
hydrogen: or
—OH; or
halogen (i.e. F, Cl, Br, I); or
a group $R^{75}$; or
alkenyl having up to 6 carbon atoms, optionally substituted by one or more halogens; or
cycloalkyl group having from 3 to 6 carbon atoms, optionally substituted by one or more $R^{75}$ groups or by one or more halogens or by a group —$COOR^{75}$; or
—$S(O)_vR^{75}$; or —COOR$^{75}$; or cyano; or —COR$^{73}$; or —CONR$^{73}$R$^{74}$ or —CSNR$^{73}$R$^{74}$; or —OR$^{75}$; or —O-phenyl-(R$^2$)$_x$; or —OCH$_2$-phenyl-(R$^2$)$_x$; or —OCOR$^{78}$; or —OCO-phenyl-(R$^2$)$_x$; or a group —OCO—Het1; or —OCONR$^{73}$R$^{74}$; or —OSO$_2$R$^{78}$; or —OSO$_2$-phenyl-(R$^2$)$_x$; or —OSO$_2$NR$^{73}$R$^{74}$; or —NR$^{73}$R$^{74}$; or —NR$^{73}$COR$^{75}$; or a group Het2;

R$^{71}$ represents:

hydrogen; or a group R$^{75}$;

or R$^{61}$ and R$^{71}$ can form with the carbon atom to which they are attached, (OR$^{75}$)$_2$ or (SR$^{75}$)$_2$ wherein R$^{75}$ is as defined above, or a cyclic ketal or cyclic thioketal having 5 or 6 atoms in the ring, optionally substituted by one or more R$^{75}$ groups;

R$^{78}$ represents:

straight- or branched-chain alkyl or alkenyl having up to 6 carbon atoms, optionally substituted by one or more halogens; or a cycloalkyl group having from 3 to 6 carbon atoms, optionally substituted by one or more R$^{75}$ groups or by one or more halogens or by a substituent —COOR$^{75}$;

Het1 represents a heterocycle having 5 or 6 atoms in the ring, one or more of which is a heteroatom selected from nitrogen, sulphur and oxygen, the ring carbon atoms being optionally substituted by a group R$^2$;

Het2 represents a heterocyclic group selected from the group consisting of pyrrol-1-yl, pyrazol-1-yl, imidazol-1-yl, 1,2,4-triazol-4-yl, 1,2,4-triazoyl-1-yl, 1,2,3-triazol-1-yl and 1,2,3-triazol-2-yl, each of which may be optionally substituted by one or more groups R$^2$;

v represents zero, 1 or 2;

n represents an integer from 1 to 5;

x represents zero or an integer from 1 to 5; and u represents zero or 1;

and agriculturally acceptable salts thereof, which possess valuable herbicidal properties.

It is to be understood that when n or x is an integer from 2 to 5 the substituents represented by R$^2$ may be the same or different.

Furthermore in certain cases the substituents R$^1$, R$^2$, R$^{61}$, R$^{71}$, R$^{73}$, R$^{74}$, R$^{75}$ and R$^{78}$ contribute to optical and/or stereoisomerism. All such forms are embraced by the present invention.

By the term "agriculturally acceptable salts" is meant salts the cations or anions of which are known and accepted in the art for the formation of salts for agricultural or horticultural uses. Preferably the salts are water-soluble. Suitable salts with bases include alkali metal (e.g. sodium and potassium), ammonium and amine (e.g. diethanolamine, triethanolamine, octylamine, morpholine and dioctylmethylamine) salts. Suitable acid addition salts of the compounds of formula I, which may incorporate an amino radical, include salts with inorganic acids, for example hydrochlorides, sulphates, phosphates and nitrates and salts with organic acids, for example acetic acid.

It is to be understood that where reference is made in the present specification to the compounds of formula I, such reference is intended to include also the salts with agriculturally acceptable acids or bases of compounds of formula I where appropriate.

In this third embodiment, preferred compounds of formula I are those wherein:

a) one of the groups represented by (R$^2$)$_n$ is in the ortho position on the phenyl ring; and/or b) where there are two groups represented by (R$^2$)$_n$, they are in the 2- and 4-positions on the phenyl ring; and/or c) R$^1$ is alkyl optionally substituted by halogen; or cycloalkyl optionally substituted by alkyl or halogen; most preferably cyclopropyl, 1-methylcyclopropyl or 1-methylethyl; and/or d) R$^2$ is halogen; or nitro; or R$^{75}$; or —S(O)$_v$R$^{75}$; or —OR$^{75}$; or alkyl substituted by —OR$^{75}$; or —COOR$^{75}$; and/or e) R$^{75}$ is alkyl (with 1 to 3 carbon atoms) optionally substituted by fluorine or chlorine; and/or f) R$^{61}$ is hydrogen, halogen, —OH, —OR$^{75}$, —OCOR$^{78}$, or alkyl (having from one to four carbon atoms) optionally substituted by one or more halogens; most preferably halogen, —OH, —OR$^{75}$ or —OCOR$^{78}$; and/or g) one of the groups R$^{61}$ or R$^{71}$ is hydrogen; and/or h) R$^{71}$ is hydrogen or alkyl having from one to four carbon atoms; and/or i) R$^{78}$ is alkyl having from one to four carbon atoms, optionally substituted by one or more halogens; and/or j) n is 2 or 3.

In a fourth embodiment, the invention provides compounds of formula I above in which R represents hydrogen, Q represents C═O, R$^1$ is R$^{41}$ as defined below and (R$^2$)$_n$ is 2-R$^{42}$-3-R$^{43}$-4-R$^{44}$ as defined below. The invention thus provides 4-benzoylisoxazole derivatives of formula IA:

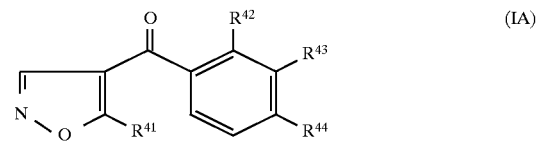

(IA)

wherein:

R$^{41}$ represents:

straight- or branched-chain alkyl having up to 4 carbon atoms;

cycloalkyl having three or four carbon atoms, optionally bearing straight- or branched-chain alkyl having up to four carbon atoms;

R$^{42}$ represents:

straight- or branched-chain alkyl or alkoxy group having up to four carbon atoms; or —S(O)$_w$R$^{40}$;

R$^{43}$ represents:

hydrogen, chlorine, bromine or fluorine; or a member selected from the group consisting of R$^{45}$, —CO$_2$R$^{45}$ and —OR$^{45}$; or straight- or branched-chain alkyl having up to four carbon atoms bearing a substituent —OR$^{45}$; or straight- or branched-chain alkoxy having up to four carbon atoms bearing a substituent —OR$^{45}$;

R$^{44}$ represents chlorine, bromine or fluorine; or straight- or branched-chain allyl or alkoxy having up to four carbon atoms, optionally bearing one or more halogens; or a group —S(O)$_w$R$^{40}$;

R$^{45}$ represents:

straight- or branched-chain alkyl having up to 4 carbon atoms, optionally bearing one or more halogens;

$R^{40}$ represents methyl or ethyl; and w represents zero, one or two;

provided that when $R^{41}$ represents methyl or cyclopropyl, $R^{42}$ represents methyl and $R^{44}$ represents —$SO_2Me$, $R^{43}$ is not —$CO_2Me$ or —$CO_2iPr$;

which possess valuable herbicidal properties.

The compounds of this embodiment, in some aspects of their herbicidal activity, show advantages over known compounds.

In this fourth embodiment, a preferred class of compounds because of their herbicidal properties are those wherein:

$R^{41}$ represents methyl, ethyl, 1-methylethyl, cyclopropyl or 1-methylcyclopropyl;

$R^{42}$ represents:
straight- or branched-chain alkyl or alkoxy having up to four carbon atoms;

$R^{43}$ represents:
hydrogen, chlorine, bromine or fluorine;
a member selected from the group consisting of $R^{45}$, —$CO_2R^{45}$ and —$OR^{45}$;
straight- or branched-chain alkyl having up to four carbon atoms bearing a substituent —$OR^{45}$; or
straight- or branched-chain alkoxy having up to four carbon atoms bearing a substituent —$OR^{45}$; and $R^{44}$ represents —$S(O)_wR^{40}$.

In this fourth embodiment, a further preferred class of compounds of formula IA are those wherein:

a) $R^{41}$ represents 1-methylethyl, cyclopropyl or 1-methylcyclopropyl;

b) $R^{42}$ represents methyl, ethyl methoxy or ethoxy; and/or c) $R^{43}$ represents:
hydrogen, chlorine, bromine or fluorine; or
a member selected from the group consisting of methyl, methoxy, ethoxy, —$CH_2OR^{45}$, —O—$(CH_2)_2OR^{45}$, and —$CO_2R^{45}$, in which $R^{45}$ represents straight- or branched-chained alkyl having up to three carbon atoms.

In this fourth embodiment, a further preferred class of compounds of formula IA are those wherein:

$R^{42}$ represents —$S(O)_wR^{40}$;

$R^{43}$ represents hydrogen; and $R^{44}$ represents:
chlorine, bromine or fluorine; or
straight- or branched-chain alkyl or alkoxy having up to four carbon atoms, optionally bearing one or more halogens, which show unexpected and remarkably high herbicidal activity in comparison with known compounds against important weed species including foxtail (*Setaria viridis* and *Setaria faberii*), barnyard grass (*Echinochloa crus-galli*), crabgrass (*Digitaria sanguinalis*) and shattercane (*Sorghum bicolor*).

In this fourth embodiment, a further preferred class of compounds of formula IA are those wherein:

a) $R^{41}$ represents methyl, ethyl, 1-methylethyl, cyclopropyl or 1-methylcyclopropyl; and/or b) $R^{42}$ represents —$S(O)_wR^{40}$;

c) $R^{43}$ represents hydrogen; and d) $R^{44}$ represents chlorine, bromine or fluorine or a member selected from the group consisting of methyl, methoxy and trifluoromethyl.

In this fourth embodiment, a further preferred class of compounds of formula IA are those wherein:

(a) $R^{41}$ represents cyclopropyl;

(b) $R^{42}$ represents —$S(O)_wR^{40}$;

(c) $R^{43}$ represents hydrogen;

(d) $R^{44}$ represents chlorine, bromine, fluorine or trifluoromethyl; and/or (e) $R^{40}$ represents methyl.

In a fifth embodiment the invention provides compounds of formula I above in which Q represents C=O, R and $R^1$ are $R^{50}$ and $R^{51}$ respectively as defined below, and $(R^2)_n$ is 2-$R^{52}$-3-$R^{53}$-4-$R^{54}$ as defined below. The invention thus provides 4-benzoylisoxazole derivatives of formula IB:

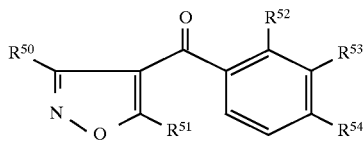

wherein:

$R^{50}$ represents hydrogen or a substituent —$CO_2R^{55}$;

$R^{51}$ represents methyl 1-methylethyl, cyclopropyl or 1-methylcyclopropyl;

$R^{52}$ represents —$S(O)_yR^{56}$;

$R^{53}$ represents:
chlorine, bromine or fluorine;
straight- or branched-chain alkyl or alkoxy having up to four carbon atoms, substituted by one or more halogens;
straight- or branched-chain alkenyl having up to six carbon atoms;
or —$CO_2R^{57}$;

$R^{54}$ represents:
chlorine, bromine or fluorine;
straight- or branched-chain alkyl having up to four carbon atoms, optionally substituted by one or more halogens;
alkoxy group having up to four carbon atoms substituted by one or more halogens;
—$S(O)_zR^{58}$ or cyano;

$R^{55}$ represents straight- or branched-chain alkyl having up to six carbon atoms, optionally substituted by one or more halogens;

$R^{56}$ and $R^{58}$, which can be the same or different, each represents straight- or branched-chain alkyl having up to four carbon atoms, optionally substituted by one or more halogens;

$R^{57}$ represents methyl or ethyl;

y represents zero, one or two; and z represents zero, one or two;

which show unexpected and remarkably high herbicidal activity in comparison with known compounds against important weed species including foxtail (*Setaria viridis* and *Setaria faberii*), barnyard grass (*Echinochloa crus-galli*), crabgrass (*Digitaria sanguinalis*) and shattercane (*Sorghum bicolor*).

In this fifth embodiment, a preferred class of compounds of formula IB because of their herbicidal activity are those wherein:

$R^{50}$ represents hydrogen or a substituent —$CO_2R^{55}$;

$R^{51}$ represents cyclopropyl;

$R^{52}$ represents —$S(O)_yR^{56}$;

$R^{53}$ represents:

chlorine, bromine or fluorine; or straight- or branched-chain alkyl or alkoxy having up to four carbon atoms, optionally substituted by one or more halogens;

$R^{54}$ represents:

chlorine, bromine or fluorine; or straight- or branched-chain alkyl having one or two carbon atoms, optionally substituted by one or more halogens;

$R^{55}$ represents straight- or branched-chain alkyl having up to six carbon atoms, optionally substituted by one or more halogens;

$R^{56}$ represents methyl or ethyl; and y represents zero, one or two.

In this fifth embodiment, a further preferred class of compounds of formula IB are those wherein:

$R^{50}$ represents hydrogen or a substituent —$CO_2R^{55}$;

$R^{51}$ represents methyl, 1-methylethyl, cyclopropyl or 1-methylcyclopropyl;

$R^{52}$ represents —$S(O)_y R^{56}$;

$R^{53}$ represents straight- or branched chain alkenyl having up to six carbon atoms;

$R^{54}$ represents:

chlorine, bromine or fluorine;

straight- or branched-chain alkyl having up to four carbon atoms, optionally substituted by one or more halogens;

alkoxy group having up to four carbon atoms substituted by one or more halogens;

—$S(O)_z R^{58}$ or cyano;

$R^{55}$ represents straight- or branched-chain alkyl having up to six carbon atoms, optionally substituted by one or more halogens;

$R^{56}$ and $R^{58}$, which can be the same or different, each represents straight- or branched-chain alkyl having up to four carbon atoms, optionally substituted by one or more halogens;

y represents zero, one or two; and z represents zero, one or two.

In this fifth embodiment, where $R^{50}$ represents —$CO_2R^{55}$, $R^{55}$ is preferably methyl or ethyl.

In this fifth embodiment, preferably $R^{51}$ represents cyclopropyl.

In this fifth embodiment, where $R^{53}$ represents alkenyl, alkenyl preferably has from two to four carbon atoms, more preferably two or three carbon atoms. Where $R^{53}$ represents —$CO_2R^{57}$, $R^{57}$ is preferably methyl. Where $R^{53}$ represents a halogen-substituted alkyl, preferably $R^{53}$ is not trifluoromethyl; preferred halogen-substituted alkyls include for example difluoromethyl, 2,2,2-trifluoroethyl, fluoromethyl and dichlorofluoromethyl. Preferred compounds include those wherein $R^{53}$ represents optionally halogen-substituted alkoxy having one or two carbon atoms, more preferably ethoxy or most preferably methoxy.

In this fifth embodiment, where $R^{54}$ represents —$S(O)_z R^{58}$, preferably z is zero and/or $R^{58}$ is ethyl or most preferably methyl.

In this fifth embodiment, a preferred class of compounds of formula IB are those wherein:

$R^{53}$ represents fluorine, chlorine or bromine; methyl or ethyl; alkoxy of one or two carbon atoms, optionally substituted by one or more halogens; alkenyl having from two to four carbon atoms; or —$CO_2R^{57}$;

$R^{54}$ represents fluorine, chlorine or bromine; alkyl of one or two carbon atoms substituted by one or more halogens; alkoxy of one or two carbon atoms substituted by one or more halogens; or —$S(O)_z R^{58}$, wherein z represents zero and $R^{58}$ is methyl or ethyl; and $R^{56}$ represents methyl or ethyl.

In this fifth embodiment, a further preferred class of compounds of formula IB because of their herbicidal activity are those wherein:

$R^{53}$ represents chlorine, bromine or fluorine; or methyl or methoxy, optionally substituted by from one to three halogens; and/or $R^{54}$ represents chlorine, bromine or fluorine; or methyl optionally substituted by from one to three halogens.

In this fifth embodiment, a particularly preferred class of compounds of formula IB because of their herbicidal activity are those wherein:

$R^{53}$ represents chlorine, bromine, fluorine, methyl, methoxy or trifluoromethyl;

$R^{54}$ represents chlorine, bromine, fluorine or trifluoromethyl;

$R^{55}$ represents methyl or ethyl.

In this fifth embodiment, a further preferred class of compounds of formula IB because of their herbicidal activity are those wherein;

$R^{53}$ represents chlorine, bromine or fluorine;

$R^{54}$ represents chlorine, bromine, fluorine or trifluoromethyl:

$R^{55}$ represents methyl or ethyl; and $R^{56}$ represents methyl.

Particularly important compounds of formula I above include the following:

1. 5-methyl-4-(2-nitro-4-trifluoromethylbenzoyl) isoxazole;
2. 5-methyl-4(2-nitrobenzoyl)isoxazole;
3. 4-(2-nitro-4-trifluoromethylbenzoyl)-5-phenylisoxazole;
4. 4-(2,4-dinitrobenzoyl)-5-methylisoxazole;
5. 5-(4-chlorophenyl)-4-(2-nitrotrifluoromethylbenzoyl) isoxazole;
6. 4-(2-chlorobenzoyl)-5-methylisoxazole;
7. 5-methyl-4-(2-nitro-4-methylsulphonylbenzoyl) isoxazole;
8. 5-(1-methylethyl)-4-(2-nitro-4-trifluoromethylbenzoyl)isoxazole;
9. 4-(4-chlorobenzoyl)-5-methylisoxazole;
10. 4-(4-methylbenzoyl)-5-methylisoxazole;
11. 5-(4-fluorophenyl)-4-(2-nitro-4-trifluoromethylbenzoyl)isoxazole;
12. 5-ethyl-4-(2-nitro-4-trifluoromethylbenzoyl) isoxazole;
13. 4-(4-chloro-2-nitrobenzoyl)-5-methylisoxazole;
14. 4-(2-nitrotrifluoromethylbenzoyl)-5-propylisoxazole;
15. 5-cyclopropyl-4-(2-nitro-4-trifluoromethylbenzoyl) isoxazole;
16. 4-(2,3-dichloro-4-methylsulphonylbenzoyl)-5-methylisoxazole;
17. 5-(1,1-methylethyl)-4-(2-nitro-4-trifluoromethylbenzoyl)isoxazole;
18. 4-(4-methoxybenzoyl)-5-methylisoxazole;
19. 5-methyl-4-(4-methyl-2-nitrobenzoyl)isoxazole;
20. 4-(2,3-dichloro-4-methylsulphonylbenzoyl)-5-(1-methylethyl)isoxazole;

21. 5-cyclopropyl-4-(2,3-dichloro-4-methylsulphonylbenzoyl)isoxazole;
22. 4-(2-nitro-4-trifluoromethylbenzoyl)-5-phenylmethylisoxazole;
23. 4-(2-chloro-4-trifluoromethylbenzoyl)-5-cyclopropylisoxazole;
24. 5-methyl-4-(2-nitro-4-pentafluoroethylbenzoyl)isoxazole;
25. 5-cyclopropyl-4-[4-(1,1-dimethylethyl)-2-nitrobenzoyl]isoxazole;
26. 4-[4-(1,1-dimethylethyl)-2-nitrobenzoyl]-5-methylisoxazole;
27. 5-cyclopentyl-4-(2-nitro-4-trifluoromethylbenzoyl)isoxazole;
28. 4-(2,4-dichlorobenzoyl)-5-methylisoxazole;
29. 4-(2-chloro-4-methylsulphonylbenzoyl)-5-methylisoxazole;
30. 4-(2-chloro-4-trifluoromethylbenzoyl)-5-methylisoxazole;
31. 5-methyl-4-(2-trifluoromethylbenzoyl)isoxazole;
32. 5-methyl(2,4-bis-trifluoromethylbenzoyl)isoxazole;
33. 4-(2-chloro-4-methylsulphonylbenzoyl)-5-cyclopropylisoxazole;
34. 5-cyclopropyl-4-(2-trifluoromethylbenzoyl)isoxazole;
35. 5-cyclopropyl-4-(2,4-dichlorobenzoyl)isoxazole;
36. 4-(2,3-dichloro-4methylsulphenylbenzoyl)-5-methylisoxazole;
37. 5-cyclopropyl-4-(2,4-bis-trifluoromethylbenzoyl)isoxazole;
38. 4-(4-chloro-2-trifluoromethylbenzoyl)-5-methylisoxazole;
39. 4-(4-cyano-2-nitrobenzoyl)-5-methylisoxazole;
40. 5-amino-4-(2-nitro-4-trifluoromethylbenzoyl)isoxazole;
41. 4-(4-chloro-2-trifluoromethylbenzoyl)-5-cyclopropylisoxazole;
42. 5-(1-methylethyl)-4-(2-nitro-4-pentafluoroethylbenzoyl)isoxazole;
43. 4-(2-chloro-4-methylsulphonylbenzoyl)-5-(1-methylethyl)isoxazole;
44. 5-cyclopropyl-4-(4-fluoro-2-nitrobenzoyl)isoxazole;
45. 5-cyclopropyl-4-(2-nitro-4-pentafluoroethylbenzoyl)isoxazole;
46. 4-(2,3-dichloro-4-methylsulphinylbenzoyl)-5-methylisoxazole;
47. 5-cyclobutyl-4-(2-nitro-4-trifluoromethylbenzoyl)isoxazole;
48. 4-(4-fluoro-2-nitrobenzoyl)-5-methylisoxazole;
49. 5-(1-methylcyclopropyl)-4-(2-nitro-4-trifluoromethylbenzoyl)isoxazole;
50. 5-(4-nitrophenyl)-4-(2-nitro-4-trifluoromethylbenzoyl)isoxazole;
51. 5-(4-methoxyphenyl)-4-(2-nitro-4-trifluoromethylbenzoyl)isoxazole;
52. 4-(2-chloro-3-ethoxy-4-methylsulphonylbenzoyl)-5-methylisoxazole;
53. 4-(3-cyanobenzoyl)-5-methylisoxazole;
54. 5-cyclopropyl-4-(4-methylsulphonyl-2-trifluoromethylbenzoyl)isoxazole;
55. 5-cyclopropyl-4-(2-nitro-4-methylsulphonylbenzoyl)isoxazole;
56. 4-(2-chloro-3-ethoxy-4-methylsulphonylbenzoyl)-5-cyclopropylisoxazole;
57. 4-(2-chloro-3-ethoxy-4-ethylsulphonylbenzoyl)-5-methylisoxazole;
58. 4(2-chloro-3-ethoxy-4-methylsulphonylbenzoyl)-5-(1-methylethyl)isoxazole;
59. 4-(2-chloro-3-ethoxy-4-ethylsulphonylbenzoyl)-5-cyclopropylisoxazole;
60. 5-(1-ethoxycarbonylcyclopropyl)-4-(2-nitro-4-trifluoromethylbenzoyl)isoxazole;
61. 4-(3-methoxycarbonyl-2-methyl-4-methylsulphonylbenzoyl)-5-methylisoxazole;
62. 5-(2-methylcyclopropyl)-4-(2-nitro-4-trifluoromethylbenzoyl)isoxazole;
63. 4-[2-chloro-3-(1-methylethoxy)-4-methylsulphonylbenzoyl]-5-methylisoxazole;
64. 5-methyl-4-[2-methyl-3-(1-methylethoxycarbonyl)-4-methylsulphonylbenzoyl]isoxazole;
65. 5-cyclopropyl-4-[2-methyl-3-(1-methylethoxycarbonyl)-4-methylsulphonylbenzoyl]isoxazole;
66. 5-(1-ethoxycarbonyl-1-methylethyl)-4-(2-nitro-4-trifluoromethylbenzoyl)isoxazole;
67. 5-cyclopropyl-4-(2,3,4-trichlorobenzoyl)isoxazole;
68. 4-[3-methoxycarbonyl-2-methyl-4-(1-methylethylsulphonyl)benzoyl]-5-methylisoxazole;
69. 5-cyclopropyl-4-(2-nitro-4-trifluoromethylsulphonyl)isoxazole;
70. 5-cyclopropyl-4-(2,6-dichloro-4-trifluoromethylbenzoyl)isoxazole;
71. 5-(1-methylcyclopropyl)-4-(methylsulphonyl-2-nitrobenzoyl)isoxazole;
72. 4-(2-chloro-4-methylsulphonylbenzoyl)-5-(1-methylcyclopropyl)isoxazole;
73. 5-(1-methylethyl)-4-(4-methyl-2-nitrobenzoyl)isoxazole;
74. 5-cyclopropyl-4-(4-methyl-2-nitrobenzoyl)isoxazole;
75. 4-(2-chloro-3-methoxy-4-methylsulphonylbenzoyl)-5-cyclopropylisoxazole;
76. 4-(2-chloro-4-nitrobenzoyl)-5-methylisoxazole;
77. 4-(2-chloro-4-nitrobenzoyl)-5-(1-methylethyl)isoxazole;
78. 4(2-chloro-4-nitrobenzoyl)-5-cyclopropylisoxazole;
79. 4-[4-(1,1-dimethylethyl)-2-nitrobenzoyl]-5-(1-methylethyl)isoxazole;
80. 5-(1-methylpropyl)-4-(2-nitro-4-trifluoromethylbenzoyl)isoxazole;
81. 5-cyclopropyl-4-(2,6-dichlorobenzoyl)isoxazole;
82. 5-(1,1-dimethylethyl)-4-(4-methylsulphonyl-2-nitrobenzoyl)isoxazole;
83. 5-cyclopropyl-4-(2-methylsulphonylbenzoyl)isoxazole;
84. 4-(2-chloro-3-cyano-4-methylsulphenylbenzoyl)-5-cyclopropylisoxazole;
85. 4-(4-bromo-2-methylbenzoyl)-5-cyclopropylisoxazole;
86. 4-(2-chloro-4-methylsulphonylbenzoyl)-5-(1,1-dimethylethyl)isoxazole;
87. 4-(2-chloro-4-methylsulphonylbenzoyl)-5-(1-methylpropyl)isoxazole;
88. 5-cyclopropyl-4-(2-methylsulphonyl-4-nitrobenzoyl)isoxazole;

89. 5-(1-methylethyl)-4-(2-methylsulphonyl-4-nitrobenzoyl)isoxazole;
90. 4-(2-chloro-4-methylsulphonyl)-5-ethylisoxazole;
91. 5-cyclopropyl-4-(2,6-dichloro-3-nitrobenzoyl)isoxazole;
92. 4-(2-chloro-4-fluorobenzoyl)-5-cyclopropylisoxazole;
93. 5-cyclopropyl-4-[2,4-bis-methylsulphonylbenzoyl]isoxazole;
94. 4-(4-bromo-2-chlorobenzoyl)-5-cyclopropylisoxazole;
95. 5-(1,1-dimethylethyl)-4-(4-methylsulphonyl-2-trifluoromethylbenzoyl)isoxazole;
96. 5-methyl-4-(2-methylsulphonylbenzoyl)isoxazole;
97. 5-methyl-4-(4-methylsulphonyl-2-trifluoromethylbenzoyl)isoxazole;
98. 5-(1-methylethyl)-4-(4-methylsulphonyl-2-trifluoromethylbenzoyl)isoxazole;
99. 5-(1-methylcyclopropyl)-4-(4-methylsulphonyl-2-trifluoromethylbenzoyl)isoxazole;
100. 4-[2-chloro-4-(1-methylethylsulphonyl)benzoyl]-5-cyclopropylisoxazole;
101. 5-(1-methylethyl)-4-(2-methylsulphonylbenzoyl)isoxazole;
102. 5-cyclopropyl-4-(2-methylsulphenylbenzoyl)isoxazole;
103. 4-(2-chloro-5-methylsulphonylbenzoyl)-5-cyclopropylisoxazole;
104. 4-[2-chloro-4-(1,1-dimethylethylsulphonyl)benzoyl]-5-cyclopropylisoxazole;
105. 5-cyclopropyl-4-(4-methylsulphenyl-2-trifluoromethylbenzoyl)isoxazole;
106. 5-cyclopropyl-4-(2-methylsulphinylbenzoyl)isoxazole;
107. 5-(1-methylcyclopropyl)-4-(2-methylsulphonylbenzoyl)isoxazole;
108. 5-(1-methylpropyl)-4-(2-methylsulphonylbenzoyl)isoxazole;
109. 5-cyclopropyl-4-(2-ethylsulphonylbenzoyl)isoxazole;
110. 4(2-chloro-4-methylsulphenylbenzoyl)-5-cyclopropylisoxazole;
111. 5-cyclopropyl-4-(4-methylsulphenyl-2-nitrobenzoyl)isoxazole;
112. 4(5-chloro-2-methylsulphonylbenzoyl)-5-cyclopropylisoxazole;
113. 4-(2-chloro-4-ethylsulphonylbenzoyl)-5-cyclopropylisoxazole;
114. 5-cyclopropyl-4-(2-fluoro-4-methylsulphonylbenzoyl)isoxazole;
115. 4-(2-chloro-4-methylsulphinylbenzoyl)-5-cyclopropylisoxazole;
116. 5-cyclopropyl-4-(4-methylsulphinyl-2-trifluoromethylbenzoyl)isoxazole;
117. 5-cyclopropyl-4-(5-fluoro-2-methylsulphonylbenzoyl)isoxazole;
118. 5-cyclopropyl-4-[2-(1-methylethylsulphonyl)benzoyl]isoxazole;
119. 5-cyclopropyl-4-(2,5-dichloro-4-methylsulphonylbenzoyl)isoxazole;
120. 5-cyclopropyl-4-(4-methylsulphinyl-2-nitrobenzoyl)isoxazole;
121. 4-(4-cyano-2-nitrobenzoyl)-5-cyclopropylisoxazole;
122. 4-(4-chloro-2-nitrobenzoyl)-5-cyclopropylisoxazole;
123. 5-cyclopropyl-4-(2,4-dibromo-3-methoxybenzoyl)isoxazole;
124. 4-(2-bromo-3-methoxy-4-methylsulphonylbenzoyl)-5-cyclopropylisoxazole;
125. 4-(2-bromo-3-methoxy-4-methylsulphonylbenzoyl)-5-methylisoxazole;
126. 4-(2-bromo-3-methoxy-4-methylsulphonylbenzoyl)-5-(1-methylcyclopropyl)isoxazole;
127. 4-(4-chloro-2-nitrobenzoyl)-5-(1-methylethyl)isoxazole;
128. 4-(2,3-dichloro-4-methylsulphonylbenzoyl)-5-(1-methylcyclopropyl)isoxazole;
129. 4-(2-chloro-4-trifluoromethoxybenzoyl)-5-cyclopropylisoxazole;
130. 5-cyclopropyl-4-(2,3-dichloro-4-trifluoromethoxybenzoyl)isoxazole;
131. 4-(2-chloro-3-methoxy-4-methylsulphonylbenzoyl)-5-(1-methylcyclopropyl)isoxazole;
132. 4(3-chloro-2-methylsulphonylbenzoyl)-5-cyclopropylisoxazole;
133. 4-(2-bromo-4-methylsulphonylbenzoyl)-5-cyclopropylisoxazole;
134. 4-(2-bromo-4-methylsulphonylbenzoyl)-5-(1-methylcyclopropyl)isoxazole;
135. 4-(2-chloro-3-methoxy-4-methylsulphonylbenzoyl)-5-methylisoxazole;
136. 4-(4-ethylsulphenyl-2-trifluoromethylbenzoyl)-5-(1-methylcyclopropyl)isoxazole;
137. 4-(4-ethylsulphenyl-2-trifluoromethylbenzoyl)-5-cyclopropylisoxazole;
138. 4-(4-ethylsulphonyl-2-trifluoromethylbenzoyl)-5-(1-methylcyclopropyl)isoxazole;
139. 4-(4-ethylsulphinyl-2-trifluoromethylbenzoyl)-5-(1-methylcyclopropyl)isoxazole;
140. 5-cyclopropyl-4-(3-methoxy-2-methylsulphonylbenzoyl)isoxazole;
141. 4-(4-fluoro-2-nitrobenzoyl)-5-(1-methylcyclopropyl)isoxazole;
142. 5-(1-methylethyl)-1-(4-methylsulphenyl-2-trifluoromethylbenzoyl)isoxazole;
143. 5-cyclopropyl-4-(4-ethylsulphonyl-2-trifluoromethylbenzoyl)isoxazole,
144. 5-cyclopropyl-4-(4-ethylsulphinyl-2-trifluoromethylbenzoyl)isoxazole;
145. 4-(4-bromo-2-nitrobenzoyl)-5-cyclopropylisoxazole;
146. 4-(2-bromo-4-ethylsulphenyl-3-methoxybenzoyl)-5-cyclopropylisoxazole;
147. 4-(2-bromo-3-difluoromethoxy-4-ethylsulphonylbenzoyl)-5-cyclopropylisoxazole;
148. 5-cyclopropyl-4-(2-methylsulphenyl-4-methylsulphonylbenzoyl)isoxazole;
149. 4-(2-bromo-4-ethylsulphinyl-3-methoxybenzoyl)-5-cyclopropylisoxazole;
150. 5-ethyl-4-(4-methylsulphonyl-2-trifluoromethylbenzoyl)isoxazole;
151. 5-methyl-4-(4-methylsulphonyl-2-trifluoromethylbenzoyl)isoxazole;

152. 5-methyl-4-(4-methylsulphinyl-2-trifluoromethylbenzoyl)isoxazole;
153. 5-(1-methylcyclopropyl)-4-(2-methylsulphenyl-4-methylsulphonyl)isoxazole;
154. 4-(2-bromo-4-methylsulphenylbenzoyl)-5-cyclopropylisoxazole;
155. 4-(2-bromo-4-methylsulphinylbenzoyl)-5-cyclopropylisoxazole;
156. 4-(2-bromo-3-methoxy-4-methylsulphenylbenzoyl)-5-cyclopropylisoxazole;
157. 5-cyclopropyl-4-(2-fluoro-6-methylsulphonylbenzoyl)isoxazole;
158. 4-[2,4-bis-methylsulphenylbenzoyl]-5-cyclopropylisoxazole;
159. 5-cyclopropyl-4-(2,4-dichloro-3-ethoxycarbonylbenzoyl)isoxazole;
160. 4(3-chloro-4-methoxy-2-methylsulphenylbenzoyl)-5-cyclopropylisoxazole;
161. 4-(3-cyano-2,4-dichlorobenzoyl)-5-cyclopropylisoxazole;
162. 5-cyclopropyl-4-(2,4-dichloro-3-methoxybenzoyl)isoxazole;
163. 4(2-fluoro-4-methylsulphonylbenzoyl)-5-(1-methylcyclopropyl)isoxazole;
164. 4-[2,4-dichloro-3-(1-methylethoxycarbonyl)benzoyl]-5-(1-methylcyclopropyl)isoxazole;
165. 4-(2-fluoro-4-methylsulphonylbenzoyl)-5-(1-methylethyl)isoxazole;
166. 4-(2-bromo-3-methoxy-4-methylsulphinylbenzoyl)-5-cyclopropylisoxazole;
167. 5-cyclopropyl-4-[2,4-dichloro-3-(1-methylethoxycarbonyl)benzoyl]isoxazole;
168. 4-(3-chloro-4-methoxy-2-methylsulphinylbenzoyl)-5-cyclopropylisoxazole;
169. 4-(3-chloro-4-methoxy-2-methylsulphonylbenzoyl)-5-cyclopropylisoxazole;
170. 4(2-chloro-3-cyano-4-methylsulphonylbenzoyl)-5-cyclopropylisoxazole;
171. 4(2-chloro-3-cyano-4-methylsulphinylbenzoyl)-5-cyclopropylisoxazole;
172. 4-[2-chloro-3-(1-methylethoxycarbonyl)-4-methylsulphenylbenzoyl]-5-cyclopropylisoxazole;
173. 4-[2-chloro-3-(1-methylethoxycarbonyl)-4-methylsulphonylbenzoyl]-5-cyclopropylisoxazole;
174. 4-[4-chloro-3-(1-methylethoxycarbonyl)-2-methylsulphenylbenzoyl]-5-cyclopropylisoxazole;
175. 4-[4-chloro-3-(1-methylethoxycarbonyl)-2-methylsulphinylbenzoyl]-5-cyclopropylisoxazole;
176. 4-[4-chloro-3-(1-methylethoxycarbonyl)-2-methylsulphonylbenzoyl]-5-cyclopropylisoxazole;
177. 4-[4-trifluoromethyl-3-(1-methylethoxycarbonyl)-2-methylsulphenylbenzoyl]-5-cyclopropylisoxazole;
178. 4-[4-trifluoromethyl-3-(1-methylethoxycarbonyl)-2-methylsulphinylbenzoyl]-5-cyclopropylisoxazole;
179. 4-[4-trifluoromethyl-3-(1-methylethoxycarbonyl)-2-methylsulphonylbenzoyl]-5-cyclopropylisoxazole;
180. 4-[2,4-dibromo-3-(2-methoxyethoxy)benzoyl]-5-cyclopropylisoxazole;
181. 4-[2-bromo-3-(2-methoxyethoxy)-4-methylsulphonylbenzoyl]-5-cyclopropylisoxazole;
182. 4-[2-bromo-3-2-methoxyethoxy)-4-methylsulphonylbenzoyl-5-(1-methylcyclopropyl)isoxazole;
183. 4-[2-bromo-3-(2-methoxyethoxy)-4-methylsulphonylbenzoyl]-5-methylisoxazole;
184. 4-[2-chloro-3-(2-methoxyethoxy)-4-methylsulphonylbenzoyl]-5-cyclopropylisoxazole;
185. 4-[2-chloro-3-(2-methoxyethoxy)-4-methylsulphonylbenzoyl]-5-(1-methylethyl)isoxazole;
186. 4-[2-chloro-3-(2-methoxyethoxy)-4-methylsulphonylbenzoyl]-5-methylisoxazole;
187. 4-[2-bromo-3-(2-methoxyethoxy)-4-methylsulphenylbenzoyl]-5-cyclopropylisoxazole;
188. 4-[2-bromo-3-(2-methoxyethoxy)-4-methylsulphinylbenzoyl]-5-cyclopropylisoxazole;
189. 4-[4-bromo-3-(2-methoxyethoxy)-2-methylsulphinylbenzoyl]-5-cyclopropylisoxazole;
190. 3-methyl-4-(2-nitro-4-trifluoromethylbenzoyl)isoxazole;
191. 3-(1-methylethyl)-4-(2-nitro-4-trifluoromethylbenzoyl)isoxazole;
192. ethyl 4-(2-nitro-4-trifluoromethylbenzoyl)-isoxazole-3-carboxylate;
193. 3-bromo-4-(2-nitro-4-trifluoromethylbenzoyl)isoxazole;
194. 4-(2-nitro-4-trifluoromethylbenzoyl)-3-trifluoromethylisoxazole;
195. 5-cyclopropyl-3-methyl-4-(2-nitro-4-trifluoromethylbenzoyl)isoxazole;
196. ethyl 5-methyl-4-(2-nitro-4-trifluoromethylbenzoyl)isoxazole-3-carboxylate;
197. 5-methyl-4-(2-nitro-4-trifluoromethylbenzoyl)isoxazole-3-carboxamide;
198. ethyl 5-cyclopropyl-4-(2-nitro-4-trifluoromethylbenzoyl)isoxazole-3-carboxylate;
199. 3-cyano-5-methyl-4-(2-nitro-4-trifluoromethylbenzoyl)isoxazole;
200. ethyl 4-(2-chloro-4-methylsulphonylbenzoyl)-5-cyclopropylisoxazole-3-carboxylate;
201. ethyl 5-cyclopropyl-4-(4-methylsulphonyl-2-trifluoromethylbenzoyl)isoxazole-3-carboxylate;
202. methyl 4-(2-chloro-4-methylsulphonylbenzoyl)-5-cyclopropylisoxazole-3-carboxylate;
203. 4-(2-chloro-4-methylsulphonylbenzoyl)-5-cyclopropylisoxazole-3-carboxamide;
204. ethyl 5-cyclopropyl-4-(2-methylsulphonylbenzoyl)isoxazole-3-carboxylate;
205. methyl 5-cyclopropyl-4-(4-methylsulphonyl-2-trifluoromethylbenzoyl)isoxazole-3-carboxylate;
206. ethyl 5-cyclopropyl-4-(2-nitro-4-methylsulphonylbenzoyl)isoxazole-3-carboxylate;
207. ethyl 5-cyclopropyl-4-(2,3-dichloro-4-methylsulphonylbenzoyl)isoxazole-3-carboxylate;
208. ethyl 4-(2-chloro-3-methoxy-4-methylsulphonylbenzoyl)-5-cyclopropylisoxazole-3-carboxylate;
209. 4-(2-chloro-4-methylsulphonylbenzoyl)-3-cyano-5-cyclopropylisoxazole;
210. ethyl 4-(4-chloro-2-methylsulphonylbenzoyl)-5-cyclopropylisoxazole-3-carboxylate;
211. ethyl 4-(4-chloro-2-nitrobenzoyl)-5-cyclopropylisoxazole-3-carboxylate;
212. ethyl 4-(4-chloro-2-trifluoromethylbenzoyl)-5-cyclopropylisoxazole-3-carboxylate;
213. ethyl 5-cyclopropyl-4-(2-methylsulphenyl-4-trifluoromethylbenzoyl)isoxazole-3-carboxylate;

214. ethyl 5-cyclopropyl-4-(4-methylsulphenyl-2-trifluoromethylbenzoyl)isoxazole-3-carboxylate;
215. ethyl 5-cyclopropyl-4-(2-methylsulphinyl-4-trifluoromethylbenzoyl)isoxazole-3-carboxylate;
216. ethyl 5-cyclopropyl-4-(4-methylsulphinyl-2-trifluoromethylbenzoyl)isoxazole-3-carboxylate;
217. ethyl 5-cyclopropyl-4-(2-methylsulphonyl-4-trifluoromethylbenzoyl)isoxazole-3-carboxylate;
218. ethyl 5-cyclopropyl-4-(2-fluoro-4-methylsulphonylbenzoyl)isoxazole-3-carboxylate;
219. ethyl 4-(2-chloro-4-ethylsulphonylbenzoyl)-5-cyclopropylisoxazole-3-carboxylate;
220. ethyl 4-(4-bromo-2-methylsulphonylbenzoyl)-5-cyclopropylisoxazole-3-carboxylate;
221. ethyl 4-(2-bromo-4-methylsulphonylbenzoyl)-5-cyclopropylisoxazole-3-carboxylate;
222. ethyl 4-(2-chloro-4-methylsulphenylbenzoyl)-5-cyclopropylisoxazole-3-carboxylate;
223. ethyl 4-(2-chloro-4-methylsulphinylbenzoyl)-5-cyclopropylisoxazole-3-carboxylate;
224. 3-acetyl-4-(2-chloro-4-methylsulphonylbenzoyl)-5-cyclopropylisoxazole;
225. 1-methylethyl 4-(2-chloro-4-methylsulphonylbenzoyl)-5-cyclopropylisoxazole-3-carboxylate;
226. methyl 4-(4-chloro-2-methylsulphonylbenzoyl)-5-cyclopropylisoxazole-3-carboxylate;
227. methyl 5-cyclopropyl-4-(2-methylsulphonyl-4-trifluoromethylbenzoyl)isoxazole-3-carboxylate;
228. methyl 4-(4-chloro-2-methylsulphenylbenzoyl)-5-cyclopropylisoxazole-3-carboxylate;
229. methyl 4-(4-chloro-2-methylsulphinylbenzoyl)-5-cyclopropylisoxazole-3-carboxylate;
230. ethyl 5-cyclopropyl-4-(2-methoxy-4-methylsulphenylbenzoyl)isoxazole-3-carboxylate;
231. ethyl 5-cyclopropyl-4-(2-methoxy-4-methylsulphinylbenzoyl)isoxazole-3-carboxylate;
232. ethyl 5-cyclopropyl-4-(2-methoxy-4-methylsulphonylbenzoyl)isoxazole-3-carboxylate;
233. ethyl 5-cyclopropyl-4-(2-methyl-4-methylsulphenylbenzoyl)isoxazole-3-carboxylate;
234. ethyl 5-cyclopropyl-4-(2-methyl-4-methylsulphinylbenzoyl)isoxazole-3-carboxylate;
235. ethyl 5-cyclopropyl-4-(2-methyl-4-methylsulphonylbenzoyl)isoxazole-3-carboxylate;
236. 1,1-dimethylethyl 4-(2-chloro-4-methylsulphenylbenzoyl)-5-cyclopropylisoxazole-3-carboxylate;
237. n-hexyl 4-(2-chloro-4-methylsulphenylbenzoyl)-5-cyclopropylisoxazole-3-carboxylate;
238. 2,2,2,-trifluoroethyl 4-(2-chloro-4-methylsulphenylbenzoyl)-5-cyclopropylisoxazole-3-carboxylate;
239. prop-2-enyl 4-(2-chloro-4-methylsulphenylbenzoyl)-5-cyclopropylisoxazole-3-carboxylate;
240. prop-2-ynyl-4-(2-chloro-4-methylsulphenylbenzoyl)-5-cyclopropylisoxazole-3-carboxylate;
241. phenyl 4-(2-chloro-4-methylsulphenylbenzoyl)-5-cyclopropylisoxazole-3-carboxylate;
242. benzyl 4-(2-chloro-4-methylsulphenylbenzoyl)-5-cyclopropylisoxazole-3-carboxylate;
243. benzyl 4-(2-chloro-4-methylsulphonylbenzoyl)-5-cyclopropylisoxazole-3-carboxylate;
244. 4-(2-chloro-4-methylsulphenylbenzoyl)-5-cyclopropyl-3-(isopropylidenaminooxycarbonyl)isoxazole;
245. 4-nitrobenzyl 4-(2-chloro-4-methylsulphenylbenzoyl)-5-cyclopropylisoxazole-3-carboxylate;
246. 4-methoxybenzyl 4-(2-chloro-4-methylsulphenylbenzoyl)-5-cyclopropylisoxazole-3-carboxylate;
247. 4-methoxybenzyl 4-(2-chloro-4-methylsulphonylbenzoyl)-5-cyclopropylisoxazole-3-carboxylate;
248. 4-(2-chloro-4-methylsulphenylbenzoyl)-5-cyclopropyl-3-(benzylidenaminooxycarbonyl)isoxazole;
249. 5-cyclopropyl-4-(2-methoxy-4-methylsulphenylbenzoyl)isoxazole;
250. 5-cyclopropyl-4-(2-methoxy-4-methylsulphonylbenzoyl)isoxazole;
251. 5-cyclopropyl-4-(2-methoxy-4-methylsulphinylbenzoyl)isoxazole;
252. 5-cyclopropyl-4-(2-methyl-4-methylsulphinylbenzoyl)isoxazole;
253. 5-cyclopropyl-4-(2-methylmethylsulphonylbenzoyl)isoxazole;
254. 5-cyclopropyl-4-(2-methyl-4-methylsulphenylbenzoyl)isoxazole;
255. 5-(1-methylcyclopropyl)-4-(2-methyl-4-methylsulphonylbenzoyl)isoxazole;
256. 5-cyclopropyl-4-(2-ethyl-4-methylsulphenylbenzoyl)isoxazole;
257. 5-cyclopropyl-4-(2-ethyl-4-methylsulphinylbenzoyl)isoxazole;
258. 5-cyclopropyl-4-(2-ethyl-4-methylsulphonylbenzoyl)isoxazole;
259. 5-cyclopropyl-4-(2-ethoxy-4-methylsulphenylbenzoyl)isoxazole;
260. 4-(4-chloro-2-methylsulphonylbenzoyl)-5-cyclopropylisoxazole;
261. 5-cyclopropyl-4-(2-methylsulphonyl-4-trifluoromethylbenzoyl)isoxazole;
262. 5-cyclopropyl-4-(2-methylsulphenyl-4-trifluoromethylbenzoyl)isoxazole;
263. 4-(4-bromo-2-methylsulphonylbenzoyl)-5-cyclopropylisoxazole;
264. 5-cyclopropyl-4-(2-methylsulphinyl-4-trifluoromethylbenzoyl)isoxazole;
265. 4-(4-chloro-2-methylsulphonylbenzoyl)-5-(1-methylcyclopropyl)isoxazole;
266. 4-(4-chloro-2-methylsulphonylbenzoyl)-5-(1-methylethyl)isoxazole;
267. 5-cyclopropyl-4-(4-fluoro-2-methylsulphonylbenzoyl)isoxazole;
268. 5-cyclopropyl-4-(4-methyl-2-methylsulphonylbenzoyl)isoxazole;
269. 5-cyclopropyl-4-(4-methoxy-2-methylsulphonylbenzoyl)isoxazole;
270. 4-(4-chloro-2-ethylsulphonylbenzoyl)-5-cyclopropylisoxazole;
271. 4-(4-chloro-2-methylsulphenylbenzoyl)-5-cyclopropylisoxazole;
272. 4-(4-chloro-2-methylsulphinylbenzoyl)-5-cyclopropylisoxazole;

273. 5-(1-methylethyl)-4-(2-methylsulphonyl-4-trifluoromethylbenzoyl)isoxazole;
274. 5-(1-methylcyclopropyl)-4-(2-methylsulphonyl-4-trifluoromethylbenzoyl)isoxazole;
275. 4-(4-chloro-2-methylsulphonylbenzoyl)-5-methylisoxazole;
276. 4-(4-chloro-2-methylsulphenylbenzoyl)-5-(1-methylethyl)isoxazole;
277. 4-(4-chloro-2-ethylsulphonylbenzoyl)-5-(1-methylcyclopropyl)isoxazole;
278. 4-(4-chloro-2-ethylsulphonylbenzoyl)-5-(1-methylethyl)isoxazole;
279. 4-(4-chloro-2-methylsulphonylbenzoyl)-5-ethylisoxazole;
280. 4-(4-chloro-2-methylsulphinylbenzoyl)-5-(1-methylethyl)isoxazole;
281. 4-(4-bromo-2-methylsulphonylbenzoyl)-5-(1-methylcyclopropyl)isoxazole;
282. 4-(4-bromo-2-methylsulphonylbenzoyl)-5-(1-methylethyl)isoxazole;
283. 5-cyclopropyl-4-(3,4-difluoro-2-methylsuphonylbenzoyl)isoxazole;
284. 5-cyclopropyl-4-(3,4-dichloro-2-methylsulphenylbenzoyl)isoxazole;
285. 5-cyclopropyl-4-(3,4-dichloro-2-methylsulphinylbenzoyl)isoxazole;
286. 5-cyclopropyl-4-(3,4-dichloro-2-methylsulphonylbenzoyl)isoxazole;
287. 5-cyclopropyl-4-(4-bromo-3-methoxy-2-methylsulphenylbenzoyl)isoxazole;
288. 5-cyclopropyl-4-(4-bromo-3-methoxy-2-methylsulphonylbenzoyl)isoxazole;
289. 5-cyclopropyl-4-(4-bromo-3-methoxy-2-methylsulphinylbenzoyl)isoxazole;
290. ethyl 5-cyclopropyl-4-(3,4-dichloro-2-methylsulphenylbenzoyl)isoxazole-3-carboxylate;
291. ethyl 5-cyclopropyl-4-(3,4-dichloro-2-methylsulphinylbenzoyl)isoxazole-3-carboxylate;
292. 4-(4-chloro-3-methoxy-2-methylsulphenylbenzoyl)-5-cyclopropylisoxazole;
293. ethyl 5-cyclopropyl-4-(3,4-dichloro-2-methylsulphonylbenzoyl)isoxazole-3-carboxylate;
294. 4-[hydroxy-(2-nitro-4-trifluoromethylphenyl)methyl]-5-cyclopropylisoxazole;
295. 4-[hydroxy-(2-nitro-4-trifluoromethylphenyl)methyl]-5-methylisoxazole;
296. 4-[hydroxy-(2-chloro-3-ethoxy-4-methylsulphonylphenyl)methyl]-5-cyclopropylisoxazole;
297. 4-[acetoxy-(2-nitro-4-trifluoromethylphenyl)methyl]-5-cyclopropylisoxazole;
298. 4-[chloro-(2-nitro-4-trifluoromethylphenyl)methyl]-5-cyclopropylisoxazole;
299. 4-[bromo-(2-nitro-4-trifluoromethylphenyl)methyl]-5-cyclopropylisoxazole;
300. 4-[N,N-dimethylamino-(2-nitro-4-trifluoromethylphenyl)methyl]-5-cyclopropylisoxazole;
301. 4-[hydroxy-(2-chloro-4-methylsulphonylphenyl)methyl]-5-cyclopropylisoxazole;
302. 4-[methoxy-(2-nitro-4-trifluoromethylphenyl)methyl]-5-cyclopropylisoxazole;
303. 4-[hydroxy-(2-nitro-4-methylphenyl)methyl]-5-cyclopropylisoxazole;
304. 4-[hydroxy-(2-chloro-3-ethoxy-4-ethylsulphonylphenyl)methyl]-5-methylisoxazole;
305. 4-[hydroxy-(2-chloro-3-ethoxy-4-ethylsulphonylphenyl)methyl]-5-cyclopropylisoxazole;
306. 4-[acetoxy-(2-chloro-4-methylsulphonylphenyl)methyl]-5-cyclopropylisoxazole;
307. 4-[methoxy-(2-chloro-4-methylsulphonylphenyl)methyl]-5-cyclopropylisoxazole;
308. 4-[hydroxy-(2-chloro-4-fluorophenyl)methyl]-5-cyclopropylisoxazole;
309. 4-[hydroxy-(2-trifluoromethyl-4-methylsulphonylphenyl)methyl]-5-cyclopropylisoxazole;
310. 4-[acetoxy-(2-trifluoromethyl-4-methylsulphonylphenyl)methyl]-5-cyclopropylisoxazole;
311. 4-[methoxy-(2-trifluoromethyl-4-methylsulphonylphenyl)methyl]-5-cyclopropylisoxazole;
312. 4-[bromo-(2-trifluoromethyl-4-methylsulphonylphenyl)methyl]-5-cyclopropylisoxazole;
313. 4-[chloro-(2-trifluoromethyl-4-methylsulphonylphenyl)methyl]-5-cyclopropylisoxazole;
314. 4-[trifluoroacetoxy-(2-trifluoromethyl-4-methylsulphonylphenyl)methyl]-5-cyclopropylisoxazole;
315. 4-[hydroxy-(2-methylsulphonylphenyl)methyl]-5-cyclopropylisoxazole;
316. 4-[hydroxy-(2,3-dichloro-4-methylsulphonylphenyl)methyl]-5-(1-methylcyclopropyl)isoxazole;
317. 4-[hydroxy-(2-methylsulphonyl-4-chlorophenyl)methyl]-5-cyclopropylisoxazole;
318. 4-[hydroxy-(2-bromo-4-methylsulphonylphenyl)methyl]-5-cyclopropylisoxazole;
319. 4-[hydroxy-(2-methylsulphonyl-4-bromophenyl)methyl]-5-cyclopropylisoxazole;
320. 4-[hydroxy-(2-methyl-4-methylsulphonylphenyl)methyl]-5-cyclopropylisoxazole;
321. 4-[hydroxy-(2-chloro-4-methanesulphenylphenyl)methyl]-5-cyclopropylisoxazole;
322. 4-[hydroxy-(2-methylsulphonyl-4-trifluoromethylphenyl)methyl]-5-cyclopropylisoxazole;
323. 4-[hydroxy-(2-chloro-4-methanesulphinylphenyl)methyl]-5-cyclopropylisoxazole;
324. 4-[hydroxy-(2-trifluoromethyl-4-methanesulphenylphenyl)methyl]-5-cyclopropylisoxazole;
325. 4-[hydroxy-(2-fluoro-4-methylsulphonylphenyl)methyl]-5-cyclopropylisoxazole;
326. 4-[hydroxy-(2-methylsulphonyl-4-chlorophenyl)methyl]-5-(1-methylethyl)isoxazole;
327. 4-[hydroxy-(2-methylsulphonyl-4-chlorophenyl)methyl]-5-(1-methylcyclopropyl)isoxazole;
328. 4-(4-chloro-3-methoxy-2-methylsulphinylbenzoyl)-5-cyclopropylisoxazole;
329. 4-(4-chloro-3-methoxy-2-methylsulphonylbenzoyl)-5-cyclopropylisoxazole;

330. 4-(4-chloro-3-methyl-2-methylsulphenylbenzoyl)-5-cyclopropylisoxazole;

331. 4-(4-chloro-3-fluoro-2-methylsulphenylbenzoyl)-5-cyclopropylisoxazole;

332. 4-(4-chloro-3-fluoro-2-methylsulphinylbenzoyl)-5-cyclopropylisoxazole;

333. 4-(4-chloro-3-fluoro-2-methylsulphonylbenzoyl)-5-cyclopropylisoxazole;

334. 4-(4-chloro-3-methyl-2-methylsulphinylbenzoyl)-5-cyclopropylisoxazole;

335. 4-(4-chloro-3-methyl-2-methylsulphonylbenzoyl)-5-cyclopropylisoxazole;

336. 5-cyclopropyl-4-(4-methoxycarbonyl-2-methylsulphenyl-4-trifluoromethylbenzoyl)isoxazole;

337. 4-(4-chloro-3-methoxycarbonyl-2-methylsulphenylbenzoyl)-5-cyclopropylisoxazole;

338. 4-(4-bromo-3-chloro-2-methylsulphenylbenzoyl)-5-cyclopropylisoxazole;

339. 4-(4-bromo-3-chloro-2-methylsulphinylbenzoyl)-5-cyclopropylisoxazole;

340. 4-(4-bromo-3-chloro-2-methylsulphonylbenzoyl)-5-cyclopropylisoxazole;

341. 4-(4-chloro-3-methoxycarbonyl-2-methylsulphinylbenzoyl)-5-cyclopropylisoxazole;

342. 4-(4-chloro-3-methoxycarbonyl-2-methylsulphonylbenzoyl)-5-cyclopropylisoxazole;

343. 4-(3-chloro-2-methylsulphenyl-4-trifluoromethylbenzoyl)-5-cyclopropylisoxazole;

344. 4-(3-chloro-2-methylsulphonyl-4-trifluoromethylbenzoyl)-5-cyclopropylisoxazole;

345. 4-(4-bromo-3-fluoro-2-methylsulphenylbenzoyl)-5-cyclopropylisoxazole;

346. 4-(4-bromo-3-fluoro-2-methylsulphinylbenzoyl)-5-cyclopropylisoxazole;

347. 4-(4-bromo-3-fluoro-2-methylsulphonylbenzoyl)-5-cyclopropylisoxazole;

348. 4-(4-chloro-3-isopropenyl-2-methylsulphenylbenzoyl)-5-cyclopropylisoxazole;

349. 5-cyclopropyl-4-(3-methyl-2,4-bis-methylsulphenylbenzoyl)isoxazole;

350. 4-(4-chloro-3-isopropenyl-2-methylsulphinylbenzoyl)-5-cyclopropylisoxazole;

351. 4(4-chloro-3-isopropenyl-2-methylsulphonylbenzoyl)-5-cyclopropylisoxazole;

352. 5-cyclopropyl-4-[2-methylsulphenyl-3-(2-methoxyethoxy)benzoyl]isoxazole;

353. 5-cyclopropyl-4-[2-methylsulphinyl-3-(2-methoxyethoxy)benzoyl]isoxazole;

354. 5-cyclopropyl-4-[2-methylsulphonyl-3-(2-methoxyethoxy)-benzoyl]isoxazole;

355. 5-cyclopropyl-4-[4-(N,N-dimethylaminosulphonyl)-2-trifluoromethylbenzoyl]isoxazole;

356. 5-cyclopropyl-4-(4-difluoromethoxy-2-methylsulphenylbenzoyl)isoxazole;

357. 4-[2-(2-chloro-1,1,2-trifluoroethoxy)-4-methylsulphenylbenzoyl]-5-cyclopropylisoxazole;

358. 4-[4-chloro-3-(2,2,2-trifluoroethoxy)-2-methylsulphonylbenzoyl]-5-cyclopropylisoxazole;

359. 5-cyclopropyl-4-[2-(1-methylpropylsulphenyl)-4-trifluoromethylbenzoyl]isoxazole;

360. 4-(4-chloro-3-difluoromethyl-2-methylsulphenylbenzoyl)-5-cyclopropylisoxazole;

361. 4-(3-acetyl-4-chloro-2-methylsulphenylbenzoyl)-5-cyclopropylisoxazole;

362. 4-(4-chloro-3-formyl-2-methylsulphenylbenzoyl)-5-cyclopropylisoxazole;

363. 4-[4-chloro-3-(N,N-dimethylcarboxamide)-2-methylsulphenylbenzoyl]-5-cyclopropylisoxazole;

364. 4-(4-chloro-3-methoxymethyl-2-methylsulphenylbenzoyl)-5-cyclopropylisoxazole;

365. 4-(4-chloro-3-methoxymethyl-2-methylsulphonylbenzoyl)-5-cyclopropylisoxazole;

366. 5-cyclopropyl-4-[3,4-dichloro-2-(2,2,2-trifluoroethylsulphenyl)benzoyl]isoxazole;

367. 4-[2-(2-chloro-1,1,2-trifluoroethylsulphenyl)-3,4-dichlorobenzoyl]-5-cyclopropylisoxazole;

368. 4-[4-bromo-2-(2,2,2-trifluoroethoxymethyl)benzoyl]-5-cyclopropylisoxazole;

369. 5-cyclopropyl-4-(3,4-dibromo-2-methylsulphenylbenzoyl)isoxazole;

370. cyclohexyl 5-cyclopropyl-4-(2-methylsulphonyl-4-trifluoromethylbenzoyl)isoxazole-3-carboxylate; and 371. 4-[benzoyloxy-(2-chloro-4-methylsulphonylphenyl)methyl]-5-cyclopropylisoxazole.

The numbers 1 to 371 are assigned to these compounds for reference and identification hereafter.

The compounds of formula I, IA and IB above can be prepared by the application or adaptation of known methods (ie. methods heretofore used or described in the chemical literature), for example as hereinafter described.

In the following description where symbols appearing in formulae are not specifically defined it is to be understood that they are 'as hereinbefore defined' in accordance with the first definition of each symbol in this specification It is to be understood that in the descriptions of the following processes, that the sequences may be performed in different orders and that suitable protecting groups may be required to achieve the compounds sought.

According to a feature of the present invention the compounds of formula I in which R is hydrogen and Q is C═O with the exception of compounds in which $R^1$ is cyano, nitro, amino or halogen may be prepared by the reaction of a compound of formula II:

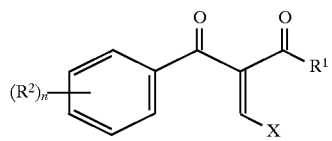

wherein $R^2$ and n are as hereinbefore defined and X is O-alkyl or N,N-dialkyl, with a salt of hydroxylamine such as hydroxylamine hydrochloride in a solvent such as ethanol or acetonitrile optionally in the presence of a base such as triethylamine at a temperature between room temperature and the reflux temperature of the solvent.

According to a further feature of the present invention the compounds of formula I in which R is hydrogen, Q is C═O and $R^2$ is halogen, alkyl alkylthio or alkoxy may be prepared by the reaction of a compound of formula III:

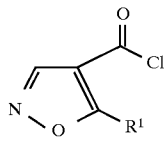

wherein $R^1$ is as hereinbefore defined, with an excess of the appropriately substituted benzene in the presence of a Lewis acid catalyst such as aluminium chloride at a temperature between room temperature and 100 C.

According to a further feature of the present invention the compounds of formula I in which R is hydrogen, Q is C=O and $R^1$ is an unsubstituted amino group may be prepared by the reaction of a compound of formula IV:

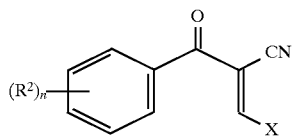

wherein $R^2$, n and X are as hereinbefore defined, with a salt of hydroxylamine such as hydroxylamine hydrochloride in a solvent such as ethanol or acetonitrile optionally in the presence of a base such as triethylamine at a temperature between room temperature and the reflux temperature of the solvent.

According to a further feature of the present invention compounds of formula I in which R is hydrogen and Q is C=O may be prepared by the reaction of a compound of formula V:

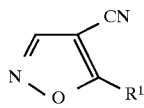

wherein $R^1$ is as hereinbefore defined, with an organometallic reagent such as a Grignard reagent in an inert solvent such as ether or tetrahydofuran at temperatures between room temperature and the reflux temperature of the solvent.

Intermediates in the preparation of compounds of formula I are prepared by the application or adaptation of known methods. For instance compounds of formula II or IV are prepared by the reaction of a diketone or ketonitrile of formula VI:

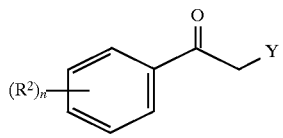

wherein $R^2$ and n are as hereinbefore defined and Y is $COR^1$ or cyano, with an ortho ester such as triethyl orthoformate in the presence of an acid catalyst such as acetic anhydride at the reflux temperature of the mixture (as described by Schwan et al; J. Heterocycl. Chem. 1976, 13,973) or by the reaction of the diketone or ketonitrile of formula VI with an amide acetal such as dimethyl formamide dimethyl acetal in an inert solvent such as toluene at a temperature between room temperature and the reflux temperature of the solvent (as described by W. D. Jones et al J. Heterocycl. Chem. 1987,24,1221).

Intermediates of formula III may be prepared from the appropriate carboxylic acids by the reaction with for example thionyl chloride at the reflux temperature of the mixture (e.g. as described by Doleschall and Seres, J. Chem. Soc. Perkin Trans. I 1988, 1973).

Intermediates of formula V may be prepared from intermediates of formula III by reaction with aqueous ammonia at a temperature between 0° C. and room temperature, followed by dehydration using for example phosphorus oxychloride at a temperature between room temperature and 100° C.

Preparation of the diketone intermediates of formula V (where Y is $COR^1$) is described extensively in the literature, for example Treibs and Hintermeier (Chem. Ber 1954, 87, 1163) describe the preparation of diketones by decarboxylation of t-butyl diketoesters with 4-toluene sulphonic acid and Hauser et al (Organic Reactions 1954, 8 59) review the preparation of diketones by acylation of ketones.

Interconversion of compounds of formula I are possible by the application or adaptation of known methods as described, for example in Comprehensive Heterocyclic Chemistry, Vol 6. For example compounds of formula I which cannot be made directly from compounds of formula II or formula III may be made by interconversion of substituents $R^1$. Examples of interconversions are indicated hereafter.

Compounds in which $R^1$ is a cyano group may be prepared from compounds in which $R^1$ is an ester by acidic hydrolysis of the carboxylic acid for example in aqueous acetic/hydrochloric acid at the reflux temperature of the mixture followed by conversion to the acid chloride using for example thionyl chloride at reflux. The acid chloride may be converted to the amide by treatment with aqueous ammonia at a temperature between 0° C. and room temperature and the amide may be converted to the cyano group by dehydration using for example phosphorus oxychloride at a temperature between room temperature and 100° C.

Compounds in which $R^1$ is an acyl group may be prepared by the reaction of compounds in which $R^1$ is cyano with an organometallic reagent such as a Grignard reagent in an inert solvent such as ether or tetrahydrofuran at temperatures between room temperature and the reflux temperature of the solvent.

Compounds in which $R^1$ is nitro may be prepared by the oxidation of compounds in which $R^1$ is unsubstituted amino using for example trifluoroperacetic acid prepared in situ from trifluoroacetic acid and aqueous hydrogen peroxide.

Compounds in which $R^1$ is a halogen may be prepared from compounds in which $R^1$ is an unsubstituted amino group by diazonzation. This may be carried out using sodium nitrite in the presence of an acid such as hydrochloric acid or hydrobromic acid followed by treatment with for example copper (I) chloride or copper (I) bromide at a temperature between room temperature and 80° C.

Alternatively diazotization may be carried out using an alkyl nitrite such as t-butyl nitrite in the presence of a halogenating agent such as copper (II) chloride or bromoform in an inert solvent such as tetrahydrofuran at a temperature between room temperature and the reflux temperature of the solvent.

Compounds in which $R^1$ is substituted amino may be prepared from compounds in which $R^1$ is halogen by displacement using the appropriate amine in an inert solvent such as toluene at a temperature between 0 C. and room temperature.

Compounds containing sulphinyl or sulphonyl groups may be prepared by oxidation of the compounds containing thioether groups using for example 3-chloroperbenzoic acid in an inert solvent such as dichloromethane at a temperature between −30° C. and the reflux temperature of the solvent.

According to a further feature of the present invention, compounds of formula I wherein R is not hydrogen, Q is C=O and $R^1$, $R^2$ and n are as hereinbefore defined, may be prepared by the reaction of a compound of the formula VII:

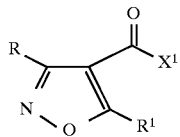

VII wherein $R^1$ is as hereinbefore defined, R is not hydrogen and $X^1$ represents a halogen (preferably a chlorine) atom, with a compound of the formula VIII:

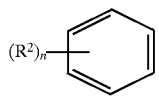

VIII wherein $R^2$ and n are as hereinbefore defined, in the presence of a Lewis acid catalyst, for example aluminium chloride. The reaction is generally performed in an inert solvent at a temperature from 0° C. to 100° C.

According to a further feature of the present invention compounds of formula I wherein R is not hydrogen, Q is C=O and $R^1$, $R^2$ and n are as hereinbefore defined may be prepared by the reaction of a compound of the formula IX:

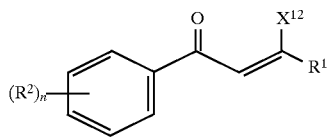

IX wherein $R^1$, $R^2$ and n are as hereinbefore defined and $X^{12}$ represents a group of the formula —N($R^{7a}$)$_2$ or —S$R^{7a}$, wherein $R^{7a}$ represents a straight- or branched-chain alkyl group of up to 4 carbon atoms, with a compound of the formula X:

$$RC(X^1)=N-OH \qquad X$$

wherein R is not hydrogen and $X^1$ is as hereinbefore defined, in the presence of an organic base, for example triethylamine or pyridine, in an inert solvent for example toluene. The reaction may also be carried out in the presence of a catalyst such as a molecular sieve or fluoride ion such as potassium fluoride in an inert solvent such as dichloromethane.

According to a further feature of the present invention compounds of formula I wherein R is not hydrogen, Q is C=O and $R^1$, $R^2$ and n are as hereinbefore defined may be prepared by the reaction of a compound of the formula XI:

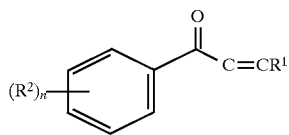

XI wherein $R^1$, $R^2$ and n are as hereinbefore defined, with a compound of formula X above wherein R is not hydrogen and $X^1$ is as hereinbefore defined, in the presence of an organic base or a catalyst in an inert solvent, such as dichloromethane. The reaction may be carried out in the presence of a catalyst, for example, a molecular sieve or fluoride ion such as potassium fluoride.

According to a further feature of the present invention compounds of formula I wherein R is not hydrogen, Q is C=O and $R^1$, $R^2$, and n are as hereinbefore defined, may be prepared by the oxidation of a compound of formula XII:

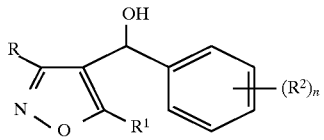

XII wherein R is not hydrogen and $R^1$, $R^2$, and n are as hereinbefore defined, to convert the hydroxy group to a ketone group, for example by means of a mixture prepared from chromium trioxide, aqueous sulphuric acid and acetone.

According to a further feature of the present invention compounds of formula I wherein R is not hydrogen, Q is C=O and $R^1$, $R^2$ and n are as hereinbefore defined may be prepared by metallation of a compound of formula XIII:

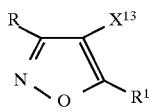

XIII wherein R is not hydrogen and $R^1$ is as hereinbefore defined and $X^{13}$ represents bromine or iodine, with for example n-butyllithium in an inert solvent such as diethyl ether or tetrahydrofuran at a temperature from −78° C. to 0° C., followed by treatment with a benzoyl chloride of formula XIV:

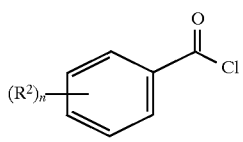

XIV in which $R^2$ and n are as hereinbefore defined.

According to a further feature of the present invention compounds of formula I wherein R is not hydrogen, Q is C=O and $R^1$, $R^2$ and n are as hereinbefore defined may be prepared by the reaction of a salt of a compound of formula XV:

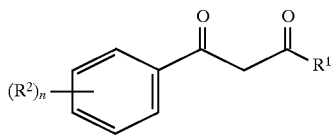

XV wherein $R^1$, $R^2$ and n are as hereinbefore defined, with a compound of formula X above, in which R is not hydrogen and $X^1$ is as hereinbefore defined. Generally the reaction is performed in an inert apolar solvent e.g. toluene from 0° C. to 80° C. Preferred salts include sodium or magnesium salts.

Intermediates used in the preparation of compounds of formula I in which R is not hydrogen and Q is C=O may be prepared by the application or adaptation of known methods, for example methods described below.

Intermediates of formula IX may be prepared by the reaction of an acetophenone of formula XVI:

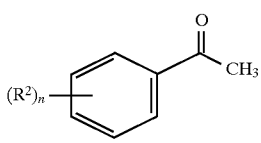

wherein $R^2$ and n are as hereinbefore defined, with an amide acetal of formula XVII:

wherein $R^1$ and $R^{7a}$ are as hereinbefore defined, optionally in the presence of an inert solvent such as toluene, at a temperature from room temperature to the reflux temperature of the mixture.

Alternatively, intermediates of formula IX may be prepared by the reaction of an enamine of formula XVIII:

wherein $R^1$ and $R^{7a}$ are as hereinbefore defined, with a benzoyl chloride of formula XIV wherein $R^2$ and n are as hereinbefore defined, in the presence of an organic base such as triethylamine in an inert solvent such as toluene or dichloromethane at a temperature from $-20°$ C. to room temperature.

Intermediates of formula XI may be prepared by metallation of the appropriate acetylene of formula XIX:

wherein $R^1$ is as hereinbefore defined, using for example n-butyllithium in an inert solvent such as ether or tetrahydrofuran at a temperature from $-78°$ to $0°$ C., followed by reaction of the metal salt thus obtained with a benzoyl chloride of formula XIV wherein $R^2$ and n are as hereinbefore defined.

Intermediates of formula XII may be prepared by the metallation of compounds of formula XIII wherein R is not hydrogen and $R^1$ and $X^{13}$ are as hereinbefore defined, with for example n-butyllithium in an inert solvent such as ether or tetrahydrofuran at a temperature from $-78°$ to $0°$ C., followed by treatment with a benzaldehyde of formula XX:

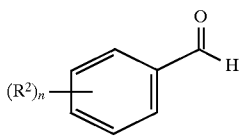

wherein $R^2$ and n are as hereinbefore defined.

Intermediates of formula XIII may be prepared by the halogenation of a compound of formula XXI:

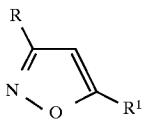

wherein R is not hydrogen and $R^1$ is as hereinbefore defined, for example by heating with bromine or iodine in the presence of concentrated nitric acid.

The agriculturally acceptable salts may be prepared from the compounds of formula I by the application or adaptation of known methods.

Compounds of formulae VII, VIII, X, XIV, XV, XVI, XVII, XVIII, XIX, XX and XXI are known or may be prepared by the application or adaptation of known methods.

Those skilled in the art will appreciate that some compounds of formula I may be prepared by the interconversion of other compounds of formula I, and such interconversions constitute yet more features of the present invention. Examples of such interconversions include:

Compounds in which R or $R^2$ represents a cyano group may be prepared from compounds in which R or $R^2$ represents a group $—CO_2R^{83}$ wherein $R^{83}$ is other than hydrogen via hydrolysis to the corresponding carboxylic acid, in which $R^{83}$ is hydrogen, conversion to the corresponding acid halide, for example by treatment with thionyl chloride or oxalyl chloride, treatment with ammonia to give the amide, and dehydration, for example by means of phosphorus oxychloride.

Compounds in which R or $R^2$ represents a group $—COR^{85}$ may be prepared from corresponding compounds in which R or $R^2$ represents a cyano group by means of a reaction with an organometallic reagent, for example a Grignard reagent of the appropriate structure.

Compounds in which $R^2$ represents $—SOR^{85}$ or $—SO_2R^{85}$ may be prepared by oxidation of compounds in which $R^2$ represents $—SR^{85}$ using for example m-chloroperbenzoic acid in an inert solvent such as dichloromethane at a temperature from $-40°$ C. to $0°$ C.

Compounds in which R or $R^2$ represent $—CO_2R^{83}$ wherein $R^{83}$ represents alkyl may be converted into other compounds in which R or $R^2$ represent $—CO_2R^{83}$ by transesterification of the ester group, for example by the reaction of a compound in which R or $R^2$ represents $—CO_2CH_3$ with an alkoxide salt of formula $M—OR^{83}$ (wherein M represents a metal cation e.g. sodium or potassium) wherein $R^{83}$ is not $CH_3$, in an alcohol solvent $R^{83}OH$ optionally in the presence of an acid catalyst such as sulphuric acid or boron trifluoride etherate. The reaction is preferably carried out at a temperature from $15°$ C. to the reflux temperature of the mixture.

Compounds in which R represents $—CO_2R^{83}$ wherein $R^{83}$ represents alkyl may be converted into other compounds in which R represents a group $—CO_2R^{83}$ or $—CO_2R^{87}$ or $—COSR^{88}$ by hydrolysis to the corresponding carboxylic acid in which $R^{83}$ represents hydrogen, conversion to the corresponding acid halide, for example by treatment with thionyl chloride or oxalyl chloride and subsequent treatment with the appropriate compound $R^{83}OH$, $R^{87}OH$ or $R^{88}SH$ or a salt of the compound such as the sodium salt optionally in the presence of an organic base such as pyridine in an inert solvent such as toluene at a temperature between $0°$ C. and room temperature.

According to a feature of the present invention the compounds of formula I in which R represents hydrogen and Q represents $—CR^{61}R^{71}—$ wherein $R^{61}$ is OH and $R^{71}$ represents hydrogen, may be prepared by the reduction of the corresponding compound of formula I in which Q represents $C=O$ using, for example sodium borohydride in a polar solvent such as ethanol and at temperatures from $0°$ to $50°$ C. It is to be understood that functionality in either $R^1$ or $R^2$ which might be reactive to these conditions is to be selectively protected.

According to a feature of the present invention the compounds of formula I in which R represents hydrogen and Q represents $—CR^{61}R^{71}—$, wherein $R^{61}$ is OH and $R^{71}$ is $R^{75}$, may be prepared by reaction of the corresponding compound of formula I in which Q represents $C=O$ with an appropriate organometallic reagent such as a Grignard reagent, in an inert solvent, such as ether or glyme and at temperatures from $0°$ C. to the refluxing temperature of the solvent.

Compounds of formula I in which R represents hydrogen and Q represents $—CR^{61}R^{71}—$ may be converted into other compounds of formula I in which R represents hydrogen and Q represents —$CR^{61}R^{71}$—.

According to a further feature of the present invention compounds of formula I in which R represents hydrogen and Q represents —$CR^{61}R^{71}$— wherein $R^{61}$ is —OH and $R^{71}$ is hydrogen or $R^{75}$, may be converted into other compounds of formula I wherein $R^{61}$ is —$OCOR^{78}$, or —OCO-phenyl-$(R^2)x$, or —$OCH_2$-phenyl-$(R^2)_x$, or —O-phenyl-$(R^2)_x$, or —OCO—Het1, or —$OCONR^{73}R^{74}$, or —$OS_2R^{78}$, or —$OSO_2$-phenyl-$(R^2)_x$, or —$OSO_2NR^{73}R^{74}$, and $R^{71}$ is hydrogen or $R^{75}$ group, by the reaction of the corresponding compound of formula I in which $R^{61}$ is hydroxy and $R^{71}$ is hydrogen or $R^{75}$, with the corresponding halogen compound in the presence of a suitable base such as pyridine in an inert solvent such as dichloromethane, and at temperatures from 0° C. to the refluxing temperature of the solvent.

Compounds of formula I in which R represents hydrogen and Q represents —$CR^{61}R^{71}$—, wherein $R^{61}$ is chlorine or bromine and $R^{71}$ is a hydrogen or $R^{75}$, may be prepared from the corresponding compound of formula I wherein $R^{61}$ is hydroxy group and $R^{71}$ is hydrogen or $R^{75}$, by reaction with a halogenating agent such as, for example phosphorus trichloride or phosphorous tribromide, in an inert solvent such as ether or dichloromethane, and at temperatures from 0° C. to the refluxing temperature of the solvent.

Alternatively, compounds of formula I in which R represents hydrogen and Q represents —$CR^{61}R^{71}$—, wherein $R^{61}$ is halogen or cyano and $R^{71}$ is hydrogen or $R^{75}$ may be prepared from the corresponding compound of formula I in which $R^{61}$ is hydroxy and $R^{71}$ is hydrogen or $R^{75}$ by first conversion of the hydroxy group to a leaving group such as the mesylate or tosylate group followed by reaction with an alkali metal halide such as sodium iodide or cesium fluoride or reaction with a tetraalkylammonium halide, for example, tetra-n-butylammonium, or an alkali metal cyanide such as potassium cyanide.

According to a further feature of the present invention compounds of formula I in which R represents hydrogen and Q represents —$CR^{61}R^{71}$—, wherein $R^{61}$ is —$OR^{75}$, —$SR^{75}$, Het2, or —$NR^{73}R^{74}$, may be prepared by substitution of the halogen atom of the corresponding compound of formula I in which $R^{61}$ is halogen, with a suitable nucleophile in an inert solvent, and at temperatures from 0° to 50° C.

According to a further feature of the present invention compounds of formula I in which R represents hydrogen and Q represents —$CR^{61}R^{71}$—, wherein $R^{61}$ is —$SOR^{75}$ or —$SO_2R^{75}$, may be prepared by oxidation of the corresponding compound of formula I in which $R^{61}$ is —$SR^{75}$ using, for example meta-chloroperoxybenzoic acid in an inert solvent, and at temperatures from 0° C. to the refluxing temperature of the solvent.

According to a further feature of the present invention, compounds of formula I in which R represents hydrogen and Q represents —$CR^{61}R^{71}$—, wherein $R^{61}$ is —$OR^{75}$ or —$SR^{75}$ and $R^{71}$ is —$OR^{75}$ or —$SR^{75}$, or $R^{61}$ and $R^{71}$ represent cyclic ketal or cyclic thioketal, may be prepared by treating the corresponding compound of formula I in which Q is C=O with the appropriate alcohol or thiol in an inert solvent such as toluene in the presence of an acid catalyst such as para-toluenesulphonic acid at from room temperature to the boiling point of the solvent.

According to a further compounds of present invention, compounds of formula I in which R represents hydrogen and Q represents —$CR^{61}R^{71}$—, wherein $R^{61}$ represents a ketone group —$COR^{73}$ in which $R^{73}$ excludes hydrogen may be prepared from the corresponding compound of formula I in which $R^{61}$ represents cyano by reaction with an organometallic reagent such as a Grignard reagent in an inert solvent such as ether or tetrahydrofuran from room temperature to the reflux temperature of the solvent.

According to a further feature of the present invention, compounds of formula I in which R represents hydrogen and Q represents —$CR^{61}R^{71}$—, wherein $R^{61}$ represents an aldehyde group —$COR^{73}$ in which $R^{73}$ represents hydrogen may be prepared from the corresponding compound of formula I in which $R^{61}$ represents cyano by reduction using diisobutylaluminium hydride in an inert solvent such as ether or tetrahydrofuran.

According to a further feature of the present invention, compounds of formula I in which R represents hydrogen and Q represents —$CR^{61}R^{71}$—, wherein $R^{61}$ represents —$NR^{73}COR^{75}$ may be prepared from the corresponding compound of formula I in which $R^{61}$ represents a group —$NHR^{73}$ by reaction with an acyl compound of formula $R^{75}CO$—$X^{20}$ wherein $X^{20}$ represents a leaving group such as chlorine.

According to a further feature of the present invention, compounds of formula I in which R represents hydrogen and Q represents —$CR^{61}R^{71}$—, wherein $R^{61}$ represents an amide group, —$CONR^{73}R^{74}$ may be prepared from the corresponding compound of formula I in which $R^{61}$ represents an ester group —$CO_2R^{75}$ by acidic hydrolysis of said ester group followed by conversion of the carboxylic acid thus obtained to the corresponding acid chloride using for example thionyl chloride. The acid chloride may be converted to the amide by treatment with an amine of formula H—$NR^{73}R^{74}$.

According to a further feature of the present invention, compounds of formula I in which R represents hydrogen and Q represents —$CR^{61}R^{71}$—, wherein $R^{61}$ represents a group —$CSNR^{73}R^{74}$ may be prepared by reacting the corresponding compound of formula I in which $R^{61}$ represents a group —$CONR^{73}R^{74}$ with Lawesson's reagent, [2,4-bis(4-methoxyphenyl)-1,3-dithia-2,4-diphosphetane-2,4-disulfide] as described in, for example Synthesis,941 (1979).

According to a further feature of the present invention, compounds of formula I in which R represents hydrogen and Q represents —$CR^{61}R^{71}$—, wherein $R^{61}$ represents a group selected from $R^{75}$; alkenyl having up to 6 carbon atoms, optionally substituted by one or more halogens; and cycloalkyl having from 3 to 6 carbon atoms, optionally substituted by one or more $R^{75}$ groups or one or more halogens or —$COOR^{75}$;

may be prepared by reaction of a compound of formula XXI:

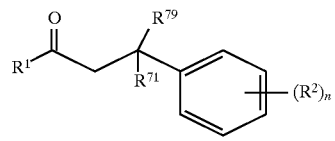

wherein $R^1$, $R^2$, $R^{71}$and n are as hereinbefore defined, $R^{79}$ represents a group selected from $R^{75}$; alkenyl having up to 6 carbon atoms, optionally substituted by one or more halogens; and cycloalkyl having from 3 to 6 carbon atoms, optionally substituted by one or more $R^{75}$ groups or one or more halogens or —$COOR^{75}$;

with a trialkylorthoformate, for example triethylorthoformate in the presence of an acid catalyst, such as acetic anhydride, followed by cyclisation to the desired isoxazole using a salt of hydroxylamine, optionally in the presence of a base such as triethylamine, in an inert solvent and at temperatures from 0° to 50° C.

According to a further feature of the present invention compounds of formula IA above may be prepared by the reaction of a compound of formula IIA:

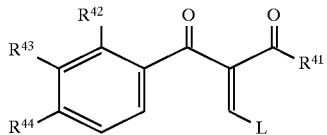

wherein $R^{41}$, $R^{42}$, $R^{43}$ and $R^{44}$ are as hereinbefore defined and L is a leaving group, with a salt of hydroxylamine. Hydroxylamine hydrochloride is generally preferred. Generally L is O-alkyl, for example ethoxy, or N,N-alkylamino, for example dimethylamino. The reaction is generally carried out in a solvent such as ethanol or acetonitrile, optionally in the presence of a base or acid acceptor such as triethylamine or sodium acetate.

According to a further feature of the present invention compounds of formula IA in which $R^{42}$ or $R^{44}$ represent a group $-SR^{40}$ may be prepared by the reaction of a compound of formula IIIA:

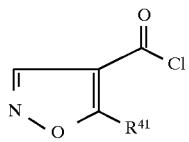

wherein $R^{41}$ is as hereinbefore defined, with a compound of formula IVA:

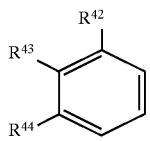

in which $R^{43}$ is as hereinbefore defined and $R^{42}$ or $R^{44}$ represent a group $-SR^{40}$. The reaction is generally carried out in the presence of a Lewis acid catalyst such as aluminium chloride at a temperature between room temperature and 100° C.

According to a further feature of the present invention compounds of formula IA may be prepared by the reaction of a compound of formula VA:

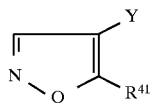

wherein $R^{41}$ is as hereinbefore defined and Y represents a carboxy group or a reactive derivative thereof (such as a carboxylic acid chloride or carboxylic ester), or a cyano group, with an appropriate organometallic reagent such as a Grignard reagent or an organolithium reagent. The reaction is generally carried out in an inert solvent such as ether or tetrahydrofuran at a temperature from 0° C. to the reflux temperature of the mixture.

Intermediates in the preparation of compounds of formula IA are prepared by the application or adaptation of known methods.

Compounds of formula IIA may be prepared by the reaction of compounds of formula VIA:

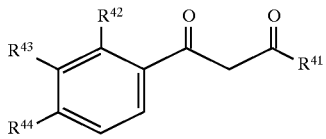

with either a trialkyl orthoformate or a dimethylformamide dialkyl acetal. Generally triethyl orthoformate or dimethylformamide dimethyl acetal are used. The reaction with a trialkyl orthoformate is generally carried out in the presence of acetic-anhydride at the reflux temperature of the mixture and the reaction with a dimethylformamide dialkyl acetal is carried out optionally in the presence of an inert solvent at a temperature from room temperature to the reflux temperature of the mixture.

The preparation of compounds of formulae IIIA, IVA, VA and VIA is described extensively in the literature.

Those skilled in the art will appreciate that some compounds of formula IA may be prepared by the interconversion of other compounds of formula IA and such interconversions constitute yet more features of the present invention. Examples of such interconversions are hereafter described.

According to a further feature of the present invention compounds in which w is 1 or 2 may be prepared by the oxidation of the sulphur atom of compounds in which w is zero. The oxidation of the sulphur atom is generally carried out using for example 3-chloroperoxybenzoic acid in an inert solvent such as dichloromethane at a temperature from −40° C. to room temperature, for example from −40° C. to 0° C.

According to a further feature of the present invention compounds of formula IB above in which $R^{50}$ represents hydrogen may be prepared by the reaction of a compound of formula IIB:

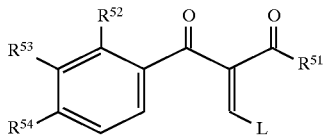

wherein $R^{51}$, $R^{52}$, $R^{53}$ and $R^{54}$ are as hereinbefore defined and L is a leaving group, with a salt of hydroxylamine. Hydroxylamine hydrochloride is generally preferred. Generally L is alkoxy, for example ethoxy, or N,N-dialkylamino, for example dimethylamino. The reaction is generally carried out in a solvent such as ethanol or acetonitrile, optionally in the presence of a base or acid acceptor such as triethylamine or sodium acetate.

According to a further feature of the present invention compounds of formula IB in which $R^{52}$ represents a group $-SR^{56}$ and $R^{50}$ represents hydrogen, may be prepared by the reaction of a compound of formula IIIB:

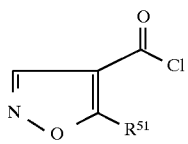

wherein $R^{51}$ is as hereinbefore defined, with a compound of formula IVB:

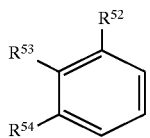

in which $R^{53}$ and $R^{54}$ are as hereinbefore defined and $R^{52}$ represents —$SR^{56}$. The reaction is generally carried out in the presence of a Lewis acid catalyst such as aluminium chloride at a temperature between room temperature and 100° C.

According to a further feature of the present invention compounds of formula IB in which $R^{50}$ represents hydrogen may be prepared by the reaction of a compound of formula VB:

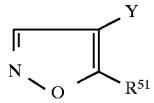

wherein $R^{51}$ is as hereinbefore defined and Y represents a carboxy group or a reactive derivative thereof (such as a carboxylic acid chloride or carboxylic ester), or a cyano group, with an appropriate organometallic reagent such as a Grignard reagent or an organolithium reagent. The reaction is generally carried out in an inert solvent such as ether or tetrahydrofuran at a temperature from 0° C. to the reflux temperature of the mixture.

According to a further feature of the invention compounds of formula IB wherein R represents a group —$CO_2R^{55}$, y is 0 or 2 and $R^{54}$ represents a group $R^{54b}$ which is as hereinbefore defined for $R^{54}$ provided that z is 0 or 2, may be prepared by the reaction of a compound of formula VIB:

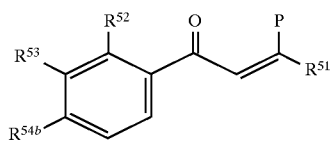

wherein $R^{51}$, $R^{52}$, $R^{53}$ and $R^{54b}$ are as hereinbefore defined, y is zero or two and P is a leaving group such as N,N-dialkylamino, with a compound of formula $R^{55}O_2CC(X^{10})$=NOH wherein $R^{55}$ is as hereinbefore defined and $X^{10}$ is a halogen atom. Generally $X^{10}$ is chlorine or bromine. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula IB in which $R^{50}$ represents a group —$CO_2R^{55}$, y is 0 or 2 and $R^{54}$ represents a group $R^{54b}$ as hereinbefore defined, may be prepared by the reaction of a compound of formula VIIB:

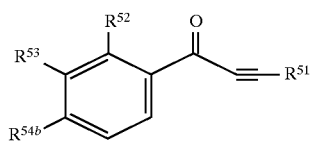

wherein $R^{51}$, $R^{52}$, $R^{53}$ and $R^{54b}$ are as hereinbefore defined and y is 0 or 2, with a compound of formula $R^{55}O_2CC(X^{10})$=NO, wherein $R^{55}$ and $X^{10}$ are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula IB wherein $R^{50}$ represents —$CO_2R^{55}$, y is 0 or 2 and $R^{54}$ represents a group $R^{54b}$ as hereinbefore defined, may be prepared by the reaction of a salt of a compound of formula VIIIB:

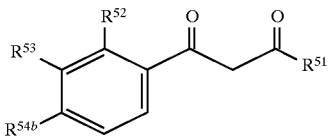

wherein $R^{51}$, $R^{52}$, $R^{53}$ and $R^{54}$ are as hereinbefore defined and y is 0 or 2, with a compound of formula $R^{55}O_2CC(X^{10})$=NOH wherein $R^{55}$ and $X^{10}$ are as hereinbefore defined. Preferred salts include sodium or magnesium salts. The reaction may be performed in an inert solvent such as dichloromethane or acetonitrile at a temperature between room temperature and the reflux temperature of the mixture.

Intermediates in the preparation of compounds of formula IB may be prepared by the application or adaptation of known methods.

Compounds of formula IIB may be prepared by the reaction of compounds of formula (VIIIB) with either a trialkyl orthoformate such as triethyl orthoformate or a dimethylformamide dialkylacetal such as dimethylformamide dimethyl acetal. The reaction with triethyl orthoformate is generally carried out in the presence of acetic anhydride at the reflux temperature of the mixture and the reaction with dimethylformamide dialkyl acetal is carried out optionally in the presence of an inert solvent at a temperature from room temperature to the reflux temperature of the mixture.

Compounds of formula VIB may be prepared by the reaction of a compound of formula IXB wherein $R^{51}$ and P are as hereinbefore defined with a benzoyl chloride of formula XB wherein $R^{52}$, $R^{53}$ and $R^{54b}$ are as hereinbefore defined:

$$R^{51}\!\!>\!\!=\quad\quad IXB$$
$$P$$

COCl  XB (benzene ring with $R^{52}$, $R^{53}$, $R^{54b}$)

The reaction is generally carried out in the presence of an organic base such as triethylamine in an inert solvent such as toluene or dichloromethane at a temperature between –20° C. and room temperature.

Compounds of formula VIIB may be prepared by the metallation of the appropriate acetylene of formula XIB:

$$R^{51}\!-\!C\!\equiv\!CH \quad\quad XIB$$

wherein $R^{51}$ is as hereinbefore defined, followed by reaction of the metal salt thus obtained with a benzoyl chloride of formula XB. The metallation is generally performed using n-butyl lithium in an inert solvent such as ether or tetrahydrofuran at a temperature from −78° C. to 0° C. The subsequent reaction with the benzoyl chloride is carried out in the same solvent at a temperature between −78° C. and room temperature.

Those skilled in the art will appreciate that some compounds of formula IB may be prepared by the interconversion of other compounds of formula IB and such interconversions constitute yet more features of the present invention. Examples of such interconversions are hereafter described.

According to a further feature of the present invention compounds in which y is one or two may be prepared by the oxidation of the sulphur atom of compounds in which y is zero or one. The oxidation of the sulphur atom is generally carried out using for example 3-chloroperoxybenzoic acid in an inert solvent such as dichloromethane at a temperature from −40° C. to room temperature, or hydrogen peroxide in acetic acid in the presence of acetic anhydride or concentrated sulphuric acid.

Benzoic acids required as intermediates in the preparation of compounds of formula IB may be prepared according to a number of processes for example as hereinafter described.

Benzoic acids or esters of formula XIIB may be prepared by diazotization of compounds of formula XIIIB followed by treatment with a dialkyl disulphide, $R^{56}S$—$SR^{56}$:

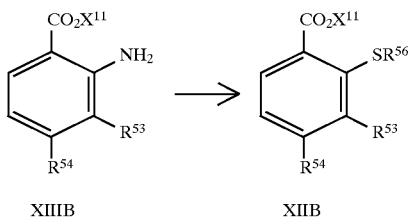

XIIIB            XIIB wherein $R^{53}$, $R^{54}$ and $R^{56}$ are as hereinbefore defined and $X^{11}$ represents hydrogen, methyl or ethyl. Diazotization may be performed using an alkyl nitrite such as t-butyl nitrite in the presence of a dialkyl disulphide in an inert solvent such as chloroform at a temperature from room temperature to the reflux temperature of the mixture. Alternatively diazotization may be carried out using sodium nitrite followed by treatment with a dialkyl disulphide in the presence of a catalyst such as copper.

Alternatively benzoic acids or esters of formula XIIB may be prepared from compounds of formula XIVB:

wherein $R^{53}$, $R^{54}$ and $X^{11}$ are as hereinbefore described and $Y^{11}$ is a halogen atom (e.g. chlorine, fluorine or bromine) or a nitro group, with an alkyl mercaptan of formula $R^{56}$—SH wherein $R^{56}$ is as hereinbefore defined, in the presence of a base. Typical bases used in the above reaction include lithium hydroxide and potassium carbonate and the reaction may be carried out in a solvent such as dimethyl formamide or acetone at a temperature from room temperature to the reflux temperature of the mixture.

Alternatively benzoic acids of formula XIIB in which $R^{53}$ represents halogen may be prepared by lithiation of compounds of formula XVB to give the lithiated intermediate XVBa:

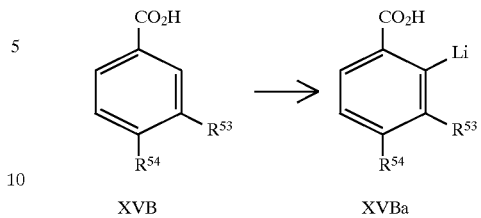

XVB            XVBa wherein $R^{54}$ is as hereinbefore defined and $R^{53}$ represents a halogen atom, which is treated with a dialkyl disulphide, $R^{56}S$—$SR^{56}$, wherein $R^{56}$ is as hereinbefore defined. The lithiation is typically carried out using alkyl lithium compounds such as n-butyl lithium or lithium diisopropylamide in an inert solvent such as tetrahydrofuran at a temperature from −70° C. to −40° C. The reaction is preferably performed under an inert atmosphere. This reaction, giving the lithiated intermediate XVBa is novel and as such constitutes a further feature of the present invention.

The benzoic acids of formula XIB may also be prepared from benzoic acids of formula XVB by first protecting the benzoic acid function as a 4,4-dimethyloxazoline to give a compound of formula XVIB:

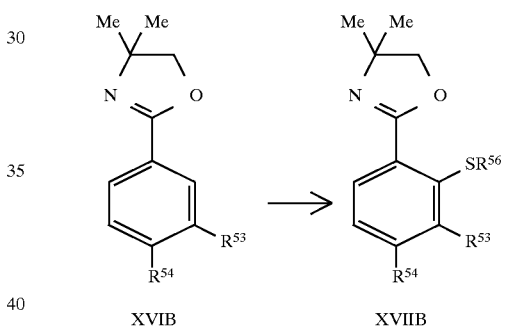

XVIB            XVIIB wherein $R^{53}$ and $R^{54}$ are as hereinbefore defined, which is then lithiated using for example n-butyllithium or lithium diisopropyl amide followed by treatment with a dialkyl disulphide of formula $R^{56}S$—$SR^{56}$, wherein $R^{56}$ is as hereinbefore defined. Compounds of formula XVIB are described in the literature, for example by A Metildan et al, Eur. J. Med. Chem. 25 (1990) 267–270. The oxazoline of formula XVIIB is then converted to the benzoic acid as described for example by A. I. Meyers J. Org. Chem. 40 (1975) 3158–3159.

Intermediates of formulae IIIB, IVB, VB, VIIIB, IXB, XB, XIB, XIIIB, XIVB and XVB are known or may be prepared by the application or adaptation of known methods.

The following Examples illustrate the preparation of compounds of formula I, IA and IB and the following Reference Examples illustrate the preparation of intermediates of the invention. In the present specification b.p. means boiling point; m.p. means melting point; Cp represents cyclopropyl; Ph is phenyl. Where the letters NMR appear the characteristics of the proton nuclear magnetic resonance spectrum follow.

EXAMPLE 1

A mixture of crude 2-ethoxymethylene-1-(2-nitro-4-trifluoromethylphenyl)butan-1,3-dione (13.25 g) and hydroxylamine hydrochloride (3.7 g) in ethanol (80 ml) was stirred for 5 hours. The solution was evaporated almost to dryness and the resultant solution was diluted with ethyl acetate (100 ml). The solution was washed with water (3×40 ml), dried (anhydrous sodium sulphate) and filtered. The filtrate was evaporated to dryness. The residue was triturated with a mixture of ether and petroleum spirit (bp 60°–80° C.) (1:1) and the resultant buff solid was filtered off. The solid was dissolved in dichloromethane (100 ml) and filtered through silica. The silica was washed with dichloromethane (100 ml) and the combined filtrates were evaporated to dryness to give 4-(2-nitro-4-trifluoromethylbenzoyl)-5-methylisoxazole (Compound 1, 4.5 g) as an off-white solid mp 85°–86° C.

By proceeding in a similar manner, the compounds described in the following table were prepared:

| Compound No. | 5 | 8 | 11 |
| --- | --- | --- | --- |
| Form | White solid | White flakes | White solid |
| mp (°C.) | 159–160 | 138–139 | 150–151 |
| NMR (where applicable) | — | — | — |
| Chromatography solvent | — | Ethyl acetate/ petroleum spirit (bp 60–80° C.) 1:2 | — |
| Recrystallization solvent | Ethyl acetate/ petroleum spirit (bp 60–80°C.) 1:1 | Cyclohexane | Triturated ethanol |
| Starting Material | 3-(4 Chlorophenyl)-2-ethoxymethylene-1-(2-nitro-4-trifluoromethylphenyl)-propan-1,3 dione | 2-Ethoxymethylene-4-methyl-1-(2-nitro-4-trifluoromethylphenyl)-pentan-1,3 dione | 2-Ethyloxymethylene-3-(4-fluorophenyl)-1-(2-nitro-4-trifluoromethylphenyl)-propan-1,3 dione |

| Compound No. | 12 | 14 | 15 |
| --- | --- | --- | --- |
| Form | Brown solid | White solid | Off-white solid |
| mp (°C.) | 86–87 | 102–103 | |
| NMR (where applicable) | — | — | — |
| Chromatography solvent | — | — | — |
| Recrystallization solvent | Ether petroleum spirit (bp 60–80° C.) 1:20 | — | Cyclohexane |
| Starting Material | 2-Ethoxymethylene-1-(2-nitro-4-trifluoromethylphenyl)-pentan-1,3-dione | 2-Ethoxymethylene-1-(2-nitro-4-trifluoromethylphenyl)-hexan-1,3-dione | 3-Cyclopropyl-2-ethoxymethylene-1-(2-nitro-4-trifluoromethylphenyl)-propan-1,3-dione |

| Compound No. | 17 | 22 | 24 |
| --- | --- | --- | --- |
| Form | Buff solid | White flakes | White solid |
| mp (°C.) | 169–170 | 86.5–87.5 | 128–129 |
| NMR (where applicable) | — | — | — |
| Chromatography solvent | Ethyl acetate/ petroleum spirit (bp 60–80° C.) 1:5 | — | Ethyl acetate/ petroleum spirit (bp 60–80° C.) 1:20 |
| Recrystallization solvent | | Petroleum spirit (bp 60–80° C.) | Toluene |
| Starting Material | 4,4-Dimethyl-2-ethoxymethylene-1-(2-nitro-4-trifluoromethylphenyl)-pentan-1,3-dione | 2-Ethoxymethylene-1-(2-nitro-4-trifluoromethylphenyl)-4-phenylbutan-1,3-dione | 2-Ethoxymethylene-1-(2-nitro-4-pentafluoroethylphenyl)-butan-1,3-dione |

| Compound No. | 27 | 39 | 40 |
| --- | --- | --- | --- |
| Form | White soild | Off-white solid | Orange flakes |
| mp (°C.) | 136.8 | 155–156 | 165–166 |
| NMR (where applicable) | — | — | — |
| Chromatography solvent | Ethyl acetate/ petroleum spirit (bp 60–80° C.) 1:5 | — | — |
| Recrystallization solvent | Cyclohexane | Triturated Ethyl acetate | Toluene |
| Starting | 3-Cyclopentyl-2- | 1-(4-Cyano-2- | 2-Ethoxymethylene-3- |

-continued

| Material | ethoxymethylene-1-(2-nitro-4-trifluoromethylphenyl)-propan-1,3-dione | nitrophenyl)-2-ethoxy-methylenebutan-1,3-dione | (2-nitro-4-trifluoromethylphenyl)-3-oxo-propionitrile |
|---|---|---|---|
| Compound No. | 42 | 45 | 60 |
| Form | White solid | Pale yellow solid | Viscous orange gum |
| mp (°C.) | 139–140.5 | 108.6–110 | — |
| NMR (where applicable) | — | — | 1.1(t,3H)1.4(m,2H) 1.6(m,2H)4.0(q,2H) 7.6(d,1H)8.0(d,1H) 8.1(s,1H)8.4(s,1H) |
| Chromatography solvent | — | — | Ether |
| Recrystallization solvent | n-hexane | Ethanol | — |
| Starting Material | 2-Ethoxymethylene-4-methyl-1-(2-nitro-4-pentafluoroethylphenyl)-pentan-1,3-dione | 3-Cyclopropyl-2-ethoxymethylene-1-(2-nitro-4-pentafluoroethylphenyl)-propan-1,3-dione | 3-(1-Ethoxycarbonyl-cyclopropyl)-2-ethoxymethylene-1-(2-nitro-4-trifluoromethylphenyl)-propan-1,3-dione |

| Compound No. | 62 | 66 |
|---|---|---|
| Form | White solid | Off-white solid |
| mp (°C.) | 106–107.5 | 108–109 |
| NMR (where applicable) | — | — |
| Chromatography solvent | Ethyl acetate/petroleum spirit (bp 60–80° C.) 1:2 | Ethyl acetate/petroleum spirit (bp 60–80° C.) 1:10 |
| Recrystallization solvent | — | — |
| Starting Material | 2-Ethoxymethylene-3-(2-methylcyclopropyl)-1-(2-nitro-4-trifluoromethylphenyl)-propan-1,3-dione | Ethyl 2,2-dimethyl-3,5-dioxo-4-ethoxymethylene-5-(2-nitro-4-trifluoromethylphenyl)-pentanoate |

| Compound No. | 71 | 80 |
|---|---|---|
| Form | Pale Yellow Solid | White solid |
| mp (°C.) | 168.6–169 | 91–92 |
| Chromatography Solvent | Ethyl Acetate/Petrolum Spirit (bp 60–80° C.) (1:1) | Ethyl acetate/hexane (1:10) |
| Recrystallization Solvent | — | — |
| Starting Material | 2-Ethoxymethylene-1-(4-methylsulphonyl-2-nitrophenyl)-3-(1-methylcyclopropyl)-propane-1,3-dione | 1-(2-Nitro-4-trifluoromethylphenyl)-2-ethoxymethylene-4-methylhexane-1,3-dione |

EXAMPLE 2

Triethylamine (1.9 g) was added to a mixture of 2-ethoxymethylene-1-(2-nitrophenyl)-butan-1,3-dione (4.9 g) and hydroxylamine hydrochloride (1.3 g) in acetonitrile (100 ml) with stirring. The mixture was stirred for 2 hours and left to stand overnight. The mixture was evaporated almost to dryness and water (100 ml) was added. The mixture was extracted with ethyl acetate (2×75 ml), dried (anhydrous magnesium sulphate) and filtered. The filtrate was evaporated to dryness to give 4(2-nitrobenzoyl)-5-methylisoxazole (compound 2, 2.4 g) as a brown solid, mp 104.5°–105.5° C.

By proceeding in a similar manner the compounds described in the following table were prepared:

| Compound No. | 3 | 4 | 6 |
|---|---|---|---|
| Form | Off-white solid | Brown solid | Yellow oil |
| mp (°C.) | 149.5–150.5 | 133–135 | — |
| NMR (where applicable) | — | — | 2.62(s,3H(7.4 (m,2H)7.49(m,2H) 8.29(s,1H) |

-continued

| | | | |
|---|---|---|---|
| Chromatography solvent | Ethyl acetate/ petroleum spirit (bp 60–80° C.) 1:5 | — | Ethyl acetate/ petroleum spirit (bp 60–80° C.) 1:5 |
| Recrystallization solvent | — | Triturated ethyl acetate | — |
| Starting Material | 2-Ethoxymethylene-1- (2-nitro-4-trifluoro- methylphenyl)-3-phenyl- propan-1,3-dione | 1-(2,4-Dinitrophenyl)- 2-ethoxy- methylenebutan- 1,3-dione | 1-(2-Chlorophenyl)- 2-ethoxymethylene- butan-1,3-dione |
| Compound No. | 7 | 13 | 16 |
| Form | White solid | Brown solid | White solid |
| mp (°C.) | 159–160 | 98–99 | 128–129 |
| NMR (where applicable) | — | — | — |
| Chromatography solvent | Ethyl acetate/ dichloromethane 1:5 | Ethyl acetate/ n-hexane 1:10 | Ethyl acetate/ n-hexane 1:5 |
| Recrystallization solvent | — | — | — |
| Starting Material | 2-Ethoxymethylene- 1-(4-methyl-sulphonyl 2-nitro-phenyl)- butan-1,3-dione | 1-(4-Chloro-2-nitro- phenyl)-2-ethoxy- methylenebutan- 1,3-dione | 1-(2,3-Dichloro-4- methyl-sulphonyl- phenyl)-2-ethoxymethyl- enebutan-1,3-dione |
| Compound No. | 19 | 20 | 21 |
| Form | Orange solid | White solid | White solid |
| mp (°C.) | 69–70 | 104–106 | 127.6–128.8 |
| NMR (where applicable) | — | — | — |
| Chromatography solvent | Ethyl acetate/ cyclohexane 1:10 | — | Ethyl acetate/ cyclohexane 1:10 |
| Recrystallization solvent | — | Triturated ether | — |
| Starting Material | 2-Ethoxymethylene- 1-(4-methyl-2- nitrophenyl)butan- 1,3-dione | 1-(2,3-Dichloro- 4-methylsulphonyl- phenyl)-2-ethoxy- methylene-4-methyl- pentan-1,3-dione | 3-Cyclopropyl-1- (2,3-dichloro-4- methylsulphonylphenyl)- 2-ethoxy-methylene- propan-1,3-dione |
| Compound No. | 23 | 25 | 26 |
| Form | White solid | Brown solid | White solid |
| mp (°C.) | 39–40 | 87–89 | 124.8–125 |
| NMR (where applicable) | — | — | — |
| Chromatography solvent | Ethyl acetate/ cyclohexane 1:20 | Ethyl acetate/ cyclohexane 1:5 | — |
| Recrystallization solvent | — | — | Cyclohexane |
| Starting Material | 1-(2-Chloro-4- trifluoromethylphenyl)- 3-cyclopropyl-2- ethoxymethylene- propan-1,3-dione | 3-Cyclopropyl-1- [4-(1,1-dimethyl- ethyl)-2-nitro- phenyl]-2-ethoxy- methylenepropan- 1,3-dione | 1-[4-(1,1-Dimethyl- ethyl)-2-nitro-phenyl]- 2-ethoxymethylene butan-1,3-dione |
| Compound No. | 28 | 29 | 30 |
| Form | Yellow oil | Orange solid | Brown solid |
| mp (°C.) | — | 113.8 | 52.1 |
| NMR (where applicable) | 2.6(s,3H)7.3 (m,2H)7.4(s,1H) 8.2(s,1H) | — | — |
| Chromatography solvent | Ethyl acetate/ cyclohexane 1:50 | — | — |
| Recrystallization solvent | — | Triturated ether | Cyclohexane |
| Starting Material | 1-(2,4-Dichlorophenyl)- 2-ethoxy- methylenebutan- 1,3-dione | 1-(2-Chloro-4-methyl- sulphonylphenyl)- 2-ethoxymethylene- butan-1,3-dione | 1-(2-Chloro-4- trifluoromethylphenyl)- 2-ethoxymethylene- butan-1,3-dione |
| Compound No. | 31 | 32 | 33 |
| Form | Yellow oil | Pale yellow oil | White solid |
| mp (°C.) | — | — | 115–117 |
| NMR (where | 2.5(s,3H)7.4 | 2.6(s,3H)7.5 | — |

-continued

| | | | |
|---|---|---|---|
| applicable) | (m,1H)7.6(m,2H) 7.7(m,1H)8.15 (s,1H) | (d,1H)7.9(d,1H) 8.0(s,1H)8.1 (s,1H) | |
| Chromatography solvent | Ethyl acetate/ cyclohexane 1:50 | Ethyl acetate/ cyclohexane 1:20 | Ethyl acetate/ toluene 1:20 |
| Recrystallization solvent | | | Ethyl acetate/ cyclohexane 1:10 |
| Starting Material | 2-Ethoxymethylene-1-(2-trifluoro-methylphenyl)-butan-1,3-dione | 1-(2,4-Bis-trifluoro-methylphenyl)-2-ethoxymethylene-butan-1,3-dione | 1-(2-Chloro-4-methylsulphonylphenyl)-3-cycloppropyl-2-ethoxymethylene-propan-1,3-dione |

| Compound No. | 34 | 35 | 36 |
|---|---|---|---|
| Form | Viscous clear oil | Pale yellow oil | Cream solid |
| mp (°C.) | — | — | 126–128 |
| NMR (where applicable) | 1.2(m,2H)1.3 (m,2H)2.55(m,1H) 7.5(m,1H)7.7 (m,2H)7.8(m,1H) 8.15(s,1H) | 1.15(m,2H)1.25 (m,2H)2.6(m,1H) 7.3(s,2H)7.4 (s,1H)8.1(s,1H) | — |
| Chromatography solvent | Ethyl acetate/ cyclohexane 1:20 | Ethyl acetate/ cyclohexane 1:50 | Ethyl acetate/ cyclohexane 1:10 |
| Recrystallization solvent | | | Ethyl acetate/ cyclohexane 1:1 |
| Starting Material | 3-Cyclopropyl-2-ethoxymethylene-1-(2-trifluoromethyl-phenyl)-propan-1,3-dione | 3-Cyclopropyl-1-(2,4-dichlorophenyl)-2-ethoxymethylene-propan-1,3-dione | 1-[2,3-Dichloro-4-(methylthio)-phenyl]-2-ethoxy-methylenebutan-1,3-dione |

| Compound No. | 37 | 38 | 41 |
|---|---|---|---|
| Form | Pale yellow solid | Pale yellow solid | Pale yellow gum |
| mp (°C.) | 74–75 | 89–89.5 | — |
| NMR (where applicable) | — | — | 1.2(m,2H)1.4 (m,2H)2.6(m,1H) 7.4(d,1H)7.7 (d,1H)7.8(s,1H) 8.1(s,1H) |
| Chromatography solvent | Ethyl acetate/ cyclohexane 1:20 | — | Ethyl acetate/ cyclohexane 1:20 |
| Recrystallization solvent | — | Cyclohexane | — |
| Starting Material | 1-(2,4-Bis-trifluoro-methylphenyl)-3-cyclopropyl-2-ethoxy-methylenepropan-1,3-dione | 1-(4-Chloro-2-trifluoromethylphenyl)-2-ethoxymethylene-butan-1,3-dione | 1-(4-Chloro-2-trifluoromethylphenyl)-3-cyclopropyl-2-ethoxymethylene-propan-1,3-dione |

| Compound No. | 43 | 44 | 47 |
|---|---|---|---|
| Form | Cream solid | Beige solid | Yellow solid |
| mp (°C.) | 126–127 | 113.8–114.2 | 147–148 |
| NMR (where applicable) | — | — | — |
| Chromatography solvent | — | — | — |
| Recrystallization solvent | Ethyl acetate/ n-hexane 1:5 | Ethyl acetate | Triturated ether/petroleum spirit (bp 60–80° C.) 1:5 |
| Starting Material | 1-(2-Chloro-4-methyl-sulphonylphenyl)-2-ethoxymethylene-4-methylpentan-1,3-dione | 3-Cyclopropyl-2-ethoxymethylene-1-(4-fluoro-2-nitro-phenyl)-propan-1,3-dione | 3-Cycloburyl-2-ethoxymethylene-1-(2-nitro-4-trifluoro-methylphenyl)-propan-1,3-dione |

| Compound No. | 48 | 49 | 50 |
|---|---|---|---|
| Form | White solid | Off-white solid | Yellow powder |
| mp (°C.) | 85–87 | 150–152 | 170–171 |
| NMR (where applicable) | — | — | — |
| Chromatography solvent | Ethyl acetate/ cyclohexane 1:10 | — | — |
| Recrystallization solvent | Ethyl acetate/ cyclohexane | Triturated ether | Toluene petroleum spirit |

-continued

| | | | |
|---|---|---|---|
| Starting Material | 1:10 2-Ethoxymethylene-1-(4-fluoro-2-nitrophenyl)-butan-1,3-dione | 2-Ethoxymethylene-3-(1-methylcyclo-propyl)-1-(2-nitro-4-trofluoromethyl-phenyl)-propan-1,3-dione | (bp 60–80° C.) 1:2 2-Ethoxymethylene-3-(4-nitrophenyl)-1-(2-nitro-4-tri-fluoromethylphenyl)-propan-1,3-dione |

| Compound No. | 51 | 52 | 53 |
|---|---|---|---|
| Form | Yellow crystals | Light brown solid | Cream solid |
| mp (°C.) | 154–155 | 104–106 | 93.8–94.4 |
| NMR (where applicable) | — | — | — |
| Chromatography solvent | — | Ethyl acetate/n-hexane 1:4 | Ethyl acetate/cyclohexane 1:5 |
| Recrystallization solvent | Toluene | | Ethyl acetate/n-hexane 1:4 |
| Starting Material | 2-Ethoxymethylene-3-(4-methoxy-phenyl)-1-(2-nitro-4-trifluoromethyl-phenyl)-propan-1,3-dione | 1-(2-Chloro-3-ethoxy-4-methyl-sulphonylphenyl)-2-ethoxymethylene-butan-1,3-dione | 1-(3-Cyanophenyl)-2-ethoxymethylene-butan-1,3-dione |

| Compound No. | 54 | 55 | 56 |
|---|---|---|---|
| Form | Off-white solid | Cream solid | White solid |
| mp (°C.) | 145.6–146.5 | 154.6–155.2 | 199–120.2 |
| NMR (where applicable) | — | — | — |
| Chromatography solvent | Ether | Ether | Ethyl acetate/cyclohexane 1:10 |
| Recrystallization solvent | — | — | Triturated cyclohexane |
| Starting Material | 3-Cyclopropyl-2-ethoxymethylene-1-(4-methylsulphonyl-2-trifluoromethyl-phenyl)-propan-1,3-dione | 3-Cyclopropyl-2-ethoxymethylene-1-(4-methylsulphonyl-2-nitrophenyl)-propan-1,3-dione | 1-(2-Chloro-3-ethoxy-4-methyl-sulphonylphenyl)-3-cyclopropyl-2-ethoxymethylene-propan-1,3-dione |

| Compound No. | 57 | 58 | 59 |
|---|---|---|---|
| Form | Cream solid | White solid | White solid |
| mp (°C.) | 108.4–109 | 82.5–84.3 | 127.4–128.2 |
| NMR (where applicable) | — | — | — |
| Chromatography solvent | — | Ethyl acetate/cyclohexane 1:20 | — |
| Recrystallization solvent | Ether/cyclohexane 1:2 | | Ether/cyclohexane 1:4 |
| Starting Material | 1-(2-Chloro-3-ethoxy-4-ethyl-sulphonylphenyl)-2-ethoxymethylene-butan-3-dione | 1-(2-Chloro-3-ethoxy-4-methyl-sulphonylphenyl)-2-ethoxymethylene-4-methylpentan-1,3-dione | 1-(2-Chloro-3-ethoxy-4-ethyl-sulphonylphenyl)-3-cyclopropyl-2-ethoxymethylene-propan-1,3-dione |

| Compound No. | 61 | 63 | 64 |
|---|---|---|---|
| Form | Yellow solid | White solid | Pale pink solid |
| mp (°C.) | 54–57 | 119–120.2 | 131–135 |
| NMR (where applicable) | — | — | — |
| Chromatography solvent | Ether | Ether | Ethyl acetate/cyclohexane 1:3 |
| Recrystallization solvent | Ether/cyclohexane 1:2 | — | — |
| Starting Material | 2-Ethoxymethylene 1-(3-methoxy-carbonyl-2-methyl-4-methylsulphonyl-phenyl)-butan-1,3-dione | 1-[2-Chloro-3-(1-methylethoxy)-4-methylsulphonyl-phenyl]-2-ethoxy-methylenebutan-1,3-dione | 2-Ethoxymethylene-1-[2-methyl-3-(1-methylethoxy-carbonyl)-4-methyl-sulphonylphenyl]-butan-1,3-dione |

| Compound No. | 65 | 67 | |
|---|---|---|---|
| Form | White | Off-white solid | |
| mp (°C.) | 164–166 | 105–107 | |

-continued

| | | |
|---|---|---|
| NMR (where applicable) | — | — |
| Chromatography solvent | Ether | Ether/ petroleum spirit (bp 60–80° C.) 1:9 |
| Recrystallization solvent | | cyclohexane |
| Starting Material | 3-Cyclopropyl-2-ethoxymethylene-1-[2-methyl-3-(1-methylethoxycarbonyl)-4-methylsulphonyl-phenyl]-propan-1,3-dione | 3-Cyclopropyl-2-ethoxymethylene-1-(2,3,4-trichloro-phenyl)-propan-1,3-dione |

| Compound No. | 68 | 69 | 70 |
|---|---|---|---|
| Form. | Yellow oil | Yellow oil | |
| mp (°C.) or NMR. | 1.3(6H,d)2.25(3H,s) 2.6(3H,s)3.3(1H,m) 3.9(3H,s)7.4(1H,d) 7.85(1H,d)8.2(1H,s) | 124.8–126.8 | 90–90.4 |
| Chromatography Solvent. | Ethyl acetate/ cyclohexane (1:5) | Ethyl acetate/ cyclohexane (1:10) | Ethyl acetate/ cyclohexane (1:1) |
| Recrystallization Solvent. | — | — | Cyclohexane |
| Starting material. | 1-[3-Methoxycarbonyl-4-(1-methylethylsulphon-yl)-2-methylphenyl]-2-ethoxymethylene-butane-1,3-dione | 1-(2-Nitro-4-trifluoromethylsulfonyl-phenyl)-2-ethoxyethylene-4-cyclopropyl-1,3-dione | 1-(2,6-Dichloro-4-trifluoromethyl-phenyl)-2-ethoxymethylene-3-cyclopropylpropan-1,3-dione |

| Compound No. | 72 | 73 | 74 |
|---|---|---|---|
| Form. | White solid | Orange solid | Orange solid |
| mp (°C.) or NMR. | 114–115 | 58.9–60.3 | 53.6–54.8 |
| Chromatography Solvent. | Ethyl acetate/ cyclohexane (1:1) | Ethyl acetate/ cyclohexane (1:2) | Ethyl acetate/ cyclohexane (1:20) |
| Recrystallization Solvent. | — | — | — |
| Starting material. | 1-(2-Chloro-4-methylsulphonyl)-2-ethoxymethylene-3-(1-methylcyclopropyl)-propan-1,3-dione | 1-(4-Methyl-2-nitrophenyl)-2-ethoxymethylene-3-isoprophylpropane-1,3-dione | 1-(4-methyl-2-nitrophenyl)-2-ethoxymethylene-3-cyclopropylpropane-1,3-dione |

| Compound No. | 75 | 76 | 77 |
|---|---|---|---|
| Form. | Orange solid | | White solid |
| mp (°C.) or NMR. | 93.8–94.4 | 69.2–70.6 | 62.2–63.8 |
| Chromatography Solvent. | Ethyl acetate/ cyclohexane (1:10) | — | Ethyl acetate/ cyclohexane (1:20) |
| Recrystallization Solvent. | — | Ether | Cyclohexane |
| Starting material. | 1-(2-Chloro-3-methoxy-4-methylsulphonyl-phenyl)-2-ethoxymethylene-3-cyclopropylpropan-1,3-dione | 1-(2-Chloro-4-nitrophenyl)-2-ethoxy-methylenebutane-1,3-dione | 1-(2-Chloro-4-nitrophenyl)-2-ethoxymethylene-3-isopropylpropane-1,3-dione |

| Compound No. | 78 | 79 | 81 |
|---|---|---|---|
| Form. | Pale orange solid | Light brown solid | Orange solid |
| mp (°C.) or NMR. | 107.3–108.3 | 68.2–69.4 | 107–109.4 |
| Chromatography Solvent. | | | |
| Recrystallization Solvent. | Cyclohexane | Cyclohexane | Cyclohexane |
| Starting material. | 1-(2-Chloro-4-nitrophenyl)-2-ethoxymethylene-3-cyclopropylpropane-1,3-dione | 1-(Nitro-4-tbutylphenyl)-2-ethoxymethylene-3-isopropylpropan-1,3-dione | 1-(2,6-Dichlorophenyl)-2-ethoxymethylene-3-cyclopropylpropan-1,3-dione |

EXAMPLE 3

3-Chloroperbenzoic acid (85%, 0.99 g) was added portionwise to a stirred solution of 4-(2,3-dichloro-4-methylsulphenylbenzoyl)-5-methylisoxazole (1.5 g) in dichloromethane (50 ml) whilst maintaining the temperature below −20° C. The mixture was stirred at −20° C. for 1 hour. Dichloromethane (50 ml) was added and the solid was removed by filtration. The filtrate was evaporated to dryness and the residue was chromatographed on silica eluted with a mixture of ethyl acetate and cyclohexane (1:5) to give 4-(2,3-dichloro4-methylsulphinylbenzoyl)-5-methylisoxazole (compound 46, 0.8 g) as a white solid, mp 125°–126.4° C.

By proceeding in a similar manner the compounds described in the following table were prepared:

| Cpd. No. | $R^1$ | V | $SR^{95}$ | m | mp/NMR |
|---|---|---|---|---|---|
| 106 | Cp | H | 2-SMe | 1 | 104–107.4° C. |
| 115 | Cp | 2-Cl | 4-SMe | 1 | 116–116.8° C. |
| 116 | Cp | 2-CF$_3$ | 4-SMe | 1 | 151.2–151.8° C. |
| 120 | Cp | 2-NO$_2$ | 4-SMe | 1 | 143.2–144.2° C. |
| 139 | 1-Me—Cp | 2-CF$_3$ | 4-SEt | 1 | 1.1(2H, m) 1.4(2H, m) 1.3(3H, t) 1.55(3H, s) 2.9(2H, q) 7.6(1H, d) 7.9(1H, d) 8.05(1H, m) 8.07(1H, s) |
| 144 | Cp | 2-CF$_3$ | 4-SEt | 1 | 161.2–162.6° C. |
| 149 | Cp | 2-Br-3-OMe | 4-SEt | 1 | 92–92.6° C. |
| 152 | Me | 2-CF$_3$ | 4-SMe | 1 | 2.7(3H, s) 2.9(3H, s) 7.5(1H, d) 8.0(1H, dd) 8.1(1H, s) 8.2(1H, s) |
| 155 | Cp | 2-Br | 4-SMe | 1 | 121.2–122.4° C. |
| 166 | Cp | 2-Br-3-OMe | 4-SMe | 1 | 111–114.8° C. |
| 168 | Cp | 3-Cl-4-OMe | 2-SMe | 1 | 161–162° C. |
| 169 | Cp | 3-Cl-4-OMe | 2-SMe | 2 | 147–149° C. |
| 170 | Cp | 2-Cl-3-CN | 4-SMe | 2 | 168–169° C. |
| 171 | Cp | 2-Cl-3-CN | 4-SMe | 1 | 157.8–158.6° C. |
| 175 | Cp | 3-CO$_2^i$Pr-4-Cl | 2-SMe | 1 | 135.2–139° C. |
| 176 | Cp | 3-CO$_2^i$Pr-4-Cl | 2-SMe | 2 | 178–180.4° C. |
| 178 | Cp | 3-CO$_2^i$Pr-4-CF$_3$ | 2-SMe | 1 | 165–166° C. |
| 179 | Cp | 3-CO$_2^i$Pr-4-CF$_3$ | 2-SMe | 2 | 212.3–216.8° C. |

EXAMPLE 4

A mixture of aluminium chloride (16 g) and 5-methylisoxazole-4-carbonyl chloride (5.0 g) in dry chlorobenzene (50 ml) was stirred in an atmosphere of nitrogen for 16 hours. The mixture was heated to 80° C. for 1 hours. The cooled mixture was quenched with excess ice and extracted with ethyl acetate (3×200 ml). The combined organic layers were washed with water (3×500 ml), dried (anhydrous magnesium sulphate) and filtered. The filtrate was evaporated to dryness. The residue was purified by chromatography on silica eluted with a mixture of ethyl acetate and cyclohexane (1:20) to give 4-(4-chlorobenzoyl)-5-methylisoxazole (compound 9, 5.2 g) as a yellow solid mp 65°–66° C.

By proceeding in a similar manner the following compound was prepared: 4-(4-methylbenzoyl)-5-methylisoxazole (compound 10), NMR (CDCl$_3$) 236(s,3H), 2.59(s,3H), 7.2–7.7(m,4H), 8.36(s,1H), starting from toluene.

EXAMPLE 5

A mixture of aluminium chloride (10 g) and 5-methylisoxazole-4-carbonyl chloride (2.7 g) in methoxybenzene (50 ml) was stirred at room temperature for 16 hours. The mixture was quenched with excess ice and extracted with ether (3×200 ml). The combined organic layers were washed with water (3×500 ml), dried (anhydrous magnesium sulphate) and filtered. The filtrate was evaporated to dryness. The residue was purified by chromatography on silica eluted with a mixture of ethyl acetate and cyclohexane (1:10) followed by HPLC on silica eluted with a mixture of ethyl acetate and hexane (1:20) to give 4-(4-methoxybenzoyl)-5-methylisoxazole (compound 18, 0.35 g) as a white solid mp 78°–79° C.

EXAMPLE 6

Sodium acetate (1.0 g) was added to a stirring mixture of hydroxylamine hydrochloride (0.85 g) and 2-ethoxymethylene-1-(4-methylsulphonyl-2-trifluoromethylphenyl)-3-(1-methylcyclopropyl)propane-1,3-dione (4.2 g) in industrial methylated spirit (200 ml). The mixture was stirred at room temperature for 3 hours. The mixture was evaporated to dryness and then suspended in ethyl acetate (100 ml). The resultant suspension was washed with water (100 ml), dried (anhydrous magnesium sulphate) and filtered. The filtrate was evaporated to dryness to give 4-(4-methylsulphonyl-2-trifluoromethylbenzoyl)-5-(1-methylcyclopropyl)isoxazole (compound 99, 3.5 g) as a white solid, m.p. 141°–142° C.

By proceeding in a similar manner the compounds described in the following table were prepared:

| Cpd. No. | $R^1$ | $(R^2)_n$ | m.p./NMR |
|---|---|---|---|
| 82 | $^t$Bu | 2-NO$_2$-4-SO$_2$Me | 173–174° C. |
| 83 | Cp | 2-SO$_2$Me | 118.4–119.4° C. |
| 84 | Cp | 2-Cl-3-CN-4-SMe | 204.4–205.4° C. |
| 85 | Cp | 2-Me-4-Br | 63–69.4° C. |
| 86 | $^t$Bu | 2-Cl-4-SO$_2$Me | 143–144° C. |
| 87 | $^s$Bu | 2-Cl-4-SO$_2$Me | 125–126° C. |
| 88 | Cp | 2-SO$_2$Me-4-NO$_2$ | 168–169° C. |

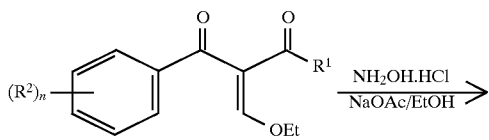
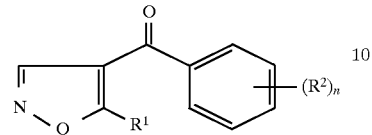

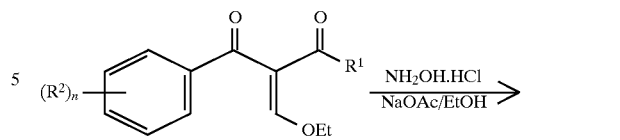

| Cpd. No. | R¹ | (R²)ₙ | m.p./NMR |
|---|---|---|---|
| 89 | $^i$Pr | 2-SO₂Me-4-NO₂ | 168.8–170.6° C. |
| 90 | Et | 2-Cl-4-SO₂Me | 89–91° C. |
| 91 | Cp | 2,6-Cl₂-3-NO₂ | 91.4–93° C. |
| 92 | Cp | 2-Cl-4-F | 82.4–84° C. |
| 93 | Cp | 2,4-(SO₂Me)₂ | 163.2–164.4° C. |
| 94 | Cp | 2-Cl-4-Br | 46.4–47.6° C. |
| 95 | $^t$Bu | 2-CF₃-4-SO₂Me | 149.5–150° C. |
| 96 | Me | 2-SO₂Me<br>MeCN added as a solvent | 110.8–111° C. |
| 97 | Me | 2-CF₃-4-SO₂Me | 91.5–92.5° C. |
| 98 | $^i$Pr | 2-CF₃-4-SO₂Me | 133–133.5° C. |
| 100 | Cp | 2-Cl-4-SO₂$^i$Pr | 140.2–142.2° C. |
| 101 | $^i$Pr | 2-SO₂Me | 84.4–88.0° C. |
| 102 | Cp | 2-SMe | 1.1(m, 2H)<br>1.25(m, 2H)<br>2.4(s, 3H)<br>2.6(m, 1H)<br>7.15(m, 1H)<br>7.4(m, 3H)<br>8.13(s, 1H) |
| 103 | Cp | 2-Cl-5-SO₂Me | 163–165° C. |
| 104 | Cp | 2-Cl-4-SO₂$^t$Bu | 158–160.8° C. |
| 105 | Cp | 2-CF₃-4-SMe | 62–63° C. |
| 107 | 1-Me–Cp | 2-SO₂Me | 116.4–117.4° C. |
| 108 | $^s$Bu | 2-SO₂Me | 74.2–75.4° C. |
| 109 | Cp | 2-SO₂Et | 116.2–117.4° C. |
| 110 | Cp | 2-Cl-4-SMe | 1.15(m, 2H)<br>1.25(m, 3H)<br>2.45(s, 3H)<br>2.6(m, 1H)<br>7.1(d, 1H)<br>7.2(s, 1H)<br>7.3(d, 1H)<br>8.15(s, 1H) |
| 111 | Cp | 2-NO₂-4-SMe | 108.8–110.4° C. |
| 112 | Cp | 2-SO₂Me-5-Cl | 141–144° C. |
| 113 | Cp | 2-Cl-4-SO₂Et | 102–102.8° C. |
| 114 | Cp | 2-F-4-SO₂Me | 115.6–116.6° C. |
| 117 | Cp | 2-SO₂Me-5-F | 155–158° C. |
| 118 | Cp | 2-SO$^i$Pr | 105.8–106.6° C. |
| 119 | Cp | 2,5-Cl₂-4-SO₂Me | 188–195° C. |
| 121 | Cp | 2-NO₂-4-CN | 146–147° C. |
| 122 | Cp | 2-NO₂-4-Cl | 127–128° C. |
| 123 | Cp | 2,4-Br-3-OMe | 79–82° C. |
| 124 | Cp | 2-Br-3-OMe-4-SO₂Me<br>MeCN added as solvent | 130.2–131.4° C. |
| 125 | Me | 2-Br-3-OMe-4-SO₂Me<br>MeCN added as solvent | 103.2–104.2° C. |
| 126 | 1-Me–Cp | 2-Br-3-OMe-4-SO₂Me | 85.6–86.4° C. |
| 127 | $^i$Pr | 2-NO₂-4-Cl | 95.4–96° C. |
| 128 | 1-Me–Cp | 2,3-Cl₂-4-SO₂Me | 85–86° C. |
| 129 | Cp | 2-Cl-4-OCF₃ | 1.1(2H, m)<br>1.3(2H, m)<br>2.6(1H, m)<br>7.2(1H, m)<br>7.4(1H, d)<br>7.3(1H, d)<br>8.1(1H, s) |
| 130 | Cp | 2,3-Cl₂-4-OCF₃ | 36–38° C. |
| 131 | 1-Me–Cp | 2-Cl-3-OMe-4-SO₂Me | 84–86° C. |
| 132 | Cp | 2-SO₂Me-3-Cl | 115.4–116.8° C. |
| 133 | Cp | 2-Br-4-SO₂Me | 109.7–110.6° C. |
| 134 | 1-Me–Cp | 2-Br-4-SO₂Me | 120–121° C. |
| 135 | Me | 2-Cl-3-OMe-4-SO₂Me | 116–117° C. |
| 136 | 1-Me–Cp | 2-CF₃-4-SEt | 0.9(2H, m)<br>1.3(2H, m)<br>1.4(3H, t)<br>1.5(3H, s)<br>3.0(2H, q)<br>7.3(1H, d)<br>7.45(1H, dd)<br>7.6(1H, d)<br>8.1(1H, s) |
| 137 | Cp | 2-CF₃-4-SEt | 47.8–49.4° C. |
| 138 | 1-Me–Cp | 2-CF₃-4-SO₂Et | 124.8–126.4° C. |
| 140 | Cp | 2-SO₂Me-3-OMe | 168.3–169.3° C. |
| 141 | 1-Me–Cp | 2-NO₂-4-F | 84–86° C. |
| 142 | $^i$Pr | 2-CF₃-4-SMe | 1.2(6H, d)<br>2.5(3H, s)<br>3.5(1H, m)<br>7.2(1H, m)<br>7.3(1H, m)<br>7.4(1H, m)<br>8.0(1H, s) |
| 143 | Cp | 2-CF₃-4-SO₂Et | 103–104.6° C. |
| 145 | Cp | 2-NO₂-4-Br | 121–122° C. |
| 146 | Cp | 2-Br-3-OMe-4-SEt | 1.15(2H, m)<br>1.25(2H, m)<br>2.55(1H, m)<br>3.85(3H, m)<br>7.05(1H, d)<br>7.15(1H, d)<br>8.15(1H, s) |
| 147 | Cp | 2-Br-3-OCHF₂-4-SO₂Me | 94–97° C. |
| 148 | Cp | 2-SMe-4-SO₂Me | 137.4–140° C. |
| 150 | Et | 2-CF₃-4-SO₂Me | 90.4–91.2° C. |
| 151 | Me | 2-CF₃-4-SO₂Me | 2.55(3H, s)<br>2.6(3H, s)<br>7.3(1H, m)<br>7.45(1H, m)<br>7.55(1H, m)<br>8.23(1H, s) |
| 153 | 1-Me–Cp | 2-SMe-4-SO₂Me | 161.9–162.8° C. |
| 154 | Cp | 2-Br-4-SMe | 67.2–68° C. |
| 156 | Cp | 2-Br-3-OMe-4-SMe | 86.4–87° C. |
| 157 | Cp | 2-F-6-SO₂Me | 123–125° C. |
| 158 | Cp | 2,4-(SMe)₂ | 92.6–93.2° C. |
| 159 | Cp | 2,4-Cl₂-3-CO₂Et | 1.15(2H, m)<br>1.3(2H, m)<br>1.4(3H, t)<br>2.5(1H, m)<br>4.4(2H, q)<br>7.3(1H, m)<br>7.4(1H, d)<br>8.1(1H, s) |
| 160 | Cp | 2-SMe-3-Cl-4-OMe | 72.3–74° C. |
| 161 | Cp | 2,4-Cl₂-3-CN | 174–175° C. |
| 162 | Cp | 2,4-Cl₂-3-OMe | 73.5–74.5° C. |
| 163 | 1-Me–Cp | 2-F-4-SO₂Me | 99.4–100.8° C. |
| 164 | 1-Me–Cp | 2,4-Cl₂-3-CO₂$^i$Pr | 0.8(2H, m)<br>1.2(2H, m)<br>1.3(6H, d)<br>1.4(3H, s)<br>5.3(1H, m) |

-continued

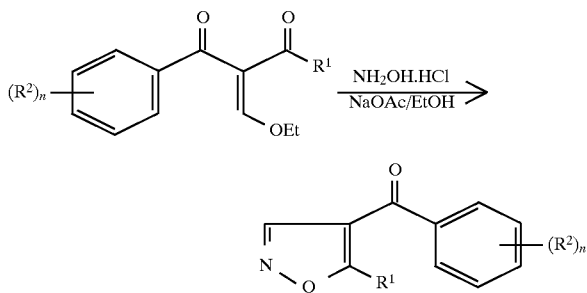

| Cpd. No. | R¹ | (R²)ₙ | m.p./NMR |
|---|---|---|---|
| | | | 7.25(1H, d) 7.4(1H, d) 8.1(1H, s) |
| 165 | ⁱPr | 2-F-4-SO₂Me | 105.6–106.4° C. |
| 167 | Cp | 2,4-Cl₂-3-CO₂ⁱPr | 88.4–89.8° C. |
| 172 | Cp | 2-Cl-3-CO₂ⁱPr-4-SMe | 98.8–99.4° C. |
| 173 | Cp | 2-Cl-3-CO₂ⁱPr-4-SO₂Me | 136.6–137.4° C. |
| 174 | Cp | 2-SMe-3-CO₂ⁱPr-4-Cl | 92.4–94.2° C. |
| 177 | Cp | 2-SMe-3-CO₂ⁱPr-4-CF₃ | 112.6–113.8° C. |
| 361 | Cp | 2-SMe-3-C(O)CH₃-4-Cl | 79.5–81.2° C. |
| 364 | Cp | 2-SMe-3-CH₂OMe-4-Cl | 56.4–57.5° C. |
| 363 | Cp | 2-SMe-3-C(O)NMe₂-4-Cl | 1.15(m, 2H) 1.3(m, 2H) 2.3(s, 3H) 2.5(m, 1H) 2.7(s, 3H) 3.1(s, 3H) 7.1(d, 1H) 7.35(d, 1H) 8.1(s, 1H) |
| 355 | Cp | 2-CF₃-4-SO₂NMe₂ | 133.6–135.2° C. |
| 366 | Cp | 2-SCH₂CF₃-3,4-Cl₂ | 1.2(m, 2H) 1.4(m, 2H) 2.6(m, 1H) 3.5(q, 2H) 7.2(d, 1H) 7.6(d, 1H) 8.1(s, 1H) |
| 357 | Cp | 2-OCF₂CHFCl-4-SMe | 1.2(m, 2H), 1.3(m, 2H) 2.5(s, 3H) 2.6(m, 1H) 5.95–6.1(m, 1H) 7.15(s, 1H) 7.2(dd, 1H) 7.45(d, 1H) 8.15(s, 1H) |
| 367 | Cp | 2-SCF₂CHFCl-3,4-Cl₂ | 0.8(m, 2H) 1.2(m, 2H) 2.5(m, 1H) 6.1–6.25(dt, 1H) 7.2(d, 1H) 7.7(d, 1H) 8.0(s, 1H) |
| 356 | Cp | 2-SMe-4-OCHF₂ | 117–119° C. |
| 368 | Cp | 2-CH₂OCH₂CF₃-4-Br | 1.2(m, 2H) 1.35(m, 2H) 2.6(m, 1H) 3.9(q, 2H) 4.9(s, 2H) 7.35(d, 1H) 7.55(dd, 1H) 7.75(d, 1H) 8.2(s, 1H) |

EXAMPLE 7

Sodium acetate (1.65 g) was added to a stirred mixture of 3-cyclopropyl-2-ethoxymethylene-1-[2-bromo-3-(2-methoxyethoxy)-4-methylsulphonylphenyl]propan-1,3-dione (8.5 g) and hydroxylamine hydrochloride (1.77 g) in ethanol. The mixture was stirred at room temperature overnight and then evaporated to dryness. The residue was dissolved in ethyl acetate and washed with water, dried (anhydrous magnesium sulphate) and filtered. The filtrate was evaporated to dryness. The residue was chromatographed on silica eluted with a mixture of ethyl acetate and cyclohexane (1:5) to give 4-[2-bromo-3-(2-methoxyethoxy)-4-methylsulphonylbenzoyl]-5-cyclopropylisoxazole (compound 181) as a yellow oil (33 g), NMR (CDCl₃), 1.3(2H, m), 1.4(2H,m), 2.6(1H,m), 3.3(3H,s), 3.5(3H,s), 3.9(2H,m), 45(2H,m), 7.3(1H,d), 8.0(1H,s), 8.1(1H,d).

By proceeding in a similar manner the following compounds of formula I in which Q represents C=O and R is hydrogen were prepared.

| Cpd. No. | R¹ | (R²)ₙ | m.p./NMR |
|---|---|---|---|
| 180 | Cp | 2,4-Br₂-3-O(CH₂)₂OMe | 1.15(2H,m) 1.3(2H,m) 2.5(1H,m) 3.4(3H,s) 3.75(2H,t) 4.1(2H,t) 6.8(1H,d) 7.5(1H,d) 8.1( 1H,s) |
| 182 | 1-Me-Cp | 2-Br-3-O(CH₂)₂OMe-4-SO₂Me | 0.9(2H,m) 1.3(2H,m) 1.4(3H,s) 3.2(3H,s) 3.4(3H,s) 3.8(2H,t) 4.4(2H,t) 7.2(1H,d) 8.0(1H,s) 8.1(1H,d) |
| 183 | Me | 2-Br-3-(CH₂)₂OMe-4-SO₂Me | 2.6(3H,s) 3.3(3H,s) 3.45(3H,s) 3.8(2H,t) 4.4(2H,t) 7.2(1H,d) 8.0(1H,d) 8.1(1H,s) |
| 184 | Cp | 2-Cl-3-O(CH₂)₂OMe-4-SO₂Me | 81.4–82.6° C. |
| 185 | iPr | 2-Cl-3-O(CH₂)₂OMe-4-SO₂Me | 84.2–86.2° C. |
| 186 | Me | 2-Cl-3-O(CH₂)₂OMe-4-SO₂Me | 107.2–107.8° C. |
| 187 | Me | 2-Br-3-O(CH₂)₂OMe-4-SMe | 94.4–94.8° C. |
| 189 | Cp | 2-SO₂Me-3-O(CH₂)₂OMe-4-Br | 104.2–105.2° C. |
| 352 | Cp | 2-SMe-3-O(CH₂)₂OMe | 59–62° C. |

EXAMPLE 8

3-Chloroperoxybenzoic acid (50–60%) (1.3 g) was added to a solution of 5-cyclopropyl-4-[2-bromo-3-(2-methoxyethoxy)-4-methylsulphenylbenzoyl]isoxazole (1.9 g) in dichloromethane whilst maintaining the temperature at around −15° C. The mixture was stirred at −15° C. for 1 hour and at room temperature for 1 hour. The solution was diluted with dichloromethane and washed with sodium bisulphite solution (2M), followed by water. The organic layer was dried (anhydrous magnesium sulphate) and filtered. The filtrate was evaporated to dryness. The residue was purified by dry column flash chromatography eluted with a mixture of ethyl acetate and cyclohexane (1:5) yielding 5-cyclopropyl-4-[2-bromo-3-(2-methoxyethoxy)-3-methylsulphinylbenzoyl]isoxazole (Compound 188, 1.52 g) as a white solid, mp 86.2°–87.0° C.

By proceeding in a similar manner the following compounds were prepared:

5-cyclopropyl-4-[2-methylsulphinyl-3-(2-methoxyethoxy)]benzoylisoxazole (compound 353), m.p. 82° to 84° C.;

5-cyclopropyl-4-[2-methylsulphonyl-3-(2-methoxyethoxy)]benzoylisoxazole (compound 354), m.p. 111° to 114° C.

EXAMPLE 9

A solution of acetohydroximoyl chloride (1.3 g) in toluene (25 ml) was added progressively to a solution of 3-(N,N-dimethylamino)-1-(2-nitro-4-trifluoromethylphenyl)prop-2-en-1-one (2.0 g) and triethylamine (1.5 g) in toluene (25 ml). The resulting suspension was stirred for 5 hours, filtered and the filtrate evaporated to dryness. The residue was subjected to chromatography, eluting with a mixture of petroleum spirit and ethyl acetate. The product was recrystallized from cyclohexane to give compound 190, (0.66 g) in the form of a white solid, m.p. 104° C.

By proceeding in a similar manner the following compounds of formula I in which Q represents C=O were prepared from the appropriately substituted starting materials:

| Cpd No. | R | $R^1$ | $(R^2)_n$ | m.p./ NMR(CDCl$_3$) |
|---|---|---|---|---|
| 191 | iPr | H | 2-NO$_2$-4-CF$_3$ | 92° C. |
| 192 | CO$_2$Et | H | 2-NO$_2$-4-CF$_3$ | 65° C. |
| 193 | Br | H | 2-NO$_2$-4-CF$_3$ | 115° C. |
| 194 | CF$_3$ | H | 2-NO$_2$-4-CF$_3$ | 117° C. |
| 196 | CO$_2$Et | CH3 | 2-NO$_2$-4-CF$_3$ | 62° C. |
| 198 | CO$_2$Et | Cp | 2-NO$_2$-4-CF$_3$ | 1.1(t,3H) 12–1.5(m,4H) 2.7(m,1H) 3.9(q,2H) 7.5(d,1H) 7.9(d,1H) 8.4(s,1H) |
| 200 | CO$_2$Et | Cp | 2-Cl-4-SO$_2$Me | 110° C. |
| 201 | CO$_2$Et | Cp | 2-CF$_3$-4-SO$_2$Me | 124.5–126° C. |
| 202 | CO$_2$Me | Cp | 2-Cl-4-SO$_2$Me | 143–144° C. |
| 204 | CO$_2$Et | Cp | 2-SO$_2$Me | 97–98° C. |
| 205 | CO$_2$Me | Cp | 2-CF$_3$-4-SO$_2$Me | 152.5–153° C. |
| 206 | CO$_2$Et | Cp | 2-NO$_2$-4-SO$_2$Me | 131–132° C. |
| 207 | CO$_2$Et | Cp | 2,3-Cl$_2$-4-SO$_2$Me | 202–203° C. |
| 208 | CO$_2$Et | Cp | 2-Cl-3-MeO-4-SO$_2$Me | 130–132° C. |
| 210 | CO$_2$Et | Cp | 2-SO$_2$Me-4-Cl | 118–119° C. |
| 211 | CO$_2$Et | Cp | 2-NO$_2$-4-Cl | 83–84° C. |
| 212 | CO$_2$Et | Cp | 2-CF$_3$-4-Cl | 59–60° C. |

EXAMPLE 10

A solution of n-butyllithium in hexane (2.5M, 20 ml) was added dropwise to a solution of 5-cyclopropyl-4-iodo-3-methylisoxazole (12.4 g) in ether (200 ml), whilst maintaining the temperature below −60° C. The mixture was stirred for 1 hour and a solution of 2-nitro-4-trifluoromethylbenzoyl chloride (12.68 g) in ether (100 ml) was added dropwise whilst maintaining the temperature below −60° C. The mixture was stirred for 1 hour and allowed to warm to 0° C. Hydrochloric acid (2M, 150 ml) was added and the layers were separated. The organic layer was washed with water, saturated sodium metabisulphate solution, water, dried (anhydrous sodium sulphate) and filtered. The filtrate was evaporated to dryness and the residue was triturated with a mixture of petroleum spirit and ether (5:1) and filtered. The solid was recrystallized from cyclohexane to give compound 195 (11.3 g) as a white solid, m.p. 110° C.

EXAMPLE 11

A mixture of ethyl 5-methyl-4-(2-nitro-4-trifluoromethylbenzoyl)isoxazole-3-carboxylate (30 g) and concentrated aqueous ammonia (60 ml) was stirred at room temperature overnight. Water (200 ml) was added and the mixture was extracted with ether. The combined extracts were washed with water, dried (anhydrous sodium sulphate) and filtered. The filtrate was evaporated to dryness and the residue was purified by chromatography on silica gel eluted with a mixture of ethyl acetate and petroleum spirit (1:5) to give compound 197 (0.44 g) as a white solid, m.p. 144° C.

By proceeding in a similar manner 4-(2-chloro-4-methylsulphonylbenzoyl)-5-cyclopropylisoxazole-3-carboxamide, compound 203 (m.p. 202°–203° C.) was prepared from the appropriately substituted starting material.

EXAMPLE 12

A mixture of 5-methyl-4-(2-nitro-4-trifluoromethylbenzoyl)isoxazole-3-carboxamide (1.2 g) and phosphorus oxychloride (10 ml) was stirred at room temperature for 1.5 hours and at 50°–60° C. for 1 hour. The mixture was poured into water (50 ml), with cooling as necessary, and extracted with dichloromethane. The combined extracts were washed with water, dried (anhydrous sodium sulphate) and filtered. The filtrate was evaporated to dryness and the residue was purified by chromatography on silica gel eluted with a mixture of ethyl acetate and petroleum spirit (1:5). The product was recrystallized from cyclohexane to give compound 199 (0.65 g) as an off-white solid, m.p. 104° C.

By proceeding in a similar manner 4-(2-chloro-4-methylsulphonylbenzoyl)-3-cyano-5-cyclopropylisoxazole, compound 209 (m.p. 123°–123.5° C.) was prepared from the appropriately substituted starting materials.

EXAMPLE 13

A mixture of 3-cyclopropyl-3-diethylamino-1-[2-(methylsulphenyl)-4-trifluoromethylphenyl]-prop-2-en-1-one (9.4 g), ethyl chloroximidoacetate (6.0 g) and 4A molecular sieve (35 g) in dichloromethane was stirred for 60 hours. The mixture was filtered and the filtrate was evaporated to dryness and the residue was recrystallized from n-hexane to give compound 213 (3.6 g) as an off-white solid, m.p. 97°–98° C.

By proceeding in a similar manner the following compounds of formula I in which Q represents C=O were prepared from the appropriately substituted starting materials:

| Cpd. No. | R | $R^1$ | $(R^2)_n$ | m.p./°C. |
|---|---|---|---|---|
| 214 | CO$_2$Et | Cp | 2-CF$_3$-4-SMe | 97–98 |
| 218 | CO$_2$Et | Cp | 2-F-4-SO$_2$Me | 116–117 |
| 219 | CO$_2$Et | Cp | 2-Cl-4-SO$_2$Et | 136–137 |
| 220 | CO$_2$Et | Cp | 2-SO$_2$Me-4-Br | 93–95 |
| 221 | CO$_2$Et | Cp | 2-Br-4-SO$_2$Me | 139–140 |
| 222 | CO$_2$Et | Cp | 2-Cl-4-SMe | 75–76 |
| 224 | COCH$_3$ | Cp | 2-Cl-4-SO$_2$Me | 121.5 |

EXAMPLE 14

3-Chloroperoxybenzoic acid (1.9 g) was added to a solution of ethyl 5-cyclopropyl-4-(2-methylsulphenyl-4-trifluoromethylbenzoyl)isoxazole-3-carboxylate (2.7 g) in dichloromethane whilst maintaining the temperature below −10° C. The mixture was stirred at −5° C. for 1.5 hours and allowed to warm to room temperature. A solution of sodium metabisulphite in water was added and the layers were separated. The organic layer was washed with water, dried (anhydrous sodium sulphate) and filtered. The filtrate was evaporated to dryness and the residue was purified by chromatography on silica eluted with a mixture of ethyl acetate and hexane (1:3) to give compound 215 (1.2 g) as a white solid, m.p. 140°–141° C.

By proceeding in a similar manner the following compounds of formula I in which Q represents C=O were prepared from the appropriately substituted starting materials.

| Cpd No. | R | $R^1$ | $(R^2)_n$ | m.p./°C. |
|---|---|---|---|---|
| 216 | $CO_2Et$ | Cp | 2-$CF_3$-4-SOMe | 65–66 |
| 217 | $CO_2Et$ | Cp | 2-$SO_2Me$-4-$CF_3$ | 101–102 |
| 223 | $CO_2Et$ | Cp | 2-Cl-4-SOMe | 100–101 |
| 229 | $CO_2Me$ | Cp | 2-SOMe-4-Cl | 82–83 |
| 231 | $CO_2Et$ | Cp | 2-OMe-4-SOMe | 96–98.5 |
| 232 | $CO_2Et$ | Cp | 2-OMe-4-$SO_2Me$ | 111–115 |
| 234 | $CO_2Et$ | Cp | 2-Me-SOMe | 83–85 |
| 235 | $CO_2Et$ | Cp | 2-Me-4-$SO_2$—Me | 128–129 |
| 243 | $CO_2CH_2$—$C_6H_5$ | Cp | 2-Cl-$SO_2Me$ | 154.5–155.5 |
| 247 | $CO_2CH_2C_6H_4$—OMe(p) | Cp | 2-Cl-4-$SO_2Me$ | 146–147 |

EXAMPLE 15

Sodium hydride (0.15 g) was added to isopropanol. This was followed by the addition of methyl 4-(2-chloro-4-methylsulphonylbenzoyl)-5-cyclopropylisoxazole-3-carboxylate (1.9 g). The mixture was stirred and heated at reflux for 2.5 hours, cooled and water was added. It was extracted with ethyl acetate and the organic layer was washed with water, dried (anhydrous sodium sulphate) and filtered. The filtrate was evaporated to dryness. The residue was triturated with ether and filtered. The solid was treated with ethyl acetate and filtered. The filtrate was passed through a short column of silica and the eluate was evaporated to dryness to give compound 225 (0.25 g) as a white solid, m.p. 149°–150° C.

EXAMPLE 16

A mixture of magnesium (0.35 g) and carbon tetrachloride (0.5 ml) in methanol was warmed until all of the magnesium had dissolved. 1-(4-chloro-2-methylsulphonylphenyl)-3-cyclopropylpropane-1,3-dione (4.0 g) was added and the mixture was stirred and heated at reflux for 2 hours. It was then cooled and evaporated to dryness. The residue was dissolved in dichloromethane and a solution of methyl chloro-oximidoacetate (2.75 g) in dichloromethane was added. The mixture was stirred at room temperature overnight, washed with hydrochloric acid (2M), water, dried (anhydrous sodium sulphate) and filtered. The filtrate was evaporated to dryness and the residue was triturated with ether and filtered. The solid was recrystallized from ethanol to give compound 226 (1.7 g) as a pale orange solid, m.p. 146°–147° C.

By proceeding in a similar manner the following compounds of formula I in which Q represents C=O were prepared from the appropriately substituted starting materials (cHex=cyclohexyl):

| Cpd. No. | R | $R^1$ | $(R^2)_n$ | m.p./°C. |
|---|---|---|---|---|
| 227 | $CO_2Me$ | Cp | 2-$SO_2Me$-4-$CF_3$ | 130–131 |
| 228 | $CO_2Me$ | Cp | 2-SMe-4-Cl | 112–113 |
| 230 | $CO_2Et$ | Cp | 2-OMe-4-SMe | 67–69 |
| 233 | $CO_2Et$ | Cp | 2-Me-4-SMe | 56.5–58.5 |
| 370 | $CO_2$cHex | Cp | 2-$SO_2Me$-4-$CF_3$ | a | a = NMR(CDCl$_3$) 1.1–1.9(m,14H), 2.3(m,1H), 3.4(s,3H), 4.75(m,1H), 7.6(d,1H), 7.95(d,1H), 8.4(s,1H).

EXAMPLE 17

Oxalyl chloride (1.3 g) was added dropwise to a suspension of 4-(2-chloro-4-methylsulphenylbenzoyl)-5-cyclopropylisoxazole-3-carboxylic acid (2.1 g) in toluene containing 2 drops of pyridine. The mixture was stirred at room temperature for 2 hours. Pyridine (0.2 ml) was added and the mixture was stirred at room temperature overnight. Pyridine (1.6 g) was added followed by n-hexyl alcohol (2.0 g) and the mixture was stirred at room temperature for 3 hours. Water was added and the layers were separated. The organic layer was washed with water, dried (Na$_2$SO$_4$) and filtered. The filtrate was evaporated to dryness and the residue was purified by dry column flash chromatography eluted with a mixture of ethyl acetate and n-hexane to give compound 237 (0.6 g) as a clear oil NMR(CDCl$_3$) 0.9 (m,3H), 1.25 (m,10H), 1.6 (m,2H), 2.35 (m,1H), 2.55(s,3H) 4.1(t,2H) 7.15 (d,1H), 7.25 (s,1H), 7.45 (d,1H).

By proceeding in a similar manner the following compounds of formula (I) in which Q is C=O were prepared from the appropriately substituted starting materials.

| Cpd No. | R | $R^1$ | $(R^2)_n$ | m.p./NMR |
|---|---|---|---|---|
| 236 | —$CO_2Bu^t$ | Cp | 2-Cl-4-SMe | 113–114° C. |
| 238 | —$CO_2CH_2CF_3$ | Cp | 2-Cl-4-SMe | NMR (a) |
| 239 | —$CO_2CH_2CH$=$CH_2$ | Cp | 2-Cl-4-SMe | 54–56° C. |
| 240 | $CO_2CH_2C$≡H | Cp | 2-Cl-4-SMe | 81–83° C. |
| 241 | —$CO_2C_6H_5$ | Cp | 2-Cl-4-SMe | 142.5–143.5° C. |
| 242 | —$CO_2CH_2C_6H_5$ | Cp | 2-Cl-4-SMe | 106.5–107.5° C. |
| 244 | —$CO_2N$=$C(CH_3)_2$ | Cp | 2-Cl-4-SMe | 90–91° C. |
| 245 | —$CO_2CH_2C_6H_4$—$NO_2$(p) | Cp | 2-Cl-4-SMe | 99.5–100° C. |
| 246 | —$CO_2CH_2C_6H_4$—OMe(p) | Cp | 2-Cl-4-SMe | 100–101° C. |
| 248 | —$CO_2N$=$CHC_6H_5$ | Cp | 2-Cl-4-SMe | 98.5–99.5° C. |

(a) NMR (CDCl$_3$) 1.15(m,2H), 1.25(m,2H), 2.2(m,1H), 2.45(s,3H), 4.45,(q,2H), 7.05(d,1H), 7.15, (s,1H)7.4(d,1H).

EXAMPLE 18

Sodium acetate (7.87 g) was added to a stirred mixture of 3-cyclopropyl-2-ethoxymethylene-1-(2-methoxy-4-methylsulphenylphenyl)propan-1,3-dione (30.6 g) and hydroxylamine hydrochloride (8.0 g) in ethanol. The mixture was stirred at room temperature overnight, then evaporated to dryness and the residue was dissolved in ethyl acetate, washed with water, dried (anhydrous magnesium sulphate) and filtered. The filtrate was evaporated to dryness and the residue was triturated with ether and filtered to give 5-cyclopropyl-4-(2-methoxy-4-methylsulphenylbenzoyl)isoxazole, compound 249 as a white solid, m.p. 107.5°–108.5° C.

By proceeding in a similar manner the following compounds of formula IA were prepared from the appropriately substituted starting materials:

| Cpd. No. | $R^{41}$ | $R^{42}$ | $R^{43}$ | $R^{44}$ | m.p./NMR |
|---|---|---|---|---|---|
| 253 | Cp | $CH_3$ | H | $SO_2Me$ | 86–87° C. |
| 254 | Cp | $CH_3$ | H | SMe | 65–66° C. |
| 255 | 1-Me-Cp | $CH_3$ | H | $SO_2Me$ | 87.5–88.5° C. |
| 256 | Cp | $CH_2CH_3$ | H | SMe | NMR (a) |
| 259 | Cp | $OCH_2CH_3$ | H | SMe | 108.8–110.6° C. |

(a) NMR (CDCl$_3$) 1.0(m,2H), 1.1(t,3H), 1.4(m,2H), 2.5(s,3H), 2.6(m,1H), 2.8(q,2H), 7.0(dd,1H), 7.1(d,1H), 7.3(d,1H), 8.3(s,1H).

EXAMPLE 19

3-Chloroperoxybenzoic acid (3.4 g) was added to a solution of 5-cyclopropyl-4-(2-methoxymethylsulphenylbenzoyl)isoxazole (3.5 g) in dichloromethane at −15° C. The mixture was stirred at −15° C. for 1 hour and at room temperature overnight. The mixture was recooled to −15° C. and 3-chloroperoxybenzoic acid (3.4 g) was added. The mixture was filtered and the filtrate was washed with aqueous sodium metabisulphite solution, water, dried (anhydrous magnesium sulphate) and filtered. The filtrate was evaporated to dryness. The residue was purified by column chromatography on silica eluted with a mixture of ethyl acetate and hexane to give 5-cyclopropyl-4-(2-methoxy-4-methylsulphonylbenzoyl) isoxazole, compound 250 (1.4 g) as a white solid, m.p. 133°–133.5° C. and 5-cyclopropyl-4-(2-methoxy-4-methylsulphinylbenzoyl)isoxazole, compound 251 (0.85 g) as an off-white solid, m.p. 100°–102° C.

By proceeding in a similar manner the following compounds of formula IA above were prepared from the appropriately substituted starting materials:

| Cpd No. | $R^{41}$ | $R^{42}$ | $R^{43}$ | $R^{44}$ | m.p./°C. |
|---|---|---|---|---|---|
| 252 | Cp | $CH_3$ | H | S(O)Me | 135–136.5 |
| 257 | Cp | $CH_2CH_3$ | H | S(O)Me | 139.9–140.6 |
| 258 | Cp | $CH_2CH_3$ | H | $SO_2Me$ | 85.8–86.8 |

EXAMPLE 20

Sodium acetate (1.93 g) was added to a mixture of 1-(4-chloro-2-methylsulphonylphenyl)-3-cyclopropyl-2-ethoxymethylenepropan-1,3-one (8.4 g) and hydroxylamine hydrochloride (1.64 g) in ethanol with stirring. The mixture was stirred at room temperature overnight. It was evaporated and the residue was dissolved in ethyl acetate, washed with water, dried (anhydrous magnesium sulphate) and filtered. The filtrate was evaporated to dryness and the residue was crystallized from ether to give 4-(4-chloro-2-methylsulphonylbenzoyl)-5-cyclopropylisoxazole, compound 260 (4.4 g) as an off-white solid, m.p. 183°–185° C.

By proceeding in a similar manner the following compounds of formula IA above were prepared from the appropriately substituted starting materials:

| Cpd No. | $R^{41}$ | $R^{42}$ | $R^{43}$ | $R^{44}$ | m.p./°C. |
|---|---|---|---|---|---|
| 261 | Cp | $SO_2Me$ | H | $CF_3$ | 132–135 |
| 262 | Cp | SMe | H | $CF_3$ | 57–58.5 |
| 263 | Cp | $SO_2Me$ | H | Br | 191–196 |
| 265 | 1-Me-Cp | $SO_2Me$ | H | Cl | 135–137 |
| 266 | iPr | $SO_2Me$ | H | Cl | 133.5–135 |
| 267 | Cp | $SO_2Me$ | H | F | 91.5–92.5 |
| 268 | Cp | $SO_2Me$ | H | $CH_3$ | 163–164 |
| 269 | Cp | $SO_2Me$ | H | $OCH_3$ | 178–179.5 |
| 270 | Cp | $SO_2Et$ | H | Cl | 174–175 |
| 271 | Cp | SMe | H | Cl | 99.5–100 |
| 273 | iPr | $SO_2Me$ | H | $CF_3$ | 99–100.5 |
| 274 | 1-Me-Cp | $SO_2Me$ | H | $CF_3$ | 79.5–80.5 |
| 275 | Me | $SO_2Me$ | H | Cl | 124–126 |
| 276 | iPr | SMe | H | Cl | 102.5–103 |
| 277 | 1-Me-Cp | $SO_2Et$ | H | Cl | 96–98 |
| 278 | iPr | $SO_2Et$ | H | Cl | 102–103 |
| 279 | Et | $SO_2Me$ | H | Cl | 97.5–98.5 |
| 281 | 1-Me-Cp | $SO_2Me$ | H | Br | 149.8–153.8 |
| 282 | iPr | $SO_2Me$ | H | Br | 154.4–160 |

EXAMPLE 21

3-Chloroperoxybenzoic acid (0.95 g) was added to a cooled solution of 5-cyclopropyl-4-(2-methylsulphenyl-4-trifluoromethylbenzoyl)isoxazole (1.2 g) in dichloromethane with stirring at −20° C. The mixture was stirred at −20° C. for 2 hours and allowed to warm slowly to 0° C. It was stirred for 1 hour and recooled to −20° C. 3-Chloroperoxybenzoic acid (0.4 g) was added at −20° C. and the mixture was allowed to warm slowly to 0° C. and stirred for 1 hour. The mixture was then filtered and the filtrate was washed with water, aqueous sodium metabisulphite solution, dried (anhydrous magnesium sulphate) and filtered. The filtrate was evaporated to dryness and the residue was triturated with ethyl acetate and filtered to give 5-cyclopropyl-4-(2-methylsulphinyl-4-trifluoromethylbenzoyl)isoxazole, compound 264 (0.59 g) as a white solid, m.p. 149°–151° C.

By proceeding in a similar manner the following compounds of formula IA above were prepared from the appropriately substituted starting materials:

| Cpd No | $R^{41}$ | $R^{42}$ | $R^{43}$ | $R^{44}$ | m.p. |
|---|---|---|---|---|---|
| 272 | Cp | S(O)Me | H | Cl | 140–140.5° C. |
| 280 | iPr | S(O)Me | H | Cl | 168–169° C. |

EXAMPLE 22

Sodium acetate (0.31 g) was added with stirring to a mixture of 3-cyclopropyl-1-[3,4-difluoro-2-(methylsulphonyl)phenyl]-2-ethoxymethylenepropane-1,3-dione (1.1 g) and hydroxylamine hydrochloride (0.26 g) in ethanol. The mixture was stirred for 2.5 hours. The mixture was evaporated to dryness and the residue was suspended in ethyl acetate, washed with water, dried (anhydrous $MgSO_4$) and filtered. The filtrate was evaporated to dryness. The residue was triturated with n-hexane and filtered to give 5-cyclopropyl-4-(3,4-difluoro-2-methylsulphonylbenzoyl)isoxazole (compound 283, 0.59 g) as an orange solid, m.p.115°–118° C.

By proceeding in a similar manner the following compounds of formula IB above were prepared from the appropriately substituted starting materials.

| Cpd | $R^{50}$ | $R^{51}$ | $R^{52}$ | $R^{53}$ | $R^{54}$ | m.p./NMR |
|---|---|---|---|---|---|---|
| 284 | H | Cp | SMe | Cl | Cl | 83.5–84.5° C. |
| 287 | H | Cp | SMe | OMe | Br | a |
| 288 | H | Cp | $SO_2Me$ | OMe | Br | 146.4–146.8° C. |
| 292 | H | Cp | SMe | OMe | Cl | b |
| 330 | H | Cp | SMe | Me | Cl | 85–87° C. |
| 331 | H | Cp | SMe | F | Cl | 73–74° C. |
| 336 | H | Cp | SMe | $CO_2Me$ | $CF_3$ | c |
| 337 | H | Cp | SMe | $CO_2Me$ | Cl | d |
| 338 | H | Cp | SMe | Cl | Br | 93–94° C. |
| 343 | H | Cp | SMe | Cl | $CF_3$ | 89–90° C. |
| 345 | H | Cp | SMe | F | Br | e |
| 348 | H | Cp | SMe | $C(CH_3)=CH_2$ | Cl | 140–141.5° C. |
| 349 | H | Cp | SMe | Me | SMe | 103–105° C. |
| 360 | H | Cp | SMe | $CHF_2$ | Cl | f |
| 369 | H | Cp | SMe | Br | Br | 107–109° C. |
| 358 | H | Cp | $SO_2Me$ | $OCH_2CF_3$ | Cl | 108–110° C. | a = NMR ($CDCl_3$): 1.2(m,2H), 1.3(m,2H), 2.4(s,3H), 2.6(m,1H), 4.0(s,3H), 7.0(d,1H), 7.6(d,1H), 8.15(s,1H).
b = NMR ($CDCl_3$): 1.2(m,2H) 1.4(m,2H), 2.4(s,3H), 2.6(m,1H), 4.0(s,3H), 7.05(d,1H), 7.45(d,1H), 8.15(s,1H).
c = NMR ($CDCl_3$): 1.25(m,2H), 1.35(m,2H), 2.4(s,3H), 2.55(m,1H), 4.0(s,3H), 7.5(d,1H), 7.8(d,1H), 8.15(s,1H).
d = NMR ($CDCl_3$): 1.2(m,2H), 1.35(m,2H),2.4(s,3H), 2.5(m,1H), 4.0(s,3H), 7,35(d,1H), 7.55(d,1H), 8.15(s,1H).
e = NMR ($CDCl_3$): 125 (m,2H), 1.35(m,2H), 2.45(s,3H), 2.65(m,1H), 7.05 (d,1H), 7.6(t,1H), 8.15(s,1H).
f = NMR ($CDCl_3$): 1.2(m,2H), 1.3(m,2H), 2.4(s,3H), 2.5(m,1H), 7.3(d,1H), 7.55(d,1H), 7.6(t,1H), 8.1(s,1H).

EXAMPLE 23

A mixture of magnesium (0.17 g) and methanol containing approximately 0.1 ml of carbon tetrachloride was heated at reflux for 0.5 hours, cooled and 3-cyclopropyl-1-(3,4-dichloro-2-methylsulphenylphenyl)propane-1,3-dione (2.0 g) was added. The mixture was stirred and heated at reflux for 2 hours. It was cooled and evaporated to dryness. The residue was dissolved in dichloromethane and a solution of ethyl chloro-oximidoacetate (1.37 g) in dichloromethane was added. The mixture was stirred at room temperature overnight. Hydrochloric acid (2M) was added and the layers were separated. The organic layer was washed with water, dried (anhydrous Na$_2$SO$_4$) and filtered. The filtrate was evaporated to dryness and the residue was purified by dry column flash chromatography eluted with a mixture of ethyl acetate and n-hexane (1:9) to give ethyl 5-cyclopropyl-4-(3,4-dichloro-2-methylsulphenylbenzoyl)isoxazole-3-carboxylate (compound 290, 2.19 g) as an orange oil NMR: (CDCl$_3$) 1.15–1.3(m,5H), 1.4(m,2H), 2.4(s,3H), 2.45(m, 1H), 4.1(q,2H), 7.2(d,1H), 7.5(d,1H).

EXAMPLE 24

3-Chloroperoxybenzoic acid (2.0 g) was added to a solution of 5-cyclopropyl-4-(3,4-dichloro-2-methylsulphenylbenzoyl)isoxazole (1.86 g) in dichloromethane while maintaining the temperature around −15° C. The mixture was stirred at −15° C. for 1 hour and at room temperature for 1 hour. It was recooled to −15° C. and filtered. The filtrate was evaporated to dryness and the residue was purified by dry column flash chromatography eluted with a mixture of ethyl acetate and n-hexane. The product was recrystallized from a mixture of ethyl acetate and n-hexane to give 5-cyclopropyl-4-(3,4-dichloro-2-methylsulphinylbenzoyl)isoxazole (compound 285, 0.3 g) as a white solid, m.p. 110°–112° C.

By proceeding in a similar manner the following compounds were prepared from the appropriately substituted starting materials:

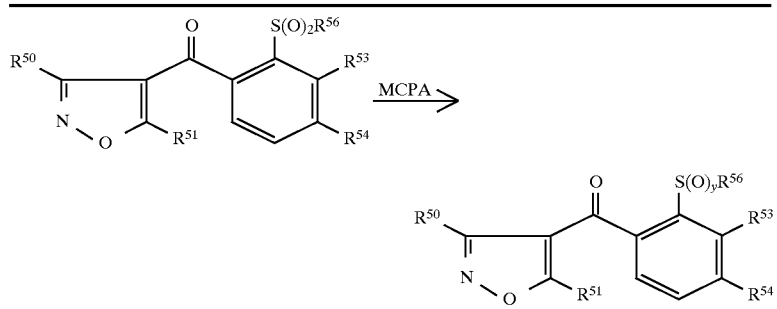

| Cpd No | R$^{50}$ | R$^{51}$ | R$^{56}$ | R$^{53}$ | R$^{54}$ | z | y | m.p (°C.)/NMR |
|---|---|---|---|---|---|---|---|---|
| 286 | H | Cp | Me | Cl | Cl | 1 | 2 | 149–150 |
| 289 | H | Cp | Me | OMe | Br | 0 | 1 | a |
| 291 | CO$_2$Et | Cp | Me | Cl | Cl | 0 | 1 | 129–130 |
| 293 | CO$_2$Et | Cp | Me | Cl | Cl | 1 | 2 | 106–107.5 |
| 328 | H | Cp | Me | OMe | Cl | 0 | 1 | 95–96 |
| 329 | H | Cp | Me | OMe | Cl | 0 | 2 | 63–67 |
| 332 | H | Cp | Me | F | Cl | 0 | 1 | 136–137 |
| 333 | H | Cp | Me | F | Cl | 0 | 2 | 151–152 |
| 334 | H | Cp | Me | Me | Cl | 0 | 1 | 115.4–118 |
| 335 | H | Cp | Me | Me | Cl | 0 | 2 | 132–134.6 |
| 339 | H | Cp | Me | Cl | Br | 0 | 1 | 133–134 |
| 340 | H | Cp | Me | Cl | Br | 0 | 2 | 147–148 |
| 341 | H | Cp | Me | CO$_2$Me | Cl | 0 | 1 | 163–164 |
| 342 | H | Cp | Me | CO$_2$Me | Cl | 0 | 2 | 123.4–132 |
| 344 | H | Cp | Me | Cl | CF$_3$ | 0 | 2 | 136–137 |
| 346 | H | Cp | Me | F | Br | 0 | 1 | 125–126 |
| 350 | H | Cp | Me | C(CH$_3$)=CH$_2$ | Cl | 0 | 1 | 215–217 |
| 351 | H | Cp | Me | C(CH$_3$)=CH$_2$ | Cl | 0 | 2 | 130–132 | a = NMR (CDCl$_3$): 1.1–1.4(m, 4H), 2.6(m, 1H), 3.0(s, 3H), 3.95(s, 3H), 7.0(d, 1H), 7.7(d, 1H), 8.1(s, 1H).

EXAMPLE 25

Hydrogen peroxide (30%; 1.3 ml) was added dropwise to a solution of 4-(4-bromo-3-fluoro-2-methylsulphenylbenzoyl)-5-cyclopropylisoxazole (1.2 g) in a mixture of acetic acid and acetic anhydride. The resultant mixture was heated at 70° C. for 4 hours. It was cooled, poured into water and extracted with ethyl acetate. The organic extract was washed with aqueous sodium bisulphite, aqueous ferrous sulphate and water, dried (MgSO$_4$) and filtered. The filtrate was evaporated to dryness and the residue was triturated with ether and filtered to give 4-(4-bromo-3-fluoro-2-methylsulphonylbenzoyl)-5-cyclopropylisoxazole (compound 347, 0.85 g) as a white solid, m.p. 144°–145° C.

EXAMPLE 26

A mixture of 4-[2-nitro-4-trifluoromethylbenzoyl]-5-cyclopropylisoxazole (8.00 g) and sodium borohydride (0.53 g) in ethanol (250 ml) was stirred at room temperature for 2 hours. The solution was evaporated almost to dryness and the resultant solution was diluted with ethyl acetate. The solution was washed with water, dried (anhydrous magnesium sulphate) and filtered. The filtrate was evaporated to dryness. The residue was purified by chromatography on silica eluted with a mixture of ether and petroleum ether to give 4-[hydroxy-(2-nitro-4-trifluoromethylphenyl)methyl]-5-cyclopropylisoxazole (compound 294, 5.95 g) as an off white solid: m.p. 76° C.

By proceeding in a similar manner the following compounds of formula I in which R is hydrogen and Q represents —CR$^{61}$R$^{71}$ were prepared:

| Cpd No. | R$^1$ | (R$^2$)n | R$^{61}$ | R$^{71}$ | m.p. |
|---|---|---|---|---|---|
| 295 | Me | 2-NO$_2$-4-CF$_3$ | H | OH | 90° |
| 296 | Cp | 2-Cl-3-OEt-SO$_2$Me | H | OH | * |

*NMR: (CDCl$_3$) 1.0 (4H,m) 1.4 (3H,t) 2.1 (1H,m) 3.16 (3H,s) 3.6 (1H,br.s) 4.37 (2H,q) 6.1(1H,m) 7.69 (1H,m) 7.8 (1H,s) 7.81 (1H,m).

| | | | | | |
|---|---|---|---|---|---|
| 301 | Cp | 2-Cl-4-SO$_2$Me | H | OH | 141° C. |
| 303 | Cp | 2-NO$_2$-4-Me | H | OH | 82° C. |
| 304 | Me | 2-Cl-3-OEt-4-SO$_2$Et | H | OH | * |

*NMR: (CDCl$_3$) 1.2 (3H,t) 1.5 (3H,t) 2.45 (3H,s) 3.4 (2H,q) 3.7 (1H,brs) 4.2 (2H,m) 6.05 (1H,s) 7.75 (1H,d) 7.85 (1H,d) 8.0 (1H,s).

| | | | | | |
|---|---|---|---|---|---|
| 305 | Cp | 2Cl-3-OEt-4SO$_2$Et | H | OH | * |

*NMR: (CDCl$_3$) 1.1 (2H, m) 1.2 (2H,m) 1.25 (3H,t) 1.5 (3H,t) 2.15 (1H,m) 2.95 (1H,d) 3.45 (2H,q) 4.2 (2H,m) 6.2 (1H,d) 7.8 (1H,d) 7.95 (1H,d) 8.0 (1H,s).

| | | | | | |
|---|---|---|---|---|---|
| 308 | Cp | 2-Cl-4-F | H | OH | * |

*NMR: (CDCl$_3$) 0.9(2H,m) 1.0(2H,m) 1.9(1H,m) 3.25 (1H, brs) 6.05 (1H,s) 7.0 (2H,m) 6.65 (1H,m) 7.8 (1H,s).

| | | | | | |
|---|---|---|---|---|---|
| 309 | Cp | 2-CF$_3$-4SO$_2$Me | H | OH | 90° C. |
| 315 | Cp | 2-SO$_2$Me | H | OH | 118° C. |
| 316 | 1-Me-Cp | 2,3-Cl$_2$-4SO$_2$Me | H | OH | 205° C. |
| 317 | Cp | 2-SO$_2$Me-4-Cl | H | OH | 91.5° C. |
| 318 | Cp | 2-Br-4-SO$_2$Me | H | OH | 148° C. |
| 319 | Cp | 2-SO$_2$Me-4-Br | H | OH | 95° C. |
| 320 | Cp | 2-CH$_3$-4-SO$_2$Me | H | OH | 136° C. |
| 321 | Cp | 2-Cl-4-SMe | H | OH | 104° C. |
| 322 | Cp | 2-SO$_2$Me-4-CF$_3$ | H | OH | 89° C. |
| 323 | Cp | 2-Cl-4-SOMe | H | OH | * |

*NMR (DMSO): 0.8 (2H,m). 0.9 (2H,m). 2.2 (1H,m) 2.8 (3H,s) 6.1 (1H,br.d) 6.3 (1H,br.d) 7.6 (2H,m) 8.0 (1H,m) 8.2 (1H, s).

| | | | | | |
|---|---|---|---|---|---|
| 324 | Cp | 2-CF$_3$-4-SMe | H | OH | 91° C. |
| 325 | Cp | 2-F-4-SO$_2$Me | H | OH | 101° C. |
| 326 | iPr | 2-SO$_2$Me-4-Cl | H | OH | 145° C. |
| 327 | 1-Me-Cp | 2-SO$_2$Me-4-Cl | H | OH | 154° C. |

EXAMPLE 27

A mixture of 4-[hydroxy-(2-nitro-4-trifluoromethylphenyl)methyl]-5-cyclopropylisoxazole (0.69 g), acetyl chloride (0.27 g) and pyridine (0.10 g) in dichloromethane (40 ml) was stirred at 0° C. for 4 hours. The mixture was quenched with water and extracted with dichloromethane. The organic extracts were dried (anhydrous magnesium sulphate) and filtered. The filtrate was evaporated to dryness. The residue was triturated with ether/petroleum ether to give 4-[acetoxy-(2-nitro-4-trifluoromethylphenyl)methyl]-5-cyclopropylisoxazole (compound 297, 0.46 g) as a yellow solid: m.p. 82° C.

By proceeding in a similar manner the following compounds of formula (I) in which R is hydrogen and Q represents —CR$^{61}$R$^{71}$ were prepared:

| Cpd No. | R$^1$ | (R$^2$)n | R$^{61}$ | R$^{71}$ | m.p |
|---|---|---|---|---|---|
| 306 | Cp | 2-Cl-4-SO$_2$Me | H | —OCOMe | * |
| 371 | Cp | 2-Cl-4-SO$_2$Me | H | —OCOPh | 147.4–148.6 |

*NMR (CDCl$_3$): 1.1 (2H,m) 1.2 (2H,m) 2.1 (3H,s) 2.2 (1H,m) 3.0 (3H,s) 7.1 (1H,s) 7.9 (3H,m) 8.0 (1H,s).

EXAMPLE 28

A mixture of 4-[hydroxy-(2-nitro-4-trifluoromethylphenyl)methyl]-5-cyclopropylisoxazole (0.89 g) and phosphorous trichloride (0.57 g) in dichloromethane (50 ml) were stirred at 0° C. for 2 hours. The reaction mixture was quenched with water and extracted with dichloromethane. The organic extracts were dried (anhydrous magnesium sulphate), filtered and evaporated to dryness. The crude product was purified by column chromatography on silica eluted with a mixture of petroleum ether/ethyl acetate to give 4-[chloro-(2-nitro-4-trifluoromethylphenyl)methyl]-5-cyclopropylisoxazole (compound 298, 0.79 g) as a yellow oil: NMR: (CDCl$_3$) 1.1 (4H,m) 1.9(1H,m) 6.9(1H,s) 7.9(1H,m) 8.0(1H,s) 8.25(2H, m).

By proceeding in a similar manner the following compound was prepared:

4-[chloro-(2-trifluoromethyl-4-methanesulphonylphenyl)methyl]-5-cyclopropylisoxazole, compound 313 m.p. 145° C.

EXAMPLE 29

A mixture of 4-[hydroxy-(2-nitro-4-trifluoromethylphenyl)methyl]-5-cyclopropylisoxazole (1.0 g), phosphorus tribromide (0.70 g) and pyridine (0.05 g) in dry ether was stirred at 0° C. for 15 hours. The reaction mixture was quenched with water and extracted with ether. The organic extracts were dried (anhydrous magnesium sulphate), filtered and the solvent evaporated yielding 4-[bromo-(2-nitro-4-trifluoromethylphenyl)methyl]-5-cyclopropylisoxazole (compound 299, 1.18 g) as a yellow oil: NMR: (CDCl$_3$) 1.1(4H,m) 1.9(1H,m) 6.9(1H,s) 7.9(1H, m) 8.0(1H,s) 8.15(2H,m).

By proceeding in a similar manner the following compound was prepared:

4-[bromo-(2-trifluoromethyl-4-methanesulphonylphenyl)methyl]-5-cyclopropylisoxazole,compound 312: mp. 146° C.

EXAMPLE 30

A mixture of 4-[bromo-(2-nitro-4-trifluoromethylphenyl)methyl]-5-cyclopropylisoxazole (1.2 g) and dimethylamine (2.0 g of a 33% solution in ethanol) in dichloromethane was stirred at 0° C. for 2 hours and then at room temperature for a further 16 hours. The reaction mixture was quenched with water and extracted with dichloromethane. The organic extracts were dried (anhydrous magnesium sulphate), filtered and evaporated to dryness. The residue was purified by column chromatography on silica eluting with petroleum ether and ethyl acetate to give 4-[N,N-dimethylamino-(2-nitro-4-trifluoromethylphenyl)methyl]-5-cyclopropylisoxazole (compound 300, 0.27 g) as a yellow oil: NMR (CDCl$_3$); 1.02(4H,m), 2.08(1H,m), 2.12(6H,s), 4.9(1H,s), 7.8(1H,m), 7.9(1H,m), 8.0(1H,s), 8.1(1H,m).

EXAMPLE 31

A mixture of 4-[bromo-(2-chloro-4-methanesulphonylphenyl)methyl-5-cyclopropylisoxazole (2.5 g) and methanol (2.0 ml) in toluene was stirred at reflux for 16 hours. The resultant solution was evaporated to dryness and the residue was dissolved in ethyl acetate. This solution was washed with water, dried (MgSO$_4$), and filtered. The filtrate was evaporated to dryness. The residue was purified by chromatography on silica eluted with ethyl acetate and petroleum ether to give 4-[methoxy-(2-chloro-4-methanesulphonylphenyl)methyl]-5-cyclopropylisoxazole (compound 307, 1.40 g) as a colourless oil, NMR: (CDCl$_3$) 1.0(4H,m), 2.1 (1H,m), 3.0(3H,s), 3.3(3H,s), 5.6(1H,s), 7.9(4H,m).

By proceeding in a similar manner the following compounds were prepared:

4-[methoxy-(2-nitro-4-trifluoromethylphenyl)methyl]-5-cyclopropylisoxazole, compound 302; NMR (CDCl$_3$): 1.0(4H,m), 2.1(1H,m), 3.3(3H,s), 6.0(1H,s), 7.8(1H,s), 7.9(1H,d), 8.0(1H,d), 8.2(1H,s);

4-[methoxy-(2-trifluoromethyl-4-methanesulphonylphenyl)methyl]-5-cyclopropylisoxazole, compound 311; m.p. 159° C.

EXAMPLE 32

A mixture of crude 2-N,N-dimethylaminomethylene-3-[2-(1-methyl-1-propylsulphenyl)-4-trifluoromethylphenyl]-3-cyclopropylpropan-1,3-dione (11.9 g) and hydroxylamine hydrochloride (2.3 g) in ethanol was stirred for 24 hours. The mixture was then cooled in an ice bath and filtered. The resultant solid was washed with water and dried over phosphorous pentoxide to give 4-[2-(1-methylpropylsulphenyl)-4-trifluoromethylbenzoyl)-5-cyclopropylisoxazole (3.8 g, Compound 359) as a white solid, m.p. 75.6°–76.4° C.

By proceeding in a similar manner 4-(4-chloro-3-formyl-2-methylsulphenylbenzoyl)-5-cyclopropylisoxazole (Compound 362) was prepared as a clear gum, NMR (CDCl$_3$) 1.2(m,2H), 1.3(m,2H), 2.2(s,3H), 2.5(m,1H), 7.3 (d,1H), 7.5(d,1H), 8.0(s,1H), 10.5(s,1H), starting from 1-(4-chloro-3-dioxalane-2-methylsulphenylphenyl)-2-N,N-dimethylaminomethylene-3-cyclopropylpropan-1,3-dione.

EXAMPLE 33

4-(4-Chloro-3-methoxymethyl-2-methylsulphenylbenzoyl)-5-cyclopropylisoxazole (0.7 g), hydrogen peroxide (2.5 ml of 30% solution), acetic anhydride (6 ml) and acetic acid (20 ml) were heated together at 70° C. for 2 hours. The mixture was allowed to cool and then poured into water and the resultant solid filtered. This solid was washed with water and dried in a desiccator yielding 4-(4-chloro-3-methoxymethyl-2-methylsulphonylbenzoyl)-5-cyclopropylisoxazole (compound 365, 0.22 g) as a white solid, m.p. 83.6°–84.2° C.

REFERENCE EXAMPLE 1

A mixture of 1-(2-nitro-4-trifluoromethylphenyl)-butan-1,3-dione (–11.0 g), triethyl orthoformate (11.3 g) and acetic anhydride (12.3 g) was stirred and heated at reflux for 3 hours. After cooling, the mixture was evaporated to dryness. Toluene (50 ml) was added and the mixture was evaporated to dryness to give 2-ethoxymethylene-1-(2-nitro-4-trifluoromethylphenyl)-butan-1,3-dione as a crude brown oil which was not further purified.

By proceeding in a similar manner the following compounds were prepared:

2-Ethoxymethylene-1-(2-nitrophenyl)-butan-1,3-dione, as a crude black gum, starting from 1-(2-nitrophenyl) butan-1,3-dione.

2-Ethoxymethylene-1-(2-nitro-4-trifluoromethylphenyl)-3-phenylpropan-1,3-dione, as a crude orange oil, starting from 1-(2-nitro-4-trifluoromethyl-phenyl)-3-phenylpropan-1,3-dione.

1-(2,4-dinitrophenyl)-2-ethoxymethylenebutan-1,3-dione, as a crude black gum, starting from 1-(2,4dinitrophenyl)-butan-1,3-dione.

3-(4-Chlorophenyl)-2-ethoxymethylene-1-(2-nitro-4-trifluoromethylphenyl)-propan-1,3-dione, as a white solid, by trituration with ether, m.p. 146°–147° C. starting from 3-(4-chlorophenyl)-1-(2-nitro-4-trifluoromethylphenyl)propan-1,3-dione.

1-(2-Chlorophenyl)-2-ethoxymethylenebutan-1,3-dione, as a crude black gum, starting from 1-(2-chlorophenyl)-butan-1,3-dione.

2-Ethoxymethylene-1-(4-methylsulphonyl-2-nitrophenyl)-butan-1,3-dione as a crude brown gum, starting from 1-(4-methylsulphonyl-2-nitrophenyl) butan-1,3-dione.

2-Ethoxymethylene-4-methyl-1-(2-nitro-4-trifluoromethylphenyl)-pentan-1,3-dione as a crude red oil, starting from 4-methyl-1-(2-nitro-4-trifluoromethylphenyl)-pentan-1,3-dione.

2-Ethoxymethylene-3-(4-fluorophenyl)-1-(2-nitro-4-trifluoromethylphenyl)-propan-1,3-dione, as an orange solid, mp 103°–104° C., starting from 3-(4-fluorophenyl)-1-(2-nitro-4-trifluoromethylphenyl)-propan-1,3-dione.

2-Ethoxymethylene-1-(2-nitro-4-trifluoromethylphenyl)-pentan-1,3-dione, as a crude brown oil, starting from 1-(2-nitro-4-trifluoromethylphenyl)-pentan-1,3-dione.

1-(4-Chloro-2-nitrophenyl)-2-ethoxymethylenebutan-1,3-dione, as a crude black gum, starting from 1-(4-chloro-2-nitrophenyl)-butan-1,3-dione.

2-Ethoxymethylene-1-(2 nitro-4-trifluoromethylphenyl)-hexan-1,3-dione, as a crude red oil, starting from 1-(2-nitro-4-trifluoromethylphenyl)-hexan-1,3-dione.

3-Cyclopropyl-2-ethoxymethylene-1-(2-nitro-4-trifluoromethylphenyl)-propan-1,3-dione, as a crude orange oil, starting from 3-cyclopropyl-1-(2-nitro-4-trifluoromethylphenyl)-propan-1,3-dione.

1-(2,3-Dichloro-4-methylsulphonylphenyl)-2-ethoxymethylenebutan-1,3-dione as a crude black gum, starting from 1-(2,3-dichloro-4-methylsulphonylphenyl)-butan-1,3-dione.

4,4-Dimethyl-2-ethoxymethylene-1-(2-nitro-4-trifluoromethylphenyl)-pentan-1,3-dione, as a white solid by trituration with petroleum spirit (bp 60°–80° C.) mp 134°–135° C., starting from 4,4-dimethyl-1-(2-nitro-4-trifluoromethylphenyl)-pentan-1,3-dione.

2-Ethoxymethylene-1-(4-methyl-2-nitrophenyl)-butan-1,3-dione as a crude black gum, starting from 1-(4-methyl-2-nitrophenyl)butan-1,3-dione.

1-(2,3-Dichloro-4-methylsulphonylphenyl)-2-ethoxymethylene-4-methylpentan-1,3-dione, as a crude black gum, starting from 1-(2,3-dichloro-4-methylsulphonylphenyl)-4-methylpentan-1,3-dione.

3-Cyclopropyl-1-(2,3-dichloro-4-methylsulphonylphenyl)-2-ethoxymethylene-propan-1,3-dione, as a crude brown gum, starting from 3-cyclopropyl-1-(2,3-dichloro-4-methylsulphonylphenyl)-propan-1,3-dione.

2-Ethoxymethylene-1-(2-nitro-4-trifluoromethylphenyl)-4-phenylbutan-1,3-dione, as an orange solid by trituration with petroleum spirit (bp 60°–80° C.) mp 145°–147° C., starting from 1-(2-nitro-4-trifluoromethylphenyl)-4-phenylbutan-1,3-dione.

1-(2-Chloro 4-trifluoromethylphenyl)-3-cyclopropyl-2-ethoxymethylenepropan-1,3-dione, as a crude brown gum, starting from 1-(2-chloro-4-trifluoromethylphenyl)-3-cyclopropylpropan-1,3-dione.

2-Ethoxymethylene-1-(2-nitro-4-pentafluoroethylphenyl)-butan-1,3-dione, as a crude brown oil, starting from 1-(2-nitro-4-pentafluoroethylphenyl)butan-1,3-dione.

3-Cyclopropyl-1-[4-(1,1-dimethylethyl)-2-nitrophenyl]-2-ethoxymethylenepropan-1,3-dione as a crude red gum, starting from 3-cyclopropyl-1-[4-(1,1-dimethylethyl)-2-nitrophenyl]-propan-1,3-dione.

1-[4-(1,1-dimethylethyl)-2-nitrophenyl]-2-ethoxymethylenebutan-1,3-dione, as a crude red gum, starting from 1-[4-(1,1-dimethylethyl)-2-nitrophenyl]-butan-1,3-dione.

3-Cyclopentyl-2-ethoxymethylene-1-(2-nitro-4-trifluoromethylphenyl)-propan-1,3-dione, as a crude red oil, starting from 3-cyclopentyl-1-(2-nitro-4-trifluoromethylphenyl-propan-1,3-dione.

1-(2,4-Dichlorophenyl)-2-ethoxymethylenebutan-1,3-dione, as a crude brown oil, starting from 1-(2,4-dichlorophenyl)-butan-1,3-dione.

1-(2-Chloro-4-methylsulphonylphenyl)-2-ethoxymethylenebutan-1,3-dione as a crude brown oil, starting from 1-(2-chloro-4-methylsulphonylphenyl)-butan-1,3-dione.

1-(2-Chloro-4-trifluoromethylphenyl)-2-ethoxymethylenebutan-1,3-dione, as a crude red oil, starting from 1-(2-chloro-4-trifluoromethylphenyl)-butan-1,3-dione.

2-Ethoxymethylene-1-(2-trifluoromethylphenyl)-butan-1,3-dione as a crude red oil, starting from 1-(2-trifluoromethylphenyl)-butan-1,3-dione.

1-(2,3-Bis-trifluoromethylphenyl)-2-ethoxymethylenebutan-1,3-dione, as a crude red gum, starting from 1-(2,4-bis-trifluoromethylphenyl)-butan-1,3-dione.

1-(2-Chloro-4-methylsulphonylphenyl)-3-cyclopropyl-2-ethoxymethylenepropan-1,3-dione as a crude golden oil, starting from 1-(2-chloro-4-methylsulphonylphenyl)-3-cyclopropylpropan-1,3-dione.

3-Cyclopropyl-2ethoxymethylene-1-(2-trifluoromethylphenyl)-propan-1,3-dione, as a crude yellow oil starting from 3-cyclopropyl-1-(2-trifluoromethylphenyl)-propan-1,3-dione.

3-Cyclopropyl-1-(2,4-dichlorophenyl)-2-ethoxymethylenepropan-1,3-dione, as a crude brown oil, starting from 3-cyclopropyl-1-(2,4-dichlorophenyl)-propan-1,3-dione.

1-(2,3-Dichloro-4-methylsulphenylphenyl)-2-ethoxymethylenebutan-1,3-dione, as a crude red oil starting from 1-(2,3-dichloro-4-methylsulphenylphenyl)-butan-1,3-dione.

1-(2,4-Bis-trifluoromethylphenyl)-3-cyclopropyl-2-ethoxymethylenepropan-1,3-dione, as a crude yellow gum, starting from 1-(2,4-bis-trifluoromethyl-phenyl)-3-cyclopropylpropan-1,3-dione.

1-(4-Chloro-2-trifluoromethylphenyl)-2-ethoxymethylenebutan-1,3-dione, as a crude black gum, starting from 1-(4-chloro-2-trifluoromethylphenyl)-butan-1,3-dione.

1-(4-Cyano-2-nitrophenyl)-2-ethoxymethylenebutan-1,3-dione, as a crude brown oil, starting from 1-(4-cyano-2-nitrophenyl)-butan-1,3-dione.

2-Ethoxymethylene-3-(2-nitro-4-trifluoromethylphenyl)-3-oxopropionitrile as a crude yellow oil, starting from 3-(2-nitro-4-trifluoromethylphenyl)-3-oxopropionitrile.

1-(4-Chloro-2-trifluoromethylphenyl)-3-cyclopropyl-2-ethoxymethylene-propan-1,3-dione as a crude yellow oil, starting from 1-(4-chloro-2-trifluoromethylphenyl)-3-cyclopropylpropan-1,3-dione.

2-Ethoxymethylene-4-methyl-1-(2-nitro-4-pentafluoroethylphenyl)-pentan-1,3-dione, as a crude red oil, starting from 4-methyl-1-(2-nitro-pentafluoroethylphenyl)-pentan-1,3-dione.

1-(2-Chloro-4-methylsulphonylphenyl)-2-ethoxymethylene-4-methylpentan-1,3-dione, as a crude brown oil, starting from 1-(2-chloro-4-methylsulphonylphenyl)-4-methylpentan-1,3-dione.

3-Cyclopropyl-2-ethoxymethylene-1-(4-fluoro-2-nitrophenyl)-propan-1,3-dione as a crude black oiL starting from 3-cyclopropyl-1-(4-fluoro-2-nitrophenyl)-propan-1,3-dione.

3-Cyclopropyl-2-ethoxymethylene-1-(2-nitro-4-pentafluoroethylphenyl)-propan-1,3-dione, as a crude brown oil, starting from 3-cyclopropyl-1-(2-nitro-4-pentafluoroethylphenyl)-propan-1,3-dione.

3-Cyclobutyl-2-ethoxymethylene-1-(2-nitro-4-trifluoromethylphenyl)-propan-1,3dione, as a crude red oil, starting from 3-cyclobutyl-1-(2-nitro-4-trifluoromethylphenyl)-propan-1,3-dione.

2-Ethoxymethylene-1-(4-fluoro-2-nitrophenyl)-butan-1,3-dione, as a crude black oil, starting from 1-(4-fluoro-2-nitrophenyl)-butan-1,3-dione.

2-Ethoxymethylene-3-(1-methylcyclopropyl)-1-(2-nitro-4-trifluoromethylphenyl)-propan-1,3-dione, as a white solid by trituration with petroleum spirit (bp 60°–80° C.) mp 124°–125° C., starting from 3-(1-methylcyclopropyl)-1-(2-nitro-4-trifluoromethylphenyl)-propan-1,3-dione.

2-Ethoxymethylene-3-(4-nitrophenyl)-1-(2-nitro-4-trifluoromethylphenyl)-propan-1,3-dione, as a crude orange semi-solid, starting from 3-(4-nitrophenyl)-1-(2-nitro-4-trifluoromethylphenyl)-propan-1,3-dione.

2-Ethoxymethylene-3-(4-methoxyphenyl)-1-(2-nitro-4-trifluoromethylphenyl)-propan-1,3-dione, as a crude brown solid, starting from 3-(4-methoxyphenyl)-1-(2-nitro-4-trifluoromethylphenyl)-propan-1,3-dione.

1-(2-Chloro-3-ethoxy-4-methylsulphonylphenyl)-2-ethoxymethylenebutan-1,3-dione, as a crude orange oil, starting from 1-(2-chloro-3-ethoxy-4-methyl-sulphonylphenyl)-butan-1,3-dione.

1-(3-Cyanophenyl)-2-ethoxymethylenebutan-1,3-dione, as a crude black oil, starting from 1-(3-cyanophenyl)-butan-1,3-dione.

3-Cyclopropyl-2-ethoxymethylene-1-(4-methylsulphonyl-2-trifluoromethylphenyl)-propan-1,3-dione, as a crude brown solid, starting from 3-cyclopropyl-1-(4-methylsulphonyl-2-trifluoromethylphenyl)-propan-1,3-dione.

3-Cyclopropyl-2-ethoxymethylene-1-(4-methylsulphonyl-2-nitrophenyl)propan-1,3-dione, as a crude red oil, starting from 3-cyclopropyl-1-(4-methylsulphonyl-2-nitrophenyl)-propan-1,3-dione.

1-(2-Chloro-3-ethoxy-4-methylsulphonylphenyl)-3-cyclopropyl-2-ethoxymethylenepropan-1,3-dione, as a crude red gum, starting from 1-(2-chloro-3-ethoxy-4-methylsulphonylphenyl)-3-cyclopropylpropan-1,3-dione.

1-(2-Chloro-3-ethoxy4-ethylsulphonylphenyl)-2-ethoxymethylenebutan-1,3-dione, as a crude red oil, starting from 1-(2-chloro-3-ethoxy-4-ethylsulphonylphenyl)-butan-1,3-dione.

1-(2-Chloro-3-ethoxy-4-methylsulphonylphenyl)-2-ethoxymethylenemethylpentan-1,3-dione, as a crude red gum starting from 1-(2-chloro-3-ethoxy-4-methylsulphonylphenyl)-4-methylpentan-1,3-dione.

1-(2-Chloro-3-ethoxy-4-ethylsulphonylphenyl)-3-cyclopropyl-2-ethoxymethylenepropan-1,3-dione, as a crude red oil, starting from 1-(2-chloro-3-ethoxy-4-ethylsulphonylphenyl)-3-cyclopropylpropan-1,3-dione.

3-(1-Ethoxycarbonylcyclopropyl)-2-ethoxymethylene-1-(2-nitro-4-trifluoromethylphenyl)-propan-1,3-dione, as a crude brown oil, starting from 3-(1-ethoxycarbonylcyclopropyl)-1-(2-nitro-4-trifluoromethylphenyl)-propan-1,3-dione.

2-Ethoxymethylene-1-(3-methoxycarbonyl-2-methyl-4-methylsulphonylphenyl)-butan-1,3-dione, as a crude brown oil, starting from 1-(3-methoxycarbonyl-2-methyl-4-methylsulphonylphenyl)-butan-1,3-dione.

2-Ethoxymethylene-3-(2-methylcyclopropyl)-1-(2-nitro-4-trifluoromethylphenyl)-propan-1,3-dione, as a crude red oil, starting from 3-(2-methylcyclopropyl)-1-(2-nitro-4-trifluoromethylphenyl)-propan-1,3-dione.

1-(2-Chloro-3-(1-methylethoxy)-4-methylsulphonylphenyl]-2-ethoxymethylenebutan-1,3-dione, as a crude black gum, starting from 1-[2-chloro-3-(1-methylethoxy)-4-methylsulphonylphenyl]-butan-1,3-dione.

2-Ethoxymethylene-1-[2-methyl-3-(1-methylethoxycarbonyl)-4-methylsulphonylphenyl]-butan-1,3-dione, as a crude red oil, starting from 1-[2-methyl-3-(1-methylethoxycarbonyl)-4-methylsulphonylphenyl]-butan-1,3-dione.

3-Cyclopropyl-2-ethoxymethylene-1-[2-methyl-3-(1-methylethoxycarbonyl)-4-methylsulphonylphenyl]-propan-1,3-dione, as a crude orange oil, starting from 3-cyclopropyl-1-[2-methyl-3-(1-methylethoxycarbonyl)-4-methylsulphonylphenyl]-propan-1,3-dione.

Ethyl 2,2-dimethyl-3,5-dioxo-4-ethoxymethylene-5-(2-nitro-4-trifluoro-methylphenyl)-pentanoate, as a crude orange oil, starting from ethyl 2,2-dimethyl-3,5-dioxo-5-(2-nitro-4-trifluoromethylphenyl)-pentanoate.

3-Cyclopropyl-2-ethoxymethylene-1-(2,3,4-trichlorophenyl)-propan-1,3-dione as a crude brown oil, starting from 3-cyclopropyl-1-(2,3,4-trichlorophenyl)-propan-1,3-dione.

In addition, by proceeding in a similar manner, the following compounds were prepared from appropriately substituted starting materials:

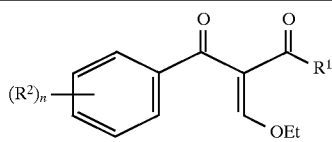

| $R^1$ | $(R^2)_n$ | m.p. |
|---|---|---|
| Cp | 2-$NO_2$-4-$SO_2CF_3$ | — |
| Me | 2-$CH_3$-3-$CO_2CH_3$-4-$SO_2^iPr$ | — |
| Cp | 2,6-$Cl_2$-4-$CF_3$ | — |
| 1-Me—Cp | 2-$NO_2$-4-$SO_2Me$ | — |
| 1-Me—Cp | 2-Cl-4-$SO_2Me$ | — |
| $^iPr$ | 2-$NO_2$-4-Me | — |
| Cp | 2-$NO_2$-4-Me | — |

-continued

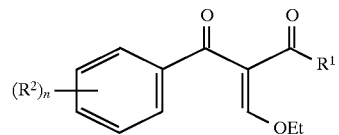

| $R^1$ | $(R^2)_n$ | m.p. |
|---|---|---|
| Cp | 2-Cl-3-OMe-4-$SO_2Me$ | — |
| Me | 2-Cl-4-$NO_2$ | — |
| $^iPr$ | 2-Cl-4-$NO_2$ | — |
| Cp | 2-Cl-4-$NO_2$ | — |
| $^iPr$ | 2-$NO_2$-4-tBu | — |
| $^sBu$ | 2-$NO_2$-4-$CF_3$ | — |
| Cp | 2,6-$Cl_2$ | — |
| $^tBu$ | 2-$NO_2$-4-$SO_2Me$ | 203.5–204.5° C. |
| Cp | 2-$SO_2Me$ | — |
| Cp | 2-Cl-3-CN-4-SMe | — |
| Cp | 2-Me-4-Br | — |
| $^tBu$ | 2-Cl-4-$SO_2Me$ | 180.5–181.5° C. |
| $^sBu$ | 2-Cl-4-$SO_2Me$ | — |
| Cp | 2-$SO_2Me$-4-$NO_2$ | — |
| $^iPr$ | 2-$SO_2Me$-4-$NO_2$ | — |
| Et | 2-Cl-4-$SO_2Me$ | — |
| Cp | 2,6-$Cl_2$-3-$NO_2$ | — |
| Cp | 2-Cl-4-F | — |
| Cp | 2,4-$(SO_2Me)_2$ | — |
| Cp | 2-Cl-4-Br | — |
| $^tBu$ | 2-$CF_3$-4-$SO_2Me$ | 188–189.2° C. |
| Me | 2-$SO_2Me$ | — |
| Me | 2-$CF_3$-4-$SO_2Me$ | — |
| $^iPr$ | 2-$CF_3$-4-$SO_2Me$ | — |
| 1-Me—Cp | 2-$CF_3$-4-$SO_2Me$ | — |
| Cp | 2-Cl-4-$SO_2^iPr$ | — |
| $^iPr$ | 2-$SO_2Me$ | — |
| Cp | 2-SMe | — |
| Cp | 2-Cl-5-$SO_2Me$ | — |
| Cp | 2-Cl-4-$SO_2^tBu$ | — |
| Cp | 2-$CF_3$-4-SMe | — |
| 1-Me—Cp | 2-$SO_2Me$ | — |
| $^sBu$ | 2-$SO_2Me$ | — |
| Cp | 2-$SO_2Et$ | — |
| Cp | 2-Cl-4-SMe | — |
| Cp | 2-$NO_2$-4-SMe | — |
| Cp | 2-$SO_2Me$-5-Cl | — |
| Cp | 2-Cl-4-$SO_2Et$ | — |
| Cp | 2-F-4-$SO_2Me$ | — |
| Cp | 2-$SO_2Me$-5-F | — |
| Cp | 2-$SO_2^iPr$ | — |
| Cp | 2,5-$Cl_2$-4-$SO_2CH_3$ | — |
| Cp | 2-$NO_2$-4-CN | 112–114° C. |
| Cp | 2-$NO_2$-4-Cl | — |
| Cp | 2,4-$Br_2$-3-OMe | — |
| Cp | 2-Br-3-OMe-4-$SO_2Me$ | — |
| Me | 2-Br-3-OMe-4-$SO_2Me$ | — |
| 1-Me—Cp | 2-Br-3-OMe-4-$SO_2Me$ | — |
| $^iPr$ | 2-$NO_2$-4-Cl | — |
| 1-Me—Cp | 2,3-$Cl_2$-4-$SO_2Me$ | 179–180° C. |
| Cp | 2-Cl-4-$OCF_3$ | — |
| Cp | 2,3-$Cl_2$-4-$OCF_3$ | — |
| 1-Me—Cp | 2-Cl-3-OMe-4-$SO_2Me$ | — |
| Cp | 2-$SO_2Me$-3-Cl | — |
| Cp | 2-Br-4-$SO_2Me$ | — |
| 1-Me—Cp | 2-Br-4-$SO_2Me$ | — |
| Me | 2-Cl-3-OMe-4-$SO_2Me$ | — |
| 1-Me—Cp | 2-$CF_3$-4-SEt | — |
| Cp | 2-$CF_3$-4-SEt | — |
| 1-Me—Cp | 2-$CF_3$-4-$SO_2Et$ | — |
| Cp | 2-$SO_2Me$-3-OMe | — |
| 1-Me—Cp | 2-$NO_2$-4-F | — |
| $^iPr$ | 2-$CF_3$-4-SMe | — |
| Cp | 2-$CF_3$-4-$SO_2Et$ | — |
| Cp | 2-$NO_2$-4-Br | — |
| Cp | 2-Br-3-OMe-4-SEt | — |
| Cp | 2-Br-3-$OCHF_2$-4-$SO_2Et$ | — |
| Cp | 2-SMe-4-$SO_2Me$ | — |
| Et | 2-$CF_3$-4-$SO_2Me$ | — |
| Me | 2-$CF_3$-4-$SO_2Me$ | — |

-continued

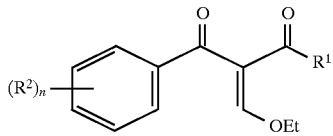

| R¹ | (R²)ₙ | m.p. |
|---|---|---|
| 1-Me—Cp | 2-SMe-4-SO₂Me | — |
| Cp | 2-Br-4-SMe | — |
| Cp | 2-Br-3-OMe-4-SMe | — |
| Cp | 2-F-6-SO₂Me | — |
| Cp | 2,4-(SMe)₂ | — |
| Cp | 2,4-Cl₂-3-CO₂Et | — |
| Cp | 2-SMe-3-Cl-4-OMe | — |
| Cp | 2,4-Cl₂-3-CN | — |
| Cp | 2,4-Cl₂-3-OMe | — |
| 1-Me—Cp | 2-F-4-SO₂Me | — |
| 1-Me—Cp | 2,4-Cl₂-3-CO₂ⁱPr | — |
| ⁱPr | 2-F-4-SO₂Me | — |
| Cp | 2,4-Cl₂-3-CO₂ⁱPr | — |
| Cp | 2-Cl-3-CO₂ⁱPr-4-SMe | — |
| Cp | 2-Cl-3-CO₂ⁱPr-4-SO₂Me | — |
| Cp | 2-SMe-3-CO₂ⁱPr-4-Cl | — |
| Cp | 2-SMe-3-CO₂ⁱPr-4-CF₃ | — |

REFERENCE EXAMPLE 2

A mixture of crude t-butyl 2-(2-nitro-4-trifluoromethylbenzoyl)-3-oxobutanoate (9.1 g) and 4-toluenesulphonic acid (0.1 g) in dry toluene (100 ml) was stirred and heated at reflux for 3 hours. The cooled mixture was extracted with aqueous sodium hydroxide solution (2M, 2×50 ml) and water (2×50 ml). The combined aqueous extracts were acidified to pH 1 and extracted with ether (3×100 ml). The combined organic layers were washed with water (50 ml), dried (anhydrous sodium sulphate) and filtered. The filtrate was evaporated to dryness and the residue was recrystallized from petroleum spirit (bp 60°–80° C.) to give 1-(2-nitro-4-trifluoromethylphenyl)-butan-1,3-dione (4.6 g) as an off white solid mp 80°–81° C.

By proceeding in a similar manner, the following compounds were prepared:

1-(2,4-Dinitrophenyl)-butan,1,3-dione, as a brown solid, NMR (CDCl₃)d 2.2(s,3H), 5.8(s,1H), 7.7(d,1H), 8.4 (dd,1H), 8.65(d,1H), starting from t-butyl 2-(2,4-dinitrobenzoyl)-3-oxobutanoate.

1-(4-Methylsulphonyl-2-nitrophenyl)-butan-1,3-dione, as a light brown solid NMR (DMSO-d⁶) 2.54(s,3H), 3.7 (s,3H), 6.4(s,1H), 8.18(d,1H), 8.58(d,1H), 8.75(s,1H), starting from t-butyl 2-(4-methylsulphonyl-2-nitrophenyl)-3-oxobutanoate.

4-Methyl-1-(2-nitro-4-trifluoromethylphenyl)-pentan-1,3-dione, as an off-white solid by chromatography in a mixture of ethyl acetate and n-hexane (1:3)mp 44°–45° C., starting from t-butyl 4-methyl-2-(2-nitro-4-trifluoromethylphenyl)-3-oxopentanoate.

1-(2-Nitro-4-trifluoromethylphenyl)-pentan-1,3-dione as an off-white solid by chromatography in a mixture of ethyl acetate and n-hexane (1:5)mp 45°–46° C., starting from t-butyl 2-(2-nitro-4-trifluoromethylbenzoyl)-3-oxopentanoate.

1-(4-Chloro-2-nitrophenyl)-butan-1,3-dione, as a light brown solid, NMR (CDCl₃) 2.1(s,3H), 5.68(s,1H), 7.2–7.8(m,3H) starting from t-butyl 2-(4-Chloro-2-nitrobenzoyl)-3-oxobutanoate.

1-(2-Nitro-4-trifluoromethylphenyl)-hexan-1,3-dione as an orange oil NMR (CDCl₃) 0.95(t,3H), 1.6(m,2H), 2.3(t,2H), 5.7(s,1H), 7.55(d,1H), 7.8 (d,1H) 8.0(s,1H), 15.2(bs,1H) starting from t-butyl 2-(2-nitro-4-trifluoromethylbenzoyl)-3-oxohexanoate.

3-Cyclopropyl-1-(2-nitro-4-trifluoromethylphenyl)-propan-1,3-dione, as an off-white solid, mp 95°–96° C. starting from t-butyl 3-cyclopropyl-2-(2-nitro-4-trifluoromethylbenzoyl)-3-oxopropionate.

1-(2,3-Dichloro-4-methylsulphonylphenyl)-butan-1,3-dione as a light brown solid, mp 135°–136° C. starting from t-butyl 2-(2,3-dichloro-4-methylsulphonyl-benzoyl)-3-oxobutanoate.

4,4-Dimethyl-1-(2-nitro-4-trifluoromethylphenyl)-pentan-1,3-dione, as a buff solid, mp 60°–61° C., starting from t-butyl 4,4-dimethyl-2-(2-nitro-4-trifluoromethylbenzoyl)-3-oxopentanoate.

1-(4-Methyl-2-nitrophenyl)-butan-1,3-dione, as an orange solid, mp 68°–69° C. starting from t-butyl 2-(4-methyl-2-nitrobenzoyl)-3-oxobutanoate.

1-(2,3-Dichloro-4-methylsulphonylphenyl)-4-methylpentan-1,3-dione as a white solid, mp 120°–121° C., starting from t-butyl 2-(2,3-dichloro-4-methylsulphonylbenzoyl)-4-methyl-3-oxopentanoate.

3-Cyclopropyl-1-(2,3-dichloro-4-methylsulphonylphenyl)-propan-1,3-dione, as an off white solid, mp 132°–134° C. starting from t-butyl 3-cyclopropyl-2-(2,3-dichloro-4-methylsulphonylbenzoyl)-3-oxopropionate.

1-(2-Nitro-4-trifluoromethylphenyl)-4-phenylbutan-1,3-dione as a brown oil NMR (CDCl₃) 3.7(s,2H), 5.7(s, 1H), 7.2(s,5H), 7.45(d,1H), 7.75(d,1H), 8.0(s,1H), 12.4–12.9(bs,1H) starting from t-butyl 2-(2-nitro-4-trifluoromethylbenzoyl)-3-oxo-4-phenylbutanoate.

1-(2-Chloro-4-trifluoromethylphenyl)-3-cyclopropylpropan-1,3-dione as a crude brown oil which was not further purified, starting from t-butyl 2-(2-chloro-4-trifluoromethylbenzoyl)-3-cyclopropyl-3-oxopropionate.

1-(2-Nitro-4-pentafluoroethylphenyl)-butan-1,3-dione as an off-white solid, mp 103°–104.8° C., starting from t-butyl 2-(2-nitro-4-pentafluorobenzoyl)-3-oxobutanoate.

3-Cyclopropyl-1-[4-(1,1-dimethylethyl)-2-nitrophenyl]-propan-1,3-dione as a crude brown solid which was not further purified, starting from t-butyl 3-cyclopropyl 2-[4-(1,1-dimethylethyl)-2-nitrobenzoyl]-3-oxopropionate.

1-[4-(1,1-dimethylethyl)-2-nitrophenyl]-butan-1,3-dione, as a yellow gum NMR (CDCl₃) 1.4(s,9H), 2.1(s,3H), 5.7(s,1H), 7.3(d,1H), 7.55(dd,1H), 7.75(d,1H) starting from t-butyl 2-[4-(1,1-dimethylethyl)-2-nitrobenzoyl]-3-oxobutanoate.

3-Cyclopentyl-1-(2-nitro-4-trifluoromethylphenyl)-propan-1,3-dione, as an off-white solid, mp 64°–65° C. starting from t-butyl 3-cyclopentyl-2-(2-nitro-4-trifluoromethylbenzoyl)-3-oxopropionate.

1-(2-Chloro-4-methylsulphonylphenyl)-butan-1,3-dione as a cream solid, mp 125.8° C., starting from t-butyl 2-(2-chloro-4-methylsulphonylbenzoyl)-3-oxobutanoate.

1-(2-Chloro-4-trifluoromethylphenyl)-butan-1,3-dione, as a yellow-gum, NMR (CDCl₃) 2.2(s,3H), 5.9(s,1H), 7.3–7.7(m,3H) starting from t-butyl 2-(2-chloro-4-trifluoromethylbenzoyl)-3-oxobutanoate.

1-(2-Trifluoromethylphenyl)-butan-1,3-dione, as a yellow oil NMR (CDCl₃) 2.15(s,3H), 5.7(s,1H), 7.6–8.4(m, 4H), starting from t-butyl 3-oxo-(2-trifluoromethylbenzoyl)-butanoate.

1-(2,4-Bis-trifluoromethylphenyl)-butan-1,3-dione as a yellow solid, mp 39.6° C., starting from t-butyl 2-(2,4-bis-trifluoromethylbenzoyl)-3-oxobutanoate.

1-(2-Chloro-4-methylsulphonylphenyl)-3-cyclopropylpropan-1,3-dione, as an off-white solid, mp 93.1° C., starting from t-butyl 2-(2-chloro-4-methylsulphonylbenzoyl)-3-cyclopropyl-3-oxopropionate.

3-Cyclopropyl-1-(2-trifluoromethylphenyl)-propan-1,3-dione as an orange oil NMR (CDCl$_3$) 0.8–1.4(m,4H), 1.5–1.9(m,1H), 5.8(s,1H), 8.0–8.6(m,4H) starting from t-butyl 3-cyclopropyl-3-oxo-2-(2-trifluoromethylbenzoyl)-propionate.

3-Cyclopropyl-1-(2,4-dichlorophenyl)-propan-1,3-dione as an off-white solid by recrystallization from cyclohexane mp 62.3° C. starting from t-butyl 3-cyclopropyl-2-(2,4-dichlorobenzoyl)-3-oxopropionate.

1-(2,3-Dichloro-4-methylthiophenyl)-butan-1,3dione as a brown solid mp 103.5° C., starting from t-butyl 2-(2,3-dichloro-4-methylthio-benzoyl)-3-oxobutanoate.

1-(2,4-Bis-trifluoromethylphenyl)-3-cyclopropylpropan-1,3-dione as a white solid, mp 40° C., starting from t-butyl 2-4-bis-trifluoromethylbenzoyl)-3-cyclopropyl-3-oxopropionate.

1-(4-Chloro-2-trifluoromethylphenyl)-butan-1,3-dione as a crude yellow gum which was not further purified, starting from t-butyl 2-(4-chloro-2-trifluoromethylbenzoyl)-3-oxobutanoate.

1-(4-Cyano-2-nitrophenyl)-butan-1,3-dione as an off-white solid by chromatography in a mixture of ethyl acetate and n-hexane (1:1) NMR (CDCl$_3$) 2.1(s,3H), 5.7(s,1H), 7.6(d,1H), 7.9(d,1H), 8.15(s,1H), 14.6–15.1 (bs,1H), starting from t-butyl 2-(4-cyano-2-nitrobenzoyl)-3-oxobutanoate.

1-(4-Chloro-2-trifluoromethylphenyl)-3-cyclopropylpropan-1,3-dione as a crude yellow gum which was not further purified, starting from t-butyl 2-(4-chloro-2-trifluoromethylbenzoyl)-3-cyclopropyl-3-oxopropionate.

4-Methyl-1-(2-nitro-4-pentafluoroethylphenyl)-pentan-1,3-dione as a crude oil which was not further purified, starting from t-butyl 4-methyl-2-(2-nitro-4-pentafluoroethylbenzoyl)-3-oxopentoate.

1-(2-Chloro-4-methylsulphonylphenyl)-4-methylpentan-1,3-dione as a yellow oil NMR (CDCl$_3$) 1.15(d,6H), 2.3–2.8(m,1H), 3.0(s,3H), 5.9(s,1H), 6.7(m,2H), 6.85 (s,1H) starting from t-butyl 2-(2-chloro-4-methylsulphonylbenzoyl)-4-methyl-3-oxopentanoate.

3-Cyclopropyl-1-(4-fluoro-2-nitrophenyl)-propan-1,3-dione as a brown solid, mp 75.1° C., starting from t-butyl 3-cyclopropyl-2-(4-fluoro-2-nitrobenzoyl)-3-oxopropionate.

3-Cyclopropyl-1-(2-nitropentafluoroethylphenyl)-propan-1,3-dione as a crude brown solid which was not further purified, starting from t-butyl 3-cyclopropyl-2-(2-nitro-4-pentafluoroethylbenzoyl)-3-oxopropionate.

3-Cyclobutyl-1-(2-nitro-4-trifluoromethylphenyl)-propan-1,3-dione as a crude orange oil which was not further purified, starting from t-butyl 3-cyclobutyl-2-(2-nitro-4-trifluoromethylbenzoyl)-3-oxopropionate.

1-(4-Fluoro-2-nitrophenyl)-butan-1,3-dione, as a tan solid, mp 98.0° C. starting from t-butyl 2-(4-fluoro-2-nitrobenzoyl)-3-oxobutanoate.

3-(1-Methylcyclopropyl)-1-(2-nitro-4-trifluoromethylphenyl)-propan-1,3-dione as an off-white solid, mp 124.5°–125° C., starting from t-butyl 3-(1-methylcyclopropyl)-2-(2-nitro-4-trifluoromethylbenzoyl)-3-oxopropionate.

1-(2-Chloro-3-ethoxy-4-methylsulphonylphenyl)-butan-1,3-dione, as a light brown solid, mp 120°–122° C., starting from t-butyl 2-(2-chloro-3-ethoxy-4-methylsulphonylbenzoyl)-3-oxobutanoate.

1-(3-Cyanophenyl)-butan-1,3-dione as an off-white solid, mp 72.8° C., starting from t-butyl 2-(3-cyanobenzoyl)-3-oxobutanoate.

3-Cyclopropyl-1-(4-methylsulphonyl-2-trifluoromethylphenyl)-propan-1,3-dione, as a crude brown solid which was not further purified, starting from t-butyl 3-cyclopropyl-2-(4-methylsulphonyl-2-trifluoromethylbenzoyl)-3-oxopropionate.

3-Cyclopropyl-1-(4-methylsulphonyl-2-nitrophenyl)-propan-1,3-dione, as a cream solid, mp 179.6°–181.6° C., starting from t-butyl 3-cyclopropyl-2-(4-methylsulphonyl-2-nitrobenzoyl)-3-oxopropionate.

1-(2-Chloro-3-ethoxy-4-methylsulphonylphenyl)-3-cyclopropylpropan-1,3-dione as an orange gum, NMR (CDCl$_3$) 1.25(m,4H), 1.6(m,4H), 3.3(s,3H), 4.35(q, 2H), 6.05(s, 1H), 7.4(d,1H), 7.9(d,1H), 14.5–15.5(bs, 1H) starting from t-butyl 2-(2-chloro-3-ethoxy-4-methylsulphonylbenzoyl)-3-cyclopropyl-3-oxopropionate.

1-(2-Chloro-3-ethoxy-4-ethylsulphonylphenyl)-butan-1,3-dione, as a yellow oil NMR (CDCl$_3$) 1.2–1.9(m,6H), 2.3(s,3H), 3.55(q,2H), 4.4(q,2H), 6.0(s,1H), 7.45(d, 1H), 7.95(d,1H), starting from t-butyl 2-(2-chloro-3-ethoxy-4-ethylsulphonylbenzoyl)-3-oxobutanoate.

1-(2-Chloro-3-ethoxy-4-methylsulphonylphenyl)-4-methylpentan-1,3-dione, as a yellow gum, NMR (CDCl$_3$) 1.1(d,6H), 1.5(t,3H), 2.4(m,1H), 3.2(s,3H), 4.2(q,2H), 5.35(s,1H), 7.25(d,1H), 7.65(d, 1H), starting from t-butyl 2-(2-chloro-3-ethoxy-4-methylsulphonylbenzoyl)-4-methyl-3-oxopentanoate.

1-(2-Chloro-3-ethoxy-4-ethylsulphonylphenyl)-3-cyclopropylpropan-1,3-dione as a yellow oil NMR (CDCl$_3$) 1.2–2.3 (m,11H), 3.75(q,2H), 4.6(q,2H), 6.3 (s,1H), 7.7(d,1H), 8.2(d,1H) starting from t-butyl 2-(2-chloro-3-ethoxy-4-ethylsulphonylbenzoyl)-3-cyclopropyl-3-oxopropionate.

3-(1-Ethoxycarbonylcyclopropyl)-1-(2-nitro-4-trifluoromethylphenyl)propan-1,3-dione, as a white solid by chromatography in a mixture of ethyl acetate, n-hexane and acetic acid (20:80:1) NMR (CDCl$_3$) 1.25(t,3H), 1.7(m,4H), 4.1(q,2H), 6.6(s,1H), 7.7(m, 2H), 8.0(s,1H), 14.2–15.0(bs,1H), starting from t-butyl 3-(1-ethoxycarbonylcyclopropyl)-2-(2-nitro-4-trifluoromethylbenzoyl)-3-oxopropionate.

1-(3-Methoxycarbonyl-2-methyl-4-methylsulphonylphenyl)-butan-1,3-dione, as an orange oil, NMR (CDCl$_3$) 2.15(s,3H), 2.4(s,3H), 3.1(s,3H), 3.9(s,3H), 5.7(s,1H), 7.45(d,1H), 7.45(d,1H), 7.8(d, 1H), starting from t-butyl 2-(3-methoxycarbonyl-2-methyl-4-methylsulphonylbenzoyl)-3-oxobutanoate.

3-(2-methylcyclopropyl)-1-(2-nitro-4-trifluoromethylphenyl)-propan-1,3-dione as a white solid, mp 70.4°–72.6° C., starting from t-butyl 3-(2-methylcyclopropyl)-2-(nitro-4-trifluoromethylbenzoyl)-3-oxopropionate.

1-[2-Chloro-3-(1-methylethoxy)-4-methylsulphonylphenyl]-butan-1,3-dione as a white solid, NMR (CDCl$_3$) 1.4(d,6H), 2.2(s,3H), 3.2(s,3H), 5.2(m,1H), 5.8(s,1H), 7.2(d,1H), 8.2(d,1H) starting from t-butyl 2-[2-chloro-3-(1-methylethoxy)-4-methylsulphonylbenzoyl]-3-oxobutanoate.

1-[2-Methyl-3-(1-methylethoxycarbonyl)-4-methylsulphonylphenyl]-butan-1,3-dione as an orange oil NMR (CDCl$_3$) 1.65(d,6H), 2.4(s,3H), 2.7(s,3H), 3.4(s,3H), 5.5(m,1H), 5.9(s,1H), 7.65(d,1H), 8.05(d, 1H), starting from t-butyl 2-[2-methyl-3-(1-methylethoxycarbonyl)-4-methylsulphonylbenzoyl]-3-oxobutanoate.

3-Cyclopropyl-1-[2-methyl-3-(1-methylethoxycarbonyl)-4-methylsulphonylphenyl]-propan-1,3-dione as an orange oil NMR (CDCl$_3$) 1.4(m,5H), 1.65(d,6H), 2.7(s,3H), 3.4(s,3H), 5.5(m,1H), 6.0(s,1H), 7.65(d,1H), 8.0(d,1H), starting from t-butyl 3-cyclopropyl-2-[2-methyl-3-(1-methylethoxycarbonyl)-4-methylsulphonylbenzoyl]-3-(1-methylethoxycarbonyl)-4-methylsulphonylbenzoyl]-3-oxopropionate.

Ethyl 2.2-dimethyl-3,5-dioxo-5-(2-nitro-4-trifluoromethylphenyl)-pentanoate as an orange oil NMR (CDCl$_3$) 1.25(t,3H), 1.5(s,6H), 4.1(q,2H), 5.8(s, 1H), 7.55(d,1H), 7.8(d,1H), 8.05(s,1H) starting from t-butyl 4-ethoxycarbonylmethyl-2-(2-nitro-4-trifluoromethylbenzoyl)-3-oxopentanoate.

3-Cyclopropyl-1-(2,3,4-trichlorophenyl)-propan-1,3-dione as a dark brown oil, NMR (CDCl$_3$) 1.2(m,4H), 1.8(s,1H), 5.95(s,1H), 7.3(s,2H), 14.6–15.5(bs,1H) starting from t-butyl 3-cyclopropyl-3-oxo-2-(2,3,4-trichlorophenyl)-propionate.

In addition, by proceeding in a similar manner the following compounds were prepared from the appropriately substituted starting materials:

| R$^1$ | (R$^2$)$_n$ | mp/NMR |
|---|---|---|
| Me | 2-Me-3-CO$_2$Me-4-SO$_2$$^i$Pr | 1.2(6H, d) 2.2(3H, s) 2.4(3H, s) 3.4(1H, m) 3.9(3H, s) 5.7(1H, s) 7.4(1H, d) 7.7(1H, d) |
| Cp | 2-NO$_2$-4-SO$_2$CF$_3$ | Not characterized |
| Cp | 2,6-Cl$_2$-4-CF$_3$ | 1.2(4H, m) 1.7(1H, m) 5.75(1H, s) 7.6(2H, s) 13.5(1H, bs) |
| 1-Me-Cp | 2-NO$_2$-4-SO$_2$Me | 105–106° C. |
| 1-Me-Cp | 2-Cl-4-SO$_2$Me | 0.9(2H, m) 1.4(2H, m) 1.4(3H, s) 3.05(3H, s) 6.0(1H, s) 7.7–7.9(3H, m) |
| $^i$Pr | 2-NO$_2$-4-Me | 1.3(6H, d) 2.7(1H, m) 2.8(3H, s) 5.75(1H, s) 7.35(2H, s) 7.5(1H, s) |
| Cp | 2-NO$_2$-4-Me | 1.1(4H, m) 1.7(1H, m) 2.5(3H, s) 6.65(1H, s) 8.5(2H, s) 8.7(1H, s) |
| Cp | 2-Cl-3-OMe-4-SO$_2$Me | Not characterized |
| Me | 2-Cl-4-NO$_2$ | 76.4–77.2° C. |
| $^i$Pr | 2-Cl-4-NO$_2$ | 1.7(6H, d) 3.0(1H, m) 6.5(1H, s) 8.1(1H, m) 8.6(2H, m) |
| Cp | 2-Cl-4-NO$_2$ | 1.3(4H, m) 2.0(1H, m) 6.1(1H, s) 7.7(1H, m) 8.1(2H, m) |
| $^i$Pr | 2-NO$_2$-4-$^t$Bu | 1.2(6H, d) 1.4(9H, s) 2.5(1H, m) 5.7(1H, s) 7.4(3H, m) |

-continued

| R$^1$ | (R$^2$)$_n$ | mp/NMR |
|---|---|---|
| $^s$Bu | 2-NO$_2$-4-CF$_3$ | 1.0(8H, m) 2.0(1H, m) 5.5(1H, s) 7.5(2H, m) 7.9(1H, s) |
| Cp | 2,6-Cl$_2$ | 1.2(4H, m) 1.7(1H, m) 5.63(1H, s) 7.18(3H, s) |
| $^t$Bu | 2-NO$_2$-4-SO$_2$Me | 140.4–141.4° C. |
| Cp | 2-SO$_2$Me | 94.0–94.8° C. |
| Cp | 2-Cl-3-CN-4-SMe | 212.2–213.0° C. |
| Cp | 2-Me-4-Br | Not characterized |
| $^t$Bu | 2-Cl-4-SO$_2$Me | 1.3(9H, s) 3.0(3H, s) 6.05(1H, s) 7.7(2H, m) 7.8(1H, s) |
| $^s$Bu | 2-Cl-4-SO$_2$Me | 1.0(8H, m) 1.7(1H, m) 3.05(3H, s) 5.9(1H, s) 7.75(3H, m) |
| Cp | 2-SO$_2$Me-4-NO$_2$ | 1.3(4H, m) 2.8(1H, m) 3.65(3H, s) 6.1(1H, s) 8.0(1H, m) 8.7(2H, m) |
| $^i$Pr | 2-SO$_2$Me-4-NO$_2$ | 1.35(6H, d) 2.7(1H, m) 3.5(3H, s) 5.9(1H, s) 7.7(1H, d) 8.5(1H, dd) 9.0(1H, d) |
| Et | 2-Cl-4-SO$_2$Me | 1.2(3H, t) 2.4(2H, q) 3.05(3H, s) 5.9(1H, s) 7.8(3H, m) |
| Cp | 2,6-Cl$_2$-3-NO$_2$ | 1.2(4H, m) 1.8(1H, m) 5.7(1H, s) 7.5(2H, m) |
| Cp | 2-Cl-4-F | Not characterized |
| Cp | 2,4-(SO$_2$Me)$_2$ | 1.4(4H, m) 2.3(1H, m) 3.6(3H, s) 3.7(3H, s) 6.4(1H, s) 8.6(3H, m) |
| Cp | 2-Cl-4-Br | 1.1(4H, m) 1.2(1H, m) 6.0(1H, s) 7.0(1H, s) 7.35(2H, m) |
| $^t$Bu | 2-CF$_3$-4-SO$_2$Me | 1.0(9H, s) 4.0(3H, s) 6.8(1H, s) 8.5(1H, m) 9.0(2H, s) |
| Me | 2-SO$_2$Me | 2.4(3H, s) 3.6(3H, s) 6.15(1H, s) 7.9(4H, m) |
| Me | 2-CF$_3$-4-SO$_2$Me | 2.6(3H, s) 3.1(3H, s) 5.8(1H, s) 7.2(1H, d) 8.0(1H, dd) 8.2(1H, d) |
| $^i$Pr | 2-CF$_3$-4-SO$_2$Me | Not characterized |
| 1-Me-Cp | 2-CF$_3$-4-SO$_2$Me | 0.8(2H, m) 1.2(2H, m) 1.3(3H, s) 3.0(3H, s) 5.7(1H, s) 7.5(1H, m) 8.0(2H, m) |
| Cp | 2-Cl-2-SO$_2$$^i$Pr | Not characterized |
| $^i$Pr | 2-SO$_2$Me | 1.5(6H, d) 2.5(1H, m) 3.7(3H, s) 6.2(1H, s) 8.0(4H, m) |
| Cp | 2-SMe | Not characterized |
| Cp | 2-Cl-5-SO$_2$Me | 1.1(4H, m) 1.6(1H, m) 3.3(3H, s) 5.8(1H, s) 7.4(2H, m) 7.9(1H, m) |
| Cp | 2-Cl-4-SO$_2$$^t$Bu | 1.1(4H, m) 1.4(9H, s) 2.0(1H, m) 6.0(1H, s) 8.7(3H, m) |
| Cp | 2-CF$_3$-4-SMe | 68–69° C. |
| 1-Me-Cp | 2-SO$_2$Me | 1.3(2H, m) 1.8(3H, s) 1.85(2H, m) 3.8(3H, s) 6.3(1H, s) 7.5(1H, m) 7.9(2H, m) 8.3(1H, m) |
| $^s$Bu | 2-SO$_2$Me | 1.3(8H, m) 1.9(1H, m) 3.6(3H, s) 6.0(1H, s) 7.7(3H, m) 8.2(1H, m) |
| Cp | 2-SO$_2$Et | 1.3(4H, m) 1.5(3H, t) 1.9(1H, m) 3.7(2H, q) 6.05(1H, s) 7.7(3H, m) 8.1(1H, m) |
| Cp | 2-Cl-4-SMe | 1.0(4H, m) 1.8(1H, m) 2.4(3H, s) 6.1(1H, s) 6.9(1H, m) 7.4(2H, m) 15.0(1H, bs) |

-continued

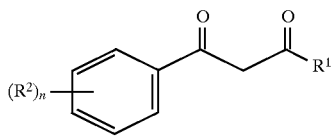

| R¹ | (R²)ₙ | mp/NMR |
|---|---|---|
| Cp | 2-NO₂-4-SMe | 98.0–98.6° C. |
| Cp | 2-SO₂Me-5-Cl | 117–121° C. |
| Cp | 2-Cl-4-SO₂Et | 2.1(7H, m) 2.75(1H, m) 3.1(2H, q) 6.0(1H, s) 7.7(3H, m) |
| Cp | 2-F-4-SO₂Me | Not characterized |
| Cp | 2-SO₂Me-5-F | 149–151° C. |
| Cp | 2-SO₂ⁱPr | 140–140.6° C. |
| Cp | 2,5-Cl₂-4-SO₂CH₃ | 145–147° C. |
| Cp | 2-NO₂-4-CN | 151–152° C. |
| Cp | 2-NO₂-4-Cl | 93–94° C. |
| Cp | 2,4-Br₂-3-OMe | 67–68° C. |
| Cp | 2-Br-3-OMe-4-SO₂Me | 1.1(4H, m) 1.6(1H, m) 3.2(3H, s) 4.0(3H, s) 5.8(1H, s) 7.15(1H, d) 7.75(1H, d) |
| Me | 2-Br-3-OMe-4-SO₂Me | 1.6(3H, s) 2.7(3H, s) 3.6(3H, s) 5.4(1H, s) 6.9(1H, d) 7.6(1H, d) |
| 1-Me-Cp | 2-Br-3-OMe-4-SO₂Me | 0.4(2H, m) 0.8(2H, m) 0.85(3H, s) 2.8(3H, s) 3.7(3H, s) 5.6(1H, s) 7.0(1H, d) 7.7(1H, d) |
| ⁱPr | 2-NO₂-4-Cl | Not characterized |
| 1-Me-Cp | 2,3-Cl₂-4-SO₂Me | 141–144° C. |
| Cp | 2-Cl-4-OCF₃ | Not characterized |
| Cp | 2,3-Cl₂-4-OCF₃ | 1.1(4H, m) 1.7(1H, m) 5.8(1H, s) 7.2(2H, m) |
| 1-Me-Cp | 2-Cl-3-OMe-4-SO₂Me | 124–125° C. |
| Cp | 2-SO₂Me-3-Cl | 211–213° C. |
| Cp | 2-Br-4-SO₂Me | 108.4–109.4° C. |
| 1-Me-Cp | 2-Br-4-SO₂Me | 0.9(2H, m) 1.3(2H, m) 1.4(3H, s) 3.1(3H, s) 5.9(1H, s) 7.7(2H, m) 8.1(1H, m) |
| Me | 2-Cl-3-OMe-4-SO₂Me | 162–163° C. |
| Cp | 2-CF₃-4-SEt | 0.8(4H, m) 1.3(3H, t) 1.7(1H, m) 3.0(2H, q) 5.7(1H, s) 6.4(3H, m) |
| 1-Me-Cp | 2-CF₃-4-SEt | 1.2(2H, m) 1.4(5H, m) 1.5(3H, s) 3.0(2H, q) 5.75(1H, s) |
| 1-Me-Cp | 2-CF₃-4-SO₂Et | 0.8(2H, m) 1.3(5H, m) 1.3(3H, s) 3.1(2H, q) 5.7(1H, s) 7.6(1H, m) 8.0(2H, m) 7.3(2H, s) 7.4(1H, s) |
| Cp | 2-SO₂Me-4-OMe | Not characterized |
| 1-Me-Cp | 2-NO₂-4-F | 112–114° C. |
| ⁱPr | 2-CF₃-4-SMe | 1.3(6H, d) 1.6(1H, m) 2.6(3H, s) 5.9(1H, s) 7.6(3H, m) |
| Cp | 2-CF₃-4-SO₂Et | 1.1(4H, m) 1.3(3H, t) 1.8(1H, m) 3.1(2H, q) 5.8(1H, s) 7.6(1H, m) 8.0(2H, m) |
| Cp | 2-NO₂-4-Br | 105–106° C. |
| Cp | 2-Br-3-OMe-4-SEt | 1.1(4H, m) 1.25(3H, t) 1.7(1H, m) 2.1(2H, q) 3.8(3H, s) 5.53(1H, s) 7.1(2H, s) |
| Cp | 2-Br-3-OCHF₂-4-SO₂Et | 1.1(4H, m) 1.2(3H, t) 1.6(1H, m) 1.3(2H, q) 5.8(1H, s) 7.0(1H, t) 7.3(1H, d) 7.8(1H, d) |
| Cp | 2-SMe-4-SO₂Me | 80.0–81.6° C. |
| Et | 2-CF₃-4-SO₂Me | 1.2(3H, t) 2.4(2H, q) 3.1(3H, s) 5.7(1H, s) 7.6(1H, m) 8.05(2H, m) |
| Me | 2-CF₃-4-SO₂Me | 2.1(3H, s) 2.5(3H, s) 5.7(1H, s) 7.2(3H, m) |

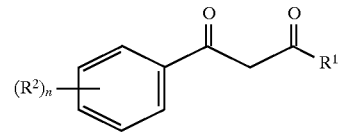

| R¹ | (R²)ₙ | mp/NMR |
|---|---|---|
| 1-Me-Cp | 2-SMe-4-SO₂Me | 0.8(2H, m) 1.2(2H, m) 1.3(3H, s) 2.6(3H, s) 3.0(3H, s) 6.1(1H, s) 8.0(3H, m) |
| Cp | 2-Br-4-SMe | 1.2(4H, m) 1.8(1H, m) 2.5(3H, s) 6.0(1H, s) 7.2(3H, m) |
| Cp | 2-Br-3-OMe-4-SMe | 1.2(4H, m) 1.7(1H, m) 2.4(3H, s) 3.8(3H, s) 5.9(1H, s) 7.0(2H, m) |
| Cp | 2-SO₂Me-6-F | 1.1(4H, m) 1.6(1H, m) 3.2(3H, s) 5.8(1H, s) 7.5.(3H, m) |
| Cp | 2,4-(SMe)₂ | 1.3(4H, m) 2.0(1H, m) 2.75(3H, s) 2.8(3H, s) 6.2(1H, s) 7.2(2H, m) 7.7(1H, m) |
| Cp | 2,4-Cl₂-3-CO₂Et | 1.1(4H, m) 1.4(3H, t) 1.7(1H, m) 4.3(2H, q) 5.9(1H, s) 7.2(2H, m) |
| Cp | 2-SMe-3-Cl-4-OMe | 45.8–47.3° C. |
| Cp | 2,4-Cl₂-3-CN | 1.0(4H, m) 1.6(1H, m) 6.0(1H, s) 7.5(2H, m) |
| Cp | 2,4-Cl₂-3-OMe | 1.0(4H, m) 1.7(1H, m) 3.8(3H, s) 5.9(1H, s) 7.1(2H, m) |
| 1-Me-Cp | 2-F-4-SO₂Me | 130.8–132.6° C. |
| 1-Me-Cp | 2,4-Cl₂-3-CO₂ⁱPr | 0.8(2H, m) 1.3(3H, s) 1.4(8H, m) 5.2(1H, m) 5.9(1H, s) 7.2(2H, m) |
| ⁱPr | 2-F-4-SO₂Me | 119–120° C. |
| Cp | 2,4-Cl₂-3-CO₂ⁱPr | 1.1(4H, m) 1.4(6H, d) 1.8(1H, m) 5.2(1H, m) 6.0(1H, m) 7.3(2H, m) |
| Cp | 2-Cl-3-CO₂ⁱPr-4-SMe | 1.0(2H, m) 1.2(2H, m) 1.4(6H, d) 1.7(1H, m) 2.5(3H, s) 5.3(1H, m) 6.1(1H, s) 7.2(1H, d) 7.6(1H, d) |
| Cp | 2-Cl-3-CO₂ⁱPr-4-SO₂Me | 1.0(2H, m) 1.2(2H, m) 1.4(6H, d) 1.7(1H, m) 3.1(3H, s) 5.3(1H, m) 6.0(1H, s) 7.7(1H, d) 8.0(1H, d) |
| Cp | 2-SMe-3-CO₂ⁱPr-Cl | 1.0(2H, m) 1.2(2H, m) 1.4(6H, d) 1.75(1H, m) 2.4(3H, s) 5.4(1H, m) 6.1(1H, s) 7.4–7.55(2H, m) |
| Cp | 2-SMe-3-CO₂ⁱPr-4-CF₃ | 1.0(2H, m) 1.2(2H, m) 1.35(6H, d) 1.7(1H, m) 2.35(3H, s) 5.3(1H, m) 6.0(1H, s) 7.5(1H, d) 7.65(1H, d) |

REFERENCE EXAMPLE 3

A mixture of magnesium turnings (4.8 g) and carbon tetrachloride (2 ml) in pure ethanol (30 ml) was stirred and warmed gently to 50° C. until the reaction was initiated (effervescence observed). Ether (100 ml) was added cautiously with stirring. A solution of t-butyl 3-oxobutanoate (31.6 g) in ether (100 ml) was added dropwise at such a rate as to maintain the mixture at reflux. Stirring and heating at reflux was continued for 2 hours. A solution of 2-nitro-4-trifluoromethylbenzoyl chloride (50.7 g) in ether (100 ml) was added dropwise and the resultant solution was stirred and heated at reflux for 25 hours. The cooled reaction mixture was treated with hydrochloric acid (2M, 100 ml) with stirring and the two layers were separated. The organic phase was extracted with aqueous sodium hydroxide solution (2M, 2×50 ml) and water (4×50 ml). The combined aqueous layers were acidified to pH 1 and extracted with ether (2×100 ml). The combined organic layers were washed with water (50 ml), dried (anhydrous sodium sulphate) and filtered. The filtrate was evaporated to dryness to give t-butyl 2-(2-nitro-4-trifluoromethylbenzoyl)-3-oxobutanoate (62.2 g) as a crude red oil which was not further purified.

By proceeding in a similar manner, the following compounds were prepared:

t-butyl 4-methyl-2-(2-nitro-4-trifluoromethylbenzoyl)-3-oxopentanoate as a crude orange oil, starting from t-butyl 4-methyl-3-oxopentanoate.

t-butyl 2-(2-nitro-4-trifluoromethylbenzoyl)-3-oxopentanoate as a crude orange oil, starting from t-butyl 3-oxopentanoate.

t-butyl 2-(2-nitro-4-trifluoromethylbenzoyl)-3-oxohexanoate as a crude orange oil, starting from t-butyl 3-oxohexanoate.

t-butyl 3-cyclopropyl-2-(2-nitro-4-trifluoromethylbenzoyl)-3-oxopropionate as a crude orange oil, starting from t-butyl 3-cyclopropyl-3-oxopropionate.

t-butyl 4,4-dimethyl-2-(2-nitro-4-trifluoromethylbenzoyl)-3-oxopentanoate, as a crude orange oil, starting from t-butyl 4,4-dimethyl-3-oxopentanoate.

t-butyl 2-(2-nitro-4-trifluoromethylbenzoyl)-3-oxo-4-phenylbutanoate as a crude orange oil, starting from t-butyl 3-oxo-4-phenylbutanoate.

t-butyl 2-(2-nitro-4-pentafluoroethylbenzoyl)-3-oxobutanoate as a crude brown oil, starting from t-butyl 3-oxobutanoate and 2-nitro-4-pentafluoroethylbenzoyl chloride.

t-butyl 3-cyclopentyl-2-(2-nitro-4-trifluoromethylbenzoyl)-3-oxopropionate as a crude orange oiL starting from t-butyl 3-cyclopentyl-3-oxopropionate.

t-butyl 2-(4-cyano-2-nitrobenzoyl)-3-oxobutanoate as a crude brown gummy solid, starting from t-butyl 3-oxobutanoate and 4-cyano-2-nitrobenzoyl chloride.

t-butyl 4-methyl-2-(2-nitro-4-pentafluoroethylbenzoyl)-3-oxopentanoate as a crude brown oil, starting from t-butyl 4-methyl-3-oxopentanoate and 2-nitro-4-pentafluoroethylbenzoyl chloride.

t-butyl 3-cyclopropyl-2-(2-nitro-4-pentafluoroethylbenzoyl)-3-oxopropionate, as a crude brown oil, starting from t-butyl 3-cyclopropyl-3-oxopropionate and 2-nitro-4-pentafluoroethylbenzoyl chloride.

t-butyl 3-cyclobutyl-2-(2-nitro-4-trifluoromethylbenzoyl)-3-oxopropionate as a crude orange oil, starting from t-butyl 3-cyclobutyl-3-oxopropionate.

t-butyl 3-(1-methylcyclopropyl)-2-(2-nitro-4-trifluoromethylbenzoyl)-3-oxopropionate, as a crude orange oil, starting from t-butyl 3-(1-methylcyclopropyl)-3-oxopropionate.

t-butyl 3-(1-ethoxycarbonylcyclopropyl)-2-(2-nitro-4-trifluoromethylbenzoyl)-3-oxopropionate as a crude white solid, starting from t-butyl 3-(1-ethoxycarbonylcyclopropyl)-3-oxopropionate.

t-butyl 3-(2-methylcyclopropyl)-2-(2-nitro-4-trifluoromethylbenzoyl)-3-oxopropionate as a crude orange oil, starting from t-butyl 3-(2-methylcyclopropyl)-3-oxopropionate.

t-butyl 4-ethoxycarbonyl-4-methyl-2-(2-nitro-4-trifluoromethylbenzoyl)-3-oxopentanoate as a crude orange oil, starting from t-butyl 4-ethoxycarbonyl-4-methyl-3-oxopentanoate.

t-butyl 3-cyclopropyl-3-oxo-2-(2,3,4-trichlorobenzoyl)-propionate, as a crude brown solid, starting from t-butyl 3-cyclopropyl-3-oxopropionate and 2,3,4-trichlorobenzoyl chloride.

REFERENCE EXAMPLE 4

Carbon tetrachloride (1 ml) was added to a stirred mixture of t-butyl 3-oxobutanoate (7.0 g) and magnesium (1.0 g) in methanol (30 ml) causing a vigorous reaction. After subsidence of the reaction the mixture was stirred for 0.25 hour and evaporated to dryness. The residue was dissolved in dry ether (70 ml) and a solution of 2,4-dinitrobenzoyl chloride (10.0 g) in dry ether (30 ml) was added dropwise. The mixture was stirred and heated at reflux for 2 hours. After cooling to room temperature, hydrochloric acid (2M, 75 ml) was added.

The layers were separated and the aqueous layer was extracted with ether (2×50 ml). The combined organic layers were extracted into aqueous sodium hydroxide (2M, 2×50 ml) and water (3×50 ml). The combined aqueous extracts were acidified to pH 1 and extracted with ether (2×75 ml). The combined organic extracts were washed with water, dried (anhydrous magnesium sulphate) and filtered. The filtrate was evaporated to dryness to give t-butyl 2-(2,4-dinitrobenzoyl)-3-oxobutanoate (15.4 g) as an orange gum which was not further purified.

By proceeding in a similar manner, the following compounds were prepared:

t-butyl 2-(4-methylsulphonyl-2-nitrobenzoyl)-3-oxobutanoate as a crude orange gum, starting from t-butyl 3-oxobutanoate and 4-methylsulphonyl-2-nitrobenzoyl chloride.

t-butyl 2-(4-chloro-2-nitrobenzoyl)-3-oxobutanoate as a crude orange gum, starting from t-butyl 3-oxobutanoate and 4-chloro-2-nitrobenzoyl chloride and replacing the dry ether by acetonitrile.

t-butyl 2-(2,3-dichloro-4-methylsulphonylbenzoyl)-3-oxobutanoate as a crude clear gum, starting from t-butyl 3-oxobutanoate and 2,3-dichloro-4-methylsulphonylbenzoyl chloride and replacing dry ether by dichloromethane.

t-butyl 2-(4-methyl-2-nitrobenzoyl)-3-oxobutanoate as a crude brown oil, starting from t- butyl 3-oxobutanoate and 4-methyl-2-nitrobenzoyl chloride.

t-butyl 2-(2,3-dichloro-4-methylsulphonylbenzoyl)-4-methyl-3-oxopentanoate as a crude white gum, starting from t-butyl 4-methyl-3-oxopentanoate and 2,3-dichloro-4-methylsulphonylbenzoyl chloride.

t-butyl 3-cyclopropyl-2-(2,3-dichloro-4-methylsulphonylbenzoyl)-3-oxo-propionate as a crude orange gum, starting from t-butyl 3-cyclopropyl-3-oxopropionate and 2,3-dichloro-4-methylsulphonylbenzoyl chloride and replacing the dry ether by dichloromethane.

t-butyl 2-(2-chloro-4-trifluoromethylbenzoyl)-3-cyclopropyl-3-oxopropionate as a crude black gum, starting from t-butyl 3-cyclopropyl-3-oxopropionate and 2-chloro-4-trifluoromethylbenzoyl chloride.

t-butyl 3-cyclopropyl-2-[4-(1,1-dimethylethyl)-2-nitrobenzoyl]-3-oxopropionate as a crude red gum, starting from t-butyl 3-cyclopropyl-3-oxopropionate and 4-(1,1-dimethylethyl)-2-nitrobenzoyl chloride.

t-butyl 2-[4-(1,1dimethylethyl)-2-nitrobenzoyl]-3-oxobutanoate as a crude yellow gum, starting from t-butyl 3-oxobutanoate and 4-(1,1-dimethylethyl)-2-nitrobenzoyl chloride.

t-butyl 2-(2-chloro-4-methylsulphonylbenzoyl)-3-oxobutanoate as a crude brown oil, starting from t-butyl 3-oxobutanoate and 2-chloro-4-methylsulphonylbenzoyl chloride and replacing the dry ether by dichloromethane.

t-butyl 2-(2-chloro-4-trifluoromethylbenzoyl)-3-oxobutanoate as a crude dark yellow oil, starting from t-butyl 3-oxobutanoate and 2-chloro-4-trifluoromethylbenzoyl chloride.

t-butyl 3-oxo-2-(2-trifluoromethylbenzoyl)-butanoate as a crude yellow oil, starting from t-butyl 3-oxobutanoate and 2-trifluoromethylbenzoyl chloride.

t-butyl 2-(2,4-bis-trifluoromethylbenzoyl)-3-oxobutanoate as a crude yellow oil, starting from t-butyl 3-oxobutanoate and 2,4-bis-trifluoromethylbenzoyl chloride.

t-butyl 2-(2-chloro-4-methylsulphonylbenzoyl)-3-cyclopropyl-3-oxopropionate as a crude yellow oil, starting from t-butyl 3-cyclopropyl-3-oxopropionate and 2-chloro-4-methylsulphonylbenzoyl chloride and replacing the dry ether by dichloromethane.

t-butyl 3-cyclopropyl-3-oxo-2-(2-trifluoromethylbenzoyl)-propionate as a crude orange gum starting from t-butyl 3-cyclopropyl-3-oxopropionate and 2-trifluoromethylbenzoyl chloride.

t-butyl 3-cyclopropyl-2-(2,4-dichlorobenzoyl)-3-oxopropionate as a crude brown oil starting from t-butyl 3-cyclopropyl-3-oxopropionate and 2,4-dichlorobenzoyl chloride.

t-butyl 2-(2,3-dichloro-4-methylsulphenylbenzoyl]-3-oxobutanoate as a crude brown oil, starting from t-butyl 3-oxobutanoate and 2,3-dichloro-4-methylsulphenylbenzoyl chloride.

t-butyl 2-(2,4-bis-trifluoromethylbenzoyl)-3-cyclopropyl-3-oxopropionate as a crude yellow oil, starting from t-butyl 3-cyclopropyl-3-oxopropionate and 2,4-bis-trifluoromethylbenzoyl chloride.

t-butyl 2-(4-chloro-2-trifluoromethylbenzoyl)-3-oxobutanoate as a crude yellow gum, starting from t-butyl 3-oxobutanoate and 4-chloro-2-trifluoromethylbenzoyl chloride.

t-butyl 2-(4-chloro-2-trifluoromethylbenzoyl)-3-cyclopropyl-3-oxopropionate as a crude yellow solid starting from t-butyl 3-cyclopropyl-3-oxopropionate and 4-chloro-2-trifluoromethylbenzoyl chloride.

t-butyl 2-(2-chloro-4-methylsulphonylbenzoyl)-4-methyl-3-oxopentanoate, as a crude brown oil, starting from t-butyl 4-methyl-3-oxopentanoate and 2-chloro-4-methylsulphonylbenzoyl chloride and replacing the dry ether by dichloromethane.

t-butyl 3-cyclopropyl-2-(4-fluoro-2-nitrobenzoyl)-3-oxopropionate as a crude brown oil starting from t-butyl 3-cyclopropyl-3-oxopropionate and 4-fluoro-2-nitrobenzoyl chloride.

t-butyl 2-(4-fluoro-2-nitrobenzoyl)-3-oxobutanoate as a crude brown oil, starting from t-butyl 3-oxobutanoate and 4-fluoro-2-nitrobenzoyl chloride.

t-butyl 2-(2-chloro-3-ethoxy-4-methylsulphonylbenzoyl)-3-oxobutanoate as a crude orange oil starting from t-butyl 3-oxobutanoate and 2-chloro-3-ethoxy-4-methylsulphonylbenzoyl chloride.

t-butyl 2-(3-cyanobenzoyl)-3-oxobutanoate as a crude orange gum, starting from t-butyl 3-oxobutanoate and 3-cyanobenzoyl chloride.

t-butyl 3-cyclopropyl-2-(4-methylsulphonyl-2-trifluoromethylbenzoyl)-3-oxopropionate as a crude red oil, starting from t-butyl 3-cyclopropyl-3-oxopropionate and 4-methylsulphonyl-2-trifluoromethylbenzoyl chloride and replacing the dry ether by dichloromethane.

t-butyl 3-cyclopropyl-2-(4-methylsulphonyl-2-nitrobenzoyl)-3-oxopropionate as a crude brown oil, starting from t-butyl 3-cyclopropyl-3-oxopropionate and 4-methylsulphonyl-2-nitrobenzoyl chloride and replacing the dry ether by acetonitrile.

t-butyl 2-(2-chloro-3-ethoxy-4-methylsulphonylbenzoyl)-3-cyclopropyl-3-oxopropionate as a crude orange gum starting from t-butyl 3-cyclopropyl-3-oxopropionate and 2-chloro-3-ethoxy-4-methylsulphonylbenzoylchloride and replacing the dry ether by dichloromethane.

t-butyl 2-(2-chloro-3-ethoxy-4-ethylsulphonylbenzoyl)-3-oxobutanoate as a crude brown gum, starting from t-butyl 3-oxobutanoate and 2-chloro-3-ethoxy-4-ethylsulphonylbenzoyl chloride and replacing the dry ether by acetonitrile.

t-butyl 2-(2-chloro-3-ethoxy-4-methylsulphonylbenzoyl)-4-methyl-3-oxopentanoate as a crude yellow oil, starting from t-butyl 4-methyl-3-oxopentanoate and 2-chloro-3-ethoxy-4-methylsulphonylbenzoyl chloride and replacing the dry ether by acetonitrile.

t-butyl 2-(2-chloro-3-ethoxy-4-ethylsulphonylbenzoyl)-3-cyclopropyl-3-oxopropionate as a crude brown oil, starting from t-butyl 3-cyclopropyl-3-oxopropionate and 2-chloro-3-ethoxy-4-ethylsulphonylbenzoyl chloride and replacing the dry ether by acetonitrile.

t-butyl 2-(3-methoxycarbonyl-2-methyl-4-methylsulphonylbenzoyl)-3-oxobutanoate as a crude orange oil, starting from t-butyl 3-oxobutanoate and 3-methoxycarbonyl-2-methyl-4-methylsulphonylbenzoyl chloride and replacing the dry ether by toluene.

t-butyl 2-[2-chloro-3-(1-methylethoxy)-4-methylsulphonylbenzoyl]-3-oxobutanoate as a crude orange gum, starting from t-butyl 3-oxobutanoate and 2-chloro-3-(1-methylethoxy)-4-methylsulphonylbenzoyl chloride and replacing the dry ether by acetonitrile.

t-butyl 2-[2-methyl-3-(1-methylethoxycarbonyl)-4-methylsulphonylbenzoyl]-3-oxobutanoate as a crude orange oil, starting from t-butyl 3-oxobutanoate and 2-methyl-3-(1-methylethoxycarbonyl)-4-methylsulphonylbenzoyl chloride and replacing the dry ether by acetonitrile.

t-butyl 3-cyclopropyl-2-[2-methyl-3-(methylethoxycarbonyl)-4-methylsulphonylbenzoyl]-3-oxopropionate as a crude orange oil, starting from t-butyl 3-cyclopropyl-3-oxopropionate and 2-methyl-3-(1-methylethoxycarbonyl)-4-methylsulphonylbenzoyl chloride and replacing the dry ether by acetonitrile.

In addition, by proceeding in a similar manner, the following compounds were prepared from the appropriately substituted starting materials.

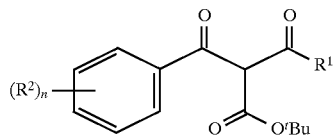

| R¹ | (R²)n | Reaction Solvent |
|---|---|---|
| Me | 2-Me-3-CO₂Me-4-SO₂$^i$Pr | CH₃CN |
| Cp | 2-NO₂-4-SO₂CF₃ | CH₃CN |
| Cp | 2,6-Cl₂-4-CF₃ | CH₃CN |
| 1-Me-Cp | 2-NO₂-4-SO₂Me | CH₃CN |
| 1-Me-Cp | 2-Cl-4-SO₂Me | CH₃CN |
| $^i$Pr | 2-NO₂-4-Me | CH₃CN |
| Cp | 2-NO₂-4-Me | CH₃CN |
| Cp | 2-Cl-3-OMe-4-SO₂Me | CH₃CN |
| Me | 2-Cl-4-NO₂ | CH₃CN |
| $^i$Pr | 2-Cl-4-NO₂ | CH₃CN |
| Cp | 2-Cl-4-NO₂ | CH₃CN |
| $^i$Pr | 2-NO₂-4-$^t$Bu | CH₃CN |
| $^s$Bu | 2-NO₂-4-CF₃ | Ether |
| Cp | 2,6-Cl₂ | CH₃CN |
| $^t$Bu | 2-NO₂-4-SO₂Me | CH₂Cl₂ |
| Cp | 2-SO₂Me | CH₃CN |
| Cp | 2-Cl-3-CN-4-SMe | Toluene |
| Cp | 2-Me-4-Br | CH₃CN |
| $^t$Bu | 2-Cl-4-SO₂Me | CH₂Cl₂ |
| $^s$Bu | 2-Cl-4-SO₂Me | CH₂Cl₂ |
| Cp | 2-SO₂Me-4-NO₂ | CH₃CN |
| $^i$Pr | 2-SO₂Me-4-NO₂ | CH₃CN |
| Et | 2-Cl-4-SO₂Me | CH₂Cl₂ |
| Cp | 2,6-Cl₂-3-NO₂ | CH₃CN |
| Cp | 2-Cl-4-F | CH₃CN |
| Cp | 2,4-(SO₂Me)₂ | CH₃CN |
| Cp | 2-Cl-4-Br | CH₃CN |
| $^t$Bu | 2-CF₃-4-SO₂Me | CH₂Cl₂ |
| Me | 2-SO₂Me | CH₃CN |
| Me | 2-CF₃-4-SO₂Me | CH₂Cl₂ |
| $^i$Pr | 2-CF₃-4-SO₂Me | CH₂Cl₂ |
| 1-Me-Cp | 2-CF₃-4-SO₂Me | CH₂Cl₂ |
| Cp | 2-Cl-4-SO₂$^i$Pr | CH₃CN |
| $^i$Pr | 2-SO₂Me | CH₃CN |
| Cp | 2-SMe | CH₃CN |
| Cp | 2-Cl-5-SO₂Me | CH₃CN |
| Cp | 2-Cl-4-SO₂$^t$Bu | CH₃CN |
| Cp | 2-CF₃-4-SMe | CH₃CN |
| 1-Me-Cp | 2-SO₂Me | CH₃CN |
| $^s$Bu | 2-SO₂Me | CH₃CN |
| Cp | 2-SO₂Et | CH₃CN |
| Cp | 2-Cl-4-SMe | CH₃CN |
| Cp | 2-NO₂-4-SMe | CH₃CN |
| Cp | 2-SO₂CH₃-5-Cl | CH₃CN |
| Cp | 2-Cl-4-SO₂Et | CH₃CN |
| Cp | 2-F-4-SO₂Me | CH₃CN |
| Cp | 2-SO₂Me-5-F | CH₃CN |
| Cp | 2-SO₂$^i$Pr | CH₃CN |
| Cp | 2-5-Cl₂-4-SO₂Me | CH₃CN |
| Cp | 2-NO₂-4-CN | CH₃CN |
| Cp | 2-NO₂-4-Cl | CH₃CN |
| Cp | 2,4-Br₂-3-OMe | Toluene |
| Cp | 2-Br-3-OMe-4-SO₂Me | CH₃CN |
| Me | 2-Br-3-OMe-4-SO₂Me | CH₃CN |
| 1-Me-Cp | 2-Br-3-OMe-4-SO₂Me | CH₃CN |
| $^i$Pr | 2-NO₂-4-Cl | CH₃CN |
| 1-Me-Cp | 2,3-Cl₂-4-SO₂Me | Toluene |
| Cp | 2-Cl-4-OCF₃ | Toluene |
| Cp | 2,3-Cl₂-4-OCF₃ | Toluene |
| Cp | 2-Cl-3-OMe-4-SO₂Me | Toluene |
| Cp | 2-SO₂Me-3-Cl | Toluene |
| Cp | 2-Br-4-SO₂Me | Toluene |
| 1-Me-Cp | 2-Br-4-SO₂Me | Toluene |
| Me | 2-Cl-3-OMe-4-SO₂Me | Toluene |
| Cp | 2-CF₃-4-SEt | Toluene |
| 1-Me-Cp | 2-CF₃-4-SEt | Toluene |
| 1-Me-Cp | 2-CF₃-4-SO₂Et | Toluene |
| Cp | 2-SO₂Me-3-OMe | Toluene |
| 1-Me-Cp | 2-NO₂-4-F | Toluene |

-continued

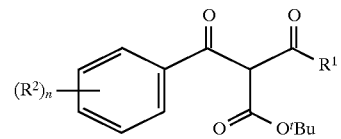

| R¹ | (R²)n | Reaction Solvent |
|---|---|---|
| $^i$Pr | 2-CF₃-4-SMe | Toluene |
| Cp | 2-CF₃-4-SO₂Et | Toluene |
| Cp | 2-NO₂-4-Br | Toluene |
| Cp | 2-Br-3-OMe-4-SEt | CH₃CN |
| Cp | 2-Br-3-OCHF₂-4-SO₂Et | Toluene |
| Cp | 2-SMe-4-SO₂Me | Toluene |
| Et | 2-CF₃-4-SO₂Me | CH₃CN |
| Me | 2-CF₃-4-SO₂Me | CH₃CN |
| 1-MeCp | 2-SMe-4-SO₂Me | Toluene |
| Cp | 2-Br-4-SMe | Toluene |
| Cp | 2-Br-3-OMe-4-SMe | CH₃CN |
| Cp | 2-SO₂Me-6-F | CH₃CN |
| Cp | 2,4-(SMe)₂ | CH₃CN |
| Cp | 2,4-Cl₂-3-CO₂Et | Toluene |
| Cp | 2-SMe-3-Cl-4-OMe | Toluene |
| Cp | 2,4-Cl₂-3-CN | Toluene |
| Cp | 2,4-Cl₂-3-OMe | Toluene |
| 1-Me-Cp | 2-F-4-SO₂Me | Toluene |
| 1-Me-Cp | 2,4-Cl₂-3-CO₂$^i$Pr | Toluene |
| $^i$Pr | 2-F-4-SO₂Me | Toluene |
| Cp | 2,4-Cl₂-3-CO₂$^i$Pr | Toluene |
| Cp | 2-Cl-3-CO₂$^i$Pr-4-SMe | Toluene |
| Cp | 2-Cl-3-CO₂$^i$Pr-4-SO₂Me | Toluene |
| Cp | 2-SMe-3-CO₂$^i$Pr-4-Cl | Toluene |
| Cp | 2-SMe-3-CO₂$^i$Pr-4-CF₃ | Toluene |

REFERENCE EXAMPLE 5

A mixture of 5-cyclopropylcarbonyl-2,2-dimethyl-1,3-dioxan-4,6-dione (23.9 g) and t-butanol (25 g) in dry toluene (80 ml) was stirred and heated at 80° C. for 4 hours. The cooled mixture was washed with water (3×30 ml), dried (anhydrous sodium sulphate), treated with decolourizing charcoal and filtered. The filtrate was evaporated to dryness and the residue was distilled to give t-butyl 3-cyclopropyl-3-oxopropionate (20.2 g) as a clear oil bp 80°–84° C./8 mmHg.

By proceeding in a similar manner the following compounds were prepared.

t-butyl 3-cyclopentyl-3-oxopropionate as an orange oil NMR (CDCl₃) 1.5(s,9H), 1.7(m,8H), 2.9(m,1H), 3.3 (s2H), starting from 5-cyclopentylcarbonyl-2,2-dimethyl-1,3-dioxan-4,6-dione.

t-butyl 3-cyclobutyl-3-oxopropionate as a clear oil bp 66°–80° C./$^-$12 mmHg, starting from 5-cyclobutylcarbonyl-2,2-dimethyl-1,3-dioxan-4,6-dione.

t-butyl 3-(2-methylcyclopropyl)-3-oxopropionate as a clear oil bp 100°–110° C./16 mmHg, starting from 2,2-dimethyl-5-(2-methylcyclopropylcarbonyl)-1,3-dioxan4,6-dione.

REFERENCE EXAMPLE 6

A mixture of 2,2-dimethyl-1,3-dioxan-4,6-dione (20.0 g) and pyridine (22,0 g) in dichloromethane (200 ml) was stirred and cooled to 0° C. in an ice bath. A solution of cyclopropylcarbonyl chloride (16.0 g) in dichloromethane (50 ml) was added dropwise with stirring in an atmosphere of nitrogen whilst maintaining the temperature below 3° C. by external cooling. The mixture was stirred at 0° C. for 1 hour and at ambient temperature for 2 hours. The resultant orange suspension was washed with hydrochloric acid (2M, 2×50 ml), water (2×50 ml), dried (anhydrous sodium sulphate) and filtered. The filtrate was evaporated to dryness. The residue was dissolved in ether (150 ml) and the solution was treated with decolourizing charcoal and filtered. The filtrate was evaporated to dryness to give 5-cyclopropylcarbonyl-2,2-dimethyl-1,3-dioxan4,6-dione (24.2 g) as a yellow solid mp 44°–46° C.

By proceeding in a similar manner the following compounds were prepared:

5-cyclopentylcarbonyl-2,2-dimethyl-1,3-dioxan-4,6-dione as an orange solid, mp 75°–76° C., starting from cylopentylcarbonyl chloride.

5-cyclobutylcarbonyl-2,2-dimethyl-1,3-dioxan-4,6-dione as an orange oil which was not further purified, starting from cyclobutylcarbonyl chloride.

2,2-dimethyl-5-(2-methylcyclopropylcarbonyl)-1,3-dioxan-4,6-dione as an orange oil which was not further purified, starting from 2-methylcyclopropylcarbonyl chloride.

REFERENCE EXAMPLE 7

A solution of n-butyllithium (2.5M in hexane, 36 ml) was added dropwise with stirring to a cooled solution of diisopropylamine (9.09 g) in dry tetrahydrofuran (i.e. tetrahydofuran) in an atmosphere of nitrogen, whilst maintaining the temperature below −70° C. The mixture was stirred for 0.25 hour and t-butyltrimethylsilylacetate (16.9 g) was added dropwise with stirring whilst maintaining the temperature below −70° C. The mixture was stirred at −78° C. for 1 hour. A suspension of 1-(1-methylcyclopropylcarbonyl)-imidazole (13.5 g) in dry tetrahydrofuran (120 ml) was added dropwise whilst maintaining the temperature below −60° C. The mixture was stirred at −78° C. for 3 hours and the temperature was allowed to rise to room temperature. Hydrochloric acid (2M, 100 ml) was added cautiously and the mixture was extracted with ether (2×100 ml). The combined extracts were washed with hydrochloric acid (2M, 3×50 ml) and water (3×50 ml), dried (anhydrous sodium sulphate) and filtered. The filtrate was evaporated to dryness to give t-butyl 3-(1-methylcyclopropyl)-3-oxopropionate as an orange oil NMR (CDCl$_3$) 0.65(m,2H), 1.1(m,2H), 1.25(s,3H), 1.4(s,9H), 3.2 (s,2H).

REFERENCE EXAMPLE 8

A solution of 1-methylcyclopropylcarbonyl chloride (11.8 g) in toluene (15 ml) was added dropwise to a solution of imidazole (13.6 g) in tetrahydrofuran (100 ml) whilst maintaining the temperature below 25° C. The mixture was stirred for 3 hours and filtered. The filtrate was evaporated to dryness to give 1-(1-methylcyclopropylcarbonyl)-imidazole (13.6 g) as a white solid, mp 34°–35° C.

REFERENCE EXAMPLE 9

A solution of n-butyllithium (2.5M in hexane, 40 ml) was added dropwise with stirring to a cooled solution of diisopropylamine (10.1 g) in anhydrous ether (100 ml) in an atmosphere of nitrogen, whilst maintaining the temperature below −70° C. The mixture was stirred at −78° C. for 5 hour and a solution of t-butyl acetate (11.6 g) in anhydrous ether (20 ml) was added dropwise, whilst maintaining the temperature below −70° C. The mixture was stirred at −78° C. for 1 hour and a solution of diethyl cyclopropane-1,1-dicarboxylate (18.6 g) in anhydrous ether (20 ml) was added dropwise whilst maintaining the temperature below −70° C. The mixture was stirred at −78° C. for 0.5 hour and the temperature was allowed to rise to room temperature. A saturated solution of ammonium chloride (150 ml) was added cautiously and the layers were separated. The organic extract was washed with water (2×50 ml) hydrochloric acid (2M, 2×50 ml) and water (2×50 ml). The solution was dried (anhydrous sodium sulphate) and filtered. The filtrate was evaporated to dryness and the residue was distilled to give t-butyl 3-(1-ethoxycarbonylcyclopropyl)-3-oxopropionate (11.66 g) as a clear oil bp 89°–90° C./0.5 mmHg.

By proceeding in a similar manner the following compound was prepared:

t-butyl 4-ethoxycarbonyl-4-methyl-3-oxopentanoate as a clear oil, bp 85°–86° C./0.8 mmHg, starting from diethyl dimethylmalonate.

REFERENCE EXAMPLE 10

A solution of 2-(2-nitrotrifluoromethylbenzoyl)-1-phenylbutan-1,3-dione (28.5 g) in ethanol (300 ml) was added to a mixture of concentrated sulphuric acid (225 ml) and ethanol (225 ml). The resultant solution was stirred and heated at 100° C. for 1 hour. The cooled solution was poured onto a mixture of ice and water (2 l) and extracted with dichloromethane (3×250 ml). The combined organic layers were washed with water (2×100 ml), dried (anhydrous sodium sulphate) and filtered. The filtrate was evaporated to dryness and the residue was recrystallized from petroleum spirit (bp 60°–80° C.) to give 1-(2-nitro-4-trifluoromethylphenyl)-3-phenylpropan-1,3-dione (19.6 g) as an off-white solid mp 101°–103° C.

By proceeding in a similar manner, the following compounds were prepared:

1-(2-Nitro-4-trifluoromethylphenyl)-3-(4-chlorophenyl)-propan-1,3-dione, as a yellow solid mp 133°–134° C., starting from 2-(2-nitrotrifluoromethylbenzoyl)-1-(4-chlorophenyl)-butan-1,3-dione.

1-(2-Nitro-4-trifluoromethylphenyl)-3-(4-fluorophenyl)-propan-1,3-dione, as a yellow solid mp 128°–130° C., starting from 2-(2-nitro-4-trifluoromethylbenzoyl)-1-(4-fluorophenyl)-butan-1,3-dione.

REFERENCE EXAMPLE 11

A mixture of magnesium turnings (3.0 g) and carbon tetrachloride (0.5 ml) in ethanol (40 ml) was warmed gently to 50° C. until the reaction initiated (effervescence observed). Ether (100 ml) was added followed by dropwise addition of a solution of 1-phenylbutan-1,3-dione (20.0 g) in ether (100 ml). The mixture was heated at reflux for 3 hours. The cooled mixture was evaporated to dryness and the residue was treated with toluene (100 ml) and re-evaporated. The residue was suspended in ether (150 ml) and a solution of 2-nitro-4-trifluoromethylbenzoyl chloride (32.8 g) was added. The mixture was stirred and heated at reflux for 2 hours. After cooling, hydrochloric acid (2M, 100 ml) was added and the two layers were separated. The organic layer was extracted with aqueous sodium bicarbonate (saturated, 5×100 ml). The combined aqueous layers were acidified to pH 1 and extracted with dichloromethane (2×150 ml). The combined organic layers were washed with water (2×50 ml), dried (anhydrous sodium sulphate) and filtered. The filtrate was evaporated to dryness to give 2-(2-nitro-4-trifluoromethylbenzoyl)-1-phenylbutan-1,3-dione (35.6 g) as a brown oil, NMR (CDCl$_3$) 2.15(s,3H), 5.25(s,1H), 7.1–8.0(m,7H), 8.2(s,1H), 16.5(bs,1H).

By proceeding in a similar manner, the following compound was prepared:

2-(2-Nitro-4-trifluoromethylbenzoyl)-1-(4-fluorophenyl)-butan-1,3-dione, as a white solid mp 90°–91° C., starting from 1-(4-fluorophenyl)-butan-1,3-dione.

REFERENCE EXAMPLE 12

A mixture of magnesium turnings (0.71 g) in methanol (20 ml) was stirred and heated at reflux for 1 hour until all of the magnesium was consumed. A solution of 1-(2-nitro-4-trifluoromethylphenyl)-butan-1,3-dione (8.0 g) in methanol (100 ml) was added dropwise at such a rate as to maintain gentle reflux. The mixture was stirred and heated at reflux for 2 hours. The cooled, cloudy solution was evaporated to dryness and the residue was dissolved in toluene (50 ml) and re-evaporated. The residue was redissolved in toluene (100 ml) and a solution 4-chlorobenzoyl chloride (5.12 g) in toluene (20 ml) was added. The mixture was stirred at ambient temperature for 16 hours. Hydrochloric acid (2M,50 ml) was added and the layers were separated. The organic layer was washed with water (50 ml), dried (anhydrous sodium sulphate) and filtered. The filtrate was evaporated to dryness. The residue was triturated with a mixture of ether and petroleum spirit (bp 60°–80° C.) (1:1) and the solid was filtered off to give 2-(2-nitro-4-trifluoromethylbenzoyl)-1-(4-chlorophenyl)-butan-1,3-dione (5.5 g) as an off-white solid mp 102.5°–103.5° C.

REFERENCE EXAMPLE 13

A mixture of magnesium turnings (0.62 g) and carbon tetrachloride (1 ml) in anhydrous methanol (120 ml) was stirred and heated at reflux for 0.5 hour until all of the magnesium was consumed. A solution of 1-(2-nitro-4-trifluoromethylphenyl)-butan-1,3-dione (7.0 g) in methanol (90 ml) was added dropwise and the mixture was stirred and heated at reflux for 2 hours. The mixture was cooled and evaporated to dryness. The residue was dissolved in toluene (50 ml) and re-evaporated to dryness. The residue was dissolved in acetonitrile (100 ml) and to this was added dropwise a solution of 4-nitrobenzoyl chloride (9.28 g) in acetonitrile (40 ml). The mixture was stirred and heated at 70° C. for 48 hours. After cooling, hydrochloric acid (2M, 50 ml) was added and the mixture was extracted with ethyl acetate (50 ml). The organic layer was extracted with aqueous sodium hydroxide (2M, 2×50 ml) and water (5×60 ml). The combined aqueous extracts were acidified to pH 1 and extracted with ethyl acetate (2×75 ml). The combined organic extracts were washed with water (2×50 ml), dried (anhydrous magnesium sulphate) and filtered. The filtrate was evaporated to dryness and triturated with ether (20 ml), to give 3-(4-nitrophenyl)-1-(2-nitro-4-trifluoromethylphenyl)-propan-1,3-dione (2.89 g) as a yellow solid, mp 139°–140° C.

By proceeding in a similar manner the following compound was prepared:

3-(4-Methoxyphenyl)-1-(2-nitro-4-trifluoromethylphenyl)-propan-1,3-dione, as a yellow solid mp 127°–129° C., starting from 4-methoxybenzoyl chloride.

REFERENCE EXAMPLE 14

A solution of 5-(2-nitro-4-trifluoromethylphenyl)-isoxazole (4.91 g) in ethanol (35 ml) was added dropwise to a solution of sodium ethoxide in ethanol (prepared from 0.6 g sodium in 25 ml ethanol). The mixture was stirred at room temperature for 3 hours, poured into water (150 ml) and acidified to pH 1. It was extracted with ether (2×75 ml) and the combined extracts were washed with water, dried (anhydrous sodium sulphate) and filtered. The filtrate was evaporated to dryness and the residue was triturated with petroleum spirit (bp 60°–80° C.) and filtered to give 3-(2-nitro-4-trifluoromethylphenyl)-3-oxopropionitrile (4.9 g) as an off-white solid mp 79.5°–80.5° C.

REFERENCE EXAMPLE 15

5-Hydroxy-5-(2-nitro-4-trifluoromethylphenyl)-isoxazoline (8.47 g) was added in portions to concentrated sulphuric acid (85 ml). The mixture was stirred for 2 hours and poured into a mixture of ice and water (200 ml). It was extracted with ether (2×100 ml) and the combined organic extracts were washed with water (2×75 ml), dried (anhydrous sodium sulphate) and filtered. The filtrate was evaporated to dryness and the residue was triturated with petroleum spirit (bp 60°–80° C.) and filtered to give 5-(2-nitro-4-trifluoromethylphenyl)-isoxazole (7.45 g) as a white solid, mp 62°–63° C.

REFERENCE EXAMPLE 16

A mixture of 3-dimethylamino-1-(2-nitro-4-trifluoromethylphenyl)-prop-2-en-1-one (41.0 g) and hydroxylamine hydrochloride (11.9 g) in dry ethanol (280 ml) was stirred at room temperature overnight. It was evaporated to dryness and the residue was dissolved in a mixture of ether (150 ml) and water (100 ml). The layers were separated and the organic layer was washed with water (100 ml), dried (anhydrous sodium sulphate) and filtered. The filtrate was evaporated to dryness and the residue was triturated with petroleum spirit (bp 60°–80° C.) (20 ml) and filtered to give 5-hydroxy-5-(2-nitrotrifluoromethylphenyl)-isoxazoline (33.9 g) as a pale yellow solid mp 122°–123° C.

REFERENCE EXAMPLE 17

A mixture of 2-nitro-4-trifluoromethylacetophenone (40.0 g) and dimethyl-formamide dimethyl acetal (89.0 g) was stirred and heated at reflux for 2.5 hours. The cooled dark red solution was evaporated to dryness and the residue was triturated with ether (30 ml) and filtered to give 3-dimethylamino-1-(2-nitro-4-trifluoromethylphenyl)-prop-2-en-1-one (41.5 g) as a bright orange solid mp 100.8°–101.3° C.

REFERENCE EXAMPLE 18

Diethyl (2-nitro-4-trifluoromethylbenzoyl)-malonate (90.75 g) was added portionwise to a mixture of concentrated sulphuric acid (38 ml), glacial acetic acid (315 ml) and water (215 ml) and the resultant mixture was stirred and heated at reflux for 2 hours. After cooling the mixture was basified by the addition of aqueous sodium hydroxide (2M) and extracted with ether (3×250 ml). The combined organic extracts were washed with water, dried (anhydrous sodium sulphate) and filtered. The filtrate was evaporated to dryness and the residue was triturated with petroleum spirit (bp 60°–80° C.) (50 ml) and filtered to give 2-nitro-4-trifluoroacetophenone (48.6 g) as an off-white solid mp 67.2°–67.7° C.

REFERENCE EXAMPLE 19

A mixture of magnesium turnings (6.1 g) and carbon tetrachloride (2 ml) in ethanol (40 ml) was stirred and warmed gently until the reaction initiated (effervescence observed). Ether (150 ml) was added cautiously followed by dropwise addition of a solution of diethyl malonate (40.2 g) in ether (200 ml). The mixture was stirred and heated at reflux for 1 hour until all of the magnesium was consumed. The solution was cooled to room temperature and a solution of 2-nitro-4-trifluoromethylbenzoyl chloride (63.4 g) in ether (200 ml) was added dropwise. The mixture was stirred and heated at reflux for 2 h. The cooled suspension was treated with hydrochloric acid (2M,200 ml) and the layers were separated. The organic layer was extracted with aqueous sodium hydroxide solution (2M, 2×100 ml) and water (3×100 ml). The combined aqueous layers were acidified to pH 1 and extracted with ether (2×150 ml). The combined organic layers were washed with water (2×75 ml) dried (anhydrous sodium sulphate) and filtered. The filtrate was evaporated to give diethyl 2-nitro-4-trifluoromethylbenzoylmalonate (90.75 g) as a white solid mp 59°–60° C.

Most of the benzoyl chlorides used in the reference examples above are described in the literature, however those which are not, are prepared by the standard reaction of the benzoic acids with thionyl chloride. The solutions were evaporated to dryness and the residual benzoyl chlorides used without purification.

REFERENCE EXAMPLE 20

2-Nitro-4-pentafluoroethyltoluene (56.6 g) and pyridine (170 ml) were added to a stirred solution of sodium hydroxide (10.0 g) in water (500 ml). The mixture was stirred and heated at reflux and potassium permanganate (174 g) was added portionwise. The mixture was stirred and heated at reflux for 1 hour until the purple colouration had disappeared. After cooling, the mixture was filtered and the solid was washed with water (3×100 ml) and ether (300 ml). The layers were separated and the aqueous layer was washed with ether and acidified to pH 1. It was extracted with ether (3×300 ml) and the combined extracts were washed with water, dried (anhydrous magnesium sulphate) and filtered. The filtrate was evaporated to dryness to give 2-nitro-4-pentafluoroethylbenzoic acid (51.6 g) as a white solid mp 124°–135° C.

REFERENCE EXAMPLE 21

A mixture of concentrated nitric acid (1 ml) and concentrated sulphuric acid (2 ml) was added to a cooled stirred suspension of 4-pentafluoroethyltoluene (2.1 g) in concentrated sulphuric acid (5 ml) whilst maintaining the temperature below 5° C. The mixture was stirred at 0° C. for 10 minutes, allowed to warm to room temperature and stirred for 1.5 hours. It was poured onto ice (30 ml) and extracted with ether (2×25 ml). The combined organic extracts were washed with aqueous sodium carbonate (2M, 2×25 ml), water (25 ml), saturated aqueous sodium chloride solution (25 ml), dried (anhydrous magnesium sulphate) and filtered. The filtrate was evaporated to dryness to give 2-nitro-4-pentafluoroethyltoluene (2.04 g) as a pale yellow oil NMR (CDCl$_3$) 2.7(s,3H), 7.45(d,1H), 7.7(d,1H), 8.1(s,1H).

The preparation of 4-pentafluoroethyltoluene is described by J. N. Freskos, Synth. Comm. 1988 18 965. He states that the product cannot be separated from toluene by distillation. However distillation through a packed column gives pure pentafluoroethyltoluene bp 137°–141° C.

REFERENCE EXAMPLE 22

Hydrogen peroxide (30%, 12.5 ml) was added dropwise with stirring to a cooled solution of 3-methoxycarbonyl-2-methyl-4-methylsulphenylbenzoic acid (4.2 g) in a mixture of acetic anhydride (2.5 ml) and acetic acid (10 ml) whilst maintaining the temperature below 5° C. The mixture was stirred at 0° C. for 20 minutes and allowed to warm to room temperature. The mixture was stirred at room temperature for 0.5 hour and heated at 65° C. for 2 hours. The cooled solution was diluted with water (50 ml) and extracted with ethyl acetate (3×50 ml). The combined extracts were washed with saturated aqueous sodium chloride solution (50 ml), aqueous ferrous sulphate solution (3×50 ml) and saturated aqueous sodium chloride solution (2×50 ml). The organic layer was extracted into aqueous sodium carbonate solution (1M, 3×50 ml). The combined aqueous extracts were acidified to pH 1 and extracted with ether (3×50 ml). The combined organic extracts were washed with water (2×50 ml), dried (anhydrous magnesium sulphate) and filtered. The filtrate was evaporated to dryness to give 3-methoxycarbonyl-2-methyl-4-methylsulphonylbenzoic acid (2.0 g) as a pale yellow solid, mp. 113°–118° C.

By proceeding in a similar manner the following compound was prepared:

2-methyl-3-(1-methylethoxycarbonyl)-4-methylsulphonylbenzoic acid as a cream solid NMR (CD$_3$CN) 1.6(d,6H), 2.7(s,3H), 3.3(s,3H), 5.4(m,1H), 8.0(m,2H), starting from 2-methyl-3-(1-methylethoxycarbonyl)-4-(methylthio)benzoic acid.

3-methoxycarbonyl-2-methyl-4-(1-methylethylsulphonyl)-benzoic acid, NMR (CDCl$_3$) 1.3(d,6H) 2.55(s,3H) 3.5(m,1H) 3.9(s,3H) 7.7(d,1H) 8.0(d,1H) 10.9(bs,1H).

2-(ethylsulphonyl)benzoic acid, NMR (DMSO D$_6$) 1.3(t, 3H) 3.5(q,2H) 7.3–8.1(m,4H) 10.9(bs,1H).

4-(ethylsulphonyl)-2-trifluoromethylbenzoic acid, NMR (CDCl$_3$) 1.25(t,3H) 3.15(q,2H) 7.7–8.2(m,3H).

ethyl 2-bromo-3-difluoromethoxy-4-(ethylsulphonyl) benzoate, NMR (CDCl$_3$) 1.25(t,3H) 1.45(t,3H) 3.4(q, 2H) 4.45(q,2H) 6.95(t,1H) 7.7(d,1H) 8.05(d,1H).

REFERENCE EXAMPLE 23

Sodium nitrite (2.4 g) was added dropwise to a stirred solution of 3-methoxycarbonyl-2-methyl-4-methylsulphenylbenzamide (4.2 g) in a mixture of concentrated sulphuric acid (50 ml), water (40 ml) and glacial acetic acid (70 ml) whilst maintaining the temperature below 5° C. The mixture was stirred without cooling for 0.5 hours. The brown solution was recooled to 0° C. and water (200 ml) was added. The mixture was extracted with ether (3×150 ml). The combined organic extracts were washed with water (2×150 ml), dried (anhydrous magnesium sulphate) and filtered. The filtrate was evaporated to dryness to give 3-methoxycarbonyl-2-methyl-4-methylsulphenylbenzoic acid (4.6 g) as a sticky orange solid NMR (CDCl$_3$) 2.1(s, 3H), 2.5(s,3H), 3.9(s,3H), 7.0(d,1H), 7.85(d,1H), 9.0(bs, 1H).

By proceeding in a similar manner the following compounds were prepared:

2-methyl-3-(1-methylethoxycarbonyl)-4-methylsulphenylbenzoic acid as an orange gum which was not further purified, from 2-methyl-3-(1-methylethoxycarbonyl)-4-methylthiobenzamide.

3-methoxycarbonyl-2-methyl-4-(1-methylethylsulphenyl)benzoic acid, NMR (CDCl$_3$) 1.3 (d,6H) 2.3(s,3H) 3.1(m,1H) 3.9(s,3H) 7.8(d,1H) 8.05 (d,1H) 11.45(bs,1H).

REFERENCE EXAMPLE 24

Hydrogen peroxide (30%, 18 ml) was added dropwise with stirring to a solution of methyl 3-cyano-2-methyl-6- methylsulphenylbenzoate (10.0 g) in ethanol (100 ml) in an atmosphere of nitrogen. A solution of sodium hydroxide (0.43 g) in water (2 ml) was added dropwise and the resultant rapid exotherm was controlled by ice cooling. After the exotherm had ceased the mixture was stirred and heated at 65° C. for 0.5 hours. The orange solution was poured into a mixture of ice and water (400 ml) and it was extracted with ether (3×100 ml). The combined organic extracts were washed with water (100 ml), aqueous ferrous sulphate solution (100 ml), water (2×100 ml), dried (anhydrous magnesium sulphate) and filtered. The filtrate was evaporated to dryness to give 3-methoxycarbonyl-2-methyl-4-methylsulphenylbenzamide (4.2 g) as an orange oil, NMR (CDCl$_3$) 2.3(s,3H), 2.4(s,3H), 3.9(s,3H), 6.5(bs,2H), 6.95(d,1H), 7.25(d,1H).

By proceeding in a similar manner, the following compounds were prepared:

2-methyl-3-(1-methylethoxycarbonyl)-4-methylsulphenylbenzamide, as an orange oil which was not further purified, starting from 1-methylethyl 3-cyano-2-methyl-6-methylthiobenzoate.

3-methoxycarbonyl-2-methyl-4-(1-methylethylsulphenyl)benzamide, NMR (CDCl$_3$) 1.2 (d,6H) 2.3(s,3H) 3.3(m,1H) 3.9(s,3H) 6.6(bs,2H) 7.5 (m,2H).

REFERENCE EXAMPLE 25

A mixture of methyl 3-iodo-2-methylmethylsulphenylbenzoate (16.6 g) and cuprous cyanide (4.4 g) in dimethyl formamide (50 ml) was stirred and heated at 150° C. for 1 hour. The mixture was cooled to 90° C. and a solution of ferric chloride (18 g) in water (28 ml) and concentrated hydrochloric acid (5 ml) was added. The mixture was stirred and heated at 90° C. for 1 hour. The cooled mixture was filtered and the solid was washed with ether. The layers in the filtrate were separated and the aqueous layer was extracted with ether (100 ml). The combined organic layers were washed with water (2×100 ml), aqueous sodium sulphate solution (10%, 2×100 ml), water (2×100 ml), aqueous sodium hydroxide solution (2×100 ml), water (3×100 ml), dried (anhydrous MgSO$_4$) and filtered. The filtrate was evaporated to dryness to give methyl 3-cyano-2-methyl-6-methylsulphenylbenzoate (10.0 g) as a brown oil NMR (CDCl$_3$) 2.5(s,6H), 3.9(s,3H), 7.05(d,1H), 7.45(d,1H).

By proceeding in a similar manner, the following compounds were prepared:

1-methylethyl 3-cyano-2-methyl-6-methylsulphenylbenzoate as an orange gum NMR (CDCl$_3$) 1.3(d,6H), 2.35(s,6H), 5.0(m,1H), 6.7–7.2(m, 2H) starting from 1-methylethyl 3-iodo-2-methyl-6-methylsulphenylbenzoate.

Methyl 3-cyano-2-methyl-6-(1-methylethylsulphenyl) benzoate, NMR (CDCl$_3$) 1.3(d,6H) 2.5(s,3H) 3.4(m, 1H) 3.9(s,3H) 7.2(d,1H) 7.45(d,1H).

REFERENCE EXAMPLE 26

A solution of sodium nitrite (6.7 g) in water was added to a stirred, cooled mixture of methyl 3-amino-2-methyl-6-(1-methylethylsulphenyl)-benzoate (18 g) in concentrated hydrochloric acid while maintaining the temperature below 0° C. The resultant mixture was added to a solution of potassium iodide (16 g) in water while maintaining the temperature at about 80° C. The resultant mixture was stirred at 80° C. for 15 mins then cooled to room temperature. It was diluted with water and extracted with dichloromethane. The organic layer was washed with sodium bicarbonate solution, water, dried (MgSO$_4$) and filtered. The filtrate was evaporated to dryness to give methyl 3-iodo-2-methyl-6-(1-methylethylsulphenyl)benzoate (20.5 g) as a red oil. NMR (CDCl$_3$) 1.25 (d,6H) 2.35(s,3H) 3.2(m,1H) 3.9(s,3H) 6.9(d,1H) 7.6(d,1H).

REFERENCE EXAMPLE 27

A suspension of methyl 3-amino-2-methyl-6-thiocyanatobenzoate (22.2 g) in ethanol was added to a solution of sodium sulphide (26.6 g) in water. The resultant mixture was stirred at room temperature for 1 hour and then cooled to 5° C. 2-Iodopropane (19.36 g) was added and the mixture was allowed to warm to room temperature and stirred for 2 hours. It was evaporated to dryness and the residue was suspended in aqueous sodium chloride solution and extracted with dichloromethane. The organic layer was dried (MgSO$_4$) and filtered. The filtrate was evaporated to dryness to give methyl 3-amino-2-methyl-6-(1-methylethylsulphenyl)benzoate (18 g) as a yellow oil NMR (CDCl$_3$) 1.2(d,6H) 2.0(s,3H) 3.0(m,1H) 3.8(bs,2H) 3.9(s, 1H) 6.5(d,1H) 7.0(d,1H).

REFERENCE EXAMPLE 28

A solution of sodium hydroxide (41.6 g) in water was added to a solution of ethyl 2,6-dichloro-4-trifluoromethylbenzoate (96.3 g) in ethanol. The mixture was heated at reflux for 2.5 hours then cooled and evaporated. It was diluted with water and extracted with ether. The aqueous layer was acidified to pH1 and extracted with ether, washed with water, dried (Na$_2$SO$_4$) and filtered. The filtrate was evaporated to dryness and the residue was triturated with n-hexane and filtered to give 2.6-dichloro-4-trifluoromethylbenzoic acid (62.3 g) as a white solid mp 138.5°–139° C.

REFERENCE EXAMPLE 29 n-Butyllithium (1.6M in hexane, 330 ml) was added dropwise with stirring to a solution of 2,6-dichloro-4-trifluoromethylbromobenzene (163.3 g) in ether while maintaining the temperature below −70° C. The mixture was stirred for 1 hour at −78° C. then ethyl chloroformate (61.7 g) was added while maintaining the temperature below −70° C. The mixture was stirred at room temperature overnight. It was cooled to 0° C. and a saturated aqueous solution of ammonium chloride was added. The layers were separated and the organic layer was washed with water, dried (Na$_2$SO$_4$) and filtered. The filtrate was evaporated to dryness and the residue was distilled to give ethyl 2,6-dichloro-4-trifluoromethylbenzoate (123.9 g) as a colourless liquid bp 90°–96° C. at 5 mmHg.

REFERENCE EXAMPLE 30

A mixture of ethyl 2-chloro-4-(1,1-dimethylethylsulphonyl)-benzoate (7.66 g) and sodium hydroxide (6.09 g) in water was stirred and heated at reflux for 2 hours. It was cooled, diluted with water and acidified to pH1. It was extracted with ethyl acetate, washed with water, dried (MgSO$_4$) and filtered. The filtrate was evaporated to dryness to give 2-chloro-4-(1,1-dimethylethylsulphonyl)benzoic acid (5.67 g) as an off white solid mp 155.2°–156.8° C.

By proceeding in a similar manner the following compound was prepared from the appropriately substituted starting material: 4Methylsulphonyl-2-(methylsulphenyl) benzoic acid mp 180.8°–181.6° C.

REFERENCE EXAMPLE 31

A solution of potassium peroxymonosulphate (34 g) in water was added to a solution of ethyl 2-chloro-4-(1,1-dimethylethylsulphenyl)benzoate (11.72 g) in ethanol while maintaining the temperature below 20° C. The mixture was stirred at room temperature for 2 hours. It was extracted with dichloromethane, washed with water, dried (MgSO$_4$) and filtered.

The filtrate was evaporated to dryness. The residue was recrystallized from a mixture of ether and cyclohexane to give ethyl 2-chloro-4-(1,1-dimethylethylsulphonyl)-benzoate (7.66 g) as a pale yellow solid mp 82.4°–83° C.

By proceeding in a similar manner the following compounds were prepared from the appropriately substituted starting materials;

3-chloro-2-(methylsulphonyl)benzoic acid mp 152°–153.6° C.

3-methoxy-2-(methylsulphonyl)benzoic acid mp 206°–208° C.

REFERENCE EXAMPLE 32

2-Methyl-2-propanethiol (7.47 g) was added to a suspension of potassium carbonate (9.52 g) in acetone. Ethyl 2-chloro-4-nitrobenzoate (10 g) was added and the mixture was stirred at room temperature overnight. Further 2-methyl-2-propanethiol (1.0 g) was added and the mixture was stirred and heated to 30° C. for 1 hour. Further 2-methyl-2-propanethiol (1.0 g) was added and the mixture was stirred and heated at reflux for 0.5 hours. Potassium carbonate (9.52 g) and 2-methyl-2-propanethiol was added and the mixture was stirred and heated at reflux overnight. Water was added and it was extracted with ethyl acetate, washed with water, dried (MgSO$_4$) and filtered. The filtrate was evaporated to dryness to give ethyl 2-chloro-4-(1,1-diethylethylsulphenyl)benzoate (12.1 g) as a red oil NMR (CDCl$_3$) 1.3 (s,9H) 1.35(t,3H) 4.3(q,2H) 7.1–7.7 (m,3H).

REFERENCE EXAMPLE 33 t-Butyl nitrite (1.52 g) was added to a mixture of 4-chloro-2-methylaniline (2.0 g) and dimethyl disulphide (14.49 g) in chloroform The mixture was heated to 70° C. to initiate the reaction. A solution of 4-chloro-2-methylaniline (9.0 g) in chloroform and t-butyl nitrite (7.25 g) were added simultaneously while maintaining the temperature in the range 60°–70° C. Further dimethyl disulphide (11.83 g) was added followed by the simultaneous addition of a solution of 4-chloro-2-methylaniline (9.0 g) in chloroform and t-butyl nitrite (7.25 g) while maintaining the temperature in the range 50°– 55° C. The mixture was stirred at room temperature for 2 hours. It was washed thoroughly with water, 2M hydrochloric acid, water, dried (MgSO$_4$) and filtered. The filtrate was evaporated to dryness to give 5-chloro-2-(methylsulphenyl)toluene (22.15 g) as a red oil which was not further characterized.

By proceeding in a similar manner the following compounds were prepared from the appropriately substituted starting materials.

5-Fluoro-2-(methylsulphenyl)toluene which was not further characterized.

2-Trifluoromethyl-4-(ethylsulphenyl)bromobenzene bp 105°–112° C. at 7 mmHg.

Ethyl 4-methylsulphonyl-2-(Methylsulphenyl)benzoate NMR (CDCl$_3$) 1.45(t,3H) 2.55(s,3H) 3.1(s,3H) 4.45(q, 2H) 7.6–8.4(m,3H).

REFERENCE EXAMPLE 34

Potassium permanganate (93.3 g) was added to a suspension of 5-chloro-2-(methylsulphenyl)toluene (22.0 g) in water while maintaining the mixture at reflux by external heating. The mixture was stirred and heated at reflux for 2 hours then filtered. The solid was washed thoroughly with water and ethyl acetate. The filtrate was extracted with ether and the aqueous layer was acidified to pH1. It was extracted with ethyl acetate, washed with water, dried (MgSO$_4$) and filtered. The filtrate was evaporated to dryness to give 5-chloro-2-(methylsulphonyl)benzoic acid (9.57 g) as a cream solid mp 138°–146° C.

By proceeding in a similar manner the following compounds were prepared from the appropriately substituted starting materials;

5-Fluoro-2-methylsulphonylbenzoic acid mp 141°–145° C.

2-Fluoro-6-methylsulphonylbenzoic acid NMR (DMSO) 3.35(s,3H) 7.6–7.9(m,3H) 14.2(bs,1H).

REFERENCE EXAMPLE 35 n-Butyllithium (2.5M in hexane, 38 ml) was added to a stirred, cooled solution of 2-chloro-4-trifluoromethoxybromobenzene (25 g) in ether while maintaining the temperature below −70° C. The mixture was stirred at −78° C. for 4 hours then poured onto solid carbon dioxide with stirring. The mixture was allowed to warm to room temperature and acidified to pH1. The layers were separated and the organic layer was washed with water, dried (MgSO$_4$) and filtered. The filtrate was evaporated to dryness and the residue was triturated with cyclohexane and filtered to give 2-chloro-4-trifluoromethoxybenzoic acid as a white solid mp 90.6°–91.2° C.

By proceeding in a similar manner the following compounds were prepared from the appropriately substituted starting materials.

4-ethylsulphenyl-2-trifluoromethylbenzoic acid mp 132.8°–134.8° C.

2-Chloro-3-cyano-4-(methylsulphenyl)benzoic acid mp 256° C.

REFERENCE EXAMPLE 36

A solution of sodium nitrite (16.31 g) in concentrated sulphuric acid was added dropwise to a solution of 2-chloro-4-trifluoromethoxyaniline (50 g) in acetic acid, while maintaining the temperature below 10° C. The mixture was stirred at 5°–10° C. for 0.5 hours then added slowly to a mixture of cuprous bromide (33.9 g) in aqueous hydrobromic acid (200 ml) and ice. The mixture was stirred at room temperature for 0.5 hours and left to stand overnight. The mixture was diluted with water and extracted with dichloromethane, washed with water, dried (MgSO$_4$) and filtered. The filtrate was evaporated to dryness to give 2-chloro-4-trifluoromethoxybromobenzene (63.64 g) as a brown oil which was not further purified.

REFERENCE EXAMPLE 37

A suspension of crude 2,3-dichloro-4-trifluoromethoxybenzoyl fluoride (2 g, containing mixed antimony halides) in water was stirred vigorously for 24 hours. The mixture was extracted with dichloromethane and filtered. The organic layer was washed with hydrochloric acid (2M), aqueous sodium chloride solution and extracted into sodium carbonate solution (2M). The aqueous extract was acidified to pH1 and the solid was filtered off and washed with water to give 2,3-dichloro-4-trifluoromethoxybenzoic acid (0.6 g) as a white solid mp 123°–126° C.

REFERENCE EXAMPLE 38

2,3-Dichloro-4-trichloromethoxybenzoyl chloride (17.2 g) was added to a mixture of antimony trifluoride (10.6 g) and antimony pentachloride (1 g). The mixture was heated at reflux for 10 mins then flash distilled to give crude 2,3-dichloro-4-trifluoromethoxybenzoyl fluoride (20 g) as a semi-solid bp 211°–215° C.

REFERENCE EXAMPLE 39

Chlorine was bubbled through a mixture of 2,3-dichloro-4-methoxybenzoyl chloride (12 g) in carbon tetrachloride while irradiating with a 100W Hanovia UV lamp for 2.5 hours. Nitrogen was passed through the mixture which was evaporated to dryness to give 2,3-dichloro-4-trichloromethoxybenzoyl chloride (17.2 g) which was used without further purification.

REFERENCE EXAMPLE 40

A mixture of 2-(3-chloro-2-methylsulphenylphenyl)-4,4-dimethyloxazoline (8.2 g) and hydrochloric acid (4.5M) was stirred and heated at reflux for 5 hours. It was cooled and extracted with dichloromethane, washed with water, dried ($Na_2SO_4$) and filtered.

The filtrate was evaporated to dryness and the residue was recrystallized from toluene to give 3-chloro-2-methylsulphenylbenzoic acid (4.2 g) as a white solid NMR ($CDCl_3$) 3.0(s,3H) 7.6–8.2(m,3H) 11.0(bs,1H).

By proceeding in a similar manner the following compound was prepared from the appropriately substituted starting material:

3-methoxy-2-(methylsulphenyl)benzoic acid as a white solid which was not further characterized.

REFERENCE EXAMPLE 41 n-Butyllithium (2.5M in hexane, 4.2 ml) was added to a solution of 2-(3-chlorophenyl)-4,4-dimethyloxazoline (2 g) in THF while maintaining the temperature below −45° C. The mixture was stirred at −65° C. for 3 hours. Dimethyl disulphide (1.0 g) was added and the mixture was stirred at −65° C. for 2.5 hours and allowed to warm to room temperature. Ether was added and the mixture was washed with water, dried ($MgSO_4$) and filtered. The filtrate was evaporated to dryness to give 2-(3-chloro-2-methylsulphenylphenyl)-4,4-dimethyloxazoline (2.35 g) as a yellow oil NMR ($CDCl_3$) 2.0(s,6H) 3.0(s,3H) 4.65(s,2H) 7.5–8.1(m,3H).

By proceeding in a similar manner the following compound was prepared from the appropriately substituted starting materials:

2-(3-methoxy-2-methylsulphenylphenyl)-4,4-dimethyloxazoline as a yellow oil which was not further characterized.

REFERENCE EXAMPLE 42

A solution of potassium hydroxide (1.46 g) in water was added to a mixture of ethyl 2-bromo-4-ethylsulphenyl-3-methoxybenzoate (3.98 g) in ethanol with stirring. The mixture was stirred and heated at reflux for 4 hours. It was cooled and evaporated then water was added and the mixture was washed with ethyl acetate then acidified to pH1. It was extracted with ethyl acetate, washed with water, dried ($MgSO_4$) and filtered. The filtrate was evaporated to dryness to give 2-bromo-4-ethylsulphenyl-3-methoxybenzoic acid as an off-white solid NMR ($CDCl_3$) 1.5(t,3H) 3.05(q,2H) 3.9(s,3H) 7.15(d,1H) 7.6(d,1H).

By proceeding in a similar manner the following compound was prepared from the appropriately substituted starting material:

2-bromo-3-difluoromethoxy-4-(ethylsulphonyl)benzoic acid NMR ($CDCl_3$) 1.1–1.4(m,3H) 3.3–3.7(m,2H) 6.9 (t,1H) 7.9 (d,1H) 8.15(d,1H)

REFERENCE EXAMPLE 43

Ethyl mercaptan (5 ml) was added to a suspension of ethyl 2,4-dibromo-3-methoxybenzoate (10.0 g) and potassium carbonate (9.0 g) in dimethylformamide (DMF). The mixture was stirred at room temperature for 48 hours, water was added and the mixture was extracted with ether, washed with water, dried ($MgSO_4$) and filtered. The filtrate was evaporated to dryness and the residue was purified by medium pressure chromatography eluted with a mixture of ethyl acetate and cyclohexane to give ethyl 2-bromo-4-(ethylsulphenyl)-3-methoxybenzoate (3.98 g) as an oil NMR ($CDCl_3$) 1.35(m,6H) 2.9(q,2H) 3.8(s,3H) 4.4(q,2H) 7.1–7.4 (m,2H).

By proceeding in a similar manner the following compound was prepared from the appropriately substituted starting material:

Ethyl 2-bromo-4-(ethylsulphenyl)-3-difluoromethoxybenzoate NMR ($CDCl_3$) 1.4(m,6H) 3.0(q,2H) 4.4(q,2H) 6.6(t,1H) 7.2(d,1H) 7.6(d,1H).

REFERENCE EXAMPLE 44

Chlorodifluoromethane was bubbled into a mixture of ethyl 2,4-dibromo-3-hydroxybenzoate (1.5 g), potassium carbonate (9.66 g) and potassium iodide (1.83 g) in DMF. The mixture was then heated at 70°–75° C. for 2.5 hours. It was evaporated and poured into water, and acidified to pH1. It was extracted with dichloromethane, washed with water, dried ($MgSO_4$) and filtered. The filtrate was evaporated to dryness and the residue was purified by column chromatography eluted with a mixture of ethyl acetate and hexane to give ethyl 2,4-dibromo-3-difluoromethoxybenzoate (10.89 g) as a white solid mp 45°–47° C.

REFERENCE EXAMPLE 45

A solution of ethyl 2-nitro-4-methylsulphonylbenzoate (10.0 g) in methanol was hydrogenated over 5% palladium on charcoal catalyst (1.2 g) at room temperature and atmospheric pressure. The resultant slurry was filtered and the filtrate was evaporated to dryness to give ethyl 2-amino-4-methylsulphonylbenzoate (6.5 g) as a yellow solid NMR ($CDC_3$) 1.4(t,3H) 3.1(s,3H) 4.35(q,2H) 6.1(bs,2H) 7.0(d, 1H) 7.2(s,1H) 7.95(d,1H).

REFERENCE EXAMPLE 46 n-Butyllithium (2.5M in hexane, 16.5 ml) was added to a solution of ethyl 2,6-dichlorobenzoate (6.89 g) in THF while maintaining the temperature below −70° C. The mixture was stirred at −78° C. for 1 hour and poured onto solid carbon dioxide pellets. The mixture was acidified to pH1 and extracted with ether, washed with water, dried ($MgSO_4$) and filtered. The filtrate was evaporated to dryness and the residue was recrystallized from a mixture of cyclohexane and ether to give 2,4-dichloro-3-ethoxycarbonylbenzoic acid (4.35 g) as a white solid mp 168° C.

REFERENCE EXAMPLE 47

A solution of lithium di-isopropylamide (2M in heptane, 25 ml) was added to a solution of 2,6-dichlorobenzonitrile (8.6 g) in THF while maintaining the temperature below −70° C. The mixture was stirred for 1.5 hours then poured onto solid carbon dioxide. It was stirred for 1 hour then diluted with ether. Water was added and the mixture was acidified to pH1. It was extracted with ether, washed with water, dried ($MgSO_4$) and filtered. The filtrate was evaporated to dryness to give 3-cyano-2,4-dichlorobenzoic acid (9.4 g) as a white solid mp 230°–232° C.

By proceeding in a similar manner the following compounds were prepared from the appropriately substituted starting materials.

2,4-dichloro-3-(1-methylethoxycarbonyl)benzoic acid NMR ($CDCl_3$) 1.4(d,6H) 5.4(m,1H) 7.4(d,1H) 8.0(d,1H).

4-Chloro-2-Fluoro-3-(1-methylethoxycarbonyl)benzoic acid NMR ($CDCl_3$) 1.35(d,6H), 5.3(m1H), 7.25(d,1H), 7.95(t,1H)

2-fluoro-3-(1-methylethoxycarbonyl)-4-trifluoromethylbenzoic acid NMR ($CDCl_3$) 1.35(d,6H), 5.35(m,1H), 7.6(d,1H), 8.15(t,1H).

REFERENCE EXAMPLE 48

Iron powder (0.5 g) and iodine (0.05 g) were added to a solution of 2-chloro-6-(methylsulphenyl)benzonitrile (10.0 g) in a mixture of carbon tetrachloride and dichloromethane. The mixture was warmed to 30° C. and bromine (9.5 g) was added. The mixture was heated at 55° C. for 5 hours. It was cooled, washed with aqueous sodium bisulphite, water, dried ($MgSO_4$) and filtered. The filtrate was evaporated to dryness and the residue was redissolved in a mixture of carbon tetrachloride and dichloromethane and treated with iron powder (0.5 g) and iodine (0.05 g). Bromine (6.5 g) was added and the mixture was heated at 55° C. for 5 hours. It was cooled and washed with sodium bisulphite, water, dried ($MgSO_4$) and filtered. The filtrate was evaporated to dryness and the residue was purified by column chromatography eluted with a mixture of ethyl acetate and n-hexane to give 3-bromo-2-chloro-6-(methylsulphenyl)benzonitrile (6.51 g) as an orange solid NMR ($CDCl_3$) 2.5(s,3H) 7.0(d,1H) 7.65 (d,1H).

REFERENCE EXAMPLE 49

Methane thiol (3.07 g) was bubbled into a solution of methyl 4-chloro-2-fluoro-3-(1-methylethoxycarbonyl) benzoate (15.9 g) in DMF. The mixture was stirred for 0.5 hours then lithium hydroxide hydrate (7.29 g) was added. The mixture was stirred at room temperature for 24 hours. It was diluted with water and acidified to pH1. It was extracted with ether, washed with water, dried ($MgSO_4$) and filtered. The filtrate was evaporated to dryness and the residue was recrystallized from cyclohexane to give 4-chloro-3-(1-methylethoxycarbonyl)-2-methylsulphenylbenzoic acid (7.5 g) as a white solid NMR ($CDCl_3$) 1.4(d,6H) 2.55(s,3H) 5.45(m,1H) 7.5(d,1H) 8.0(d,1H).

By proceeding in a similar manner the following compound was prepared from the appropriately substituted starting material:

3-(1-methylethoxycarbonyl)-2-(methylsulphenyl)-4-trifluoromethylbenzoic acid NMR ($CDCl_3$) 1.4(d,6H) 2.5(s,3H) 5.4(m,1H) 7.75(d,1H) 8.0(d,1H).

REFERENCE EXAMPLE 50

A mixture of 4-chloro-2-fluoro-3-(1-methylethoxycarbonyl)benzoic acid (19.77 g) and thionyl chloride was stirred and heated at reflux for 2 hours. After cooling to room temperature, the mixture was evaporated to dryness. Toluene was added and the mixture was re-evaporated. The residue was dissolved in methanol and heated at reflux for 48 hours. It was cooled and evaporated to dryness to give methyl 4-chloro-2-fluoro-3-(1-methylethoxycarbonyl)benzoate (20.3 g) as an orange oil NMR ($CDCl_3$) 1.35(d,6H) 3.85(s,3H) 5.2(m,1H) 7.2(d,1H) 7.85(t,1H).

By proceeding in a similar manner the following compound was prepared from the appropriately substituted starting materials:

Methyl 2-fluoro-3-(1-methylethoxycarbonyl)-4-trifluoromethylbenzoate, NMR ($CDCl_3$) 1.4(d,6H), 4.0 (s,3H), 5.35(m,1H), 7.55(d,1H), 8.1(t,1H).

REFERENCE EXAMPLE 51

A mixture of 3-cyclopropyl-1-[2-bromo-3-(2-methoxyethoxy)-4-methylsulphonylphenyl]propan-1,3-dione (7.5 g) and triethylorthoformate (10.3 g) in acetic anhydride was stirred and heated at reflux for 3 hours. It was evaporated to dryness and the residue was treated with xylene and re-evaporated to give crude 3-cyclopropyl-1-[2-bromo-3-(2-methoxyethoxy)-4-methylsulphonylphenyl]-2-ethoxymethylenepropan-1,3-dione (8.5 g) as a dark brown oil which was not purified further.

By proceeding in a similar manner the following compounds were prepared (but not purified) from the appropriately substituted starting materials.

| $R^1$ | $(R^2)n$ |
|---|---|
| Cp | 2,4-$Br_2$-3-O($CH_2$)$_2$OMe |
| 1-Me-Cp | 2-Br-3-O($CH_2$)$_2$OMe-4-$SO_2$Me |
| Me | 2-Br-3-O($CH_2$)$_2$OMe-4-$SO_2$Me |
| Cp | 2-Cl-3-O($CH_2$)$_2$OMe-4-$SO_2$Me |
| $^i$Pr | 2-Cl-3-O($CH_2$)$_2$OMe-4-$SO_2$Me |
| Me | 2-Cl-3-O($CH_2$)$_2$OMe-4-$SO_2$Me |
| Cp | 2-Br-3-O($CH_2$)$_2$OMe-4-SMe |
| Cp | 2-$SO_2$Me-3-O($CH_2$)$_2$OMe-4-Br |
| Cp | 2-SMe-3-O($CH_2$)$_2$OMe |

REFERENCE EXAMPLE 52

A mixture of crude t-butyl 2-[2-bromo-3-(2-methoxyethoxy)-4-methylsulphonylbenzoyl]-3-cyclopropyl-3-oxopropanoate (10.2 g) and 4-toluenesulphonic acid (2 g) in dry toluene was stirred and heated at reflux for 2 hours. The cooled mixture was washed with water, dried (anhydrous magnesium sulphate) and filtered. The filtrate was evaporated to dryness to give 3-cyclopropyl-1-[2-bromo-3-(2-methoxyethoxy)-4-methylsulphonylphenyl]propan-1,3-dione (7.5 g) as a brown oil which was not purified further NMR($CDCl_3$) 0.9(4H,m), 1.5(1H,m), 3.1(3H,s), 3.3(3H,s), 3.6(2H,t), 4.2(2H,t), 5.7 (1H,s), 7.15(1H,d), 7.8(1H,d).

By proceeding in a similar manner the following compounds were prepared from the appropriately substituted starting materials.

[Structure: (R²)ₙ-phenyl-C(=O)-CH₂-C(=O)-R¹]

| R¹ | (R²)n | m.p./NMR |
|---|---|---|
| Cp | 2,4-Br₂-3-O(CH₂)₂OMe | 1.5(4H, m) 2.1(1H, m) 3.9(3H, s) 4.2(2H, t) 4.6(2H, t) 6.3(1H, s) 7.4(1H, d) 7.9(1H, d) |
| 1-Me-Cp | 2-Br-3-O(CH₂)₂OMe-4-SO₂Me | 1.2(2H, m) 1.5(2H, m) 1.7(3H, s) 3.6(3H, s) 3.8(3H, s) 4.15(2H, t) 4.7(2H, t) 6.2(1H, s) 7.65(1H, d) 8.3(1H, d) |
| Me | 2-Br-3-O(CH₂)₂OMe-4-SO₂Me | 2.4(3H, s) 3.5(3H, s) 3.7(3H, s) 4.0(2H, t) 4.6(2H, t) 6.1(1H, s) 7.55(1H, d) 8.15(1H, d) |
| Cp | 2-Cl-3-O(CH₂)₂OMe-4-SO₂Me | 1.1(4H, m) 1.7(1H, m) 3.3(3H, s) 3.5(3H, s) 3.8(2H, t) 4.3(2H, t) 5.9(1H, s) 7.3(1H, d) 7.7(1H, d) |
| ⁱPr | 2-Cl-3-O(CH₂)₂OMe-4-SO₂Me | 1.1(6H, d) 2.4(1H, m) 3.1(3H, s) 3.3(3H, s) 3.6(2H, t) 4.2(2H, t) 5.7(1H, s) 7.1(1H, d) 7.7(1H, d) |
| Me | 2-Cl-3-O(CH₂)₂OMe-4-SO₂Me | 2.4(3H, s) 3.5(3H, s) 3.7(3H, s) 4.0(2H, t) 4.6(2H, t) 6.0(1H, s) 7.4(1H, d) 8.0(1H, d) |
| Cp | 2-Br-3-O(CH₂)₂OMe-4-SMe | 1.2(4H, m) 1.8(1H, m) 2.5(3H, s) 3.5(3H, s) 3.8(2H, t) 4.2(2H, t) 6.0(1H, s) 7.1(2H, m) |
| Cp | 2-SO₂Me-3-O(CH₂)₂OMe-4-Br | 1.0(4H, m) 2.0(1H, m) 3.3(3H, s) 3.5(3H, s) 3.9(2H, t) 4.4(2H, t) 5.75(1H, s) 7.0(1H, d) 7.7(1H, d) |
| Cp | 2-SMe-3-O(CH₂)₂OMe | — |

REFERENCE EXAMPLE 53

Carbon tetrachloride (1 ml) was added to a stirred mixture of t-butyl-3-cyclopropyl-3-oxopropionate (4.5 gl) and magnesium (0.68 g) in methanol (30 ml), causing a vigorous reaction. The mixture was stirred for 0.25 hours and evaporated to dryness. The residue was dissolved in acetonitrile (100 ml) and a solution of 2-bromo-3-(2-methoxyethoxy)-4-methylsulphonylbenzoyl chloride in acetonitrile (50 ml) was added and the resultant mixture stirred at room temperature for 2 hours then left to stand overnight. The acetonitrile was removed under reduced pressure and the residue was suspended in toluene. The toluene suspension was washed with 2M HCl, followed by water. The resultant organic solution was dried (anhydrous magnesium sulphate) and filtered. The filtrate was evaporated to dryness to give crude tert-butyl 2-[2-bromo-3-(2-methoxyethoxy)-4-methylsulphonylbenzoyl]-3-cyclopropyl-3-oxopropionate (10.27 g) as a crude brown oil which was not purified further.

By proceeding in a similar manner the following compounds were prepared (but not purified) from the appropriately substituted starting materials.

[Structure: (R²)ₙ-phenyl-C(=O)-CH(CO₂tBu)-C(=O)-R¹]

| R¹ | (R²)n | Reaction Solvent |
|---|---|---|
| Cp | 2,4-Br₂-3-O(CH₂)₂OMe | CH₃CN |
| 1-Me-Cp | 2-Br-3-O(CH₂)₂OMe-4-SO₂Me | Toluene |
| Me | 2-Br-3-O(CH₂)₂OMe-4-SO₂Me | Toluene |
| Cp | 2-Cl-3-O(CH₂)₂OMe-4-SO₂Me | CH₃CN |
| ⁱPr | 2-Cl-3-O(CH₂)₂OMe-4-SO₂Me | CH₃CN |
| Me | 2-Cl-3-O(CH₂)₂OMe-4-SO₂Me | CH₃CN |
| Cp | 2-Br-3-O(CH₂)₂OMe-4-SMe | CH₃CN |
| Cp | 2-SO₂Me-3-O(CH₂)₂OMe-4-Br | CH₃CN |
| Cp | 2-SMe-3-O(CH₂)₂OMe | CH₃CN |

Benzoyl chlorides were prepared by heating the appropriately substituted benzoic acids at reflux with thionyl chloride for 3 hours.

REFERENCE EXAMPLE 54

Ethyl 2-bromo-3-(2-methoxyethoxy)-4-methylsulphenylbenzoate (24.3 g) was added to a solution of potassium hydroxide (9.1 g) in water (25 ml) and industrial methylated spirits (300 ml). The resultant mixture was heated at reflux for 4 hours and then allowed to cool to room temperature overnight. The mixture was evaporated and the residue dissolved in water and washed with ether. The aqueous layer was acidified to pH 1 with 2M HCl and extracted with ethyl acetate. The ethyl acetate layer was washed with water, dried (anhydrous magnesium sulphate) and filtered. The filtrate was evaporated to dryness yielding 2-bromo-3-(2-methoxyethoxy)-4-methylsulphenyl benzoic acid (19.4 g) as a white solid, NMR (CDCl₃) 2.2(3H,s), 3.25(3H,s), 3.6(2H,t), 3.8(2H,t), 7.0(2H,m).

By proceeding in a similar manner 4-bromo-3-(2-methoxyethoxy)-2-methylsulphonylbenzoic acid was prepared as a white solid mp 156°–157.8° C. starting from ethyl 4-bromo-3-(2-methoxyethoxy)-2-methylsulphonylbenzoate.

REFERENCE EXAMPLE 55

Ethyl 4-bromo-3-(2-methoxyethoxy)-2-methylsulphenylbenzoate (5.0 g) was stirred in acetic acid (8.0 ml) and acetic anhydride (2.0 ml) at 0° C. To the mixture was added hydrogen peroxide (11 ml). The mixture was stirred at 0° C. for 1 hour and then overnight at room temperature. The mixture was then heated at 85° C. for 1 hour. After cooling to room temperature, the mixture was diluted with ethyl acetate and washed with water, followed by ferrous sulphate, followed by water. The organic extract was dried (anhydrous magnesium sulphate) and filtered. The filtrate was evaporated to dryness yielding ethyl 4-bromo-3-(2-methoxyethoxy)-2-methylsulphonylbenzoate (4.7 g) NMR (CDCl₃) 1.8(3H,t), 3.4(3H,s), 3.8(3H,s), 4.15(2H,t), 4.3(2H,q), 4.6(2H,t), 7.15(H,d), 7.85(1H,d).

REFERENCE EXAMPLE 56

Ethyl 2,4-dibromo-3-(2-methoxyethoxy)benzoate(32.2 g) was stirred in DMF (80 ml) with potassium carbonate (36 g). To the resultant suspension was added a solution of methane thiol (13 ml) in DMF (20 ml). The resultant mixture was stirred overnight at room temperature. It was then diluted with ether, and the mixture washed with water, dried (anhydrous magnesium sulphate) and filtered. The filtrate was evaporated to dryness. The residue was purified by column chromatography on silica eluting with ethyl acetate and cyclohexane (1:20) which yielded ethyl 4-bromo-3-(2-methoxyethoxy)-2-methylsulphenylbenzoate (3.5 g) as an oil which was not further characterized.

REFERENCE EXAMPLE 57

A mixture of 2-nitro-4-trifluoromethylacetophenone (10 g) and dimethylformamide dimethylacetal (20 ml) was heated at reflux for 2 hours, then evaporated to dryness and the residue was mixed with cyclohexane (20 ml), filtered to give 3-(N,N-dimethylamino)-1-(2-nitro-4-trifluoromethylphenyl)prop-2-en-1-one, (12.1 g), in the form of a red solid, m.p. 107° C.

REFERENCE EXAMPLE 58

A mixture of diethyl 2-nitro-4-trifluoromethylbenzoylmalonate (74.2 g), concentrated sulphuric acid (30 ml), water (170 ml) and glacial acetic acid (250 ml) was heated at reflux for 2 hours, then cooled, basified with aqueous sodium hydroxide solution (2M) and extracted with diethyl ether. The organic phase was washed with water, dried over anhydrous sodium sulphate, and filtered. The filtrate was evaporated to dryness and the resulting residue was recrystallized from a mixture of diethyl ether and n-hexane (1:10 v/v), to give 2-nitro-4-trifluoromethylacetophenone (30.4 g), in the form of an off-white solid, m.p. 65° C.

REFERENCE EXAMPLE 59

A mixture of magnesium turnings (4.94 g) and carbon tetrachloride (2 ml) in ethanol (35 ml) was warmed to 50° C. until the reaction started. Diethyl ether (150 ml) was then added cautiously, with stirring. A solution of diethyl malonate (32.5 g) in diethyl ether (50 ml) was then added dropwise, then stirred and heated at reflux for 2 hours. After cooling the mixture, diethyl ether (150 ml) was added. A solution of 2-nitro-4-trifluoromethylbenzoyl chloride (50.7 g) in diethyl ether (100 ml) was added dropwise. The mixture was heated at reflux for 2 hours. After cooling, hydrochloric acid (2M,200 ml) was added and the layers were separated. The organic layer was washed with water, dried (anhydrous sodium sulphate), and filtered. The filtrate was evaporated to dryness, to give diethyl 2-nitro-4-trifluoromethylbenzoylmalonate (72.6 g), in the form of an off-white solid, m.p. 60° C.

REFERENCE EXAMPLE 60

A mixture of 2-nitro-4-trifluoromethylbenzoyl chloride (8.0 g) and triphenylphosphine (16.5 g) in dry acetone (75 ml) was treated with bis-(triphenylphosphine) tetrahydroboratocopper(I) (19.8 g). The resulting suspension was stirred for 1 hour, filtered and washed with diethyl ether. The filtrate was evaporated to dryness and the resulting residue was subjected to chromatography, eluting with a mixture of diethyl ether and n-hexane (1:5 v/v), to give 2-nitro-4-trifluoromethylbenzaldehyde (5.91 g) in the form of an off-white solid, m.p. 63° C.

REFERENCE EXAMPLE 61

Concentrated nitric acid (10 ml) was added dropwise to a stirred heated mixture of iodine (23.8 g) and 5-cyclopropyl-3-methylisoxazole (24. 6 g containing approximately 20% 3-cyclopropyl-5-methylisoxazole) whilst maintaining the temperature in the range 90°–95° C. The mixture was stirred and heated at 95°–100° C. for 1 hour. It was cooled, poured into cold water and extracted with ether. The combined extracts were washed with aqueous sodium bicarbonate solution (saturated), aqueous sodium metabisulphate solution (saturated), water, dried over anhydrous sodium sulphate and filtered. The filtrate was evaporated to dryness and the residue was triturated with petroleum spirit and filtered. The solid was recrystallized from petroleum spirit to give 5-cyclopropyl-4-iodo-3-methylisoxazole (25.6 g) as a white solid, m.p. 71° C.

REFERENCE EXAMPLE 62

A mixture of 1-cyclopropylbutan-1,3-dione (65.3 g), hydroxylamine hydrochloride (36.6 g) and anhydrous potassium carbonate (71.8 g) in ethanol (375 ml) was stirred and heated at reflux for 2 hours. The mixture was cooled and filtered and the filtrate was evaporated to dryness. The residue was distilled under reduced pressure to give 5-cyclopropyl-3-methyl isoxazole containing approximately 20% 3-cyclopropyl-5-methylisoxazole (51.85 g) as a clear oil, b.p. 74° C./12 mm.Hg.

REFERENCE EXAMPLE 63

A solution of 2-nitro-4-trifluoromethylacetophenone (20.7 g) and dimethylacetamide dimethyl acetal (13.2 g) in toluene (100 ml) was stirred and heated at reflux overnight. Further dimethylacetamide dimethyl acetal (13.2 g) was added and the mixture was stirred and heated at reflux for 1.5 hours. The mixture was cooled, washed with water, dried (anhydrous sodium sulphate) and filtered. The filtrate was evaporated to dryness and the residue was triturated with a mixture of ether and cyclohexane (1:20) and filtered. The yellow solid was recrystallized from cyclohexane to give 3-dimethylamino-1-(2-nitro-4-trifluoromethylphenyl)-but-2-en-1-one (13.95 g) as a yellow solid, m.p. 122° C.

REFERENCE EXAMPLE 64

2-nitro-4-trifluoromethylbenzoyl chloride (9.4 g) was added dropwise to a cooled mixture of 1-cyclopropyl-1-diethylaminoethene (5.1 g) and triethylamine (3.7 g) in toluene (100 ml) whilst maintaining the temperature below 10° C. The mixture was then stirred at room temperature for 1 hour. The suspension was treated with decolourising charcoal and filtered. The filtrate was evaporated and the residue was purified by chromatography on silica gel eluted with a mixture of ethyl acetate and dichloromethane (1:9) to give 3-cyclopropyl-3-diethylamino-1-(2-nitro-4-trifluoromethylphenyl)-prop-2-en-1-one (4.1 g) as a red oil with its $^1$H NMR (in CDCl$_3$) giving peaks at d=0.7–1.8(m, 11H), 3.5(q, 4H), 5.0(s, 1H), 7.5(d, 1H), 7.7(d, 1H),and 7.95(s, 1H).

By proceeding in a similar manner the following compounds were prepared from the appropriately substituted starting materials:

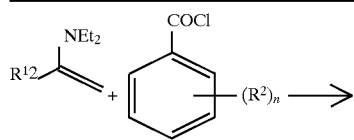

| $R^1$ | $(R^2)n$ | NMR |
|---|---|---|
| Cp | 2-Cl-4-SO$_2$Me | (CDCl$_3$): 0.6–1.8(m, 11H) 3.0(s, 3H) 3.5(q, 4H) 5.05(s, 1H) 7.4 (d, 1H) 7.65(d, 1H) 7.75(s, 1H). |
| Cp | 2-CF$_3$-4-SO$_2$Me | (CDCl$_3$): 0.5–1.8(m, 11H) 3.1(s, 3H) 3.5(q, 4H) 5.0(s, 1H) 7.5(d, 1H) 7.95(d, 1H) 8.05(s, 1H). |
| Cp | 2-SO$_2$Me | (CDCl$_3$): 0.7–1.8(m, 11H) 3.4(s, 3H) 3.5(q, 4H) 5.1(s, 1H) 7.2–7.5(m, 3H) 7.75–8.0 (m, 1H). |
| Cp | 2-NO$_2$-4-SO$_2$Me | Crude red oil not further purified. |
| Cp | 2,3-Cl$_2$-4-SO$_2$Me | (CDCl$_3$): 0.5–1.8(m, 11H) 3.25(s, 3H) 3.55(q, 4H) 5.0(s, 1H) 7.3(d, 1H) 7.9(d, 1H). |
| Cp | 2-Cl-3-OMe-4-SO$_2$Me | (CDCl$_3$): 0.6–1.8(m, 11H) 3.2(s, 3H) 3.5(q, 4H) 4.0(s, 3H) 5.0(s, 1H) 7.1(d, 1H) 7.65(d, 1H). |
| Cp | 2-SO$_2$Me-4-Cl | Crude red oil not further purified. |
| Cp | 2-CF$_3$-4-Cl | (CDCl$_3$): 0.5–1.7(m, 11H) 3.45(q, 4H) 5.0(s, 1H) 7.3(s, 2H) 7.4(s, 1H). |
| Cp | 2-SMe-4-CF$_3$ | Crude orange oil not further purified. |
| Cp | 2-CF$_3$-4-SMe | Crude orange oil not further purified. |
| Cp | 2-F-4-SO$_2$Me | Crude red oil not further purified. |
| Cp | 2-SO$_2$Me-4-Br | Crude red oil not further purified. |
| Cp | 2-Cl-4-SO$_2$Et | Crude red oil not further purified. |
| Cp | 2-Br-4-SO$_2$Me | (CDCl$_3$): 0.6–1.9(m, 11H) 3.05(s, 3H) 3.55(q, 4H) 5.05(s, 1H) 7.4(d, 1H) 7.7(d, 1H) 7.95(s, 1H). |
| Cp | 2-Cl-4-SMe | (CDCl$_3$): 0.5–1.8(m, 11H) 2.45(s, 3H) 3.45(q, 4H) 5.15(s, 1H) 6.9(d, 1H) 7.0(s, 1H) 7.25(d, 1H). |

REFERENCE EXAMPLE 65

A solution of titanium tetrachloride (10.4 g) in n-hexane (30 ml) was added dropwise with stirring to a solution of cyclopropyl methyl ketone (8.4 g) and diethylamine (43.9 g) in n-hexane (100 ml) whilst maintaining the temperature below 25° C. The mixture was stirred for 5 hours, filtered and the filtrate was evaporated to dryness to give 1-cyclopropyl-1-diethylaminoethene (5.3 g) as a pale yellow oil, NMR (CDCl$_3$) d=0.5–0.8(m, 4H), 1.1(t, 6H), 1.4(m, 1H), 3.2(q, 4H), 3.45(s, 1H), 3.5(s, 1H).

REFERENCE EXAMPLE 66

A mixture of magnesium (1.5 g) and carbon tetrachloride (0.5 ml) in methanol was stirred until the magnesium had completely dissolved. t-Butyl 3-cyclopropyl-3-oxopropionate (11.3 g) was added and the mixture was stirred and heated at reflux for 2 hours. The mixture was evaporated to dryness and the residue was dissolved in toluene. 4-Chloro-2-methylsulphonylbenzoyl chloride was added and the mixture was stirred at room temperature overnight. It was washed with hydrochloric acid and dried by azeotropic removal of water. 4-Toluenesulphonic acid (0.5 g) was added and the mixture was heated at reflux for 5 hours. The cooled solution was washed with water, dried (anhydrous sodium sulphate) and filtered. The filtrate was evaporated to dryness to give 1-(4-chloro-2-methylsulphonylphenyl)-3-cyclopropylpropan-1,3-dione (16.2 g) as an orange oil, NMR (CDCl$_3$) 0.8–1.2(m,4H) 1.5–1.9(m,1H) 3.3(s,3H) 5.8(s,1H) 7.3–7.6(m2H) 7.9(s,1H).

By proceeding in a similar manner the following compounds were prepared from the appropriately substituted starting materials.

| $R^1$ | $(R^2)n$ | NMR (CDCl$_3$) |
|---|---|---|
| Cp | 2-SO$_2$Me-4-CF$_3$ | 0.8–1.4(m, 4H) 1.5–1.8(m, 1H) 3.3(s, 3H) 5.85(s, 1H) 7.5 (d, 1H) 7.8(d, 1H) 8.2(s, 1H) |
| Cp | 2-SMe-4-Cl | 0.7–1.35(m, 4H) 1.4–1.9(m, 1H) 2.4(s, 3H) 6.1(s, 1H) 7.0–7.9(m, 3H) |
| Cp | 2-OMe-4-SMe | 0.7–1.2(m, 4H) 1.4–2.0(m, 1H) 2.4(s, 3H) 3.75(s, 3H) 6.4(s, 1H) 6.6(s, 1H) 6.6(d, 1H) 7.65(d, 1H) |
| Cp | 2-Me-4-SMe | 0.8–1.2(m, 4H) 1.4–1.8(m, 1H) 2.45(s, 6H) 5.8(s, 1H) 6.7–7.5(m, 3H) |

REFERENCE EXAMPLE 67

Potassium permanganate (316 g) was added with stirring to a suspension of 4-bromo-2-methylsulphenyltoluene (90.5 g) in water whilst maintaining the mixture at reflux. The mixture was stirred and heated at reflux for 3 hours. The mixture was filtered and the residue was washed with hot water. The filtrate was cooled to room temperature and extracted with ethyl acetate. The aqueous solution was acidified to pH 1, saturated with sodium chloride and extracted with ethyl acetate. The organic layer was washed with water, dried (anhydrous magnesium sulphate) and filtered. The filtrate was evaporated to dryness to give 4-bromo-2-methylsulphonylbenzoic acid (44.6 g) as a light brown solid, m.p. 220°–220.5° C.

By proceeding in a similar manner the following compounds were prepared from the appropriately substituted starting materials:

4-chloro-2-methylsulphonylbenzoic acid; NMR (CDCl$_3$+ DMSO-d$_6$): 3.35 (s,3H), 7.5–7.8(m,2H), 7.9 (s,1H), 8.2–8.6 (bs,1H);

2-fluoro-4-methylsulphonylbenzoic acid; m.p. 187°–189° C.

REFERENCE EXAMPLE 68

Hydrogen peroxide (30%) was added to a cooled solution of 2-methylsulphenyltrifluoromethylbenzoic acid (6.0 g) and acetic anhydride(3.6 ml) in acetic acid at 10° C. The mixture was allowed to warm slowly to room temperature and stirred for 0.5 hours. It was stirred and heated at 65° C. for 3 hours. After cooling the mixture was poured into ice and extracted with ether. The organic layer was washed with water, aqueous ferrous sulphate solution, dried (anhydrous magnesium sulphate) and filtered. The filtrate was evaporated to dryness to give 2-methylsulphonyl-4-trifluoromethylbenzoic acid (5.54 g) as a white solid, m.p. 155.5°–156.5° C.

REFERENCE EXAMPLE 69 n-Butyllithium (25M solution in hexane; 25 ml) was added under an inert atmosphere to a stirred solution 4-bromo-3-methylsulphenylbenzotrifluoride (16.4 g) in ether whilst maintaining the temperature below −70° C. The mixture was stirred at −70° C. for 2 hours and then poured onto solid carbon dioxide pellets. The mixture was stirred for 10 minutes and aqueous hydrochloric acid was added. The layers were separated and the aqueous layer was extracted with ether. The combined organic layers were washed with water, dried (anhydrous magnesium sulphate) and filtered. The filtrate was evaporated and the residue was triturated with cyclohexane and filtered to give 2-methylsulphenyl-4-trifluoromethylbenzoic acid (12.4 g) as a white solid, NMR [$CDCl_3$+DMSO-$d_6$]: 2.45 (s,3H), 7.2(d,1H), 7.3(s,1H), 8.0 (d,1H), 10.7–11.1 (bs,1H).

REFERENCE EXAMPLE 70 t-Butyl nitrite (4 ml) was added to a mixture of 5-chloro-2-methylaniline (4 g) and dimethyl disulphide (26.3 g) in chloroform. After the reaction started t-butyl nitrite (17.7 ml) and 5-chloro-2-methylaniline (16 g) were added simultaneously. The mixture was stirred at room temperature for 2 hours and left to stand overnight. The mixture was washed with water, aqueous hydrochloric acid (2M), water, dried (anhydrous magnesium sulphate) and filtered. The filtrate was evaporated to dryness to give 4-chloro-2-methylsulphenyltoluene (24.6 g) as a red oil, NMR ($CDCl_3$): 2.2(s,3H), 2.4(s,3H), 6.85(s,2H), 7.0(s,1H).

By proceeding in a similar manner the following compounds were prepared from the appropriately substituted starting materials:

4-bromo-3-methylsulphenylbenzotrifluoride, b.p. 84°–88° C. at 2 mm Hg;

2-fluoro-4-methylsulphenyltoluene, NMR ($CDCl_3$): 2.2 (s,3H), 2.45 (s,3H), 6.6–7.1 (m,3H).

REFERENCE EXAMPLE 71

A cooled solution of sodium nitrite (5.8 g) in concentrated sulphuric acid (50 ml) was added dropwise to a stirred solution of 4-methyl-3-methylsulphenylaniline (12.8 g) in glacial acetic acid at 20° C. The resulting suspension was added to a mixture of copper (I) bromide (12 g), aqueous hydrobromic acid (48–50%) and ice. The mixture was stirred at room temperature for 3 hours then diluted with water and extracted with ethyl acetate. The organic layer was washed with water, aqueous sodium hydroxide (2M), dried (anhydrous magnesium sulphate) and filtered. The filtrate was evaporated to dryness. The residue was triturated with hot cyclohexane and filtered. The filtrate was evaporated to dryness to give 4-bromo-2-methylsulphenyltoluene (8.6 g) as a brown oil, NMR ($CDCl_3$): 2.15(s,3H), 2.2(s,3H), 6.5–7.1 (m,3H).

REFERENCE EXAMPLE 72

Concentrated hydrochloric acid (128 ml) was added slowly to a suspension of 2-methylsulphenyl-4-nitrotoluene (36.6 g) in methanol. Iron powder (36 g) was added with stirring whilst maintaining the temperature below 50° C. The mixture was stirred at room temperature for 4 hours. The mixture was poured into water, neutralized (by the addition of sodium carbonate), filtered and the residue was extracted with dichloromethane. The aqueous layer was extracted with dichloromethane and the combined organic layers were washed with aqueous sodium chloride solution, dried (anhydrous magnesium sulphate) and filtered. The filtrate was evaporated to dryness and the residue was purified by column chromatography on silica eluted with a mixture of ethyl acetate and n-hexane to give 4-methyl-3-methylsulphenylaniline (12.8 g) as an orange solid, NMR ($CDCl_3$) 2.2(s,3H), 2.35 (s,3H), 3.45 (s,2H), 6.1–6.9 (m,3H).

REFERENCE EXAMPLE 73

A solution of 4-chloro-2-trifluoromethyliodobenzene (100 g) in ether was added to a suspension of magnesium (8 g) in ether at a such a rate as to maintain the mixture at reflux. The mixture was stirred at reflux for 1 hour and then cooled to 0° C. Carbon dioxide was then passed into the stirred mixture for 3 hours. Hydrochloric acid (2M) was added and the resulting layers separated. The organic layer was washed with water and then extracted into aqueous sodium carbonate solution and this aqueous extract was acidified to pH 1 and extracted with ether. The ether layer was washed with saturated sodium chloride solution, dried (anhydrous magnesium sulphate) and the solvent evaporated to give 4-chloro-2-trifluoromethylbenzoic acid (57.1 g) as a brown solid, m.p. 106.5°–108° C.

REFERENCE EXAMPLE 74

Ethyl 4-(2-chloro-4-methylsulphenylbenzoyl]-5-cyclopropylisoxazole-3-carboxylate (2.4 g) was added to a stirred solution of sodium hydroxide (2.2 g) in ethanol and water while maintaining the temperature below 0° C. The mixture was stirred at below 0° C. for 2 hours. The mixture was carefully acidified to pH1 at 0° C. and the solid was filtered off and dried to give 4-(2-chloro-4-methylsulphenylbenzoyl)-5-cyclopropylisoxazole-3-carboxylic acid (2.1 g) as an off-white solid, m.p. 106°–108° C. (decomposition).

REFERENCE EXAMPLE 75

A mixture of 3-cyclopropyl-1-(2-methoxy-4-methylsulphenylphenyl)-propan-1,3-dione (25.4 g) and triethyl orthoformate (39 g) in acetic anhydride was stirred and heated at reflux for 3 hours. After cooling the mixture was evaporated to dryness and the residue was dissolved in toluene and re-evaporated to dryness to give 3-cyclopropyl-2-ethoxymethylene-1-(2-methoxy-4-methylsulphenylphenyl)-propan-1,3-dione (30.6 g) as a red gum which was not further purified.

By proceeding in a similar manner the following compounds were prepared from the appropriately substituted starting materials:

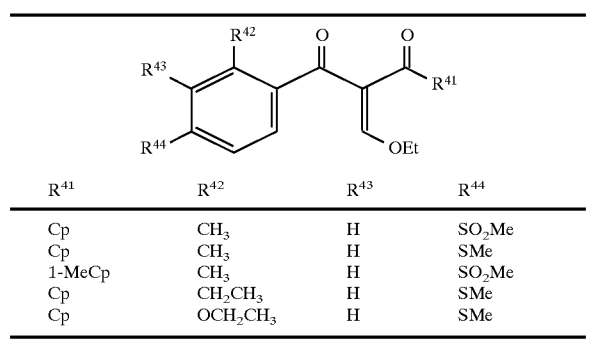

| $R^{41}$ | $R^{42}$ | $R^{43}$ | $R^{44}$ |
|---|---|---|---|
| Cp | $CH_3$ | H | $SO_2Me$ |
| Cp | $CH_3$ | H | SMe |
| 1-MeCp | $CH_3$ | H | $SO_2Me$ |
| Cp | $CH_2CH_3$ | H | SMe |
| Cp | $OCH_2CH_3$ | H | SMe |

REFERENCE EXAMPLE 76

A solution of t-butyl 3-cyclopropyl-2-(2-methoxy-4-methylsulphenylbenzoyl)-3-oxopropionate (35.1 g) and 4-toluenesulphonic acid (1.2 g) in toluene was stirred and heated at reflux for 8 hours. After cooling, it was washed with water, dried (anhydrous magnesium sulphate) and filtered. The filtrate was evaporated to dryness to give 3-cyclopropyl-1-(2-methoxy-4-methylsulphenylphenyl)-propan-1,3-dione (25.8 g) as a red solid, NMR (CDCl$_3$); 0.7–1.2 (m,4H), 1.4–2.0 (m,1H), 2.4(s,3H), 3.75 (s,3H), 6.4(s,1H), 6.6(s,1H), 6.65 (d,1H) and 7.65 (d,1H).

By proceeding in a similar manner the following compounds were prepared from the appropriately substituted starting materials:

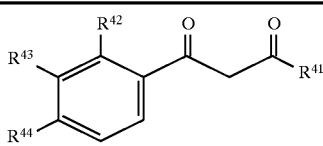

| $R^{41}$ | $R^{42}$ | $R^{43}$ | $R^{44}$ | NMR (CDCl$_3$) |
|---|---|---|---|---|
| Cp | CH$_3$ | H | SO$_2$Me | 0.8–1.3(m, 4H), 1.5–1.9(m, 1H), 1.5(s, 3H), 3.0(s, 3H), 5.8 (s, 1H), 7.5–8.1(m, 3H). |
| Cp | CH$_3$ | H | SMe | 0.8–1.2 (m, 4H), 1.4–1.8 (m, 1H), 2.45 (s, 6H), 5.8 (s, 1H), 6.7–7.5 (m, 3H). |
| 1-Me-Cp | CH$_3$ | H | SO$_2$Me | 0.7–1.1 (m, 2H), 1.2–1.5 (m, 5H), 2.4 (s, 3H), 3.0 (s, 3H), 5.75 (s, 1H) 7.4–7.8 (m, 3H). |
| Cp | CH$_2$CH$_3$ | H | SMe | Not characterized |
| Cp | OCH$_2$CH$_3$ | H | SMe | 0.9(m, 2H), 1.1(m, 2H), 1.4 (t, 3H), 1.7(m, 1H), 2.5(s, 3H) 4.0(q, 2H) 6.6(s, 1H) 6.8(m, 2H) 7.9(m, 1H) |

REFERENCE EXAMPLE 77

Carbon tetrachloride (2 ml) was added to a suspension of magnesium (2.67 g) in methanol and the mixture was stirred and heated at reflux for 0.5 hours. After cooling t-butyl 3-cyclopropyl-3-oxopropionate (18.4 g) was added. The mixture was stirred and heated at reflux for 0.5 hours. The mixture was evaporated to dryness and toluene was added to the residue. It was re-evaporated and the residue was suspended in acetonitrile. A solution of 2-methoxy-4-methylsulphenylbenzoyl chloride (21.8 g) in acetonitrile was added and the mixture was stirred for 4 hours. It was evaporated to dryness and the residue was dissolved in ethyl acetate, washed with aqueous hydrochloric acid (2M), water, dried (anhydrous magnesium sulphate) and filtered. The filtrate was evaporated to dryness to give t-butyl 3-cyclopropyl-2-(2-methoxy-4-methylsulphenylbenzoyl)-3-oxopropionate (36 g) as a brown oil which was not purified further.

By proceeding in a similar manner the following compounds were prepared from the appropriately substituted starting materials:

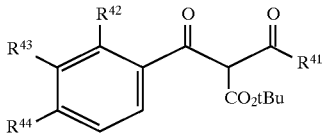

| $R^{41}$ | $R^{42}$ | $R^{43}$ | $R^{44}$ |
|---|---|---|---|
| Cp | CH$_3$ | H | SO$_2$Me |
| Cp | CH$_3$ | H | SMe |
| 1-MeCp | CH$_3$ | H | SO$_2$Me |
| Cp | CH$_2$CH$_3$ | H | SMe |
| Cp | OCH$_2$CH$_3$ | H | SMe |

REFERENCE EXAMPLE 78

A mixture of 1-(4-chloro-2-methylsulphonylphenyl)-3-cyclopropylpropan-1,3-dione (7.1 g) and triethyl orthoformate (6.9 g) in acetic anhydride was stirred and heated at reflux for 2 hours. The mixture was evaporated to dryness, toluene was added and the solution was re-evaporated to give 1-(4-chloro-2-methylsulphonylphenyl)-3-cyclopropyl-2-ethoxymethylenepropan-1,3-dione (8.4 g) as a red gum which was not purified further.

By proceeding in a similar manner the following compounds were prepared from the appropriately substituted starting materials:

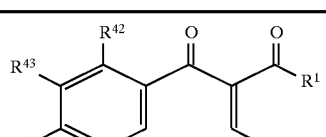

| $R^1$ | $R^{42}$ | $R^{43}$ | $R^{44}$ |
|---|---|---|---|
| Cp | SO$_2$Me | H | CF$_3$ |
| Cp | SMe | H | CF$_3$ |
| Cp | SO$_2$Me | H | Br |
| 1-MeCp | SO$_2$Me | H | Cl |
| iPr | SO$_2$Me | H | Cl |
| Cp | SO$_2$Me | H | F |
| Cp | SO$_2$Me | H | CH$_3$ |
| Cp | SO$_2$Me | H | OCH$_3$ |
| Cp | SO$_2$Et | H | Cl |
| Cp | SMe | H | Cl |
| iPr | SO$_2$Me | H | CF$_3$ |
| 1-MeCp | SO$_2$Me | H | CF$_3$ |
| Me | SO$_2$Me | H | Cl |
| iPr | SMe | H | Cl |
| 1-MeCp | SO$_2$Et | H | Cl |
| iPr | SO$_2$Et | H | Cl |
| Et | SO$_2$Me | H | Cl |
| 1-MeCp | SO$_2$Me | H | Br |
| iPr | SO$_2$Me | H | Br |

REFERENCE EXAMPLE 79

A mixture of t-butyl 2-(4-chloro-2-methylsulphonylbenzoyl)-3-cyclopropyl-3-oxopropionate (9.5 g) and 4-toluenesulphonic acid (15 g) in toluene was stirred and heated at reflux for 3 hours. After cooling, the mixture was washed with water, dried (anhydrous magnesium sulphate) and filtered. The filtrate was evaporated to dryness to give 1-(4-chloro-2-methylsulphonylphenyl)-3-cyclopropylpropan-1,3-dione, (7.1 g) as an orange gum, NMR (CDCl$_3$): 0.8–1.2 (m, 4H), 1.5–1.9 (m,1H), 3.3 (s, 3H), 5.8 (s,1H), 7.3–7.6 (m,2H), 7.9 (s,1H).

By proceeding in a similar manner the following compounds were prepared from the appropriately substituted starting materials:

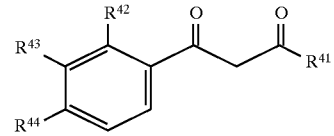

| $R^{41}$ | $R^{42}$ | $R^{44}$ | NMR (CDCl$_3$) |
|---|---|---|---|
| Cp | SO$_2$Me | CF$_3$ | 0.8–1.4(m, 4H), 1.5–1.8(m, 1H), 3.3(s, 3H), 5.85(s, 1H), 7.5 (d, 1H), 7.8(d, 1H), 8.2(s, 1H). |
| Cp | SMe | CF$_3$ | 0.8–1.3(m, 4H) 1.5–1.7(m, 1H), 2.45(s, 3H), 5.95(s, 1H), 7.1–7.6(m, 3H). |
| Cp | SO$_2$Me | Br | 0.9–1.35(m, 4H), 1.5–1.9(m, 1H), 3.45(s, 3H), 6.0(s, 1H), 7.5(d, 1H), 7.95(d, 1H), 8.4(s, 1H). |
| 1-Me-Cp | SO$_2$Me | Cl | 0.7–1.0(m, 2H), 1.1–1.6(m, 5H), 3.3(s, 3H), 5.8(s, 1H), 7.3–7.6(m, 2H), 7.95(s, 1H). |
| iPr | SO$_2$Me | Cl | 1.15(d, 6H), 2.4–2.8(m, 1H), 3.3(s, 3H), 5.7(s, 1H), 7.4–7.6(m, 2H), 7.9(s, 1H). |
| Cp | SO$_2$Me | F | 0.9–1.3(m, 4H), 1.5–1.9 (m, 1H), 3.35(s, 3H), 5.85(s, 1H), 7.1–7.9(m, 3H). |
| Me | SO$_2$Me | Cl | 2.15(s, 3H), 3.35(s, 3H), 6.7(s, 1H), 7.3–7.6(m, 2H), 7.95(s, 1H). |
| Et | SO$_2$Me | Cl | 1.2(t, 3H), 2.4(q, 2H) 3.35(s, 3H), 5.75(s, 1H), 7.2–7.6(m, 2H), 7.95(s, 1H). |

| $R^{41}$ | $R^{42}$ | $R^{43}$ | $R^{44}$ | m.p./NMR(CDCl$_3$) |
|---|---|---|---|---|
| Cp | SO$_2$Me | H | OMe | 100.5–102° C. |
| Cp | SO$_2$Et | H | Cl | 98–101° C. |
| Cp | SMe | H | Cl | NMR: 0.7–1.35(m, 4H), 1.4–1.9 (m, 1H), 2.4(s, 3H), 6.1(s, 1H), 7.0–7.9(m, 3H). |
| iPr | SO$_2$Me | H | CF$_3$ | NMR: 1.2(d, 6H), 2.2–2.8(m, 1H), 3.35(s, 3H), 5.85(s, 1H), 7.6–7.9(m, 2H), 8.25(s, 1H). |
| 1-Me-Cp | SO$_2$Me | H | CF$_3$ | NMR: 0.7–1.0 (m, 2H), 1.1–1.5(m, 5H), 3.3(s, 3H), 5.8(s, 1H), 7.5–7.8(m, 2H), 8.15 (s, 1H). |
| iPr | SMe | H | Cl | NMR: 1.2(d, 6H), 2.4–2.7 (m, 1H), 2.5(s, 3H), 6.0(s, 1H), 7.0–7.9(m, 3H). |
| 1-Me-Cp | SO$_2$Et | H | Cl | 133–134° C. |
| iPr | SO$_2$Et | H | Cl | 73–76° C. |
| 1-Me-Cp | SO$_2$Me | H | Br | NMR: 0.8(m, 2H) 1.3(s, 3H) 1.4(m, 2H) 3.4(s, 3H) 5.9(s, 1H) 7.4(d, 1H) 7.8(dd, 1H) 8.3(d, 1H) |
| iPr | SO$_2$Me | H | Br | NMR: 1.2(d, 6H) 2.5(m, 1H) 3.4(s, 3H) 5.8(s, 1H) 7.3(m, 1H) 7.8(m, 1H) 8.2(m, 1H) |

REFERENCE EXAMPLE 80

Magnesium turnings (0.46 g) were suspended in methanol and carbon tetrachloride (0.5 ml) was added. The mixture was stirred and heated at reflux for 10 minutes. t-Butyl 3-cyclopropyl-3-oxopropionate (3.5 g) was added and the mixture was stirred and heated at reflux for 0.5 hours. After cooling, the solution was evaporated to dryness and the residue was dissolved in toluene. The solution was evaporated to dryness and the residue was redissolved in toluene. 4-Methyl-2-methylsulphonylbenzoyl chloride (4.0 g) was added to the toluene solution and the mixture was stirred overnight. Aqueous hydrochloric acid (2M) was added and the resulting layers were separated. The organic layer was dried by azeotropic removal of water. 4-Toluenesulphonic acid (0.3 g) was added and the mixture was stirred and heated at reflux for 5 hours. After cooling, the mixture was washed with water, dried (anhydrous magnesium sulphate) and filtered. The filtrate was evaporated to dryness and the residue was triturated with a mixture of petroleum spirit and ether to give 3-cyclopropyl-1-(4-methyl-2-methylsulphonylphenyl)-propan-1,3-dione (3.8 g) as a brown solid, m.p. 129°–131° C.

By proceeding in a similar manner the following compounds were prepared from the appropriately substituted starting materials:

REFERENCE EXAMPLE 81

Carbon tetrachloride (2 ml) was added to a mixture of magnesium (0.57 g) and t-butyl 3-cyclopropyl-3-oxopropionate (4.36 g) in methanol. The mixture was stirred for 0.5 hours. It was evaporated to dryness and the residue was dissolved in toluene. The solution was evaporated to dryness and the residue was suspended in acetonitrile. 4Chloro-2-methylsulphonylbenzoyl chloride (6.0 g) was added and the mixture was stirred for 3 hours. It was evaporated to dryness and the residue was dissolved in ethyl acetate. The mixture was washed with aqueous hydrochloric acid (2M), water, dried (anhydrous magnesium sulphate) and filtered. The filtrate was evaporated to dryness to give t-butyl 2-(4-chloro-2-methylsulphonylbenzoyl)-3-cyclopropyl-3-oxopropionate (9.6 g) as a brown oil which was not further purified.

By proceeding in a similar manner the following compounds were prepared from the appropriately substituted starting materials:

| $R^{41}$ | $R^{42}$ | $R^{43}$ | $R^{44}$ |
|---|---|---|---|
| Cp | SO$_2$Me | H | CF$_3$ |
| Cp | SMe | H | CF$_3$ |
| Cp | SO$_2$Me | H | Br |
| 1-MeCp | SO$_2$Me | H | Cl |
| iPr | SO$_2$Me | H | Cl |

-continued

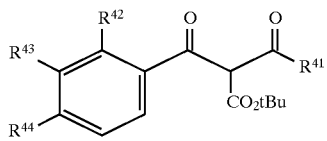

| R[41] | R[42] | R[43] | R[44] |
|---|---|---|---|
| Cp | SO$_2$Me | H | F |
| Me | SO$_2$Me | H | Cl |
| Et | SO$_2$Me | H | Cl |

REFERENCE EXAMPLE 82

Potassium permanganate (316 g) was added with stirring to a suspension of 4-bromo-2-methylsulphenyltoluene (90.5 g) in water whilst maintaining the mixture at reflux. The mixture was stirred and heated at reflux for 3 hours. The mixture was filtered and the residue was washed with hot water. The filtrate was cooled to room temperature and extracted with ethyl acetate. The aqueous solution was acidified to pH 1, saturated with sodium chloride and extracted with ethyl acetate. The organic layer was washed with water, dried (anhydrous magnesium sulphate) and filtered. The filtrate was evaporated to dryness to give 4-bromo-2-methylsulphonylbenzoic acid (44.6 g) as a light brown solid, m.p. 220°–220.5° C.

By proceeding in a similar manner the following compounds were prepared from the appropriately substituted starting materials:

4chloro-2-methylsulphonylbenzoic acid; NMR (CDCl$_3$+DMSO-d$_6$): 3.35 (s,3H), 7.5–7.8(m,2H), 7.9 (s,1H), 8.2–8.6 (bs,1H);

4-fluoro-2-methylsulphonylbenzoic acid; NMR (CDCl$_3$+DMSO-d$_6$) 3.35(s,3H), 7.1–7.8(m,3H), 10.4–10.8 (bs, 1H);

4-chloro-2-ethylsulphonylbenzoic acid; m.p.119°–120° C.

REFERENCE EXAMPLE 83

Hydrogen peroxide (30%) was added to a cooled solution of 2-methylsulphenyl-4-trifluoromethylbenzoic acid (6.0 g) and acetic anhydride(3.6 ml) in acetic acid at 10° C. The mixture was allowed to warm slowly to room temperature and stirred for 0.5 hours. It was stirred and heated at 65° C. for 3 hours. After cooling the mixture was poured into ice and extracted with ether. The organic layer was washed with water, aqueous ferrous sulphate solution, dried (anhydrous magnesium sulphate) and filtered. The filtrate was evaporated to dryness to give 2-methylsulphonyl-4-trifluoromethylbenzoic acid (5.54 g) as a white solid, m.p. 155.5°–156.5° C.

REFERENCE EXAMPLE 84

A solution of potassium peroxymonosulphate (23.8 g) in water was added to a solution of 4-methyl-2-methylsulphenylbenzoic acid (4.7 g) in methanol. The mixture was stirred for 5 hours and left to stand overnight at room temperature. The methanol was removed by evaporation and the resulting suspension was diluted with water and extracted with chloroform. The organic layer was dried (anhydrous magnesium sulphate) and filtered. The filtrate was evaporated to dryness and the residue was triturated with a mixture of ether and cyclohexane to give 4-methyl-2-methylsulphonylbenzoic acid (4.4 g) as a cream solid, m.p. 174°–174.5° C.

By proceeding in a similar manner the following compound was prepared from the appropriately substituted starting material:

4-methoxy-2-methylsulphonylbenzoic acid, m.p. 180°–180.5° C.

REFERENCE EXAMPLE 85 n-Butyllithium (2.5M solution in hexane; 25 ml) was added under an inert atmosphere to a stirred solution of 4-bromo-3-methylsulphenylbenzotrifluoride (16.4 g) in ether whilst maintaining the temperature below −70° C. The mixture was stirred at 70° C. for 2 hours and then poured onto solid carbon dioxide pellets. The mixture was stirred for 10 minutes and aqueous hydrochloric acid was added. The layers were separated and the aqueous layer was extracted with ether. The combined organic layers were washed with water, dried (anhydrous magnesium sulphate) and filtered. The filtrate was evaporated and the residue was triturated with cyclohexane and filtered to give 2-methylsulphenyl-4-trifluoromethylbenzoic acid (12.4 g) as a white solid, NMR (CDCl$_3$+DMSO-d$_6$): 2.45 (s,3H), 7.2(d,1H), 7.3(s,1H), 8.0 (d,1H), 10.7–11.1 (bs,1H).

By proceeding in a similar manner the following compound was prepared from the appropriately substituted starting material:

4-methyl-2-methylsulphenylbenzoic acid, m.p. 178.5°–179° C.

REFERENCE EXAMPLE 86 t-Butyl nitrite (4 ml) was added to a mixture of 5-chloro-2-methylaniline (4 g) and dimethyl disulphide (26.3 g) in chloroform. After the reaction started t-butyl nitrite (17.7 ml) and 5-chloro-2-methylaniline (16 g) were added simultaneously. The mixture was stirred at room temperature for 2 hours and left to stand overnight. The mixture was washed with water, aqueous hydrochloric acid (2M), water, dried (anhydrous magnesium sulphate) and filtered. The filtrate was evaporated to dryness to give 4-chloro-2-methylsulphenyltoluene (24.6 g) as a red oil, NMR (CDCl$_3$): 2.2(s,3H), 2.4(s,3H), 6.85(s,2H), 7.0(s,1H).

By proceeding in a similar manner the following compounds were prepared from the appropriately substituted starting materials:

4-bromo-3-methylsulphenylbenzotrifluoride, bp 84°–88° C. (2 mm Hg);

4-bromo-3-methylsulphenyltoluene, b.p. 118°–124° C. (7 mm Hg);

4-chloro-2-ethylsulphenyltoluene, b.p. 118°–128° C. (9.5 mm Hg).

REFERENCE EXAMPLE 87

A cooled solution of sodium nitrite (5.8 g) in concentrated sulphuric acid (50 ml) was added dropwise to a stirred solution of 4-methyl-3-methylsulphenylaniline (12.8 g) in glacial acetic acid at 20° C. The resulting suspension was added to a mixture of copper (I) bromide (12 g), aqueous hydrobromic acid (48–50%) and ice. The mixture was stirred at room temperature for 3 hours then diluted with water and extracted with ethyl acetate. The organic layer was washed with water, aqueous sodium hydroxide (2M), dried (anhydrous magnesium sulphate) and filtered. The filtrate was evaporated to dryness. The residue was triturated with hot cyclohexane and filtered. The filtrate was evaporated to dryness to give 4-bromo-2-methylsulphenyltoluene (8.6 g) as a brown oil, NMR (CDCl$_3$): 2.15(s,3H), 2.2(s,3H), 6.5–7.1 (m,3H).

REFERENCE EXAMPLE 88

Concentrated hydrochloric acid (128 ml) was added slowly to a suspension of 2-methylsulphenyl-4-nitrotoluene (36.6 g) in methanol. Iron powder (36 g) was added with stirring whilst maintaining the temperature below 50° C. The mixture was stirred at room temperature for 4 hours. The mixture was poured into water neutralized (by the addition of sodium carbonate), filtered and the residue was extracted with dichloromethane. The aqueous layer was extracted with dichloromethane and the combined organic layers were washed with aqueous sodium chloride solution, dried (anhydrous magnesium sulphate) and filtered. The filtrate was evaporated to dryness and the residue was purified by column chromatography on silica eluted with a mixture of ethyl acetate and n-hexane to give 4-methyl-3-methylsulphenylaniline (12.8 g) as an orange solid, NMR (CDCl$_3$) 2.2(s,3H), 2.35 (s,3H), 3.45 (s,2H), 6.1–6.9 (m,3H).

REFERENCE EXAMPLE 89

A mixture of 3-cyclopropyl-1-(3,4-difluoro-2-methylsulphonylphenyl)propane-1,3-dione (0.85 g) and triethyl orthoformate (1.04 g) in acetic anhydride was stirred and heated at reflux for 4 hours. It was evaporated to dryness and the residue was treated with toluene and re-evaporated to give 3-cyclopropyl-1-(3,4-difluoro-2-methylsulphonylphenyl)-2-ethoxy methylenepropane-1,3-dione (1.13 g) as a brown oil which was not purified further.

By proceeding in a similar manner the following compounds were prepared from the appropriately substituted starting materials:

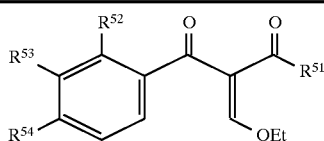

| $R^{51}$ | $R^{52}$ | $R^{53}$ | $R^{54}$ |
|---|---|---|---|
| Cp | SMe | Cl | Cl |
| Cp | SMe | OMe | Br |
| Cp | SO$_2$Me | OMe | Br |
| Cp | SMe | OMe | Cl |
| Cp | SMe | Me | Cl |
| Cp | SMe | F | Cl |
| Cp | SMe | CO$_2$Me | CF$_3$ |
| Cp | SMe | CO$_2$Me | Cl |
| Cp | SMe | Cl | Br |
| Cp | SMe | Cl | CF$_3$ |
| Cp | SMe | F | Br |
| Cp | SMe | C(CH$_3$)=CH$_2$ | Cl |
| Cp | SMe | Me | SMe |
| Cp | SMe | CHF$_2$ | Cl |
| Cp | SMe | Br | Br |
| Cp | SO$_2$Me | OCH$_2$CF$_3$ | Cl |

REFERENCE EXAMPLE 90

Magnesium (0.17 g) was suspended in methanol containing carbon tetrachloride (approximately 0.1 ml) and the mixture was warmed to initiate the reaction. t-Butyl 3-cyclopropyl-3-oxopropionate (1.32 g) was added and the mixture was stirred for 1 hour. The mixture was evaporated to dryness and the residue was dissolved in toluene and re-evaporated. The residue was dissolved in acetonitrile and 3,4-difluoro-2-(methylsulphonyl)benzoyl chloride (1.83 g) was added. The mixture was stirred at room temperature for 4 hours and left to stand overnight. The mixture was evaporated to dryness and the residue was partitioned between toluene and hydrochloric acid (2M). The layers were separated and the organic layer was washed with water then dried by azeotropic removal of water. 4-Toluene sulphonic acid (0.5 g) was added to the mixture which was heated at reflux for 4 hours. After cooling it was washed with water, dried (anhydrous MgSO$_4$) and filtered. The filtrate was evaporated to dryness to give 3-cyclopropyl-1-(3,4-difluoro-2-methylsulphonylphenyl)propane-1,3-dione (0.86 g) as a brown solid which was not purified further.

By proceeding in a similar manner the following compounds were prepared from the appropriately substituted starting materials. In all cases the acetonitrile is replaced by toluene

| $R^{51}$ | $R^{52}$ | $R^{53}$ | $R^{54}$ | m.p/NMR |
|---|---|---|---|---|
| Cp | SMe | Cl | Cl | 57–58.5° C. |
| Cp | SMe | OMe | Br | a |
| Cp | SO$_2$Me | OMe | Br | — |
| Cp | SMe | OMe | Cl | b |
| Cp | SMe | F | Cl | Not purified further |
| Cp | SMe | CO$_2$Me | CF$_3$ | Not purified further |
| Cp | SMe | CO$_2$Me | Cl | Not purified further |
| Cp | SMe | Cl | Br | c |
| Cp | SMe | Cl | CF$_3$ | Not purified further |
| Cp | SMe | F | Br | d |
| Cp | SMe | C(CH$_3$)=CH$_2$ | Cl | 61–63° C. |
| Cp | SMe | CHF$_2$ | Cl | e |
| Cp | SMe | Br | Br | 71–72° C. |
| Cp | SO$_2$Me | OCH$_2$CF$_3$ | Cl | 113–115° C. | a = NMR (CDCl$_3$): 0.9–1.4(m, 4H), 1.7–1.9(m, 1H), 2.5(s, 3H), 3.95(s, 3H), 5.9(s, 1H), 7.0(d, 1H), 7.4(d, 1H).
b = NMR (CDCl$_3$) 0.8–1.4(m, 4H), 1.5–1.9(m, 1H), 2.45(s, 3H), 4.0(s, 3H), 6.0(s, 1H), 7.15(d, 1H), 7.4(d, 1H).
c = NMR (CDCl$_3$): 1.0(m, 2H), 1.2(m, 2H), 1.75(m, 1H), 2.5(s, 3H), 5.95(s, 1H), 7.2(d, 1H), 7.65(d, 1H) 15.7–16.1(bs, 1H).
d = NMR (CDCl$_3$): 1.0(m, 2H), 1.25(m, 2H), 1.75(m, 1H), 2.5(s, 3H), 6.0(s, 1H), 7.2(d, 1H) 7.55(dd, 1H) 15.7–16.0(bs, 1H).
e = NMRCDCl$_3$): 1.0(m, 2H), 1.2(m, 2H), 2.4(s, 3H), 6.0(s, 1H), 7.4(q, 2H), 7.65(t, 1H).

REFERENCE EXAMPLE 91

A mixture of methyl 4-chloro-3-methyl-2-(methylsulphenyl)benzoate (19.5 g) and cyclopropyl methyl ketone (13.4 g) in dry tetrahydrofuran was added to a stirred heated suspension of sodium hydride (80% oil dispersion, 4.8 g) in dry tetrahydrofuran. The mixture was stirred and heated at reflux for 2 hours. It was cooled and hydrochloric acid (2 ml) was added. The layers were separated and the aqueous layer was extracted with ether. The combined organic layers were washed with water, saturated aqueous sodium bicarbonate, water, dried (Na$_2$SO$_4$) and filtered. The filtrate was evaporated to dryness to give 1-(4-chloro-3-methyl-2-methylsulphenylphenyl)-3-cyclopropylpropan-1,3-dione (20.19 g) as a yellow oil, NMR(CDCl$_3$) 0.9(m,2H), 1.2 (m,2H), 1.7(m,1H), 2.3(s,3H), 2.65(s,3H), 5,85 (s,1H), 7.15(d,1H), 7.3(d,1H), 15.7–16.0(bs,1H).

By proceeding in a similar manner the following compound was prepared from the appropriately substituted starting material:

![structure]

| R⁵¹ | R⁵² | R⁵³ | R⁵⁴ | m.p/NMR |
|-----|-----|-----|-----|---------|
| Cp  | SMe | Me  | SMe | a       | a = NMR (CDCl₃) 1.0(m, 2H), 1.2(m, 2H), 1.75(m, 1H), 2.3(s, 3H), 2.5(s, 3H), 2.6(s, 3H), 6.0(s, 1H), 7.1(d, 1H), 7.3(d, 1H), 15.8–16.1(bs, 1H).

REFERENCE EXAMPLE 92

Hydrogen peroxide (11 ml) was added with stirring to a cooled solution of 3,4-difluoro-2-(methylsulphenyl)benzoic acid (3.0 g) and acetic anhydride (2.1 ml) in acetic acid while maintaining the temperature below 5° C. The mixture was stirred at 0° C. for 0.5 hours then warmed to room temperature. Further acetic acid was added and the mixture was stirred at room temperature for 0.5 hours and at 65° C. for 2.5 hours. After cooling to room temperature water was added and the mixture was extracted with ethyl acetate, washed with water, aqueous ferrous sulphate solution and water, dried (anhydrous MgSO₄) and filtered. The filtrate was evaporated to dryness and the residue was recrystallised from a mixture of cyclohexane and ether to give 3,4-difluoro-2-(methylsulphonyl)-benzoic acid (10 g) as a white solid, m.p. 194° C.

By proceeding in a similar manner the following compound was prepared from the appropriately substituted starting material:

4-chloro-3-fluoro-2-methylsulphonyl-benzoic acid as a white solid m.p. 206°–209° C.

REFERENCE EXAMPLE 93 n-Butyllithium (2.5 m in hexane, 35 ml) was added with cooling to a solution of 3,4-difluorobenzoic acid (5.5 g) in dry tetrahydrofuran while maintaining the temperature below −70° C. The mixture was stirred for 2 hours at −70° C. A solution of dimethyl disulphide (19.8 g) in tetrahydrofuran was added and the mixture was stirred at −70° C. for 1.5 hours. It was allowed to warm to room temperature, diluted with ether and washed with water. The aqueous layer was acidified to pH 1 and extracted with ether, washed with water, dried (anhydrous MgSO₄) and filtered. The filtrate was evaporated to dryness and the residue was recrystallised from a mixture of cyclohexane and ether to give 3,4-difluoro-2-(methylsulphenyl)benzoic acid (5.9 g) as a white solid, m.p. 149.2°–149.6° C.

By proceeding in a similar manner the following compounds were prepared from the appropriately substituted starting materials:

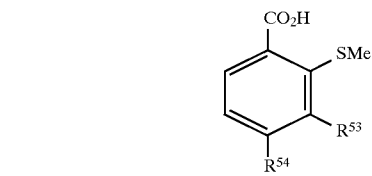

| R⁵³ | R⁵⁴ | Reaction temp | m.p. |
|-----|-----|---------------|------|
| F   | Cl  | −40° C.       | 145–146° C. |
| Cl  | CF₃ | −40° C.       | 97–100° C. |

REFERENCE EXAMPLE 94

A solution of sodium nitrite (4.53 g) in water was added to a stirred suspension of 3,4-dichloroanthranillic acid (15 g) in acetic acid and concentrated hydrochloric acid while maintaining the temperature below 5° C. The mixture was stirred at below 5° C. for 2 hours then poured into a solution of dimethyl disulphide (8.4 g) and copper powder (0.1 g) in acetic acid. The mixture was stirred at room temperature for 1 hour and poured into water. The solid was filtered off, dried and recrystallized from cyclohexane to give 3,4-dichloro-2-(methylsulphenyl)benzoic acid (12.02 g) as a pale yellow solid, NMR (DMSO-D₆) 2.4(s,3H), 7.5(d,1H), 7.7(d,1H), 13.5(bs,1H).

REFERENCE EXAMPLE 95

A solution of potassium hydroxide (2.0 g) in water was added to a solution of ethyl 4-bromo-3-methoxy-2-(methylsulphenyl)-benzoate (4.5 g) in ethanol. The resulting solution was stirred and heated at reflux for 3 hours. After cooling, the mixture was evaporated to dryness and the residue was dissolved in water and washed with ethyl acetate. The aqueous solution was acidified to pH 1 and extracted with ethyl acetate, dried (anhydrous MgSO₄) and filtered. The filtrate was evaporated to dryness to give 4-bromo-3-methoxy-2-(methylsulphenyl)benzoic acid as a white solid, NMR (CDCl₃) 2.5(s,3H), 3.9(s,3H), 7.4(s,2H), 10.9(bs,1H).

By proceeding in a similar manner the following compound was prepared from the appropriately substituted starting material:

4-Bromo-3-methoxy-2-(methylsulphonyl)benzoic acid NMR (CDCl₃) 3.3(s,3H), 4.1(s,3H), 7.1(d,1H), 7.75(d, 1H), 8.2(bs,1H).

REFERENCE EXAMPLE 96

A solution of methanethiol (47 ml) in dimethyl formamide was added to a mixture of ethyl 2,4-dibromo-3-methoxybenzoate (105 g) and potassium carbonate (131 g) in dimethyl formamide and the resultant suspension was stirred at room temperature overnight. Water was added and the mixture was extracted into ether, washed with water, dried (MgSO₄) and filtered. The filtrate was evaporated to dryness and the residue was purified by column chromatography eluted with a mixture of ethyl acetate and cyclohexane to give as the minor component ethyl 4-bromo-3-methoxy-2-(methylsulphenyl)-benzoate (4.5 g) as a white solid, NMR (CDCl₃) 1.5(t,3H), 2.6(s,3H), 4.05(s,3H), 4.5(q,2H), 7.35 (m,2H).

REFERENCE EXAMPLE 97

Hydrogen peroxide (11.3 ml) was added to a cooled solution of ethyl 4-bromo-3-methoxy-2-(methylsulphenyl)

benzoate (3.7 g) and acetic anhydride (2.0 ml) in acetic acid at 0° C. The mixture was stirred at 0° C. for 1 hour then warmed to room temperature and heated at 85° C. for 3 hours. After cooling to room temperature the mixture was diluted with ethyl acetate and washed with water, aqueous ferrous sulphate solution, water, dried (MgSO$_4$) and filtered. The filtrate was evaporated to dryness to give ethyl 4-bromo-3-methoxy-2-(methylsulphonyl)benzoate (3.6 g) as a yellow oil, NMR (CDCl$_3$) 1.6(t,3H), 3.5(s,3H), 4.3(s, 3H), 4.55(q,2H), 7.2(d,1H), 7.95(d,1H).

REFERENCE EXAMPLE 98

A mixture of 2-[4-chloro-3-methoxy-2-(methylsulphenyl)-phenyl]-4,4-dimethyloxazoline (9.0 g) and hydrochloric acid (5M) was stirred and heated at reflux for 5 hours. After cooling, the mixture was diluted with water and extracted with dichloromethane. It was dried (MgSO$_4$), filtered and the filtrate was evaporated to dryness to give 4-chloro-3-methoxy-2-(methylsulphenyl)benzoic acid as a white solid, m.p. 98°–99° C.

REFERENCE EXAMPLE 99 n-Butyllithium (2.5M in hexane, 54 ml) was added with cooling to a stirred solution of 2-(4-chloro-3-methoxyphenyl)-4,4-dimethyloxazoline (27.0 g) in tetrahydrofuran while maintaining the temperature below –40° C. The mixture was stirred at –78° C. overnight. A solution of dimethyl disulphide (26.5 g) in tetrahydrofuran was added dropwise and the mixture was stirred at –40° C. overnight. After allowing to warm to room temperature the mixture was treated with hydrochloric acid (2M). The organic layer was washed with water, dried (MgSO$_4$) and filtered. The filtrate was evaporated to dryness and the residue was purified by dry column flash chromatography eluted with a mixture of ethyl acetate and n-hexane to give 2-[4-chloro-3-methoxy-2-(methylsulphenyl)-phenyl]-4,4-dimethyloxazoline (11.1 g) as a white solid, m.p. 50°–52° C.

REFERENCE EXAMPLE 100 n-Butyllithium (2.5M in hexane, 63 ml) was added to a solution of diisopropylamine in dry tetrahydrofuran while maintaining the temperature at 0° C. Once addition was complete the cooling bath was removed and the mixture stirred for 30 minutes at room temperature. The resulting solution of lithium di-isopropylamide (LDA) was then added to a solution of 4-bromo-3-fluorobenzoic acid (14.6 g) in tetrahydrofuran while maintaining the temperature at –50° C. The mixture was then stirred for 5 hours at –30° C. A solution of dimethyl disulphide (21 g) in tetrahydrofuran was then added and the cooling bath was removed and the mixture allowed to stir at room temperature overnight. The mixture was diluted with ether and washed with water. The aqueous layer was acidified to pH 1 with 2M hydrochloric acid and extracted with ether, washed with water, dried (MgSO$_4$) and filtered. The filtrate was evaporated to dryness and the residue triturated with petroleum spirit (b.p. 60°–80° C.) to give 4-bromo-3-fluoro-2-(methylsulphenyl)benzoic acid (14 g) as a white solid, m.p. 152°–154° C.

By proceeding in a similar manner from the appropriately substituted starting material 4-bromo-3-chloro-2-(methylsulphenyl)benzoic acid was prepared, m.p. 126°–129° C.

3,4-Dibromo-2-methylsulphenylbenzoic acid m.p. 140°–142° C.

REFERENCE EXAMPLE 101

A solution of 4-bromo-3-fluorotoluene (35 g) and sodium hydroxide (7.7 g) in pyridine and water was stirred and heated to reflux. Potassium permanganate (123 g) was added to the mixture over 2 hours. The resulting suspension was heated at reflux for a further 3 hours. The mixture was filtered hot through hyflo. The hyflo was washed with boiling water, followed by ethyl acetate. The cooled aqueous layer was acidified to pH 1 with concentrated hydrochloric acid and extracted with ethyl acetate. The organic extract was washed with water, dried (MgSO$_4$) and filtered. The filtrate was evaporated to dryness and the residue triturated with petroleum spirit (bp 60°–80° C.) to give 4-bromo-3-fluorobenzoic acid as a white solid (21.25 g), m.p. 213°–215° C.

REFERENCE EXAMPLE 102

Lithium hydroxide monohydrate (1.87 g) was added to a solution of methyl 3-methoxycarbonyl-2-(methylsulphenyl)-4-trifluoromethylbenzoate (13.71 g) in methanol and water. The mixture was stirred at room temperature overnight and the methanol was removed by evaporation. The residual aqueous solution was acidified to pH 1 and extracted with ether, washed with water, dried (MgSO$_4$) and filtered. The filtrate was evaporated to dryness to give 3-methoxycarbonyl-2-(methylsulphenyl)-4-trifluoromethylbenzoic acid (10.85 g) as an off-white solid, NMR (CDCl$_3$) 2.45(s, 3H), 3.95(s,3H), 5.45–6.1(bs,1H), 7.2(d,1H), 7.95(d,1H).

By proceeding in a similar manner the following compound was prepared from the appropriately substituted starting material:

4-chloro-3-methoxycarbonyl-2-(methylsulphenyl) benzoic acid, NMR (CDCl$_3$) 2.5 (s,3H), 4.0 (s, 3H), 7.55(d,1H), 8.0(d,1H).

REFERENCE EXAMPLE 103

Sodium thiomethoxide (6.83 g) was added to a solution of methyl 2-fluoro-3-methoxycarbonyl-4-trifluoromethylbenzoate (24.85 g) in xylene. After stirring for 0.5 hours lithium hydroxide monohydrate (4.10 g) was added and the mixture was stirred for 48 hours. Hydrochloric acid (2M) was added. It was extracted with ether, washed with water, dried (MgSO$_4$) and filtered. The filtrate was evaporated to dryness and the residue was triturated with cyclohexane. The solid was filtered off and the filtrate was evaporated to dryness to give methyl 3-methoxycarbonyl-2-(methylsulphenyl)-4-trifluoromethylbenzoate (13.71 g) as a yellow oil NMR (CDCl$_3$) 2.4(s,3H), 3.95 (s,6H), 7.65 (s,2H).

By proceeding in a similar manner methyl 4-chloro-3-methoxycarbonyl-2-(methylsulphenyl)benzoate was prepared from the appropriately substituted starting material.

REFERENCE EXAMPLE 104

A solution of 2-fluoro-3-methoxycarbonyl-4-trifluoromethylbenzoic acid (23.43 g) in thionyl chloride was stirred and heated at reflux for 2 hours, cooled and evaporated to dryness. The residue was dissolved in methanol and the resultant solution was stirred and heated at reflux overnight. It was cooled and evaporated to dryness. The residue was purified by chromatography eluted with a mixture of ether and cyclohexane to give methyl 2-fluoro-3-methoxycarbonyl-4-trifluoromethylbenzoate (25.85 g) as a yellow oil, NMR (CDCl$_3$) 4.0(s, 6H), 7.55(d,1H), 8.15(t, 1H).

By proceeding in a similar manner the following compounds were prepared from the appropriately substituted starting material:

methyl 4-chloro-2-fluoro-3-methoxycarbonylbenzoate NMR (CDCl$_3$) 3.9(s,3H), 4.0(s,3H), 7.3(d,1H), 7.95(t, 1H);

methyl 4-chloro-2-fluoro-3-methylbenzoate NMR (CDCl$_3$) 2.35(d,3H), 3.95(s,3H), 7.2(d,1H) 7.7(t,1H);

methyl 4-chloro-2-fluoro-3-isopropenylbenzoate NMR (CDCl$_3$) 2.1(s,3H), 3.95(s,3H), 5.0(s,1H) 5.45(s,1H) 7.3(d,1H) 7.8(t,1H).

REFERENCE EXAMPLE 105

A solution of lithium diisopropyl amide in dry tetrahydrofuran (prepared from diisopropylamine (17.0 ml) and n-butyllithium (48.4 ml) in dry tetrahydrofuran)was added to a solution of methyl 2-fluoro-6-trifluoromethylbenzoate (22.39 g) in dry tetrahydrofuran while maintaining the temperature below −70° C. The mixture was stirred at −78° C. for 3 hours. The solution was poured onto solid carbon dioxide pellets and stirred until it had warmed to room temperature. The mixture was evaporated and treated with hydrochloric acid (2M). It was extracted with ether, washed with water, dried (MgSO$_4$) and filtered. The filtrate was evaporated to dryness to give 2-fluoro-3-methoxycarbonyl-4-trifluoromethylbenzoic acid (24.43 g) as an off-white solid, NMR (CDCl$_3$) 3.95(s,3H), 7.55(d,1H), 8.15(t,1H).

By proceeding in a similar manner the following compound was prepared from the appropriately substituted starting material:

4-chloro-2-fluoro-3-methoxycarbonylbenzoic acid, NMR (CDCl$_3$) 4.0(s,3H), 7.4(d,1H), 8.1(t,1H).

REFERENCE EXAMPLE 106

Potassium carbonate (48.37 g) was added to a solution of methanethiol (16.84 g) in dry dimethyl formamide. Methyl 4-chloro-2-fluoro-3-methylbenzoate (35.45 g) was added to the resulting suspension. The mixture was stirred for 60 hours. It was poured into water, extracted with ether, washed with water, dried (Na$_2$SO$_4$) and filtered. The filtrate was evaporated to dryness and the residue was separated by chromatography eluted with a mixture of ether and hexane to give methyl 4-chloro-3-methyl-2-(methylsulphenyl)benzoate (19.53 g) as a clear oil, NMR (CDCl$_3$) 2.35(s,3H), 2.7(s,3H), 3.95(s,3H), 7.25(d,1H), 7.4(d,1H), and methyl 3-methyl-2, 4-bis(methylsulphenyl)benzoate (9.29 g) as a yellow solid NMR (CDCl$_3$) 2.3 (s,3H), 2.5 (s,3H), 2.6 (s,3H), 3.95 (s,3H), 7.1 (d,1H), 7.4 (d,1H).

REFERENCE EXAMPLE 107 n-Butyllithium (2.5M in hexane, 100 ml) was added to a cooled solution of 2-chloro-6-fluorotoluene (36.1 g) in dry tetrahydrofuran while maintaining the temperature below −60° C. The mixture was stirred at −78° C. overnight then poured onto solid carbon dioxide pellets. The mixture was stirred and allowed to warm to room temperature. It was acidified to pH 1 and extracted with ether. The organic layer was extracted into aqueous sodium hydroxide solution (2M) and water. The combined aqueous extracts were acidified to pH 1 and the solid formed was filtered off and washed with water and n-hexane to give 4-chloro-2-fluoro-3-methylbenzoic acid (40.35 g) as a white solid, NMR (DMSO-d$_6$) 2.3(d,3H), 7.4(d,1H) 7.7(t,1H).

By proceeding in a similar manner the following compound was prepared from the appropriately substituted starting material:

4chloro-2-fluoro-3-isopropenylbenzoic acid m.p. 201°–202° C.

REFERENCE EXAMPLE 108

A solution of sodium hydroxide (7.0 g) in water was added to methyl 4-chloro-3-isopropenyl-2-(methylsulphenyl)benzoate (7.3 g) and the resulting mixture was heated at reflux for 2 hours. Ethanol was added and the mixture was heated at reflux for 1 hour. The ethanol was removed by evaporation and the aqueous residue was acidified to pH 1. It was extracted with ethyl acetate, washed with water, dried (MgSO$_4$) and filtered. The filtrate was evaporated to dryness to give 4-chloro-3-isopropenyl-2-(methylsulphenyl)benzoic acid (6.15 g) NMR (CDCl$_3$) 2.05 (s,3H), 2.4 (s,3H), 4.85 (s,1H), 5.35 (s,1H), 7.45 (d,1H), 7.85 (d,1H).

REFERENCE EXAMPLE 109

A mixture of methyl 4-chloro-2-fluoro-3-isopropenylbenzoate (8.6 g) and sodium thiomethoxide (3.15 g) in dimethyl formamide was heated at 50° C. for 3 hours and stirred at room temperature overnight. Ether was added and the mixture was washed with water, dried (MgSO$_4$) and filtered. The filtrate was evaporated to dryness and the residue was purified by chromatography eluted with a mixture of ethyl acetate and hexane to give methyl 4-chloro-3-isopropenyl-2-(methylsulphenyl)benzoate (5.95 g) as a clear oil NMR (CDCl$_3$) 2.1(s,3H), 2.35(s,3H), 3.95(s,3H), 4.9(s,1H), 5.4(s,1H), 7.45(s,2H).

REFERENCE EXAMPLE 110

A mixture of 2-(2-chloro-6-fluorophenyl)propan-2-ol (19.0 g), concentrated sulphuric acid and water was heated at reflux for 2 hours. It was cooled and extracted with ether, washed with water, dried (MgSO$_4$) and filtered. The filtrate was evaporated to dryness and the residue was purified by chromatography eluted with hexane to give 2-(2-chloro-6-fluorophenyl)-propene (11.6 g) as a clear oil, NMR (CDCl$_3$) 1.95(s,3H) 4.95(s,1H), 5.85(s,1H), 6.85–7.0(m,1H), 7.05–7.2(m,2H).

REFERENCE EXAMPLE 111

A solution of methyl 2-chloro-6-fluorobenzoate (40.0 g) in ether was added to a solution of methyl magnesium iodide in ether (prepared from methyl iodide (120.0 g) and magnesium turnings (20.6 g) in ether). The resulting solution was stirred and heated at reflux for 5 hours, poured onto a mixture of ice and concentrated sulphuric acid and the layers separated. The organic layer was washed with water, saturated aqueous sodium bisulphite, water, dried (anhydrous magnesium sulphate) and filtered. The filtrate was evaporated to dryness to give 2-(2-chloro-6-fluorophenyl)-propan-2-ol (36.8 g) as an orange oil, NMR (CDCl$_3$) 1.8(d,6H), 3.5–3.7(bs,1H), 6.9–7.05(m,1H), 7.1–7.25(m,2H).

REFERENCE EXAMPLE 112

A mixture of 3-cyclopropyl-1-[2-(1-methylpropylsulphenyl)-4-trifluoromethylphenyl]propan-1, 3-dione (10.2 g) and dimethylformamide dimethyl acetal (3.9 g) in toluene (50 ml) was stirred at room temperature overnight. The mixture was then evaporated to give 3-cyclopropyl 2-N,N-dimethylaminomethylene-1-[2-(1-methylpropylsulphenyl)-4-trifluoromethylphenyl]propan-1, 3-dione (11.9 g) as a red oil which was not purified.

By proceeding in a similar manner 3-cyclopropyl-2-N,N-dimethylaminomethylene-1-(4-chloro-3-dioxalane-2-methylsulphenylphenyl)propan-1,3-dione was prepared as a red gum, which was not purified.

REFERENCE EXAMPLE 113

Sodium hydride (80%) (3.4 g) was suspended in THF under an inert atmosphere and heated to reflux. A solution of methyl 4-chloro-3-dioxalane-2-methylsulphenylbenzoate and cyclopropyl methyl ketone in THF was added to the refluxing suspension over 30 minutes. After complete addition the mixture was heated at reflux for 70 minutes and then allowed to cool. The mixture was quenched with methanol and diluted with water. The mixture was extracted with ether and the aqueous extract acidified to pH 1 with 2M HCl and extracted with ethyl acetate. The organic phase was washed with water, dried (anhydrous magnesium sulphate) and filtered. The filtrate was evaporated to dryness to give 1-(4-chloro-3-dioxalane-2-methylsulphenylphenyl)-3-cyclopropylpropan-1,3-dione (8.05 g) as a beige solid, m.p. 113°–114° C.

By proceeding in a similar manner 1-(4-chloro-3-methoxymethyl-2-methylsulphenylphenyl)-3-cyclopropylpropan-1,3-dione was prepared from the appropriately substituted starting materials as a pink solid, NMR (CDCl$_3$) 0.9(m,2H), 1.2(m,2H), 1.7(m,1H), 2,3(s,3H), 3.4 (s,3H), 4.8(s,2H), 6.0(s,1H), 7.25(d,1H), 7.35(d,1H).

REFERENCE EXAMPLE 114

Methyl 4-chloro-3-dioxalane-2-fluorobenzoate (20.1 g) was dissolved in THF and to this solution was added sodium thiomethoxide (5.4 g). The resultant suspension was heated at 40° C. for 6 hours and then allowed to cool. The mixture was diluted with ether and washed with water. The organic phase was dried (anhydrous magnesium sulphate) and filtered. The filtrate was evaporated to dryness yielding methyl 4-chloro-3-dioxalane-2-methylsulphenylbenzoate (14.5 g) as a yellow solid NMR (CDCl$_3$); 2.45(s,3H), 3.9(s,3H), 4.1(m,2H), 4.35(m,2H), 6.75(s,1H), 7.4(m,2H).

By proceeding in a similar manner the following compounds were prepared from the appropriately substituted starting materials.

Ethyl 4-chloro-3-acetyl-2-methylsulphenylbenzoate as a brown oil, NMR (CDCl$_3$) 1.3(t,3H), 2.25(s,3H), 2.5(s, 3H), 4.3(q,2H), 7.3(d,1H), 7.5(d,1H).

Ethyl 4-chloro-3-methoxymethyl-2-methylsulphenylbenzoate as a brown oil, NMR (CDCl$_3$) 1.3(t,3H), 2.3(s,3H), 3.4(s,3H), 4.3(q,2H), 4.9 (s,2H), 7.3(m,2H).

Methyl 4-chloro-3-(N,N-dimethylcarboxamido 2-methylsulphenylbenzoate as a brown oil NMR (CDCl$_3$) 2.5(s,3H), 2.7(s,3H), 3.2(s,3H), 3.8(s,3H), 7.4 (d,1H), 7.5(d,1H).

REFERENCE EXAMPLE 115

4-Chloro-3-dioxalane-2-fluorobenzoic acid (128 g) was dissolved in DMF and to this was added potassium carbonate (69 g) followed by methyl iodide (63 ml). The resultant mixture was heated at 60° C. for 5 hours. After cooling the mixture was diluted with water and extracted with ether. The organic phase was washed with water, dried (anhydrous magnesium sulphate) and filtered. The filtrate was evaporated to dryness yielding methyl 4-chloro-3-dioxalane-2-fluorobenzoate as an orange oil (130 g), NMR (CDCl$_3$) 3.9(s,3H), 4.1(m,2H), 4.25(m,2H), 6.4(s,1H), 7.2(m,1H), 7.9(m,1H).

By proceeding in a similar manner the following compounds were prepared from the appropriately substituted starting materials:

Ethyl 4-chloro-2-fluoro-3-(1-t-butyldimethylsilyloxyethyl)benzoate as a clear oil, NMR (CDCl$_3$): –0.1(s,3H), 0.0(s,3H), 0.8(s,9H), 1.4(t, 3H), 1.55(d,3H), 4.4(q,2H), 5.5(q,1H), 7.1(d,1H), 7.9 (t,1H).

Ethyl 4-chloro-3-methoxymethyl-2-fluorobenzoate as an oil, NMR (CDCl$_3$): 1.3(t,3H), 3.3(s,3H), 4.3(q,2H), 4.6(s,2H), 7.15(d,1H), 7.8(t,1H).

REFERENCE EXAMPLE 116

2Chloro-6-fluorobenzaldehyde (100 g), ethylene glycol (192 g) and p-toluenesulphonic acid (17 g) were dissolved in toluene and heated under reflux for four days using a Dean and Stark adapter to collect the water. After cooling the mixture was washed with water, dried (anhydrous magnesium sulphate) and filtered. The filtrate was evaporated to dryness yielding 2-(2-chloro-6-fluorophenyl)-1,3-dioxalone (149 g) as an orange oil, NMR (CDCl$_3$) 4.05(m,2H), 4.3(m, 2H), 6.35(s,1H), 7.2(m,3H).

REFERENCE EXAMPLE 117

Methyl 4-chloro-3-difluoromethyl-2-methylsulphenylbenzoate (9.1 g) and lithium hydroxide (2.2 g) were dissolved in methanol and water and the mixture stirred overnight at room temperature. The mixture was then evaporated and the residue dissolved in water and washed with ethyl acetate. The aqueous layer was acidified to pH 1 with 2M HCl and extracted with ethyl acetate. The organic extract was washed with water, dried (anhydrous magnesium sulphate) and filtered. The filtrate was evaporated to dryness yielding 4-chloro-3-difluoromethyl-2-methylsulphenylbenzoic acid (8.02 g) as a beige solid NMR (CDCl$_3$) 2.5(s,3H), 7.5(d,1H), 7.65(t,1H), 7.8(d,1H).

By proceeding in a similar manner 4chloro-3-(N,N-dimethylcarboxamido)-2-methylsulphenylbenzoic acid was prepared from the appropriately substituted starting material as a yellow solid, NMR (CDCl$_3$) 2.5(s,3H), 2.8(s,3H), 3.2(s,3H), 7.4(d,1H), 7.9(d,1H).

REFERENCE EXAMPLE 118

Methyl 4-chloro-3-formyl-2-methylsulphenylbenzoate (9.0 g) was dissolved in dichloromethane and cooled to –2° C., diethylaminosulphur trifluoride (5.1 ml) was added and the resultant solution allowed to warm to room temperature and stirred overnight. The mixture was quenched with saturated ammonium chloride solution and extracted with dichloromethane. The organic extract was dried (anhydrous magnesium sulphate) and filtered. The filtrate was evaporated to dryness yielding methyl 4-chloro-3-difluoromethyl 2-fluorobenzoate (9.1 g) as a brown oil NMR (CDCl$_3$) 2.3(s,3H), 3.8(s,3H), 7.4(q,2H), 7.6(t,1H).

REFERENCE EXAMPLE 119

Methyl 4-chloro-3-dioxalane-2-methyl-sulphenylbenzoate (16.8 g) was dissolved in THF and 1M HCl (124 ml) and stirred at room temperature for 4 days. The mixture was extracted with ethyl acetate, dried (anhydrous magnesium sulphate) and filtered. The filtrate was evaporated to dryness. The residue was crystallized from cold petroleum spirit (bp 40°–60° C.) yielding methyl 4-chloro-3-formyl-2-methylsulphenylbenzoate (9.6 g) as a yellow solid, m.p. 66.5°–68.1° C.

REFERENCE EXAMPLE 120

Pyridinium chlorochromate (27.6 g) was suspended in dichloromethane and ethyl 4-chloro-2-fluoro-3-(1-hydroxyethyl)benzoate (14.1 g) was added. The mixture was stirred at room temperature for 2 hours and then heated at reflux for 2 hours. After cooling the solvent was evaporated and the residue purified by column chromatography eluted with a mixture of ethyl acetate and n-hexane (1:5) to give ethyl 4-chloro-3-acetyl-2-fluorobenzoate as a yellow oil (13 g), NMR (CDCl$_3$) 1.3(t,3H), 2.5(s,3H), 4.3(q,2H), 7.1(d, 1H), 7.8(t,1H).

REFERENCE EXAMPLE 121

Ethyl 4-chloro-2-fluoro-3-(1-t-butyldimethylsilyloxyethyl)benzoate (25 g) and tetrabutylammonium fluoride (210 ml of 1.0M solution in THF) were dissolved in THF and stirred for 4 hours at room temperature. The mixture was diluted with ether and washed with water. The organic extract was dried (anhydrous magnesium sulphate) and filtered. The filtrate was evaporated to dryness yielding ethyl 4chloro-2-fluoro-3-(1-hydroxyethyl)benzoate (16.8 g) as a clear oil, NMR (CDCl$_3$) 1.3(t,3H), 1.5(d,3H), 2.5(bs,1H), 4.3(q,2H), 5.3(q,1H), 7.1(d,1H), 7.7(t,1H).

REFERENCE EXAMPLE 122

1-(2-Chloro-6-fluorophenyl)ethanol (85 g), imidazole (8.1 g) and t-butyldimethylsilylchloride (8.71 g) were stirred in DMF for 24 hours. The mixture was diluted with ether and washed with water, dried (anhydrous magnesium sulphate) and filtered. The filtrate was evaporated to dryness to give 1-(2-chloro-6-fluorophenyl)ethyl(t-butyldimethylsilyl)ether (13.3 g) as a clear oil, NMR (CDCl$_3$) −0.1(s,3H), 0.05(s, 3H), 0.85(s,9H), 1.5(d,3H), 5.4(q,1H), 6.9(m,1H), 7.05(m, 2H).

REFERENCE EXAMPLE 123

2-(1-Methylpropylsulphenyl)-4-trifluoromethylbenzonitrile (8.6 g), 10M sodium hydroxide (120 ml) and ethanol were combined and heated at reflux for 24 hours. The cooled mixture was poured into water and acidified to pH 1 with concentrated hydrochloric acid. The mixture was extracted with ethyl acetate. The organic phase was washed with water, dried (anhydrous magnesium sulphate) and filtered. The filtrate was evaporated to dryness yielding 2-(1-methylpropylsulphenyl)-4-trifluoromethylbenzoic acid (8.1 g) as a white solid, mp. 99.8°–101° C.

REFERENCE EXAMPLE 124

2-Nitro-4-trifluoromethylbenzonitrile (10.8 g) and potassium carbonate (8.3 g) were heated to reflux in acetonitrile. A solution of 1-methylpropanethiol (5 g) in acetonitrile was added. The resultant suspension was heated at reflux for 4.5 hours. After cooling water was added and the mixture extracted with ethyl acetate. The organic extracts were washed with water. The organic extracts was washed with water, dried (anhydrous magnesium sulphate) and filtered. The filtrate was evaporated to dryness and the residue purified by column chromatography eluting with ethyl acetate in cyclohexane to give 2-(1-methylpropylsulphenyl) -4-trifluoromethylbenzonitrile (9.7 g) as a yellow oil, NMR (CDCl$_3$) 1.0(t,3H), 1.2(d,3H), 1.5(m,1H), 3.4(m,1H), 7.3(m, 1H), 7.6(m,2H).

REFERENCE EXAMPLE 125

2-Chloro-6-fluorobenzyl alcohol (50 g) was stirred in dichloromethane and a solution of sodium hydroxide (32 g) in water was added. After 30 minutes stirring the mixture was cooled to 0° C. when dimethyl sulphate (47 g) and tetrabutyl-ammonium hydrogen-sulphate (1 g) were added dropwise. The mixture was allowed to warm to room temperature and stirred for 3 hours. It was quenched with water and extracted with dichloromethane. The organic extract was washed with water, dried (anhydrous magnesium sulphate) and filtered. The filtrate was evaporated to dryness and the residue distilled under reduced pressure yielding 1-chloro-3-fluoro-2-methoxymethylbenzene (27.3 g) b.p. 82°–95° C./24 mm Hg.

REFERENCE EXAMPLE 126

Sodium hydride (1.05 g of 80% powder) was suspended in THF and to this was added a solution of 2,2,2-trifluoroethanol (1.9 g) in THF, followed by a solution of 4-chloro-3-fluoro-2-methylsulphonylbenzoic acid (4 g) in THF. The resultant mixture was stirred for 2 hours and then acidified with 2M HCl. The mixture was extracted with ether, washed with water, dried (anhydrous magnesium sulphate) and filtered. The filtrate was evaporated to dryness yielding 4-chloro-2-methylsulphonyl-3-(2,2,2-trifluoroethoxy)benzoic acid (5.26 g) as a white solid, NMR (DMSO d$_6$) 2.5(s,3H), 4.8(q,2H), 7.5(d,1H), 8.0(d,1H).

REFERENCE EXAMPLE 127

A mixture of 4-(N,N-dimethylsulphamoyl)-2-trifluoromethylbenzamide (1.38 g), acetic acid (10 ml) and concentrated sulphuric acid (0.5 ml) were heated to 70° C. and isoamyl nitrite (15 ml) was added over 4 hours. After cooling the mixture was poured into water and extracted with ethyl acetate and washed with water. The organic phase was extracted with 2M sodium carbonate and the aqueous layer acidified to pH 1 with 2M HCl. This was extracted with ethyl acetate, washed with water, dried (anhydrous magnesium sulphate) and filtered. The filtrate was evaporated to dryness and the residue passed through a short silica column eluting with dichloromethane-ethyl acetate to give 4-(N,N-dimethylsulphamoyl)-2-trifluoromethylbenzoic acid (0.98 g) as a white solid, m.p. 188.8°–189.4° C.

REFERENCE EXAMPLE 128

A mixture of 4-(N,N-dimethylsulphamoyl)-2-trifluoromethylbenzonitrile (2.78 g), sodium hydroxide (130 mg) and ethanol was heated to 40° C. Hydrogen peroxide (7 ml of 30% solution) was then added and the mixture heated at 40° C. for 3 hours. After cooling the mixture was poured into water and extracted with ethyl acetate. The organic phase was washed with water, dried (anhydrous magnesium sulphate) and filtered. The filtrate was evaporated to dryness and the residue recrystallised from ethyl acetate/toluene to give 4-(N,N-dimethylsulphamoyl)-2-trifluoromethylbenzamide (1.39 g) as a white solid, m.p. 149°–156° C.

REFERENCE EXAMPLE 129

5-Amino-2-cyanobenzotrifluoride (1.86 g) was dissolved in acetic acid (5 ml) and cooled to 5° C. A solution of sodium nitrite (0.7 g) in water (1 ml) and concentrated hydrochloric acid (10 ml) was added and the resultant mixture stirred for 30 minutes at 5° C. and then allowed to warm to 15° C. This mixture was added to a solution of sulphur dioxide (10 ml), acetic acid (10 ml) and copper (I) chloride (0.6 g) and stirred for 45 minutes. The mixture was then poured into water and extracted with dichloromethane. The organic extract was washed with water, dried (anhydrous magnesium sulphate) and filtered. The filtrate was evaporated to dryness. The residue was dissolved in dichloromethane and cooled to 0° C. Dimethylamine was added and the reaction mixture stirred overnight at room temperature. The mixture was evaporated and the residue dissolved in ethyl acetate, washed with water, dried (anhydrous magnesium sulphate) and filtered. The filtrate was evaporated to dryness yielding 4-(N,N-dimethylsulphamoyl)-2-trifluoromethylbenzonitrile as a beige solid, m.p. 133.4°–135.8° C.

REFERENCE EXAMPLE 130

A mixture of ethyl 3,4-dichloro-2-mercaptobenzoate (7.95 g), 2,2,2-trifluoroethyl-p-toluene-sulphonate (9.66 g) and potassium carbonate (6.56 g) in DMF was heated at 90° C. for 4.5 hours. After cooling, water was added and the reaction mixture extracted with ether. The organic extracts were washed with water, dried (anhydrous magnesium sulphate) and filtered. The filtrate was evaporated to dryness and the residue purified by column chromatography eluting with ether/n hexane to give ethyl 3,4-dichloro-2-trifluoroethylsulphenylbenzoate as a yellow oil, (3.53 g) NMR $CDCl_3$; 1.4(t,3H), 3.5(q,2H), 4.4(q,2H), 7.45(d,1H), 7.55(d,1H).

REFERENCE EXAMPLE 131

A solution of 3,4-chloro-2-mercaptobenzoic acid (17.78 g) and concentrated sulphuric acid (3.75 ml) in ethanol was heated at reflux for 20 hours. After cooling the mixture was evaporated and the residue suspended in dichloromethane, washed with water, sodium bicarbonate, water, dried (anhydrous magnesium sulphate) and filtered. The filtrate was evaporated to dryness. The residue was triturated with hexane to give ethyl 3,4-dichloro-2-mercaptobenzoate (7.96 g) as a yellow solid NMR ($CDCl_3$) 1.3(t,3H), 4.25(q,2H), 6.75(s,1H), 7.15(d,1H), 7.8(d,1H).

REFERENCE EXAMPLE 132

To a solution of 3,4-dichlorobenzoic acid (19.1 g) in THF at −75° C. under an inert atmosphere was added n-butyllithium (88 ml of 2.5M solution in hexane). The resultant suspension was stirred overnight at −75° C. Sulphur (3.84 g) was added in one portion and the resultant mixture stirred at −70° C. for 30 minutes and then at room temperature for 6 hours. The mixture was extracted with ether and the combined organic layers were washed with water, dried (anhydrous magnesium sulphate) and filtered. The filtrate was evaporated to dryness and the residue triturated with hexane to give 3,4-dichloro-2-mercaptobenzoic acid as a yellow solid (17.79 g) which was not characterised.

REFERENCE EXAMPLE 133

To a solution of ethyl 4-chloro-2-(2-chloro-2-fluoro-1-difluoroethoxy)benzoate (4.5 g) in DMF at −10° C. was added sodium thiomethoxide (1.5 g). The mixture was stirred at −10° C. for 2 hours and then allowed to warm to room temperature. The mixture was poured into water and extracted with dichloromethane. The organic layer was washed with water, dried (anhydrous magnesium sulphate) and filtered. The filtrate was evaporated to dryness and the residue purified by dry column chromatography eluting with hexane/ether to give ethyl 2-(2-chloro-2-fluoro-1-difluoroethoxy)-4-methylsulphenylbenzoate (3.5 g) as a yellow oil, NMR ($CDCl_3$); 1.3(t,3 H), 2.45(s,3H), 4.3(q,2H), 6.35–6.45(dt,1H), 7.05(s,1H), 7.2(dd,1H), 7.8(d,1H).

REFERENCE EXAMPLE 134

A mixture of ethyl 4chloro-2-hydroxybenzoate (10.4 g) potassium carbonate (14.33 g), potassium iodide (2.9 g) and chlorotrifluoroethylene was heated at 70° C. After cooling the mixture was poured into water (500 ml) and extracted with dichloromethane. The organic layer was washed with water. The organic layer was washed with water, dried (anhydrous magnesium sulphate) and filtered. The filtrate was evaporated to dryness and the residue purified using dry column chromatography eluting with hexane/ether to give ethyl 2-(2-chloro-2-fluoro-1-difluoroethoxy)-4-chlorobenzoate (11.06 g) as a yellow oil, NMR ($CDCl_3$): 1.7(t,3H), 4.3(q,2H), 6.25–6.4(dt,1H), 7.3(m,2H), 7.85 (d,1H).

REFERENCE EXAMPLE 135

A mixture of ethyl 3,4-dichloro-2-mercaptobenzoate (15 g), potassium carbonate (16.6 g), potassium iodide (3,4 g) and chlorotrifluoroethylene (14 g) in DMF was stirred for 3.5 hours. The mixture was poured into water and extracted with ether. The organic extract was washed with water, dried (anhydrous magnesium sulphate) and filtered. The filtrate was evaporated to dryness and the residue purified by column chromatography eluting with ether/hexane to give ethyl 2-(2-chloro-2-fluoro-1-difluoroethylsulphenyl)-3,4-dichlorobenzoate as a yellow oil (6.6 g), NMR ($CDCl_3$): 1.4(t,3H), 4.4(q,2H), 6.25–6.4(m,1H), 7.5(d,1H), 7.7(d,1H).

REFERENCE EXAMPLE 136

A mixture of ethyl 2-methylsulphenyl-4-hydroxybenzoate (5.0 g), potassium iodide (1.17 g) and potassium carbonate (6.5 g) was stirred in DMF and a steady stream of chlorodifluoromethane was bubbled through for 1.5 hours. The mixture was then heated at 70° C. for 1.5 hours, with a steady flow of chlorodifluoromethane passing through the solution. After cooling, the mixture was diluted with water and extracted with ether. The organic extract was washed with water, dried (anhydrous magnesium sulphate) and filtered. The filtrate was evaporated to dryness and the residue purified by column chromatography eluting with hexane/ethyl acetate to give ethyl 4-difluoromethoxy-2-methylsulphenylbenzoate (1.73 g) as a white solid, m.p. 83°–85° C.

REFERENCE EXAMPLE 137

Sodium hydride (4 g of a 60% oil) was heated to 70° C. in dimethyl sulphoxide (DMSO) for 40 minutes. At this time a solution of benzaldehydeoxine (11.04 g) in DMSO was added. After addition stirring was continued for 30 minutes at 70° C. and the mixture allowed to cool. A solution of ethyl 2-nitro-4-methylsulphenylbenzoate (10 g) in DMSO was added and the resultant mixture stirred overnight. The mixture was diluted with water, acidified to pH 1 with 2M HCl and extracted with ether. The organic extract was washed with water, dried (anhydrous magnesium sulphate) and filtered. The filtrate was evaporated to dryness and the residue triturated with hexane/ether to give ethyl 4-hydroxy-2-methylsulphenylbenzoate (8.63 g) as an orange solid, m.p. 132°–135.8° C.

REFERENCE EXAMPLE 138

To a suspension of NaH (0.5 g of 60% dispersion in oil) in DMF (10 ml) was added trifluoroethanol (0.92 ml) and the mixture stirred for 30 minutes. After this time the mixture was cooled to 0° C. and a solution of methyl 4bromo-2-bromomethylbenzoate (3.52 g) in DMF was added, and the resultant mixture stirred at room temperature for 1 hour. 0.5M HCl was added and the mixture extracted with ether.

The organic extract was washed with water, dried (anhydrous magnesium sulphate) and filtered. The filtrate was evaporated to dryness to yield methyl 4-bromo-2-trifluoroethoxymethylbenzoate (3.89 g) as a yellow oil, NMR (CDCl$_3$) 3.9(s,3H), 4.0(q,2H), 5.1(s,2H), 7.5(dd,1H), 7.85(d,1H), 7.9(s,1H).

In the description that follows, it will be understood that where reference is made to compounds of formula I, such reference includes compounds of formula IA and IIB as defined above.

According to a feature of the present invention, there is provided a method for controlling the growth of weeds (i.e. undesired vegetation) at a locus which comprises applying to the locus a herbicidally effective amount of at least one isoxazole derivative of formula I. For this purpose, the isoxazole derivatives are normally used in the form of herbicidal compositions (i.e. in association with compatible diluents or carriers and/or surface active agents suitable for use in herbicidal compositions), for example as hereinafter described.

The compounds of formula I show herbicidal activity against dicotyledonous (i.e. broad-leafed) and monocotyledonous (i.e. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula I may be used to control the growth of:

broad-leafed weeds, for example, *Abutilon theophrasti, Amaranthus retroflexus, Bidens pilosa, Chenopodium album, Galium aparine*, Ipomoea spp. e.g. *Ipomoea purpurea, Sesbania exalta, Sinapis arvensis, Solanum nigrum* and *Xanthium strumarium*, and grass weeds, for example *Alopecurus myosuroides, Avena fatua, Digitaria sanguinalis, Echinochloa crus-galli, Sorghum bicolor, Eleusine indica* and Setaria spp, e.g. *Setaria faberii* or *Setaria viridis*, and sedges, for example, *Cyperus esculentus.*

The amounts of compounds of formula I applied vary with the nature of the weeds, the compositions used, the time of application, the climatic and edaphic conditions and (when used to control the growth of weeds in crop-growing areas) the nature of the crops. When applied to a crop-growing area the rate of application should be sufficient to control the growth of weeds without causing substantial permanent damage to the crop. In general taking these factors into account, application rates between 0.01 kg and 5 kg of active material per hectare give good results. However, it is to be understood that higher or lower application rates may be used, depending upon the particular problem of weed control encountered.

The compounds of formula I may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops. e.g. the crops hereinbefore mentioned, application rates between 0.01 kg and 4.0 kg, and preferably between 0.01 kg and 2.0 kg, of active material per hectare are particularly suitable.

The compounds of formula I may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula I may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula I may be incorporated into the soil in which the weeds are expected to emerge. It will be appreciated that when the compounds of formula I are used to control the growth of weeds by post-emergence application, i.e. by application to the aerial or exposed portions of emerged weeds, the compounds of formula I will also normally come into contact with the soil and may also then exercise a pre-emergence control on later-germinating weeds in the soil.

Where especially prolonged weed control is required, the application of the compounds of formula I may be repeated if required.

According to a further feature of the present invention, there are provided compositions suitable for herbicidal use comprising one or more of the isoxazole derivatives of formula I, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula I]. The term "homogeneously dispersed" is used to include compositions in which the compounds of formula I are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula I.

The herbicidal compositions may contain both a diluent or carrier and surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of formula I with solid diluents or by impregnating the solid diluents or carriers with solutions of the compounds of formula I in volatile solvents, evaporating the solvents and, if necessary, grinding the products so as to obtain powders. Granular formulations may be prepared by absorbing the compounds of formula I (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula I may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are:

aqueous suspension concentrates which comprise from 10 to 70% of one or more compounds of formula I, from 2 to 10% of surface-active agent, from 0.1 to 5% of thickener and from 15 to 87.9% of water;

wettable powders which comprise from 10 to 90% of one or more compounds of formula I, from 2 to 10% of surface-active agent and from 8 to 88% of solid diluent or carrier;

water soluble or water dispersible powders which comprise from 10 to 90% of one or more compounds of formula I, from 2 to 40% of sodium carbonate and from 0 to 88% of solid diluent;

liquid water soluble concentrates which comprise from 5 to 50%, e.g. 10 to 30%, of one or more compounds of formula I, from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula I, from 5 to 15% of surface-active agent, from 0.1 to 5% of thickener and from 10 to 84.9% of organic solvent;

granules which comprise from 1 to 90%, e.g 2 to 10% of one or more compounds of formula I, from 0.5 to 7%, e.g. 0.5 to 2%, of surface-active agent and from 3 to 98.5%, e.g. 88 to 97.5%, of granular carrier, and emulsifiable concentrates which comprise 0.05 to 90%, and preferably from 1 to 60% of one or more compounds of formula I, from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine[2-chloro-4-ethylamino-6-isopropylamino-1,3,5-triazine], bromoxynil[3,5-dibromo-4-hydroxybenzonitrile], chlortoluron[N'-(3-chloro-4-methylphenyl)-N,N-dimethylurea], cyanazine[2-chloro-4-(1-cyano-1-methylethylamino)-6-ethylamino-1,3,5-triazine], 2,4-D[2,4- dichlorophenoxy-acetic acid], dicamba[3,6-dichloro-2-methoxybenzoic acid], difenzoquat[1,2-dimethyl-3,5-diphenylpyrazolium salts], flampropmethyl[methyl N-2-(N-benzoyl-3-chloro-4-fluoroanilino)-propionate], fluometuron [N'-(3-trifluoromethylphenyl)-N,N-dimethylurea], isoproturon[N'-(4-isopropylphenyl)-N,N diethylurea], insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chloro-phenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the isoxazole derivatives of formula I or, as is preferred, a herbicidal composition as hereinbefore described, and preferably a herbicidal concentrate which must be diluted before use, comprising at least one of the isoxazole derivatives of formula I within a container for the aforesaid derivative or derivatives of formula I, or a said herbicidal composition, and instructions physically associated with the aforesaid container setting out the manner in which the aforesaid derivative or derivatives of formula I or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the isoxazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% w/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 is obtained then making up to volume with water.

Similar soluble concentrates may be prepared as described above by replacing the isoxazole (compound 1) with other compounds of formula I.

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compound 1) with other compounds of formula I.

EXAMPLE C3

A water soluble powder is formed from:

| | |
|---|---|
| Active ingredient (compound 1) | 50% w/w |
| Sodium dodecylbenzene sulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the isoxazole (compound 1) with other compounds of formula I.

The compounds of the invention have been used in herbicidal applications according to the following procedures.

METHOD OF USE OF HERBICIDAL COMPOUNDS a) General

Appropriate quantities of the compounds used to treat the plants were dissolved in acetone to give solutions equivalent to application rates of up to 4000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| Weed species | Approx number of seeds/pot |
|---|---|
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium stumarium | 2. |
| 2) Grass weeds | |
| Alopecurus myosuroides | 15 |

|  | Approx number of seeds/pot |
| --- | --- |
| Avena fatua | 10 |
| Echinochloa crus-galli | 15 |
| Setaria viridis | 20. |
| 3) Sedges | |
| Cyperus esculentus | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

|  | Number of plants per pot | Growth stage |
| --- | --- | --- |
| 1) Broad leafed weeds | | |
| Weed species | | |
| Abutilon theophrasti | 3 | 1–2 leaves |
| Amaranthus retroflexus | 4 | 1–2 leaves |
| Galium aparine | 3 | 1st whorl |
| Ipomoea purpurea | 3 | 1–2 leaves |
| Sinapis arvensis | 4 | 2 leaves |
| Xanthium strumarium | 1 | 2–3 leaves. |
| 2) Grass weeds | | |
| Weed species | | |
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |
| 3) Sedges | | |
| Weed species | | |
| Cyperus esculentus | 3 | 3 leaves. |
| 1) Broad leafed | | |
| Crops | | |
| Cotton | 2 | 1 leaf |
| Soya | 2 | 2 leaves. |
| 2) Grass | | |
| Crops | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

The compounds of the invention have shown an excellent level of herbicidal activity together with crop tolerance on the weeds used in the foregoing experiments.

When applied pre-emergence at 4000 g/ha compounds 1, 2, 4, 5, 6, 7, 8, 9, 11, 12, 13, 15, 16, 19, 22, 27, 28, 29, 30, 31, 32, 35, 39, 40, 42, 44, 49 gave at least 90% reduction in growth of one or more weed species.

When applied post-emergence at 4000 g/ha compounds 1, 2, 4, 7, 8, 9, 10, 11, 12, 13, 15, 16, 19, 22, 27, 28, 29, 30, 31, 32, 35, 39, 40, 42, 44, 49, 53 gave at least 90% reduction in growth of one or more weed species.

When applied pre-emergence at 2000 g/ha compounds 3, 14, 17, 18, 20, 21, 23, 24, 25, 33, 34, 36, 37, 38, 41, 43, 45, 46, 47, 48, 51, 52 gave at least 90% reduction in growth of one or more weed species.

When applied post-emergence at 2000 g/ha compounds 3, 14, 17, 18, 20, 21, 23, 24, 25, 26, 33, 34, 36, 37, 38, 41, 43, 45, 46, 48, 50, 52 gave at least 70% reduction in growth of one or more weed species.

When applied pre-emergence at 1000 g/ha compounds 54, 55, 56, 57, 58, 59, 60, 61, 62, 63, 64, 65, 66, 67 gave at least 80% reduction in growth of one or more weed species.

When applied post-emergence at 1000 g/ha compounds 54, 55, 56, 57, 58, 59, 60, 61, 62, 63, 64, 65, 66, 67 gave at least 70% reduction in growth of one or more weed species.

When applied pre-emergence at 2000 g/ha compounds 68, 69, 71 to 86, 88 to 101, 103 to 107, 109 to 156, 158 to 176, 179 and 180 to 189 gave at least 80% reduction in growth of one or more weed species:

When applied post-emergence at 1000 g/ha compounds 68, 69, 71, 72 to 75, 78 to 81, 83 to 88, 90 to 101, 103 to 179 and 180 to 189 gave at least 70% reduction in the growth of one or more weed species:

When applied post-emergence at 1000 g/ha compounds 54, 55, 56, 57, 58, 59, 60, 61, 62, 63, 64, 65, 66, 67 gave at least 70% reduction in growth of one or more weed species.

When applied pre-emergence at 694 g/ha compound 102 gave at least 80% reduction in growth of one or more of the weed species.

When applied post-emergence at 694 g/ha compound 102 gave at least 70% reduction in growth of one or more of the weed species.

When applied post-emergence at 4000 g/ha compounds 190, 192, 193, 194 and 195 gave at least 90% reduction in growth of one or more of the weed species.

When applied pre-emergence at 1000 g/ha compounds 196 to 248 gave at least 90% reduction in growth of one or more of the weed species.

When applied post-emergence at 1000 g/ha compounds 196, 198 and 200 to 248 gave at least 90% reduction in growth of one or more of the weed species.

Crop tolerance was observed on at least one of the cereal crops for compounds 190 to 248 either pre- or post-emergence with less than 30% damage showing that the compounds had good potential for selective control in cereal crops.

When applied pre- or post-emergence at 1000 g/ha compounds 249 to 282 gave at least 90% reduction in growth of one or more of the weed species.

When applied pre- or post-emergence at 1000 g/ha compounds 283 to 292 and 328 to 351 gave at least 90% reduction in growth of one or more of the weed species.

When applied pre-emergence at 4000 g/ha compounds 294, 298 and 308 gave at least 90% reduction in growth of one or more weed species.

When applied post-emergence at 4000 g/ha compounds 294, 298 and 308 gave at least 90% reduction in growth of one or more weed species.

When applied pre-emergence at 2000 g/ha compound 295 gave at least 90% reduction in growth of one or more weed species.

When applied post-emergence at 2000 g/ha compound 295 gave at least 90% reduction in growth of one or more weed species.

When applied pre-emergence at 1000 g/ha compounds 296, 297, 300, 301, 302, 303, 304, 305, 306, 307 and 309 to 327 gave at least 90% reduction in growth of one or more weed species.

When applied post-emergence at 1000 g/ha compounds 296, 297, 301, 302, 303, 304, 305, 306, 307, 309 and 310 to 327 gave at least 70% reduction in growth of one or more weed species.

When applied pre- or post-emergence at 1000 g/ha compounds 352 to 371 gave at least 90% reduction in growth of one or more of the weed species.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What we claim is:

1. A compound of the formula:

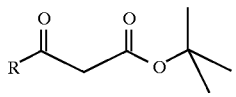

wherein R is cycloalkyl having from three to five carbon atoms; or 2-methylcyclopropyl.

2. A compound according to claim 1, wherein R is cycloalkyl having from three to five carbon atoms.

3. The compound according to claim 2, wherein R is cyclopropyl.

4. A process for the preparation of a compound as claimed in claim 1, said process comprising reacting a compound of the formula:

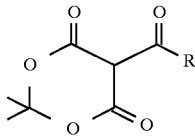

wherein R is as defined in claim 1, with t-butanol in a solvent.

5. A process according to claim 4, wherein the solvent is toluene.

6. A process according to claim 4, wherein R is cycloalkyl having from three to five carbon atoms.

7. The process according to claim 6, wherein R is cyclopropyl.

* * * * *